US010111888B2

(12) United States Patent
Kreppner et al.

(10) Patent No.: US 10,111,888 B2
(45) Date of Patent: Oct. 30, 2018

(54) INTRANASAL 0.15% AND 0.24% TESTOSTERONE GEL FORMULATIONS AND USE THEREOF FOR TREATING ANORGASMIA OR HYPOACTIVE SEXUAL DESIRE DISORDER

(71) Applicant: Acerus Pharmaceuticals SRL, Christ Church (BB)

(72) Inventors: Wayne Kreppner, Georgetown (CA); Siobhan Fogarty, Blackrock (IE); Werner Oberegger, Waterdown (CA); Paul José Pierre Marie Maes, Visé (BE)

(73) Assignee: ACERUS BIOPHARMA INC., Ontario (CA)

( * ) Notice: Subject to any disclaimer, the term of this patent is extended or adjusted under 35 U.S.C. 154(b) by 0 days.

(21) Appl. No.: 14/922,070

(22) Filed: Oct. 23, 2015

(65) Prior Publication Data

US 2016/0271144 A1 Sep. 22, 2016

Related U.S. Application Data

(63) Continuation of application No. 14/644,414, filed on Mar. 11, 2015, now abandoned, which is a continuation of application No. 13/471,450, filed on May 14, 2012, now abandoned.

(60) Provisional application No. 61/598,335, filed on Feb. 13, 2012, provisional application No. 61/513,499, filed on Jul. 29, 2011, provisional application No. 61/486,254, filed on May 14, 2011, provisional application No. 61/518,903, filed on May 13, 2011.

(51) Int. Cl.
*A61K 31/56* (2006.01)
*A61K 31/568* (2006.01)
*A61K 9/00* (2006.01)
*A61K 47/02* (2006.01)
*A61K 47/44* (2017.01)
*A61K 9/06* (2006.01)
*A61K 47/14* (2017.01)

(52) U.S. Cl.
CPC .......... *A61K 31/568* (2013.01); *A61K 9/0043* (2013.01); *A61K 9/06* (2013.01); *A61K 47/02* (2013.01); *A61K 47/14* (2013.01); *A61K 47/44* (2013.01)

(58) Field of Classification Search
USPC ....................................................... 514/170
See application file for complete search history.

(56) References Cited

U.S. PATENT DOCUMENTS

| | | |
|---|---|---|
| 3,923,190 A | 12/1975 | Roth |
| 4,051,265 A | 9/1977 | Kirshenbaum et al. |
| 4,071,623 A | 1/1978 | van der Vies |
| 4,083,973 A | 4/1978 | van der Vies |
| 4,123,417 A | 10/1978 | Finberg |
| RE29,892 E | 1/1979 | Bayne |
| 4,315,925 A | 2/1982 | Hussain et al. |
| 4,546,882 A | 10/1985 | Hsu et al. |
| 4,581,225 A | 4/1986 | Su et al. |
| 4,752,425 A | 6/1988 | Martin et al. |
| 4,786,678 A | 11/1988 | Dobreski et al. |
| 4,812,448 A | 3/1989 | Knepper |
| 4,826,852 A | 5/1989 | Haffer et al. |
| 5,049,387 A | 9/1991 | Amkraut |
| 5,130,137 A | 7/1992 | Crowley, Jr. |
| 5,248,501 A | 9/1993 | Parnell |
| 5,397,771 A | 3/1995 | Bechgaard et al. |
| 5,455,286 A | 10/1995 | Amidon et al. |
| 5,500,261 A | 3/1996 | Takei et al. |
| 5,514,673 A | 5/1996 | Heckenmuller et al. |
| 5,554,378 A | 9/1996 | Uda et al. |
| 5,578,588 A | 11/1996 | Mattern et al. |
| 5,624,960 A | 4/1997 | Wenzel et al. |
| 5,635,203 A | 6/1997 | Gale et al. |
| 5,645,856 A | 7/1997 | Lacy et al. |
| 5,739,176 A | 4/1998 | Dunn et al. |
| 5,747,058 A | 5/1998 | Tipton et al. |
| 5,756,071 A | 5/1998 | Mattern et al. |
| 5,855,905 A | 1/1999 | Oettel et al. |
| 5,863,554 A | 1/1999 | Ilium |
| 5,877,216 A | 3/1999 | Place et al. |
| 5,891,462 A | 4/1999 | Carrara |
| 5,891,920 A | 4/1999 | Hirano et al. |
| 5,897,894 A | 4/1999 | Glass |
| 5,908,638 A | 6/1999 | Huber et al. |
| 5,948,492 A | 9/1999 | Cargile |
| 6,096,733 A | 8/2000 | Lubkin |
| 6,187,323 B1 | 2/2001 | Aiache et al. |
| 6,231,662 B1 | 5/2001 | Atkinson |
| 6,248,363 B1 | 6/2001 | Patel et al. |
| 6,262,021 B1 | 7/2001 | Uvnas-Moberg et al. |
| 6,287,588 B1 | 9/2001 | Shih et al. |
| 6,306,841 B1 | 10/2001 | Place et al. |
| 6,309,663 B1 | 10/2001 | Patel et al. |
| 6,310,089 B1 | 10/2001 | Watts et al. |
| 6,319,905 B1 | 11/2001 | Mandel et al. |
| 6,319,913 B1 | 11/2001 | Mak et al. |
| 6,333,313 B1 | 12/2001 | Copland, III et al. |

(Continued)

FOREIGN PATENT DOCUMENTS

| | | |
|---|---|---|
| CA | 2135203 A1 | 12/1993 |
| CA | 2463384 A1 | 4/2003 |

(Continued)

OTHER PUBLICATIONS

Ahmed et al. "Transdermal Testosterone Therapy in the Treatment of Male Hypogonadism." J Clin Endocrinol Metab, 1988; 66(3):546-551.

(Continued)

*Primary Examiner* — Rei Tsang Shiao
(74) *Attorney, Agent, or Firm* — Lewis Brisbois Bisgaard & Smith LLP

(57) ABSTRACT

The present invention relates to lower dosage strength pernasal testosterone gel formulations for intranasal administration and treatment methods for using the lower dosage strength pernasal testosterone gel formulations for treating a female subject with anorgasmia and/or hypoactive sexual desire disorder.

12 Claims, 29 Drawing Sheets

(56) References Cited

U.S. PATENT DOCUMENTS

| | | |
|---|---|---|
| 6,423,701 B1 | 7/2002 | Hussain |
| 6,432,440 B1 | 8/2002 | Watts et al. |
| 6,451,339 B2 | 9/2002 | Patel et al. |
| 6,503,894 B1 | 1/2003 | Dudley et al. |
| 6,562,790 B2 | 5/2003 | Chein |
| 6,583,129 B1 | 6/2003 | Mazer et al. |
| 6,589,549 B2 | 7/2003 | Shih et al. |
| 6,610,670 B2 | 8/2003 | Backensfeld et al. |
| 6,669,879 B1 | 12/2003 | Spengler et al. |
| 6,720,001 B2 | 4/2004 | Chen et al. |
| 6,737,084 B2 | 5/2004 | Crosby et al. |
| 6,761,903 B2 | 7/2004 | Chen et al. |
| 6,800,363 B2 | 10/2004 | Su et al. |
| 6,815,506 B2 | 11/2004 | Takashima et al. |
| 6,833,478 B2 | 12/2004 | Bottaro et al. |
| 6,838,091 B2 | 1/2005 | Lipari et al. |
| 6,881,423 B2 | 4/2005 | Dohi et al. |
| 6,958,142 B2 | 10/2005 | Daniels et al. |
| 6,982,281 B1 | 1/2006 | Chen et al. |
| 7,029,657 B2 | 4/2006 | Pike et al. |
| 7,186,706 B2 | 3/2007 | Rosario-Jansen et al. |
| 7,198,801 B2 | 4/2007 | Carrara et al. |
| 7,404,965 B2 | 7/2008 | Carrara et al. |
| 7,459,445 B2 | 12/2008 | Hill et al. |
| 7,470,433 B2 | 12/2008 | Carrara et al. |
| 7,479,478 B2 | 1/2009 | Bringhurst et al. |
| 7,731,990 B2 | 6/2010 | Dohi et al. |
| 7,749,989 B2 | 7/2010 | Hill et al. |
| 7,799,337 B2 | 9/2010 | Levin |
| 7,799,769 B2 | 9/2010 | White et al. |
| 8,067,399 B2 | 11/2011 | Lehman et al. |
| 8,574,622 B2 | 11/2013 | Mattern |
| 8,609,043 B2 | 12/2013 | Mattern |
| 8,784,869 B2 | 7/2014 | Mattern |
| 8,784,882 B2 | 7/2014 | Mattern |
| 8,877,230 B2 | 11/2014 | Mattern |
| 2001/0055569 A1 | 12/2001 | Davis et al. |
| 2002/0032171 A1 | 3/2002 | Chen et al. |
| 2002/0114933 A1 | 8/2002 | Gould |
| 2002/0136752 A1 | 9/2002 | Whittle et al. |
| 2002/0198136 A1 | 12/2002 | Mak et al. |
| 2003/0022877 A1 | 1/2003 | Dudley |
| 2003/0139384 A1 | 7/2003 | Dudley |
| 2003/0153540 A1 | 8/2003 | Rosario-Jansen et al. |
| 2004/0005275 A1 | 1/2004 | Gizurarson et al. |
| 2004/0022738 A1 | 2/2004 | Pike et al. |
| 2004/0022739 A1 | 2/2004 | Daniels et al. |
| 2004/0028613 A1 | 2/2004 | Quay |
| 2004/0044086 A1 | 3/2004 | Schulze et al. |
| 2004/0115226 A1 | 6/2004 | Li et al. |
| 2005/0020552 A1 | 1/2005 | Aschkenasy et al. |
| 2005/0042268 A1 | 2/2005 | Aschkenasy et al. |
| 2005/0049233 A1 | 3/2005 | Dudley |
| 2005/0070516 A1 | 3/2005 | Wilson et al. |
| 2005/0100564 A1 | 5/2005 | Mattern |
| 2005/0112181 A1 | 5/2005 | Dudley et al. |
| 2005/0113353 A1 | 5/2005 | Dudley et al. |
| 2005/0129756 A1 | 6/2005 | Podhaisky et al. |
| 2005/0142173 A1 | 6/2005 | Dudley et al. |
| 2005/0152956 A1 | 7/2005 | Dudley |
| 2005/0153946 A1 | 7/2005 | Hirsh et al. |
| 2005/0187188 A1 | 8/2005 | Stein et al. |
| 2005/0245494 A1 | 11/2005 | Thompson et al. |
| 2006/0008420 A1 | 1/2006 | Daniels et al. |
| 2006/0140820 A1 | 6/2006 | Mattern |
| 2006/0147385 A1 | 7/2006 | Pike et al. |
| 2006/0153905 A1 | 7/2006 | Carrara et al. |
| 2006/0210622 A1 | 9/2006 | Pace et al. |
| 2006/0211664 A1 | 9/2006 | Dudley |
| 2006/0270642 A1* | 11/2006 | Lehman ............... A61K 9/0014 514/170 |
| 2007/0134332 A1 | 6/2007 | Turnell et al. |
| 2007/0149454 A1* | 6/2007 | Mattern ............... A61K 31/568 424/434 |
| 2007/0190120 A1 | 8/2007 | Rosario-Jansen et al. |
| 2007/0264312 A1 | 11/2007 | Skaggs et al. |
| 2009/0062244 A1 | 3/2009 | Schwarz et al. |
| 2009/0227550 A1 | 9/2009 | Mattern |
| 2009/0299156 A1 | 12/2009 | Simpson et al. |
| 2009/0318398 A1 | 12/2009 | Dudley et al. |
| 2010/0136105 A1 | 6/2010 | Chen et al. |
| 2010/0173882 A1 | 7/2010 | Giliyar et al. |
| 2010/0273838 A1 | 10/2010 | Cui et al. |
| 2010/0311707 A1* | 12/2010 | Mattern ............... A61K 31/568 514/179 |
| 2011/0009318 A1 | 1/2011 | White et al. |
| 2011/0172196 A1 | 7/2011 | Dudley et al. |
| 2011/0195114 A1 | 8/2011 | Carrara et al. |
| 2011/0237562 A1 | 9/2011 | Mattern |
| 2011/0245215 A1 | 10/2011 | Carrara et al. |
| 2011/0284579 A1 | 11/2011 | Pardes et al. |
| 2011/0306582 A1 | 12/2011 | Dudley et al. |
| 2011/0306583 A1 | 12/2011 | Malladi |
| 2012/0005987 A1 | 1/2012 | Mattern |
| 2012/0009249 A1 | 1/2012 | Mattern |
| 2012/0009250 A1 | 1/2012 | Mattern |
| 2012/0058176 A1 | 3/2012 | Mattern |
| 2012/0058981 A1 | 3/2012 | Dudley et al. |
| 2012/0083480 A1 | 4/2012 | Mattern |
| 2012/0277202 A1 | 11/2012 | Mattern |
| 2012/0297730 A1 | 11/2012 | Mattern |
| 2013/0040922 A1 | 2/2013 | Kreppner et al. |
| 2013/0040923 A1 | 2/2013 | Kreppner et al. |
| 2013/0045958 A1 | 2/2013 | Kreppner et al. |
| 2013/0059827 A1 | 3/2013 | Kreppner et al. |
| 2015/0005271 A1 | 1/2015 | Mattern |

FOREIGN PATENT DOCUMENTS

| | | |
|---|---|---|
| CN | 101801388 A | 8/2010 |
| DE | 943792 C | 6/1956 |
| DE | 1569286 A1 | 7/1969 |
| EP | 0084922 A2 | 8/1983 |
| EP | 0160501 A2 | 11/1985 |
| EP | 0349091 A1 | 1/1990 |
| EP | 1530965 A1 | 5/2005 |
| EP | 2068825 A1 | 6/2009 |
| EP | 2191833 A1 | 6/2010 |
| GB | 761618 A | 11/1956 |
| GB | 2237510 A | 5/1991 |
| JP | 50144579 | 11/1975 |
| JP | 54072192 | 6/1979 |
| JP | 01016716 | 1/1989 |
| JP | 01160916 | 6/1989 |
| JP | 2002541111 A | 12/2002 |
| JP | 2003509453 A | 3/2003 |
| JP | 2003519085 A | 6/2003 |
| JP | 2007524589 A | 8/2007 |
| JP | 2007530446 A | 11/2007 |
| JP | 2008522997 A | 7/2008 |
| JP | 2008536851 A | 9/2008 |
| KR | 200282242 | 7/2002 |
| TW | 175318 | 12/1991 |
| WO | WO-9520945 A1 | 8/1995 |
| WO | WO-9740823 A1 | 11/1997 |
| WO | WO-9809166 A1 | 3/1998 |
| WO | WO-9834621 A1 | 8/1998 |
| WO | WO-9847535 A1 | 10/1998 |
| WO | WO-0059512 A1 | 10/2000 |
| WO | WO-0141732 A1 | 6/2001 |
| WO | WO-0195888 A1 | 12/2001 |
| WO | WO-02051452 A1 | 7/2002 |
| WO | WO-03011301 A1 | 2/2003 |
| WO | WO-03063833 A1 | 8/2003 |
| WO | WO-03088974 A1 | 10/2003 |
| WO | WO-2008040488 A1 | 4/2008 |
| WO | WO-2009133352 A2 | 11/2009 |
| WO | WO-2012022446 A1 | 2/2012 |
| WO | WO-2012156820 A1 | 11/2012 |

(56) References Cited

FOREIGN PATENT DOCUMENTS

| WO | WO-2012156821 A1 | 11/2012 |
|----|------------------|---------|
| WO | WO-2012156822 A1 | 11/2012 |

OTHER PUBLICATIONS

Aleman et al. "A single administration of testosterone improves visuospatial ability in young women." Psychoneuroendocrinology. 2004; 29, 612-617.
Alexander et al. "Testosterone and libido in surgically and naturally menopausal women." Women's Health 2006; 2(3):459-77.
Alexander et al. "The effects of postmenopausal hormone therapies on female sexual functioning: a review of double-blind, randomized controlled trials." Menopause. 2004; 11 (6) 749-765.
Amaral et al. "Topographic organization of projections from the amygdala to the visual cortex in the macaque monkey." Neuroscience. 2003; 118: 1099-1120.
Amiaz et al. Testosterone gel replacement improves sexual function in depressed men taking serotonergic antidepressants: a randomized, placebo-controlled clinical trial. J. of Sex and Marital Therapy. 2011; 37: 243-254.
Andersen et al. The association of testosterone, sleep, and sexual function in men and women. Brain Res. 2011; 1416:80-104.
Anonymous. "Advisory Committee Briefing Document: Intrinsa® (testosterone transdermal system). NDA No. 21-769." Procter & Gamble Pharmaceuticals, Inc. 2004.
Araujo et al. "Prevalence of symptomatic androgen deficiency in men." J Clin Endocrinol Metab. 2007; 92 (11): 4241-7.
Arnow et al. "Women with hypoactive sexual desire disorder compared to normal females: a functional magnetic resonance imaging study." Neuroscience 2009, 158: 484-502.
Arora et al. "Permeability issues in nasal drug delivery." Drug Discov Today. 2002; 7(18):967-975.
Aspide et al. "Non-selective attention and nitric oxide in putative animal models of Attention-Deficit Hyperactivity Disorder." Behav. Brain Res. 1998; 95, 123-133.
Aspide et al. "Non-selective attention in a rat model of hyperactivity and attention deficit: subchronic methylphenydate and nitric oxide synthesis inhibitor treatment." Neurosci. Biobehav. Rev. 2000; 24, 59-71.
Bachmann et al. "Female androgen insufficiency: the Princeton consensus statement on definition, classification, and assessment." Fertility & Sterility. 2002; 77 (4): 660-665.
Bagger et al. "The potential of nasal application for delivery to the central brain—a microdialysis study of fluorescein in rats." Eur J Pharm Sci. 2004; 21: 235-242.
Baird et al. "The amygdala and sexual drive: Insights from temporal lobe epilepsy surgery." Ann Neurol. 2004; 55(1):87-96.
Bals-Pratsch et al. "Substitution Therapy of Hypogonadal Men with Transdermal Testosterone Over One Year." Acta Endocrinologica (Copenh), 1988; 118:7-13.
Bals-Pratsch et al. "Transdermal testosterone substitution therapy for male hypogonadism." Lancet. 1986; 943-946.
Banks et al. "Brain uptake of glucagon-like peptide-1 antagonist exendin(9-39) after intranasal administration." J Pharmacol Exp Ther. 2004; 309(2):469-475.
Banks et al. "Delivery of testosterone to the brain by intranasal administration: Comparison to intravenous testosterone," Journal of Drug Targeting. 2008;17(2):91-7.
Behre et al. "Intramuscular injection of testosterone undecanoate for the treatment of male hypogonadism: phase I studies." Eur J Endocrinol 1999; 140(5): 414-419.
Benedict et al. "Intranasal insulin improves memory in humans." Psychoneuroendocrinology 2004; 29 (10) 1326-1334.
Beral et al. "Evidence from randomised trials on the long-term effects of hormone replacement therapy." Lancet 2002; 360(9337):942-4.
Berman et al. "Female sexual dysfunction." Urol Clin North Am 2001; 28 (2) 405-416.

Berner et al. "Pharmacokinetic Characterisation of Transdermal Delivery System", Clin Pharmacokinet, 1994; 26(2):121-134.
Bhasin et al. "Androgens in Men Guideline Task Force. Testosterone therapy in adult men with androgen deficiency syndromes: An Endocrine Society clinical practice guideline." J Clin Endocrinol Metab 2010; 95(6):2536-2559.
Bhasin. "Clinical Review 34—Androgen Treatment of Hypogonadal Men." J. Clinical Endocrinology and Metabolism, 1992; 74(6):1221-1225.
Bhowmick et al. "Sexual Precocity in a 16-Month-Old Boy Induced by Indirect Topical Exposure to Testosterone." Clinical Pediatrics 2007; 46(6): 540-543.
Bjork et al. "Degradable starch microspheres as a nasal delivery system for insulin." Int. J. Pharm. 1988; 47, 233-238.
Born et al. "Sniffing neuropeptides: a transnasal approach to the human brain." Nat Neurosci. 2002; 5(6):514-516.
Bouloux. "Testim 1% testosterone gel for the treatment of male hypogonadism." Clin Ther. 2005; 27(3):286-98.
Brachet et al. "Children's Virilization and the Use of a Testosterone Gel by Their Fathers." Eur. J. Pediatr. 2005; 164: 646-647.
Braunstein et al. Safety and efficacy of a testosterone patch for the treatment of hypoactive sexual desire disorder in surgically menopausal women: A randomized, placebo-controlled trial. Archives of Internal Medicine. 2005; 165, 1582-1589.
Braunstein. "Androgen insufficiency in women." Growth Horm ME Res. 2006; 16: Suppl1:109-17.
Brittebo et al. "Metabolism of Xenobiotics and Steroid Hormones in the Nasal Mucosa." Toxicology of the Nasal Passages. C.S. Barrow Editor. 1986. Washington.
Brittebo et al. "Steroid Metabolism by Rat Nasal Mucosa: Studies on Progesterone and Testosterone." J. Steroid Biochem. 1984; 20(5): 1147-1151.
Brittebo et al. "Taurine in the olfactory system: effects of the olfactory toxicant dichlobenil." Neurotoxicology. 1995; 16(2), 271-280.
Brittebo. "N-demethylation of aminopyrine by the nasal mucosa in mice and rats." Acta Pharmacol. Toxicol. 1982; 51: 227-232.
Brocks et al. "Pharmacokinetics of testosterone in hypogonadal men after transdermal delivery: influence of dose." J Clin Pharmacol. 1996; 36(8):732-739.
Buddenberg et al. "Behavioral actions of intranasal application of dopamine: effects on forced swimming, elevated plus-maze and open field parameters." Neuropsychobiology. 2008;57(1-2):70-9.
Burger et al. "Effect of combined implants of oestradiol and testosterone on libido in postmenopausal women." Br Med J (Clin Res Ed) 1987; 294(6577):1417-8.
Buster et al. "Testosterone patch for low sexual desire in surgically menopausal women: a randomized trial." Obstet. Gynecol. 2005; 105 (5 Pt. 1): 944-952.
Cahill. "Why sex matters for neuroscience." Nat Rev Neurosci 2006; 7: 477-484.
Cameron et al. "Androgen replacement therapy in women." Fertil Steril 2004; 82 (2) 273-289.
Cardozo et al. "The effects of subcutaneous hormone implants during the climacteric." Maturitas 1984; 5(3):177-84.
Carey et al. "Transdermal Testosterone Treatment of Hypogonadal Men." J. of Urology, 1988; (140):76-79.
Center for Drug Evaluation & Research. Application No. 21-015. Medical Review. Feb. 15, 2000.
Center for Drug Evaluation and Research. Application No. 021463Orig1s000. Medical Reviews. Jun. 30, 2010.
Center for Drug Evaluation and Research. Application No. 022504Orig1s000. Medical Reviews. Nov. 19, 2010.
Char et al. "Nasal delivery of [14c]dextromethorphan hydrochloride in rats: levels in plasma and brain." J. Pharm. Sci. 1992; 81(8), 750-752.
Chen et al. "Delivery of nerve growth factor to the brain via the olfactory pathway." J. Alzheimer's Dis. 1998; 1:35-44.
Cherrier et al. "Cognitive changes associated with supplementation of testosterone or dihydrotestosterone in mildly hypogonadal men: a preliminary report." J Androl 2003; 24(4):568-76.

(56) References Cited

OTHER PUBLICATIONS

Chiang et al. "Testosterone gel monotherapy improves sexual function of hypogonadal men mainly through restoring erection: Evaluation by IIEF Score." Urology. 2009; 73(4): 762-766.
Chien et al. [editors] "Nasal systemic drug delivery". Drugs and the pharmaceutical sciences. vol. 39 New York, Marcel Dekker Inc. 1989. pp. 1-19, 27-32, 39-78, and 200-219.
Chou et al. "Lidocaine distribution into the CNS following nasal and arterial delivery: a comparison of local sampling and microdialysis techniques." Int. J. Pharm. 1998; 171, 53-61.
Chow et al. "Direct nose-brain transport of benzoylecgonine following intranasal administration in rats." J Pharm Sci. 2001; 90:1729-1735.
Chow et al. "Direct transport of cocaine from the nasal cavity to the brain following intranasal cocaine administration in rats." J. Pharm. Sci. 1999; 88(8), 754-758.
Chu et al. "Formulations and use of androgens in women." Mayo Clin Proc. 2004; 79(Suppl.): S3-7.
Cicinelli et al. "Administration of unmodified progesterone by nasal spray in fertile women," Gynecol. Endocrinol., vol. 9, pp. 289-293, 1995.
Cicinelli et al. "Nasal spray administration of unmodified progesterone: evaluation of progesterone serum levels with three different radioimmunoassay techniques", Maturitas Journal of the Climacteric & Postmenopause, 19(1994), pp. 43-52.
Cicinelli et al. "Progesterone administration by nasal spray in menopausal women: comparison between two different spray formulations", Gynecol. Endocrinol., 6(1992), pp. 247-251.
Cicinelli et al. "Progesterone administration by nasal spray", Fertility and Sterility, vol. 56, No. 1, Jul. 1991, pp. 139-141.
Cicnelli et al. "Nasally-administered progesterone: comparison of ointment and spray formulations," Maturitas, vol. 13, pp. 313-317, 1991.
Cincinelli et al. "Effects of the repetitive administration of progesterone by nasal spray in postmenopausal women." FertiL SteriL 1993; 60(6): 1020-1024.
Clayton et al. "Validation of the Sexual Interest and Desire Inventory-Finale in Hypoactive Sexual Desire Disorder." J. Sex Med. 2010; 7(12): 3918-3928.
Clayton. "Epidemiology and neurobiology of female sexual dysfunction." J Sex Med. 2007; 4:260-8.
Cofrancesco et al. "Transdermal testosterone delivery systems." The Endocrinologist 1996; 6: 207-213.
Corbo et al. "Drug absorption through mucosal membranes: effect of mucosal route and penetrant hydrophilicity." Pharm. Res. 1989; 6(10): 848-852.
Corbo et al. "Nasal delivery of progestational steroids in ovariectomized rabbits. II. Effect of penetrant hydrophilicity," International Journal of Pharmaceutics, vol. 50, pp. 253-260, 1989.
Corbo et al. "Nasal delivery of progestational steroids in ovariectomized rabbits: I. progesterone—comparison of pharmacokinetics with intravenous and oral administration." International Journal of Pharmaceutics, 1988; vol. 46, Issues 1-2, pp. 133-140.
Corona et al. "Six-month administration of 1% testosterone gel is able to restore erectile function in hypogonadal patients with erectile dysfunction." Arch It Ural AndroL 2008; 80(3):103-8.
Corona et al. Update in testosterone therapy for men. The Journal of Sexual Medicine. 2011; 8(3):639-54.
Cunningham et al. "Testosterone Replacement Therapy and Sleep—Related Erections in Hypogonadal Men." J. Clinical Endocrinology and Metabolism, 1990; 70(3):792-797.
Cunningham et al. "Testosterone replacement with transdermal therapeutic systems: physiological serum testosterone and elevated dihydrotestosterone levels." JAMA. 1989; 261(17):2525-2530.
Cutter. "Compounded Percutaneous testosterone gel: use and effects in Hypogonadal men." J Am Board Fam Pract. 2001; 14(1):22-32.
Czerniawska. "Experimental investigations on the penetration of Au from nasal mucous membrane into cerebrospinal fluid." Acta Otolaryng. 1970; 70, 58-61.

Dabbs et al. "Salivary testosterone measurements among women: relative magnitude of Circadian and menstrual cycles." Hormone Research 1991; 35:182-184.
Dahlin et al. "Transfer of Dopamine in the Olfactory Pathway Following Nasal Administration in Mice," Pharmaceutical Research, vol. 17, No. 6, pp. 737-742, 2000.
Dahlin et al. Levels of dopamine in blood and brain following nasal administration to rats. Eur J Pharm Sci. Aug. 2001;14(1):75-80.
Dahlin, "Nasal Administration of Compounds Active in the Central Nervous System—Exploring the Olfactory Pathway," Acta Universitatis Upsaliensis, Comprehensive Summaries of Uppsala Dissertations from the Faculty of Pharmacy 240, 48 pages, 2000.
Danner et al. "Androgen Substitution with Testosterone Containing Nasal Drops," International Journal of Andrology, vol. 3, No. 4, pp. 429-435, 1980.
David et al. "Bioavailability of progesterone enhanced by intranasal spraying," Experientia, vol. 37, pp. 533-534, 1981.
Davis et al. "Androgen replacement in women: a commentary." J. Clin. EndrocrinoL Metab 1999; 84(6): 1886-1891.
Davis et al. "Circulating androgen levels and self-reported sexual function in women." JAMA. 2005; 294(1):91-96.
Davis et al. "Effects of aromatase inhibition on sexual function and well-being in postmenopausal women treated with testosterone: a randomized, placebo-controlled trial." Menopause 2006; 13(1):37-45.
Davis et al. "Efficacy and safety of a testosterone patch for the treatment of hypoactive sexual desire disorder in surgically menopausal women: a randomized, placebo-controlled trial." Menopause. 2006; 13(3): 387-396.
Davis et al. "Perceived effects of testosterone replacement therapy in perimenopausal and postmenopausal women: an internet pilot study." Health Care Women Int. 2003; 24(9):831-848.
Davis et al. "The incidence of invasive breast cancer among women prescribed testosterone for low libido." J Sex Med 2009; 6:1850-1856.
Davis et al. "What are 'normal' testosterone levels for women?" J. Clinical Endocrinology and Metabolism. 2001; vol. 86, No. 4, p. 1842-1843.
Davis et al. Testosterone for Low Libido in Postmenopausal Women not Taking Estrogen. N. Engl. J. Med. 2008; 359: 2005-2017.
Davis. "The effects of tibolone on mood and libido." Menopause 2002. 9(3): 162-170.
Davison et al. "Androgen levels in adult females: changes with age, menopause, and oophorectomy." J Clin Endocrinol Metab.2005; 90(7):3847-3853.
Dazzi et al. "Progesterone enhances ethanol-induced modulation of mesocortical dopamine neurons: antagonism by finasteride." J Neurochem. 2002; 83:1103-1109.
de Souza et al. Dopaminergic and serotonergic activity in neostriatum and nucleus accumbens enhanced by intranasal administration of testosterone. European Neuropsychopharmacology. 2009; 19, 53-63.
De Souza Silva et al. "Increased neostriatal dopamine activity after intraperitoneal or intranasal administration of L⎕DOPA: On the role of benserazide pretreatment." Synapse. 1997;27:294-302.
De Souza Silva et al. "Intranasal administration of the dopaminergic agonists L-DOPA, amphetamine, and cocaine increases dopamine activity in the neostriatum: a microdialysis study in the rat." J Neurochem. 1997;68(1):233-9.
De Souza Silva et al. "Intranasal dopamine application increases dopaminergic activity in the neostriatum and nucleus accumbens and enhances motor activity in the open field." Synapse. 2008;62(3):176-84.
Derad et al. "Intranasal angiotensin II directly influences central nervous regulation of blood pressure." American Journal of Hypertension. 1998; 11, 971-977.
Derogatis et al. "The Female Sexual Distress Scale (FSDS): initial validation of a standardized scale for assessment of sexually related personal distress in women." Journal of Sex and Marital therapy, 2002; 28, 317-330.
Derogatis et al. "Validation of the Female Sexual Distress Scale-Revised for Assessing Distress in Women with Hypoactive Sexual Desire Disorder." J. Sex Med. 2008; 5(2): 357-364.

(56) References Cited

OTHER PUBLICATIONS

Dluzen et al. "The effects of intranasal infusion of 1-methyl-4-phenyl-1,2,3,6-tetrahydropyridine (MPTP) upon catecholamine concentrations within olfactory bulbs and corpus striatum of male mice." Brain Res. 1996; 741, 215-219.
Dobs et al. "Pharmacokinetic characteristics, efficacy, and safety of buccal testosterone in hypogonadal males: a pilot study." J Clin Endocrinol.Metab. 1998; 83 (1) 33-39.
Dobs et al. "Pharmacokinetics, efficacy, and safety of a permeation-enhanced testosterone transdermal system in comparison with bi-weekly injections of testosterone enanthate for the treatment of hypogonadal men." J. Clin EndocrinoLMetab. 1999; 84(10):3469-3478.
Dondeti et al. "Bioadhesive and formulation parameters affecting nasal absorption", International Journal of Pharmaceutics, 127 (1996) 115-133.
Draghia et al. "Gene delivery into the central nervous system by nasal instillation in rats." Gene Therapy. 1995; 2, 418-423.
Ducharme et al. "Brain distribution and behavioral effects of progesterone and pregnenolone after intranasal or intravenous administration." Eur J PharmacoL Sep. 1, 2010;641(2-3):128-34.
During et al. "Glucagon-like peptide-1 receptor is involved in learning and neuroprotection." Nature Med. 2003; 9(9):1173-1179.
Eden. "A pilot study of andro-feme cream (1% testosterone)." In: Proceedings of the 4th Annual Congress of the Australasian Menopause Society. 2000; Adelaide, SA, Australia. Abstract.
Eli Lilly and Company. "Highlights of Prescribing Information for Axiron". 2010.
Eriksson et al. "Transfer of some carboxylic acids in the olfactory system following intranasal administration." J. Drug Target. 1999; 7(2): 131-142.
Ernesti et al. "Absorption and Metabolism of Topically Applied Testosterone in an Organotypic Skin Culture" Skin Pharmacol, 1992; 5(3):146-153.
European Search Report for Application No. EP 03025769.5, dated Apr. 6, 2004. (Corresponding to US 2012/0083480).
Examination Report for Australian Application No. 2012257490, dated May 24, 2016.
Examination Report for Australian Application No. 2012257491, dated Jun. 27, 2016.
Examination Report for Australian Application No. 2012257492, dated Jun. 27, 2016.
Examination Report for Gulf Cooperation Council Application No. 2012-22792, dated Jan. 27, 2016.
Examination Report for Gulf Cooperation Council Application No. 2012-22793, dated Jan. 27, 2016.
Fabbri et al. Testosterone treatment to mimic hormone physiology in androgen replacement therapy. A view on testosterone gel and other preparations available. Expert Opin Biol Ther. 2007; 7(7):1093-1106.
Faber. "The nasal mucosa and the subarachnoid space." Am. J. Anat. 1937; 62, 121-148.
Ferguson. "Clinical trial development in female sexual dysfunction." J. Sex Marital Ther. 2002; 28(s):77-83.
Findlay et al. "Treatment of primary hypogonadism in men by the transdermal administration of testosterone." J. Clin. EndocrinoL Metab. 1989; 68(2):369-373.
Fisher et al. "Di-iodo-L-tyrosine-labelled dextrans as molecular size markers of nasal absorption in the rat." J. Pharm. PharmacoL 1992; 44: 550-554.
Fisher et al. "The effect of molecular size on the nasal absorption of water-soluble compounds in the albino rat." J. Pharm. PharmacoL 1987; 39, 357-362.
Floter et al. "Addition of testosterone to estrogen replacement therapy in oophorectomized women: effects on sexuality and well-being." Climacteric 2002; 5:357-365.
Floter et al. "Administration of testosterone undecanoate in post-menopausal women: effects on androgens, estradiol, and gonadotrophins." Menopause 2000; 7(4):251-256.

Frey et al. "Delivery of 125I-NGF to the brain via the olfactory route." Drug Deliv. 1997; 4, 87-92.
Frey. "Bypassing the blood-brain barrier to deliver therapeutic agents to the brain and spinal cord." Drug Development & Delivery. 2002; 2(5):46-49.
Gelfand et al. "Androgen and estrogen-androgen hormone replacement therapy: a review of the safety literature, 1941 to 1996." Clin Ther 1997; 19(3):383-404; discussion 367-8.
Giagulli et al. "Evidence-based medicine update on testosterone replacement therapy (TRT) in male hypogonadism: focus on new formulations." Curr Pharm Des. 2011; 17:1500-11.
Gizurarson. "Animal models for intranasal drug delivery studies." Acta Pharm. Nord. 1990; 2(2):105-122.
Goldstat et al. "Transdermal testosterone therapy improves well-being, mood, and sexual function in premenopausal women." Menopause. 2003; 10(5): 390-398.
Goldstein et al. "Hormonal cycle modulates arousal circuitry in women using functional magnetic resonance imaging." J Neurosci 2005; 25(40): 9309-9316.
Goldstein et al. "National Differences in Patient-Clinician Communication Regarding Hypoactive Sexual Desire Disorder." J. Sex Med. 2009; 6(5): 1349-1357.
Goudsmit et al. "Testosterone fails to reverse spatial memory decline in aged rats and impairs retention in young and middle-aged animals." Behav. Neural Biol. 1990; 53:6-20.
Goudsmit et al. "Testosterone locally increases vasopressin content but fails to restore choline acetyltransferase activity in other regions in the senescent male rat brain." Neurosci. Lett. 1990; 112, 290-296.
Goudsmit et al. "Testosterone supplementation restores vasopressin innervation in the senescent rat brain." Brain Res. 1988; 473:306-313.
Gracia et al. "Predictors of decreased libido in women during the late reproductive years." Menopause 2004; 11(2):144-150.
Graham et al. "The Sexual Excitation/Sexual Inhibition Inventory for Women: Psychometric Properties." Archives of Sexual Behavior 2006; 35: 397-409.
Graham. "The DSM Diagnostic Criteria for Female Orgasmic Disorder." Archives of Sexual Behavior 2010; 39: 256-270.
Gray et al. "Dose-dependent effects of testosterone on sexual function, mood, and visuospatial cognition in older men." J. Clinical Endocrinology and Metabolism. 2005; 90(7): 3838-3846.
Greenblatt. "Androgenic therapy in women." The Journal of Clinical Endocrinology 1942; 2:665-6.
Grober et al. "Efficacy of changing testosterone gel preparations (Androgel or Testim) among suboptimally responsive hypogonadal men." Int J Impot Res. 2008; 20: 213-7.
Gu et al. "Cytochrome P450 and steroid hydroxylase activity in mouse olfactory and vomeronasal mucosa." Biochem. Biophys. Res Comm. 1999; 266 (1) 262-267.
Guay et al. "Serum androgen levels in healthy premenopausal women with and without sexual dysfunction: Part A. Serum androgen levels in women aged 20-49 years with no complaints of sexual dysfunction." Int.J Impot.Res 2004; 16 (2) 112-120.
Guay et al. "Serum androgen levels in healthy premenopausal women with and without sexual dysfunction: Part B: Reduced serum androgen levels in healthy premenopausal women with complaints of sexual dysfunction." Int.J Impot.Res 2004. 16 (2) 121-129.
Guay. "Commentary on androgen deficiency in women and the FDA advisory board's recent decision to request more safety data." International Journal of Impotence Research 2005; 17, 375-376.
Guay. "Decreased testosterone in regularly menstruating women with decreased libido: a clinical observation." J Sex Marital Ther 2001; 27 (5) 513-519.
Hacker et al. "Androgenic substitution for the ageing male by nasal administraton of a precursor of testosterone," First World Congress on Aging Male, Geneva, Switzerland, 1998, Abstract.
Harris et al. "Intranasal administration of peptides: nasal deposition, biological response, and absorption of desmopressin." J Pharm Sci 1986; 75(11): 1085-1088.
Hayes et al. "Relationship between hypoactive sexual desire disorder and aging." Fertil SteriL 2007; 87(1)107-112.

(56) References Cited

OTHER PUBLICATIONS

Hayes et al. "The impact of aging on sexual function and sexual dysfunction in women: a review of population-based studies." J Sex Med. 2005; 2(3):317-330.
Heard-Davison et al. "Genital and Subjective Measurement of the Time Course Effects of an Acute Dose of Testosterone vs. Placebo in Postmenopausal Women." J. Sexual Medicine 2007; 4: 209-217.
Heiman. "A Psychophysiological Exploration of Sexual Arousal Patterns in Females and Males." Psychophysiology 1977; 14(3): 266-274.
Henriksson et al. "Uptake of inorganic mercury in the olfactory bulbs via olfactory pathways in rats." Environ. Res. 1998; 77, 130-140.
Henriksson. "Uptake of manganese and some other metals into the CNS via the olfactory pathway." PhD thesis, Uppsala University. 1999.
Henry et al. "A pharmacokinetic study of midazolam in dogs: nasal drop vs. atomizer administration." Pediatr. Dent. 1998; 20(5), 321-326.
Hirai et al. "Absorption of drugs from the nasal mucosa of rat." Int. J. Pharm. 1981; 7, 317-325.
Hubayter et al. "Testosterone therapy for sexual dysfunction in postmenopausal women." Climacteric. 2008; 11:181-91.
Hussain et al. "Intranasal absorption of physostigmine and arecoline." J. Pharm. Sci. 1991; 80(8), 750-751.
Hussain et al. "Intranasal Drug Delivery," Advanced Drug Delivery Reviews, vol. 29, pp. 39-49, 1998.
Hussain et al. "Nasal Absorption of Propranolol from Different Dosage Forms by Rats and Dogs," Journal of Pharmaceutical Sciences, vol. 69, No. 12, pp. 1411-1413, Dec. 1980.
Hussain et al. "Nasal Absorption of Testosterone in Rats," Journal of Pharmaceutical Sciences, vol. 73, No. 9, pp. 1300-1301, Sep. 1984.
Hussain et al. "Nasal administration of a cognition enhancer provides improved bioavailability but not enhanced brain delivery." J. Pharm. Sci. 1990; 79(9), 771-772.
Hussain et al. "Physiochemical considerations in intranasal drug administrations." In: Chien, Y.W: (Ed.) Transnasal systemic medications. Fundamentals, developmental concepts and biomedical assessments. Elsevier, Amsterdam. 1985; 121-137.
Hussain et al. "Testosterone 17β-N, N-Dimethylglycinate Hydrochloride: A Prodrug with a Potential for Nasal Delivery of Testosterone", Journal of Pharmaceutical Sciences, vol. 91, No. 3, Mar. 2002, pp. 785-789.
Huston et al. "Intranasal administration of testosterone increases dopaminergic and serotonergic activities in the neostriatum and nucleus accumbens of the male rat." International Journal of Neuropsychopharmacology. 2008, 11:210. (P-05.08).
Ikeda et al. Enhancement of bioavailability of dopamine via nasal route in beagle dogs. Chem Pharm Bull (Tokyo). Aug. 1992;40(8):2155-8.
Illum "Is nose-to-brain transport of drugs in man a reality?" J. Pharm. Pharmacol. 2004; 56, 3-17.
Illum, "Transport of drugs from the nasal cavity to the central nervous system," European Journal of Pharmaceutical Sciences, vol. 11, pp. 1-18, 2000.
International Search Report for PCT Application No. PCT/EP2004/012122, dated Mar. 31, 2005.
International Search Report for PCT Application No. PCT/EP2007/008409, dated Dec. 21, 2007.
International Search Report for PCT Application No. PCT/IB2012/001112, dated Sep. 27, 2012.
International Search Report for PCT Application No. PCT/IB2012/001113, dated Sep. 27, 2012.
International Search Report for PCT Application No. PCT/IB2012/001127, dated Sep. 27, 2012.
International Search Report for PCT Application No. PCT/IB2013/002913, dated May 19, 2014.
International Search Report for PCT Application No. PCT/IB2013/002920, dated Aug. 11, 2014.
International Search Report for PCT Application No. PCT/IB2013/002925, dated Aug. 11, 2014.
International Search Report for PCT Application No. PCT/IB2013/003121, dated Jul. 18, 2014.
Javanbakht et al. "Pharmacokinetics of a Novel Testosterone Matrix Transdermal System in Healthy, Premenopausal Women and Women Infected with the Human Immunodeficiency Virus." J. Clin. EndocrinoL Metab. 2000; 85(7):2395-2401.
Jockenhovel. "Testosterone Therapy—What, When and to Whom?" Aging Male. 2004; 7:319-24.
Jones et al. "Testosterone replacement in hypogonadal men with type 2 diabetes and/or metabolic syndrome (the TIMES2 Study)." Diabetes Care. 2011; 34: 828-837.
Jung et al. "Prolonged delivery of nicotine in rats via nasal administration of proliposomes," Journal of Controlled Release, vol. 66, pp. 73-79, 2000.
Junginger et al. "Mucoadhesive Hydrogels in Drug Delivery." in Encyclopedia Pharm. Technol. Swarbrick and Boylan editors. 2002; New York, p. 1848-1863.
Kaufman et al. "Efficacy and safety study of 1.62% testosterone gel for the treatment of hypogonadal men." J Sex Med. 2011; 8:2079-89.
Kaufman. "Efficacy and Safety of a New, Topical Testosterone Gel (T-gel) For Male Hormonal Supplementation." International Journal of Impotence Research. 2000; 12(Supplement 3):S75 (B9).
Kern et al. "Central nervous system effects of intranasally administered insulin during euglycemia in men." Diabetes. 1999; 48:557-563.
Khera et al. "Improved sexual function with testosterone replacement therapy in hypogonadal men: real-world data from the Testim Registry in the United States (TRiUS)." J Sex Med. 2011; 8:3204-13.
Kim et al. "Effects of Ovariectomy and Steroid Hormones on Vaginal Smooth Muscle Contractility." Int. J. Impot. Res. 2004; 16(1): 43-50.
Kimura et al. "Relationship between nasal absorption and physicochemical properties of quaternary ammonium compounds." Arch Int Pharmacodyn Ther., 1991; 310:13-21.
Kingsberg et al. "Female Sexual Disorders: Assessment, Diagnosis, and Treatment." CNS Spectr. 2011. 16:2 p. 49-62.
Kingsberg. "Testosterone treatment for hypoactive sexual desire disorder in postmenopausal women." J Sex Med. 2007; 4 Suppl 3:227-34.
Klugo et al. "Response of Micropenis to Topical Testosterone and Gonadotropin." J. Urology, 1978; 119:667-668.
Ko et al. "Emulsion formulations of testosterone for nasal administration," Journal of Microencapsulation. 1998, vol. 15, No. 2, pp. 197-205.
Korenman et al. "Androgen Therapy of Hypogonadal Men with Transscrotal Testosterone Systems." Am. J. Med., 1987; 83(3):471-478.
Kuhnert et al. Testosterone substitution with a new transdermal, hydroalcoholic gel applied of scrotal or non-scrotal skin: a multicentre trial. Eur J.; Endocrinol. Aug. 2005; 153(2):317-26.
Kuile et al. The Female Sexual Function Index (FSFI) and the Female Sexual Distress Scale (FSDS): Psychometric properties within a Dutch population. Journal of Sex and Marital Therapy, 2006; 32, 289-304.
Kumar et al. "A New Approach to Fertility Regulation by Interfering with Neuroendocrine Pathways," Neuroendocrine Regulation of Fertility, Int. Symp., Simla, pp. 314-322, 1974.
Kumar et al. "Pharmacokinetics of progesterone after its administration to ovariectomized rhesus monkeys by injection, infusion, or nasal spraying," Proc. Natl. Acad. Sci. USA, vol. 79, pp. 4185-4189, Jul. 1982.
Kumar et al. "Uptake of radioactivity by body fluids and tissues in rhesus monkeys after intravenous injection or intranasal spray of tritium-labeled oestradiol and progesterone." Curr. Sci. 1974a; 43, 435-439.
Kunz et al. "Virilization of Young Children After Topical Androgen Use by Their Parents." Pediatrics. 2004; 114: 282-284.
Laan et al. "Assessment of female sexual arousal: response specificity and construct validity." Psychophysiology 1995; 32:476-485.

(56) References Cited

OTHER PUBLICATIONS

Laan et al. "Genital responsiveness in healthy women with and without sexual arousal disorder." Journal of Sexual Medicine, 2008; 5, 1424-1435.
Laan et al. "Standard Operating Procedures for Female Orgasmic Disorder: Consensus of the International Society for Sexual Medicine." Journal of Sexual Medicine. 2013;10:74-82.
Laan et al. "Women's sexual and emotional responses to male- and female-produced erotica." Archives of Sexual Behavior, 1994; 23, 153-169.
Laughlin et al. "Hysterectomy, oophorectomy, and endogenous sex hormone levels in older women: the Rancho Bernado Study." J Clin Endocrinol Metab. 2000; 85(2):645-651.
Laughlin et al. "Postmenopausal Testosterone." J. Clinical Endocrinology and Metabolism. 2001; vol. 86, No. 4, pp. 1843-1844.
Laumann et al. "Sexual dysfunction in the United States: prevalence and predictors." JAMA. Feb. 10, 1999;281(6):537-44.
Lewis et al. "Definitions/epidemiology/risk factors for sexual dysfunction." Journal of Sexual Medicine, 2010; 7, 1598-1607.
Liu et al. "Intranasal administration of insulin-like growth factor-I bypasses the blood-brain barrier and protects against focal cerebral ischemic damage." J Neurol Sci. 2001; 187:91-97.
Liu et al. "Treatment of Naturally Menopausal Women with Hypoactive Sexual Desire Disorder: Effect of Transdermal Testosterone Patch in the NM2 Trial." Abstract presented at the ISSESH Meeting 2008.
Lobo et al. Comparative effects of oral esterified estrogens with and without methyltestosterone on endocrine profiles and dimensions of sexual function in postmenopausal women with hypoactive sexual desire. Fertil Steril 2003; 79(6):1341-52.
Lobo. "Androgens in postmenopausal women: production, possible role, and replacement options." Obstet Gynecol Surv. 2001; 56 (6) 361-376.
Longo et al. "Comparison of drug metabolizing system in nasal mucosa and liver of Sprague Dawley rats." Ital. J. Biochem. (Meeting). 1988;37(1):31A-32A.
Longo et al. "Drug-metabolizing enzymes in liver, olfactory, and respiratory epi-thelium of cattle." J Biochem. Toxicot. 1991;6(2):123-128.
Lowhagen et al. "The nasal route of cerebrospinal fluid drainage in man. A light-microscope study." Neuropathol. Appl. Neurobiol. 1994;20:543-550.
Lupo et al. "Testosterone metabolism in the olfactory epithelium of intact and castrated male rats." Neurosci. Lett. 1986;69(3):259-262.
Luthold et al. "Serum testosterone fractions in women: normal and abnormal clinical states." Metabolism. 1993;42(5):638-643.
Madrid et al. "Intranasal drug delivery to the central nervous system." In 18th Int. Symp. Control. Rel. Bioact. Mater. 1991; 283-284.
Marbury et al. "Evaluation of the pharmacokinetic profiles of the new testosterone topical gel formulation, Testim, compared to AndroGel." Biopharm Drug Dispos. 2003; 24:115-20.
Marynick et al. "Studies on the Transfer of Steroid Hormones Across the Blood-Cerebrospinal Fluid Barrier in the Rhesus Monkey," Endo, vol. 99, No. 2, pp. 400-405, 1976.
Mathiowitz et al. [editors] Bioadhesive Drug Delivery Systems: Fundamentals, Novel Approaches, and Development. Marcel Dekker, Inc. NYC, USA. 1999;523-525.
Mathison et al. "Nasal Route for Direct Delivery of Solutes to the Central Nervous System: Fact or Fiction?," Journal of Drug Targeting. 1998;5(6):415-441.
Mattern et al. "Development of a drug formulation for nasal administration of a testosterone precursor and test of its bioavailability," First World Congress on Aging Male, Geneva, Switzerland, 1998, Abstract.
Mattern et al. "Testosterone supplementation for hypogonadal men by the nasal route," The Aging Male, vol. 11, No. 4, pp. 171-178, Dec. 2008.

Mattsson et al. "Clinical equivalence of intranasal and oral 17beta-estradiol for postmenopausal symptoms." Am J Obstet GynecoL 2000; 182:545-552.
Mazer et al. "Comparison of the steady-state pharmocokinetics, metabolism, and variability of a transdermal testosterone patch versus a trasndermal testosterone gel in hypogonadal men." J Sex Med. Mar. 2005; 2(2):213-26.
Mazer et al. "Enhanced transdermal delivery of testosterone: a new physiological approach for androgen replacement in hypogonadal men." J Controlled Release. 1992;19(1-3):347-361.
Mazer. "New Clinical Applications of Transdermal Testosterone Delivery in Men and Women." J Controlled Release, 2000; 65(1-2):303-315.
Mazer. Testosterone deficiency in women: etiologies, diagnosis, and emerging treatments. Int J Fer-til. Women Med. 2002;47(2):77-86.
McClellan et al. "Transdermal Testosterone, ADIS New Drug Profile." Drugs, 1998;55(2):253-258.
McClure et al. "Hypogonadal Impotence Treated by Transdermal Testosterone." Urology, 1991; 37(3):224-228.
McMartin et al. "Analysis of structural requirements for the absorption of drugs and macromolecules from the nasal cavity." J. Pharm. Sci. 1987;76(7):535-540.
McNicholas et al. "A novel testosterone gel formulation normalizes androgen levels in hypogonadal men, with improvements in body composition and sexual function." BJU Int. 2003; 91:69-74.
McNicholas et al. "Review of Testim gel." Expert Opin Pharmacother. 2006; 7(4):477-84.
Meikle et al. "Enhanced transdermal delivery of testosterone across non-scrotal skin produces physiological concentrations of testosterone and its metabolites in hypogonadal men." J. Clin. Endocrinol Metab. 1992;74(3):623-628.
Meikle et al. "Pharmacokinetics and Metabolism of a Permeation-Enhanced Testosterone Transdermal System in Hypogonadal Men: Influence of Application Site—a Clinical Research Center Study." J. Clin. Endocrinol Metab. 1996;81(5)1832-1840.
Meikle et al. "Transdermal testosterone gel: pharmacokinetics, efficacy of dosing and application site in hypogonadal men." BJU Int. 2004; 93:789-95.
Meston et al. "Disorders of Orgasm in Women." J. Sex Med. 2004; 1(1): 66-68.
Meston et al. "Update on female sexual function." Curt. Opin Urol. 2001;11 (6):603-609.
Meston. "Validation of the Female Sexual Function Index (FSFI) in women with female orgasmic disorder and in women with hypoactive sexual desire disorder." J Sex Marital Ther. 2003;29(1):39-46.
Miller et al. "Transdermal testosterone administration in women with acquired immunodeficiency syndrome wasting: a pilot study." J Clin Endocrinol Metab. 1998; 83(8):2717-25.
Miller et al. Pharmacokinetics and relative bioavailability of absorbed testosterone after administration of a 1.62% testosterone gel to different application sites in men with hypogonadism. Endocr Pract. 2011; 17(4):574-83.
Miller et al. Femal Sexual Dysfunction: Review of the Disorder and Evidence for Available Treatment Alternatives. Journal of Pharmacy Practice. 2003;16(3):200-208.
Min et al. "Effects of ovariectomy and estrogen and androgen treatment on sildenafil-mediated changes in female genital blood flow and vaginal lubrication in the animal model." Ant J Obstet Gynecol. 2002;187(5):1370-1376.
Minn et al. "Drug transport into the mammalian brain: the nasal pathway and its specific metabolic barrier." J Drug Target. 2002;10(4):285-296.
Misra et al. "Biphasic testosterone delivery profile observed with two different transdermal formulations." Pharm Res. 1997, 14(9):1264-8.
Misra et al. "Formulation of a transdermal system for biphasic delivery of testosterone." J. Controlled Release. 1996; 39 1-7.
Modelska et al. "Female sexual dysfunction in postmenopausal women: sys-tematic review of placebo-controlled trials." Am J Obstet Gynecol. 2003; 188(1):286-293.
Morales et al. "Testosterone supplementation for hypogonadal impotence: assessment of biochemical measures and therapeutic outcomes." J Urol. 1997; 157:849-54.

(56) References Cited

OTHER PUBLICATIONS

Muller et al. "Androgenic deficiencies of the ageing male and psychophysiological performance-test system for clinical diagnosis," First World Congress on Aging Male, Geneva, Switzerland, 1998, Abstract.
Munarriz et al. "Androgen replacement therapy with dehydroepiandrosterone for androgen insufficiency and female sexual dysfunction: androgen and questionnaire results." J Sex Marital Ther. 2002;28(Suppl 1):165-173.
Nathorst-Boos et al. "Treatment with percutaneous testosterone gel in postmenopausal women with decreased libido—effects on sexuality and psychological general well-being." Maturitas. 2006; 53(1):11-18.
Nieschlag et al. "Bioavilability and LH-suppressing effect of different testosterone preparations in normal and hypogonadal men." Horm. Res. 1976; 7:138-145.
Nieschlag et al. "Transdermal Testosterone." The Lancet. May 20, 1989; 1146-1147.
Nieschlag et al. Tesosterone: Action, Deficiency, Substition. 3rd Edition, Cambridge University Press, Cambridge, UK, 2004.
Nieschlag. "Testosterone Treatment Comes of Age: New Options for Hypogonadal Men." Clin. Endocrinol. (Oxf.). 2006; 65: 275-281.
Nijland et al. "Female sexual satisfaction and pharmaceutical intervention: a critical review of the drug intervention studies in female sexual dysfunction." J Sex Med. 2006; 3(5):763-777.
Nobre et al. "Prevalence and comorbidity of sexual dysfunctions in a Portuguese clinical sample." Journal of Sex and Marital Therapy, 2006; 32: 173-182.
Nogueira et al. "In-Vivo monitoring of neostriatal dopamine activity after nasal drug administration in the rat: relevance to Parkinson's Disease and addiction," Neuroscience Meeting, San Diego, California, 1995, Abstract.
Notice of Allowance dated Mar. 19, 2014 in U.S. Appl. No. 13/547,774 (now U.S. Pat. No. 8,784,869).
Notice of Allowance dated Mar. 25, 2013 in U.S. Appl. No. 13/194,928 (US 2012/0009250).
Notice of Allowance dated Apr. 9, 2014 in U.S. Appl. No. 13/194,853 (now U.S. Pat. No. 8,784,882).
Notice of Allowance dated Jul. 5, 2013 in U.S. Appl. No. 13/194,928 (US 2012/0009250).
Notice of Allowance dated Jul. 7, 2014 in U.S. Appl. No. 13/316,494 (now U.S. Pat. No. 8,877,230).
Office Action for Chinese Application No. 201280034554.2, dated Dec. 2, 2014.
Office Action for Chinese Application No. 201280034554.2, dated Jul. 5, 2016.
Office Action for Chinese Application No. 201280034554.2, dated Oct. 21, 2015.
Office Action for Chinese Application No. 201280035150.5, dated Dec. 26, 2014.
Office Action for Chinese Application No. 201280035150.5, dated Nov. 18, 2015.
Office Action for Chinese Application No. 201280035162.8, dated Jan. 26, 2016.
Office Action for Chinese Application No. 201280035162.8, dated Mar. 9, 2015.
Office Action for Eurasian Application No. 201391701/28, dated Aug. 11, 2015.
Office Action for European Application No. 12735327.4, dated Sep. 7, 2015.
Office Action for European Application No. 12738595.3, dated Sep. 7, 2015.
Office Action for European Application No. 12748245.3, dated Sep. 7, 2015.
Office Action for Japanese Application No. 2014-509855, dated Mar. 1, 2016.
Office Action for Japanese Application No. 2014-510900, dated Mar. 22, 2016.
Office Action for Japanese Application No. 2014-510901, dated Mar. 22, 2016.
Office Action for Mexican Application No. MX/a/2013/013236, dated Apr. 20, 2016.
Office Action dated Jan. 6, 2011 in U.S. Appl. No. 12/418,917 (US 2009/0227550).
Office Action dated Jan. 13, 2009 in U.S. Appl. No. 11/027,699 (US 2006/014820).
Office Action dated Jan. 13, 2012 in U.S. Appl. No. 12/796,165 (US 2010/0311707).
Office Action dated Jan. 15, 2009 in U.S. Appl. No. 10/772,964 (US 2005/0100564).
Office Action dated Feb. 3, 2010 in U.S. Appl. No. 11/027,699 (US 2006/014820).
Office Action dated Feb. 5, 2008 in U.S. Appl. No. 11/560,187 (US 2007/0149454).
Office Action dated Feb. 6, 2012 in U.S. Appl. No. 13/194,663 (US 2012/0005987).
Office Action dated Feb. 7, 2014 in U.S. Appl. No. 13/471,452.
Office Action dated Feb. 10, 2014 in U.S. Appl. No. 13/471,449.
Office Action dated Feb. 10, 2014 in U.S. Appl. No. 13/471,450.
Office Action dated Feb. 15, 2012 in U.S. Appl. No. 13/194,928 (US 2012/0009250).
Office Action dated Mar. 8, 2011 in U.S. Appl. No. 12/418,917 (US 2009/0227550).
Office Action dated Mar. 17, 2008 in U.S. Appl. No. 10/772,964 (US 2005/0100564).
Office Action dated Mar. 18, 2009 in U.S. Appl. No. 11/560,187 (US 2007/0149454).
Office Action dated Mar. 22, 2013 in U.S. Appl. No. 13/194,853 (US 2012/0058176).
Office Action dated Mar. 22, 2013 in U.S. Appl. No. 13/316,494 (US 2012/0083480).
Office Action dated Apr. 4, 2007 in U.S. Appl. No. 10/772,964 (US 2005/0100564).
Office Action dated Apr. 11, 2013 in U.S. Appl. No. 13/194,926 (US 2012/0009249).
Office Action dated Apr. 25, 2008 in U.S. Appl. No. 11/027,699 (US 2006/014820).
Office Action dated May 5, 2008 in U.S. Appl. No. 10/772,964 (US 2005/0100564).
Office Action dated May 6, 2010 in U.S. Appl. No. 11/027,699 (US 2006/014820).
Office Action dated May 30, 2012 in U.S. Appl. No. 13/194,926 (US 2012/0009249).
Office Action dated Jun. 5, 2013 in U.S. Appl. No. 13/547,774 (US 2012/0277202).
Office Action dated Jul. 2, 2013 in U.S. Appl. No. 13/471,450.
Office Action dated Jul. 3, 2012 in U.S. Appl. No. 13/194,853 (US 2012/0058176).
Office Action dated Jul. 3, 2012 in U.S. Appl. No. 13/316,494 (US 2012/0083480).
Office Action dated Jul. 3, 2013 in U.S. Appl. No. 13/471,449.
Office Action dated Jul. 5, 2013 in U.S. Appl. No. 13/471,452.
Office Action dated Jul. 7, 2009 in U.S. Appl. No. 11/027,699 (US 2006/014820).
Office Action dated Jul. 8, 2010 in U.S. Appl. No. 10/772,964 (US 2005/0100564).
Office Action dated Jul. 14, 2011 in U.S. Appl. No. 13/152,882 (US 2011/0237562).
Office Action dated Aug. 14, 2012 in U.S. Appl. No. 13/194,853 (US 2012/0009249).
Office Action dated Aug. 20, 2008 in U.S. Appl. No. 11/560,187 (US 2007/0149454).
Office Action dated Sep. 14, 2007 in U.S. Appl. No. 11/560,187 (US 2007/0149454).
Office Action dated Sep. 19, 2012 in U.S. Appl. No. 13/194,926 (US 2012/0009249).
Office Action dated Sep. 29, 2009 in U.S. Appl. No. 10/772,964 (US 2005/0100564).
Office Action dated Oct. 19, 2012 in U.S. Appl. No. 13/567,878 (US 2012/0297730).

(56) References Cited

OTHER PUBLICATIONS

Office Action dated Oct. 29, 2008 in U.S. Appl. No. 11/560,187 (US 2007/0149454).

Office Action dated Oct. 31, 2013 in U.S. Appl. No. 13/471,445.

Office Action dated Nov. 3, 2008 in U.S. Appl. No. 11/027,699 (US 2006/014820).

Office Action dated Nov. 5, 2012 in U.S. Appl. No. 13/194,928 (US 2012/0009250).

Office Action dated Nov. 9, 2011 in U.S. Appl. No. 13/194,928 (US 2012/0009250).

Office Action dated Nov. 16, 2009 in U.S. Appl. No. 11/560,187 (US 2007/0149454).

Ohman et al. "17β-Estradiol Levels in Blood and Cerebrospinal Fluid After Ocular and Nasal Administration in Women and Female Rhesus Monkeys (*Macaca mulatta*)," Contraception, vol. 22, No. 4, pp. 349-358, Oct. 1980.

Oldendorf et al. "Lipid solubility and drug penetration of the blood brain barrier." Proc. Soc. Exp. Biol. Med. 1974; 147:813-816.

Pabla et al. "A comparative permeation/release study of different testosterone gel formulations." Drug Deliv. 2007; 14:389-96.

Padero et al. "Androgen supplementation in older women: too much hype, not enough data." J Am Geriatr Soc. 2002; 50:1131-40.

Panay et al. "Testosterone Treatment of HSDD in Naturally Menopausal Women: The ADORE Study." Climacteric 2010; 3(2): 121-131.

Pardridge. "Brain drug delivery and blood-brain barrier transport." Drug Deliv. 1993; 1: 83-101.

Parker et al. "Experience with transdermal testosterone replacement therapy for hypogonadal men." Clin Endocrinology. 1999; 50 (1) 57-62.

Patentability Report for Eurasian Application No. 201391702/28, dated May 14, 2015.

Patentability Report for Eurasian Application No. 201391703/28, dated May 14, 2015.

Pharmacopeia (USP). "Androgens (Systemic)" in USP DI-Drug Information for the Health Care Professional (23rd Ed.) (Micromedex—USP DI Editorial Group: Englewood). 2003; 132-141.

Pharmacopeia (USP). "Guidance for Industry—Nasal Spray and Inhalation Solution, Suspension, and Spray Drug Products—Chemistry, Manufacturing, and Controls Documentation." 2002.

Place et al. "Transdermal delivery of testosterone with Testoderm to provide a normal circadian pattern of testosterone." Ann. 1 V. Y. Acad Sci. 1991; 618 (1): 441-449.

Provasi et al. "Nasal delivery progesterone powder formulations comparison with oral administration," Bol. Chim. Farmaceutico, Anno 132—n.10 poster, 1993;402-404.

Pum et al. "Effects of intranasally applied dopamine on behavioral asymmetries in rats with unilateral 6-hydroxydopamine lesions of the nigro-striatal tract." Neuroscience. Aug. 4, 2009; 162(1):174-83.

Redmond. "Hormones and sexual function." Int J Fertil Womens Med 1999; 44 (4) 193-197.

Revay et al. "Dopamine transporter immunohistochemistry in median eminence, amygdala, and other areas of the rat brain." Synapse. 1996; 22: 93-99.

Reyes-Vallejo et al. Subjective sexual response to testosterone replacement therapy based on initial serum levels on total testosterone. J. Sex Med. 2007; 4:1757-1762.

Rolf et al. "Pharmacokinetics of a new transdermal testosterone gel in gonadotropin-suppressed normal men." Eur J EndocrinoL 2002; 146 (5) 673-679.

Rosen et al. "Minimal clinically important differences in the erectile function domain of the international index of erectile function scale." European Urology. 2011; 60: 1010-1016.

Rosen et al. "Prevalence of Sexual Dysfunction in Women: Results of a Survey Study of 329 Women in an Outpatient Gynaecological Clinic." J. Sex Martial Ther. 1993; 19(3): 171-188.

Rosen et al. "The Female Sexual Function Index (FSFI): A Multi-dimensional Self-Report Instrument for the Assessment of Female Sexual Function." J. Sex and Marital Therapy. 2000; 26: 191-208.

Ruocco et al. "Intranasal application of dopamine reduces activity and improves attention in Naples High Excitability rats that feature the mesocortical variant of ADHD." Eur Neuropsychopharmacol. Oct. 2009;19(10):693-701.

Saad et al. "A Dose-Response Study of Testosterone on Sexual Dysfunction and Features of the Metabolic Syndrome Using Testosterone Gel and Parenteral Testosterone Undercanoate." J Androl. 2008; 29:102-5.

Sakane et al. "Direct drug transport from the rat nasal cavity to the cerebrospinal fluid: the relation to the molecular weight of drugs." J. Pharm. Pharmacol. 1995; 47: 379-381.

Sakane et al. "The transport of a drug to the cerebrospinal fluid directly from the nasal cavity: the relation to the lipophilicity of the drug." Chem. Pharm. Bull. 1991;39(9):2456-2458.

Sakane et al. "Transport of cephalexin to the cerebrospinal fluid directly from the nasal cavity." J. Pharm. PharmacoL 1991; 43, 449-451.

Salehian et al. "Pharmacokinetics, bioefficacy, and safety of sublingual testosterone cyclodextrin in hypogonadal men: comparison to testosterone enanthate—a clinical research center study." J Clin Endocrinol Metab. 1995; 80(12):3567-3575.

Salmon et al. "Effect of Androgens upon Libido in Women." J. Clinical Endrocrinol. 1943; 3: 235-238.

Salonia. "Minimal clinically important differences in the erectile function domain: Tough and challenging is beautiful." European Urology. 2011; 60: 1017-1019.

Sarrel et al. "Estrogen and estrogen-androgen replacement in post-menopausal women dissatisfied with estrogen-only therapy. Sexual behavior and neuroendocrine responses." J Reprod Med 1998;43(10):847-856.

Schultheiss et al. "Pilot study of the transdermal application of testosterone gel to the penile skin for the treatment of hypogonadotropic men with erectile dysfunction". World J Urol. 2000; 18: 431-435.

Seftel et al. "Restorative increases in serum testosterone levels are significantly correlated to improvements in sexual functioning." J Androl. 2004; 25(6):963-72.

Segraves et al. "Hypoactive Sexual Desire Disorder: Prevalence and Comorbidity in 906 Subjects." J. Sex and Marital Therapy 1991; 17(1): 55-58.

Sharma et al. "Testosterone Implants in Specific Neural Sites Activate Female Sexual Behaviour." J. Neuroendocrinol. 1994; 6: 423-432.

Sherwin et al. "Androgen enhances sexual motivation in females: a prospective, crossover study of sex steroid administration in the surgical menopause." Psychosom Med. 1985; 47(4):339-351.

Sherwin et al. "The role of androgen in the maintenance of sexual functioning in oophorectomized women." Psychosomatic Med. 1987; 49: 397-409.

Sherwin. "Randomized clinical trials of combined estrogen-androgen preparations: effects on sexual functioning." Fertil Steril. 2002; 77(Suppl 4):S49-54.

Shifren et al. "Sexual Problems and Distress in United States Women: Prevalence and Correlates." Obstet Gynecol. 2008; 112(5): 970-978.

Shifren et al. "Testosterone patch for the treatment of hypoactive sexual desire disorder in naturally menopausal women: results from the Intimate NM1 study." Menopause 2006;13(5):770-779.

Shifren et al. "Transdermal testosterone treatment in women with impaired sexual function after oophrectomy." New Eng. J. Med. 2000; 343(10): 682-688.

Shifren et al. Position Statement. The role of testosterone therapy in postmenopausal women: position statement of the North American Menopause Society. Menopause. 2005; vol. 12, No. 5, pp. 497-511.

Shifren. "Androgen deficiency in the oophorectomized woman." Fertil Steril. 2002; 77(Suppl 4): S60-62.

Shifren. "The role of androgens in female sexual dysfunction." Mayo Clin Proc 2004; 79(4 Suppl):S19-24.

Shipley. "Transport of molecules from nose to brain: transneuronal anterograde and retrograde labeling in the rat olfactory system by wheat ge m agglutinin-horseradish peroxidase applied to the nasal epithelium." Brain Res. Bull. 1985; 15, 129-142.

Sigurdsson et al. "Olfactory absorption of insulin to the brain." Drug Deliv. 1997; 4: 195-200.

(56) References Cited

OTHER PUBLICATIONS

Simon et al. "Testosterone patch increases sexual activity and desire in surgically menopausal women with hypoactive sexual desire disorder." J. Clin. Endocrinol. Metab. 2005; 90(9): 5226-5233.
Singh et al. "Pharmacokinetics of a transdermal testosterone system in men with end stage renal disease receiving maintenance hemodialysis and healthy hypogonadal men." J Clin Endocrinol Metab. 2001; 86 (6): 2437-2445.
Sitruk-Ware. "Transdermal delivery of steroids." Contraception 1989; 39 (1) 1-20.
Skipor et al. "Local transport of testosterone from the nasal mucosa to the carotid blood and the brain in the pig," Polish Veterinary Sciences, vol. 3, No. 1, pp. 19-22, 2000.
Slater et al. "Pharmacokinetics of testosterone after percutaneous gel or buccal administration." Fertil Steril. 2001; 76 (1) 32-37.
Slayden. "Risks of menopausal androgen supplementation." Semin Reprod Endocrinol 1998; 16(2):145-52.
Somboonporn. "Testosterone therapy for postmenopausal women: efficacy and safety." Semin Reprod Med 2006; 24(2):115-23.
Spielberg. "Abnormal Testosterone Levels in Partners of Patients Using Testosterone Gels." J. Sex Med. 2005; 2(2): 278.
Steege et al. "Bioavailability of nasally administered progesterone", Fertility and Sterility, vol. 46, No. 4, 1986, pp. 727-729.
Steidle et al. "North American AA2500 T Gel Study Group. AA2500 Testosterone gel normalizes androgen levels in aging males with improvements in body composition and sexual function." J Clin Endocrinol Metab. 2003; 88(6):2673-81.
Stein. "Brain damage, sex hormones and recovery: a new role for progesterone and estrogen?" Trends Neurosci. 2001; 24(7):386-391.
Sturgeon et al. "Serum levels of sex hormones and breast cancer risk in premenopausal women: a case-control study (USA)." Cancer Causes Control 2004; 15(1):45-53.
Swerdloff et al. "Long Term Pharmacokinetics of Transdermal Testosterone Gel Versus Testosterone Patch in Hypogonadal Men." Jun. 22, 2000; 2347 Male Reproductive Poster Session, Board 578.
Swerdloff et al. "Long-term pharmacokinetics of transdermal testosterone gel in hypogonadal men." J Clin Endocrinot Metab. 2000; 85 (12) 4500-4510.
Talengaonkar et al. "Intranasal Delivery: An Approach to Bypass the Blood Brain Barrier." Indian J. Pharmacol. 2004; vol. 36, Issue 3, 140-147.
Tavares et al. Effects of intra-nasally administered testosterone on sexual proceptive behavior in female capuchin monkeys (*0Cebus apella*). Behav Brain Res. Apr. 16, 2007;179(1):33-42.
Thorne et al. "Delivery of insulin-like growth factor-I to the rat brain and spinal cord along olfactory and trigeminal pathways following intranasal administration." Neuroscience. 2004; 127:481-496.
Thorne et al. "Delivery of neurotropic factors to the central nervous system: pharmacokinetic considerations." Clin. Pharmacokinet. 2001; 40(12) 907-946.
Thorne et al. "Quantitative analysis of the olfactory pathway for drug delivery to the brain." Brain Res. 1995; 692: 278-282.
Tjalve et al. "Uptake of manganese and cadmium from the nasal mucosa into the central nervous system via olfactory pathways in rats." Pharmacol. Toxicol. 1996; 79: 347-356.
Topic et al. "Evidence for antidepressant-like action of intranasal application of testosterone," CINP Biennial International Congress, Munich, Germany, Jul. 13-17, 2008, Abstract.
Topic et al. Prolonged effects of intra-nasally administered testosterone on proceptive behavior in female capuchin monkeys (*Cebus apella*). Behav Brain Res. Apr. 16, 2007;179(1):60-8.
Traish et al. "Testosterone therapy in women with gynecological and sexual disorders: a triumph of clinical endocrinology from 1938 to 2008." J. Sex. Med. 2009; 6: 334-351.
Tremblay et al. "Pharmacokinetic modeling of a novel testosterone formulation in hypoganadal subjects." Clinical Pharmacology & Therapeutics, 2008; 83: S90.

Tuiten et al. "Can Sublingual Testosterone Increase Subjective and Physiological Measures of Laboratory-Induced Sexual Arousal?" Archives of General Psychiatry 2002; 59: 465-473.
Tuiten et al. "Discrepancies between genital responses and subjective sexual function during testosterone substitution in women with hypothalamic amenorrhea." Psychosomatic Medicine, 1996; 58, 234-241.
Tuiten et al. "Time Course of Effects of Testosterone Administration on Sexual Arousal in Women." Archives of General Psychiatry. 2000; 57: 149-153.
Turna et al. "Women with low libido: correlation of decreased androgen levels with female sexual function index." Int J Impot Res. 2005; 17, 148-153.
van Den Berg et al. "Uptake of estradiol or progesterone into the CSF following intranasal and intravenous delivery in rats". Eur J Pharm Biopharm. 2004; 58:131-135.
van Honk et al. "A single administration of testosterone induces cardiac accelerative responses to angry faces in healthy young women." Behav Neurosci. 2001; 115:238 -242.
van Wingen et al. "Testosterone biases automatic memory processes in women towards potential mates." NeuroImage. 2008; 43: 114-120.
van Wingen et al. "Testosterone reduces amygdala-orbitofrontal complex coupling." Psychoneuroendocrinology 2010; vol. 35, Issue 1, pp. 105-113.
van Wingen et al. Testosterone increases amygdala reactivity in middle-aged women to a young adulthood level. Neuropsychopharmacology. 2008; 1-9.
Viggiano et al. "Behavioural, pharmacological, morpho-functional molecular studies reveal a hyperfunctioning mesocortical dopamine system in an animal model of attention deficit and hypersctivity disorder," Neurosci. Biobehav. Rev. vol. 27, pp. 683-689, 2003.
Viggiano et al. "The Naples High- and Low-Excitability rats: selective breeding, behavioral profile, morphometry, and molecular biology of the mesocortical dopamine system." Behav. Genet. 2002; 32(5):315-333.
Wang et al. "Brain uptake of dihydroergotamine after intravenous and nasal administration in the rat." Biopharmaceutics and Drug Disposition. 1998; 19, 571-575.
Wang et al. "Effects of Transdermal Testosterone Gel on Bone Turnover Markers and Bone Mineral Density in Hypogandal Men." Clinical Science: Reproduction (Male)—Prostate, Jun. 22, 2000; Male Reproduction Poster Session, No. 579.
Wang et al. "Effects of Transdermal Testosterone Gel on Bone Turnover Markers and Bone Mineral Density in Hypogonadal Men." Clinical Endocrinology, 2001; 54: 739-750.
Wang et al. "ISA, ISSAM, EAU, EAA and ASA recommendations: investigation, treatment and monitoring of late-onset hypogonadism in males." Int J. of Impotence Research. 2009; 21(1): 1-8. Epub Sep. 3, 2008.
Wang et al. "Long-term testosterone gel (AndroGel), Treatment maintains Beneficial Effects on sexual Function and mood, Lean and Fat Mass, and Bone Mineral Density in Hypogonadal Men." J Clin Endocrinol Metab. 2004; 89(5):2085-98.
Wang et al. "Pharmacokinetics of Transdermal Testosterone Gel in Hypogonadal Men." 80th Annual Meeting of the Endocrine Society, Jun. 24 to 27, 1998; Poster Session, No. P2-51.
Wang et al. "Pharmacokinetics of transdermal testosterone gel in hypogonadal men: application of gel at one site versus four sites: a General Clinical Research Center Study." J Clin Endocrinol. Metab. 2000; 85(3):964-969.
Wang et al. "Transdermal Testosterone Gel Improves Sexual Function, Mood, Muscle Strength, and Body Composition Parameters in Hypogonadal Men." Basic Science: Reproduction-Gonadal Control (Male), Jun. 24, 2000; Male Reproduction Oral Session, No. 1360.
Wang et al. "Transdermal testosterone gel improves sexual function, mood, muscle strength, and body composition parameters in hypogonadal men." J. Clinical Endocrinology Metab. 2000; 85(8):2839-2853.
Warnock et al. "Combined esterified estrogens and methyltestosterone versus esterified estrogens alone in the treatment of loss of sexual interest in surgically menopausal women." Menopause 2005; 12(4):374-84.

(56) References Cited

OTHER PUBLICATIONS

Watson et al. "Development and validation of brief measures of positive and negative affect: the PANAS Scales." J. of Personality and Social Psychology. 1988; 54(6): 1063-1070.

Wattanakumtornkul et al. "Intranasal hormone replacement therapy," Menopause: The Journal of The North American Menopause Society, vol. 10, No. 1, pp. 88-98, 2003.

Welling et al. "Raised salivary testosterone in women is associated with increased attraction to masculine faces." Hormones and Behavior. 2007; 52: 156-161.

Wiegel et al. "The Female Sexual Function Index (FSFI): Cross-Validation and Development of Clinical Cutoff Scores." J. Sex and Marital Therapy 2005; 31:1-20.

Wierman et al. "Androgen therapy in women: an Endocrine Society Clinical Practice guideline." Journal of Clinical Endocrinology & Metabolism. 2006; 91(10):3697-3710.

Winters et al. "Serum LH Concentrations in Hypogonadal Men During Transdermal Testosterone Replacement Through Scrotal Skin: Further Evidence that Ageing Enhances Testosterone Negative Feedback. The Testoderm Study Group." Clin Endocrinol, 1997; 47(3):317-322.

Written Opinion of the International Search Authority for PCT Application No. PCT/IB2012/001113, dated Sep. 27, 2012.

Xing et al. "Transdermal testosterone delivery in castrated Yucatan minipigs: pharmacokinetics and metabolism." J. Control Release. 1998; 52 (1-2) 89-98.

Yassin et al. "Improvement of sexual function in men with late-onset hypogonadism treated with testosterone only." J Sex Med. 2007; 4:497-501.

Yialamas et al. "Androgens and the ageing male and female." Best Pract Res. Clin Endocrinol. Metab. 2003;17(2):223-236.

Yoffey. "Passage of fluid and other substances through the nasal mucosa." J. Laryngol. Otol. 1958; 72, 377-383.

Yu et al. "Testosterone pharmacokinetics after application of an investigational transdermal system in hypogonadal men." J Clin Pharmacol. 1997; 37(12):1139-1145.

Yu et al. "Transdermal testosterone administration in hypogonadal men: comparison of pharmacokinetics at different sites of application and at the first and fifth days of application." J Clin Pharmacol. 1997; 37(12) 1129-1138.

Office Action for Chinese Application No. 201280035150.5, dated Aug. 15, 2016.

Office Action for Japanese Application No. 2014-509855, dated Oct. 4, 2016.

Aurora, J. Development of Nasal Delivery Systems: A Review. Drug Development & Delivery. 2002. <http://drug-dev.com/main/back-issues/development-of-nasal-delivery-systems-a-review-489.aspx>.

Office Action for European Patent Application No. 12738595.3, dated Feb. 1, 2017.

Office Action for Mexican Application No. MX/a/2013/013236, dated Oct. 14, 2016.

Office Action for Mexican Application No. MX/a/2013/013369, dated Oct. 17, 2016.

\* cited by examiner

| | TBS-2 Day1 HSDD | TBS-2 Day3 HSDD | Intrinsa Da | Intrinsa Day3 HSDD |
|---|---|---|---|---|
| 0 | 0.085 | 0.251521136 | 0.108878 | 0.483399 |
| 15 | 0.548 | 0.487430593 | 0.099734 | 0.502445 |
| 30 | 0.613 | 0.55467768 | 0.091888 | 0.534195 |
| 45 | 0.672 | 0.59192806 | 0.090008 | 0.483488 |
| 60 | 0.647 | 0.637465497 | 0.095893 | 0.492026 |
| 90 | 0.575 | 0.709483507 | 0.110125 | 0.50149 |
| 120 | 0.668 | 0.547832314 | 0.106288 | 0.516723 |
| 180 | 0.531 | 0.499222011 | 0.14755 | 0.582705 |
| 240 | 0.638 | 0.417635523 | 0.220853 | 0.660928 |
| 300 | 0.586 | 0.450241114 | 0.319595 | 0.614123 |
| 360 | 0.585 | 0.510927601 | 0.387495 | 0.625783 |
| 480 | 0.474 | 0.541546186 | 0.499111 | 0.61994 |
| 720 | 0.438 | 0.529080604 | 0.672451 | 0.709529 |

FIG. 6

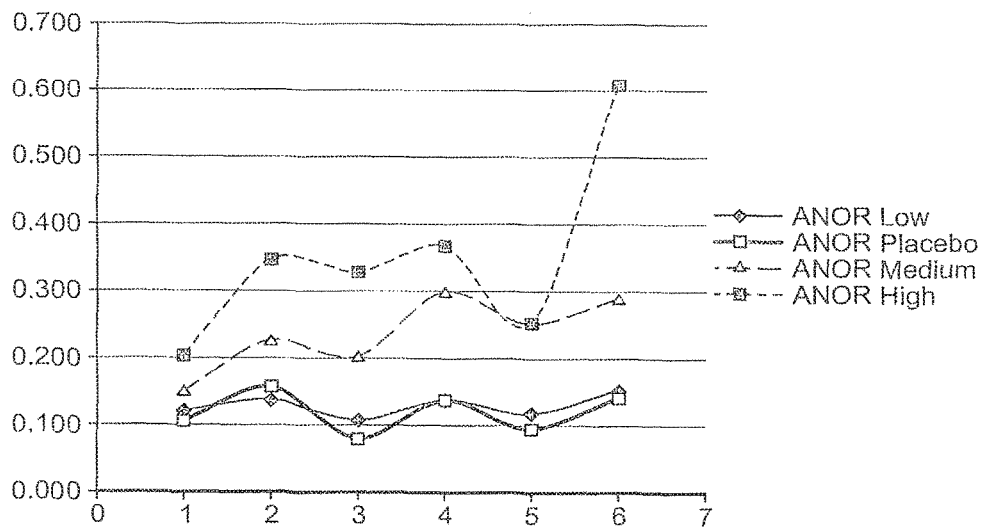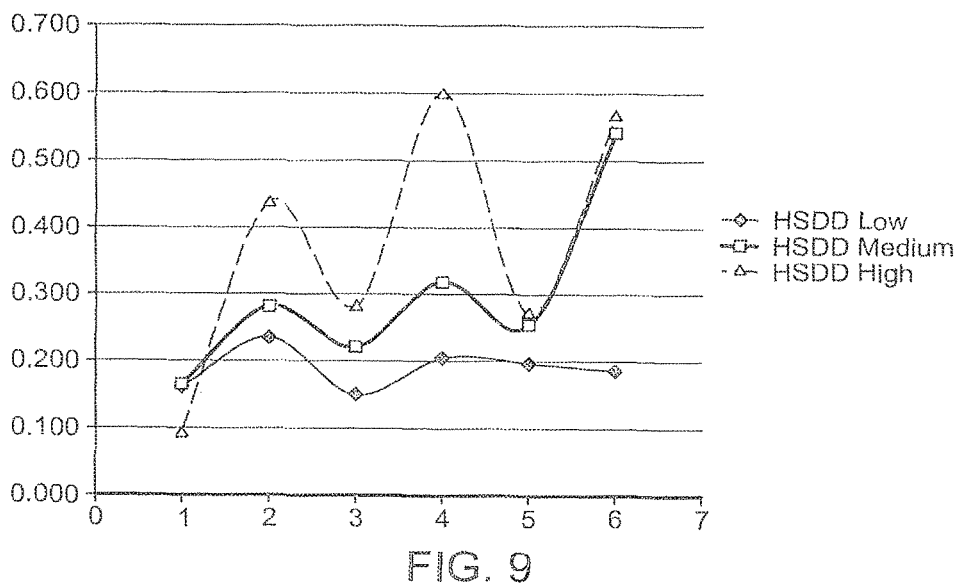
FIG. 9

|  | Placebo | | Low | | Medium | | High | | Intrinsa | |
|---|---|---|---|---|---|---|---|---|---|---|
|  | ANOR | HSDD | ANOR | HSDD | ANOR | HSDD | ANOR | HSDD | ANOR | HSDD |
| AUC12 Day 1 | 84.016 |  | 154.468 | 159.337 | 232.064 | 290.543 | 261.208 | 415.519 |  | 265.943 |
| AUC12 Day 3 | 100.328 |  | 182.745 | 162.478 | 321.319 | 434.447 | 405.019 | 491.815 |  | 479.142 |
| Cavg12 Day 1 | 7.001 |  | 12.872 | 13.278 | 19.339 | 24.212 | 21.767 | 34.627 |  | 22.162 |
| Cavg12 Day 3 | 8.361 |  | 15.229 | 13.540 | 26.777 | 36.204 | 33.752 | 40.985 |  | 39.929 |
| Cmax12 Day 1 | 0.154 |  | 0.301 | 0.304 | 0.553 | 0.786 | 0.727 | 1.192 |  | 0.685 |
| Cmax12 Day 3 | 0.157 |  | 0.356 | 0.287 | 0.799 | 0.937 | 0.750 | 1.197 |  | 0.712 |

ANOR

| Testosterone | Placebo | Placebo | Placebo | Placebo | Mean | Low | Low | Low | Low | Mean | Medium | Medium | Medium | Mean | High | High | High | High | Mean |
|---|---|---|---|---|---|---|---|---|---|---|---|---|---|---|---|---|---|---|---|
| Patient Initials | MT | AN | RS | ISE |  | JSC | LK | WY | AFO |  | JS | MG | JSA |  | ER | KK | CZS |  |  |
| Subject # | 1020 | 1024 | 2025 | 2029 |  | 1017 | 1022 | 2028 | 2030 |  | 1019 | 1021 | 2027 |  | 1018 | 1023 | 2026 |  |  |
| Day 1 2000 | 0.191 | 0.0598 | 0.171 | 0.105 | 0.120 | 0.182 | 0.175 | 0.164 | 0.0943 | 0.149 | 0.118 | 0.175 | 0.16 | 0.149 | 0.666 | 0.125 | 0.0995 |  | 0.202 |
| Day 2 0800 | 0.18 | 0.0756 | 0.163 | 0.154 | 0.135 | 0.263 | 0.213 | 0.202 | 0.329 | 0.247 | 0.173 | 0.261 | 0.253 | 0.225 | 0.332 | 0.474 | 0.26 |  | 0.345 |
| Day 2 2000 | 0.158 | 0.0551 | 0.187 | 0.0794 | 0.107 | 0.167 | 0.154 | 0.207 | 0.13 | 0.162 | 0.159 | 0.276 | 0.186 | 0.201 | 0.374 | 0.396 | 0.235 |  | 0.326 |
| Day 3 0800 | 0.207 | 0.0693 | 0.175 | 0.135 | 0.136 | 0.192 | 0.179 | na | 0.565 | 0.269 | 0.242 | 0.324 | 0.335 | 0.297 | 0.412 | 0.383 | 0.307 |  | 0.355 |
| Day 3 2000 | 0.195 | 0.0654 | 0.150 | 0.0936 | 0.116 | 0.173 | 0.178 | na | 0.169 | 0.173 | 0.255 | 0.238 | 0.253 | 0.249 | 0.348 | 0.284 | 0.161 |  | 0.252 |
| Day 4 0800 | 0.245 | 0.0734 | 0.207 | 0.139 | 0.151 | 0.240 | 0.178 | na | 0.325 | 0.240 | 0.251 | 0.274 | 0.347 | 0.288 | 0.869 | 0.438 | 0.579 |  | 0.604 |

HSDD

| Testosterone | Intrinsa | Intrinsa | Intrinsa | Intrinsa | Low | Low | Low | Mean | Medium | Medium | Medium | Mean | High | High | High | High | Mean |
|---|---|---|---|---|---|---|---|---|---|---|---|---|---|---|---|---|---|
| Patient Initials | BK | AO | MG | HJ | WN | RK | RST |  | ER | AHOO | TISC |  | EK | DB | RKE |  |  |
| Subject # | 1004 | 1006 | 1104 | 1105 | 1002 | 1007 | 2010 |  | 1003 | 1005 | 2012 |  | 1001 | 1008 | 2009 |  |  |
| Day 1 2000 | 0.0689 | 0.189 | 0.112 | 0.133 | 0.154 | 0.268 | 0.101 | 0.161 | 0.190 | 0.183 | 0.129 | 0.165 | 0.085 | 0.105 | 0.0912 |  | 0.093 |
| Day 2 0800 |  |  |  |  | 0.199 | 0.305 | 0.216 | 0.235 | 0.292 | 0.328 | 0.233 | 0.282 | 0.516 | 0.569 | 0.286 |  | 0.438 |
| Day 2 2000 |  |  |  |  | 0.181 | 0.168 | 0.111 | 0.150 | 0.279 | 0.211 | 0.186 | 0.222 | 0.186 | 0.424 | 0.285 |  | 0.282 |
| Day 3 0800 |  |  |  |  | 0.227 | 0.214 | 0.176 | 0.204 | 0.306 | 0.364 | 0.294 | 0.320 | 0.508 | 1.060 | 0.402 |  | 0.600 |
| Day 3 2000 |  |  |  |  | 0.233 | 0.237 | 0.141 | 0.198 | 0.256 | 0.313 | 0.206 | 0.255 | 0.199 | 0.422 | 0.242 |  | 0.273 |
| Day 4 0800 | 0.758 | 1.02 | 0.462 | 0.366 | 0.186 | 0.214 | 0.163 | 0.187 | 0.633 | 0.407 | 0.621 | 0.543 | 0.603 | 1.400 | 0.219 |  | 0.570 |

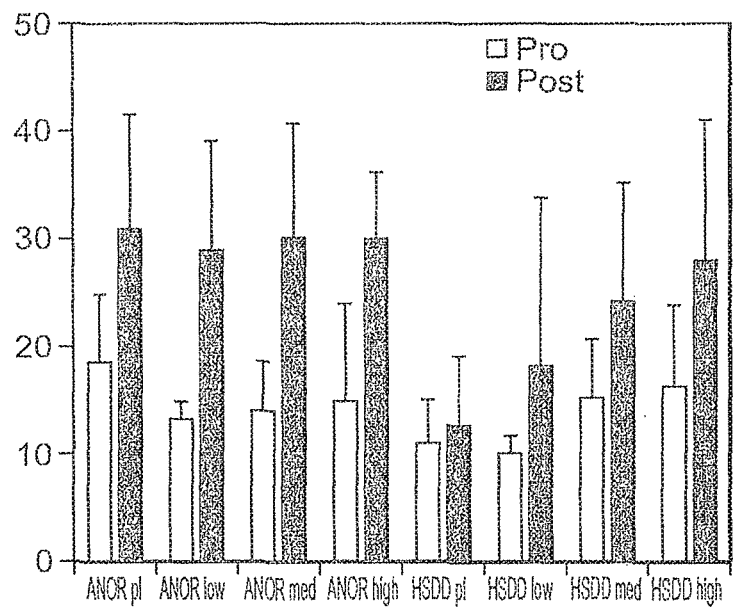
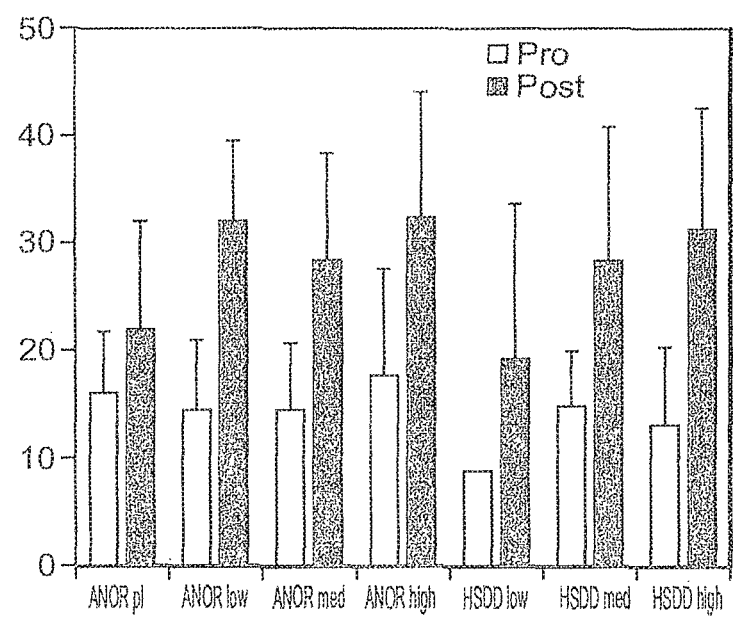
FIG. 13

INTRANASAL 0.15% AND 0.24% TESTOSTERONE GEL FORMULATIONS AND USE THEREOF FOR TREATING ANORGASMIA OR HYPOACTIVE SEXUAL DESIRE DISORDER

CROSS-REFERENCE TO RELATED APPLICATIONS

This application is a continuation of U.S. Ser. No. 14/644,414, filed Mar. 11, 2015, which is a continuation of U.S. Ser. No. 13/471,450, filed on May 14, 2012, which claims under 35 U.S.C. § 119(e) the benefit of U.S. provisional patent application No. 61/598,335, filed Feb. 13, 2012, U.S. provisional application No. 61/513,499 filed Jul. 29, 2011, U.S. provisional application No. 61/486,254, filed May 14, 2011, and U.S. provisional application No. 61/518,903, filed on May 13, 2011, the contents of all of which are hereby incorporated by reference.

FIELD OF THE INVENTION

The present invention relates to lower dosage strength intranasal testosterone gels for providing intranasal delivery of testosterone to a female and intranasal treatment methods for treating females with anorgasmia and/or hypoactive sexual desire disorder (HSDD). In particular, the present invention relates to improved methods and lower dosage strength intranasal testosterone gel formulations for treating female anorgasmia and/or HSDD. The present invention also relates to a system for dispensing intranasally a precise dosage amount of such gels at an optimal anatomical location within each nostril of the female, so that an effective amount of testosterone is deposited within each nostril at the optimal anatomical location to effectively treat female anorgasmia and/or HSDD.

BACKGROUND

Reduced levels of endogenous steroid hormones in humans often lead to a variety of undesirable clinical symptoms. For example, low testosterone levels in men (hypogonadism) may result in clinical symptoms including impotence, lack of sex drive, muscle weakness, and osteoporosis. Similarly, in women, reduced levels of testosterone and/or estrogen may result in female sexual disorder, which include clinical symptoms such as lack of sex drive, lack of arousal or pleasure, decreased energy levels or fatigue with blunted motivation, flat mood or depression, reduced sense of well-being, insomnia, irritability, partial decreases in vaginal lubrication, and osteoporosis. Moreover, reduced levels of estrogen and/or progesterone in women, as observed during menopause, often result in clinical symptoms including hot flashes, night sweats, vaginal atrophy, decreased libido, and osteoporosis.

Testosterone has historically been thought of as a male hormone, but it is also synthesized in women in small amounts, primarily by the ovaries and adrenal glands. The physiological functions of testosterone in women include, among others, development of pubic and axillary hair, sexual libido; effects on bone density and muscle tone, sexual libido, and overall vitality and sense of psychological well-being. Testosterone plasma concentrations in premenopausal women normally fluctuate during the menstrual cycle, with the total testosterone plasma concentrations generally ranging between about 15 ng/dL and about 65 ng/dL. However, in the years leading to post-menopause, levels of circulating testosterone begin to decline, generally thought to be due to age-related reductions in ovarian and adrenal secretion. Generally, women with testosterone deficiency have total testosterone levels of less than about 20-25 ng/dL, while oophorectomized women can have testosterone levels of less than about 10 ng/dL.

In the National health and Social Life Survey of over 1,700 women aged 18-59, 43% acknowledged a form of female sexual dysfunction (FSD). See, e.g., Laumanri et al.: Sexual dysfunction in the United States: prevalence and predictors; JAMA, 281: 537-544 (1999).

Hypoactive sexual desire disorder (HSDD), the most common women's sexual problem, is a condition characterized by the lack or absence of sexual fantasies and desire for sexual activity which causes marked distress or interpersonal difficulties. The sexual dysfunction is not accounted for by another psychiatric disorder nor is it a result of direct physiological effects of a substance (i.e., drug abuse) or a general medical condition.

Anorgasmia, the second most frequently reported women's sexual problem, is considered to be the persistent or recurrent delay in, or absence of, orgasm following a normal sexual excitement phase, causing marked distress or interpersonal difficulty. When a woman has sexual activity that is not accompanied by good quality orgasmic release, sexual activity may become a chore or a duty rather than a mutually satisfying, intimate experience. This may also lead to secondary loss of sexual interest and/or interpersonal difficulties.

Hypoactive sexual disorder disease and anorgasmia affect millions of women in the United States.

Sexual response is a complex and finely tuned process that can be disrupted at various time points in the reproductive life cycle (pre and postpartum, peri and postmenopausal) which likely accounts for the high prevalence of reported sexual dysfunction in the general population of healthy women. See, e.g., Laumann et al., Supra.

It is hypothesized that testosterone has central and peripheral effects on sexual function. The decline of androgen levels following surgically induced menopause has supported the hypothesis that a decrease in testosterone levels is related to a decrease in sexual desire. Testosterone, the primary circulation androgen in women, is a naturally occurring steroid. In women, androgens are derived from three sources: the adrenal glands, the ovaries and peripheral conversion. Androgens are secreted by the ovaries and the adrenal glands. Contrary to the sudden drop in estrogen during menopause, serum levels of androgens fall gradually as women age, primarily due to a decrease in the production of adrenal androgen precursors. See, e.g. Goldstat et al.: Transdermal testosterone therapy improves well-being, mood, and sexual function in pre-menopausal women; Menopause, 10(5): 390-398 (2003). As indicated above, this is likely due to a decline in ovarian and adrenal function with age.

A recent cross sectional study in woman ages 18-75 shows that total and free testosterone levels significantly decrease with age starting in the early reproductive years. In contrast to naturally occurring menopause, women who have undergone bilateral oopherectomy experience a dramatic decline in testosterone production with levels decreasing as much as 50%.

It has been reported that testosterone plays a role in mood, body composition, and bone mineral density and has central and peripheral effects on sexual function. See, e.g., Davis et al.: Androgen replacement in women: a commentary; Menopause, J Clin Endocrinol Metab, 84(6): 1886-1891 (1999);

and Goldstat et al., Supra. In the periphery, testosterone is required for nitric oxide to stimulate vasocongestion for the engorgement of clitoral tissue and vaginal lubrication during sexual arousal.

Recent studies have shown that testosterone is effective in increasing the number of sexually satisfying events, increasing sexual desire and decreasing personal distress in bilaterally oophorectomized and hysterectomized women suffering from HSDD.

Central effects of testosterone are less well characterized. Testosterone stimulates dopamine release in various brain structures implicated in motivation and reward systems, including sexual desire. Testosterone was found to stimulate dopamine release in the medial preoptic area of the anterior hypothalamus under basal conditions and with sexual stimulation in rats. See, e.g., Halaris A.: Neurochemical aspects of the sexual response cycle; CNS Spectrums, 9: 211-216 (2003). An fMRI study in healthy women of different ages showed a testosterone level dependent modulation of amygdala activity, suggesting that an age-related decline in androgen levels contributes to the decrease in amygdala reactivity. In addition, it has been reported that a decreased amygdala reactivity in older women may be restored to levels of young women with intranasal exogenous testosterone. See e.g., van Wingen et al.: Testosterone increases amygdala reactivity in middle-aged women to a young adulthood level; Neuropsychopharmacology, February: 34(3) 539-547 (2009).

The use of androgens to increase women's sexual libido was reported in 1940 by Loeser. Salmon (1942) observed that a number of young, married women who formerly considered themselves "frigid" were able to experience "a marked increase in coital gratification, culminating in an orgasm" after testosterone propionate injections. The effects wore off within several weeks after the discontinuation of the injections. See, e.g., Traish et al.: Testosterone therapy in women with gynecological and sexual disorders: a triumph of clinical endocrinology from 1938 to 2008; J Sex Med 4:609-619 (2009). In the 1980s, the role of androgens in maintaining sexual function was studied in oophrectomized women. See, e.g., Sherwin et al.: The role of androgen in the maintenance of sexual functioning in oophorectomized women; Psychosomatic Medicine, 49:397-409 (1987). In the Sherwin et al. study, a three (3) month prospective open-label study of 44 women, it was reported that monthly injections of estrogen and testosterone increased rates of sexual desire, sexual arousal, and number of fantasies. It was further reported in the Sherwin et al. study that rates of intercourse and orgasm were higher in women treated with androgens and estrogen compared to the controls.

Over the past two decades, over 80 studies have been conducted in post-menopausal women with HSDD using exogenous testosterone through the oral, transdermal, sublingual or parental route of administration with or without concomitant estrogen therapy, in which some degree of an increase in sexual desire, arousal, frequency of satisfactory sexual activity, pleasure and responsiveness was allegedly observed. See, Traish et al. Supra, 2009.

Fewer studies have been performed in pre-menopausal women with low libido. Goldstat et al., Supra, apparently studied the effects of transdermal testosterone therapy on well-being, mood and sexual function in eugonadal, pre-menopausal women presenting with low libido. Testosterone therapy resulted in statistically significant improvements in the composite scores of the Psychological General Well-Being Index, the Sabbatsberg Sexual Self-Rating Scale and the Beck Depression Inventory when compared with placebo. These effects were found while the mean total testosterone levels were in the low end of the normal range before treatment, and at the high end of the normal range during treatment. On the different sub-scales of the Sabbatsberg Sexuality Scale, however, there was a significant effect of testosterone treatment on orgasm. This study suggests that, although most previous studies with testosterone have addressed decreased sexual desire in post-menopausal women, there are also measurable effects in pre-menopausal women both on general sexual well-being and on orgasm specifically.

Intrinsa® is a testosterone slow-release transdermal patch. Intrinsa® is indicated for the treatment of hypoactive sexual desire disorder (HSDD) in bilaterally oophorectomized and hysterectomized (surgically induced menopause) women receiving concomitant estrogen therapy. Clinical studies using Intrinsa® have shown enhancement of sexual desire and number of satisfactory sexual events with mild androgenic skin effects as the primary safety concern in post-menopausal women with HSDD. See, e.g., Shifren et al.: Transdermal testosterone treatment in women with, impaired sexual function after oophorectomy; N Eng N Med, 343(10): 682-688 (2000); Braunstein et al.: Safety and efficacy of a testosterone patch for the treatment of hypoacytive sexual desire disorder in surgically menopausal women: a randomized placebo-controlled trial; Arch Intern Med, 165(14): 1582-1589 (2005); Buster et al.: Testosterone Patch for low sexual desire in surgically menopausal women: a randomized trial; Obstet Gynecol, 105(5 Pt 1): 944-952 (2005); Simon et al.: Testosterone patch increases sexual activity and desire in surgically menopausal women with hyposactive sexual desire disorder; J Clin Endocrinol Metab, 90(9) 5226-5233 (2005); Davis et al.: Efficacy and safety of a testosterone patch for the treatment of hypoactive sexual desire disorder in surgically menopausal women: a randomized, placebo-controlled trial; Menopause, 13(3): 387-396 (2006); and Shifren et al.: Testosterone patch for the treatment of hypoactive sexual desire disorder in naturally menopausal women: results from the INTIMATE1 study; Menopause, 143:770-779 (2006).

LibiGel is a gel formulation of testosterone that is applied on the upper arm of a female. It is reported that treatment with LibiGel increases the number of satisfying sexual events versus baseline and placebo treated individuals It is further reported that the effective dose of LibiGel produces testosterone blood levels within the normal range for pre-menopausal women. See, e.g., www.libigel.org.

Zestra® is a blend of botanical oils and extracts, including: Borage Seed Oil, Evening Primrose Oil, *Angelica* Extract, *Coleus Forskohlii* Extract, Theobromine, Anti-Oxidants {Ascorbyl Palmitate (Vitamin C), Tocopherol (Vitamin E)}; and Flavor (U.S. Pat. No. 6,737,084) that may benefit some women with anorgasmia. Zestra® has demonstrated significant improvements in the measures of desire, arousal and sexual satisfaction in women. See, e.g., www.zestra.com.

ArginMax™ is a mixture of L-arginine, ginseng, ginkgo, damiana, calcium, and iron. ArginMax™ for Women was formulated specifically for women. It contains calcium and iron to help relieve fatigue issues specific to women. The American ginseng in the men's product has been replaced with Damiana, an aromatic herb which helps calm anxiety and induce a relaxed state of mind. ArginMax™ for Women provides 100% of the RDA of vitamins A, C, E and the B-complex vitamins. ArginMax™ safely enhances the female sexual experience by improving circulation. Sufficient blood flow is critical to female arousal, engorgement and lubrication. See, e.g., www.arginimax.com.

In view of the fact that millions of women in the United States, as well as through out the world, suffer from HSDD and anorgasmia, there is a real and immediate need for an effective medical therapy that can treat these diseases, so that the quality of life of these individuals can be improved. One therapeutic goal of such therapy to solve this immediate need might be to restore testosterone levels in women to young adulthood levels or to at least the natural pre-menopausal state in hopes to alleviate the symptoms generally associated with HSDD and/or anaorgasmia due possibly to testosterone deficiency.

BRIEF SUMMARY OF THE INVENTION

The present invention overcomes the limitations and disadvantages associated with the treatment of anorgasmia and/or HDDD using available therapies through the discovery of novel lower dosage strength pernasal testosterone gels and methods of use to treat HSDD and/or anorgasmia. Particularly, the present invention overcomes the limitations and disadvantages of currently available options for administration of testosterone through the discovery of novel and improved lower dosage strength testosterone gel formulations specifically designed for intranasal administration to deliver therapeutically effective amounts of testosterone to treat females who suffer from and/or have been diagnosed with HSDD and/or anorgasmia.

The term "a therapeutically effective amount" means an amount of testosterone sufficient to induce a therapeutic or prophylactic effect for use in testosterone replacement or supplemental therapy to treat female sexual dysfunction ("FSD"), namely, hypoactive sexual desire disorder ("HSDD") and/or female orgasmic disorder ("anorgasmia") in females.

Thus, generally speaking, the present invention provides for new and improved, substantially less-irritating, lower dosage strength testosterone gel formulations formulated with testosterone in amounts ranging from between about 0.10% to about 1.5% by weight, for nasal administration to deliver a therapeutically effective amount of testosterone to effectively treat anorgasmia and/or HSDD.

The present invention is also directed to novel methods for pernasal administration of the nasal testosterone gels. Generally speaking, the novel methods involve depositing the intranasal testosterone gels topically into the nasal cavity of each nostril to deliver a therapeutically effective amount of testosterone, e.g., from about 150 mcg/nostril to about 600 mcg/nostril per application, over dose life for providing constant effective testosterone brain and/or blood levels for use in testosterone replacement or supplemental therapy, especially for effectively treating females in need of testosterone to treat anorgasmia and/or HSDD.

In accordance with the novel methods of the present invention, the intranasal testosterone gels are topically deposited on the outer external walls (opposite the nasal septum) inside the naval cavity of each nostril, preferably at about the middle to about the upper section of the outer external wall (opposite the nasal septum) just under the cartilage section of the outer external wall inside the naval cavity of each nostril. Once gel deposition is complete within each nostril of the nose, the outer nose is then gently and carefully squeezed and/or rubbed by the subject, so that the deposited gel remains in contact with the mucosal membranes within the nasal cavity for sustained release of the testosterone over dose life. Typical testosterone gel dosage amounts deposited pernasal application is between about 50 to about 150 microliters per nostril, and preferably about 100 microliters per nostril.

In carrying out the methods of the present invention, approximately between 50 microliters and about 150 microliters of a lower dosage strength testosterone gel of the present invention is applied to each nostril of a subject once or twice daily, e.g., for one, two, three, four or more consecutive weeks, or for two, three, four, five or six consecutive days or more, or intermittently such as every other day or once, twice or three times weekly, or on demand once or twice during the same day, to treat HSDD and/or anorgasmia.

While the present invention has identified what it believes to be preferred concentrations of intranasal testosterone gel formulations, numbers of applications per day, durations of therapy, pernasal methods and pre-filled, multi-dose applicator systems, it should be understood by those versed in this art that any effective low dosage concentration of testosterone, i.e., between about 0.10% and about 1.5% by weight, in an intranasal gel formulation that delivers an effective amount of testosterone and any numbers of applications per day, week, month or year, as described herein, that can effectively treat anorgasmia and/or HSDD without causing unwanted testosterone treatment limiting reactions or related adverse events is contemplated by the present invention.

The present invention therefore provides for a new and improved treatment for anorgasmia and/or HSDD, wherein nasal administration of a lower dosage strength testosterone gel formulation of the present invention provides for: (1) rapid delivery of testosterone due to the highly permeable nasal tissue both systemically and across the blood-brain barrier into the brain; (2) fast onset of action; (3) avoidance of hepatic first-pass metabolism; (4) ease of administration to improve sexual experience; (5) avoidance of irritation from transdermal administration, particularly, no exposition to contacts, no transference from topical gels, and no local irritability from topical patch products; and (6) a more pleasant mode of administration, as compared to injections and buccal or sublingual tablets.

In other words, the present invention provides for a new and improved anorgasmia and/or HSDD treatment that (a) is easy and convenient to use either according to a prescribed treatment regimen or on-demand, (b) rapidly delivers therapeutically effective amounts of testosterone, thereby improving female sexual function in a timely manner, (c) provides for simple use, (d) has reduced side effects associated with prior exogenous systemic testosterone therapies, (e) avoids local irritability associated with prior topical gels and topical patches, and (f) eliminates the need for invasive and painful testosterone injections.

The present invention, in one embodiment, provides numerous surprising advantages over currently available therapies for anorgasmia and HSDD. For example, the present invention provides for (1) a rapid increase in the plasma testosterone plasma level (e.g., an increase in the plasma testosterone to a level of at least about 0.4 ng/ml within about 15 minutes immediately after nasal administration of the testosterone gel formulation of the invention); (2) a sustained increase in the plasma testosterone plasma level (e.g., an increase in the plasma testosterone level that is maintained in a subject for at least about 6 hours following nasal administration of the testosterone gel formulation of the invention); and (3) a higher maximum level of plasma testosterone as compared to the maximum level of plasma testosterone following administration of Intrinsa® within about 100 minutes immediately following administration (e.g., an increase in the plasma testosterone level to at least about 0.7 ng/ml as compared to about 0.1 ng/ml for Intrinsa®.).

As demonstrated in FIG. 1, an improved testosterone gel formulation of the invention provide advantages over therapies for treating anorgasmia and HSDD that are currently available. For example, a testosterone gel formulation of the invention comprising about 0.6% testosterone by weight of the gel formulation is administered intranasally to subjects. In comparison, control subjects, who are treated with an Intrinsa® patch, receive a testosterone dose of about 2100-2800 mcg/day, up to approximately 3.5-4.5 times the testosterone received by women treated with the lower dosage strength testosterone gels of the present invention (i.e., about 600, 1800, or 2400 mcg/day, for the 0.15%, 0.45%, and 0.6% testosterone gels of the invention, respectively, or about 600, 1200 or 1800 mcg/day, for the 0.24%, 0.48% or 0.72% testosterone gels of the invention, respectively). Importantly, unlike the Intrinsa® patch, testosterone levels return to baseline after about 12 hours after treatment with the lower dosage strength testosterone gels of the present invention (at least for the 0.15% and 0.45% gel formulations of the invention).

One unique pharmacokinetic profile, as compared to Intrinsa®, is presented in FIG. 1. The improved 0.6% testosterone gel formulation for nasal administration of the present invention provides a plasma testosterone concentration, following nasal administration wherein (a) a plasma testosterone level of at least about 0.4 ng/ml is achieved; (b) a plasma testosterone level of at least about 0.7 ng/ml is achieved; (c) an increase in plasma testosterone level is achieved within at least about 10 minutes following nasal administration to a subject; (d) a plasma testosterone level of at least about 0.4 ng/ml is achieved and maintained for at least about 6 hours immediately following nasal administration to a subject; (e) a plasma testosterone level of at least about 0.3 ng/ml is achieved and maintained for at least about 13 hours immediately following nasal administration to a subject; and (f) a plasma testosterone level of at least about 0.7 ng/ml is achieved within about 100 minutes immediately following nasal administration to the subjects (see FIG. 1).

In contrast, following treatment with Intrinsa®, as illustrated in FIG. 1, the plasma testosterone level does not increase until at least about 3 hours following administration of Intrinsa®. Even then, a plasma testosterone concentration of at least about 0.4 ng/ml is not observed in the Intrinsa® treated subjects until at least about 6.5 hours following administration. The maximum plasma testosterone level of a subject treated with Intrinsa® (only about 0.68 ng/ml) is not observed until about 12 hours following administration of Intrinsa®.

Thus, one improved testosterone (0.6%) gel formulation for nasal administration of the present invention may provide one or more of the following plasma testosterone concentrations, following nasal administration:

(a) a plasma testosterone concentration of at least about 0.4 ng/ml within less than hour following administration;

(b) a plasma testosterone concentration of at least about 0.7 ng/ml within less than about 100 minutes following administration;

(c) a plasma testosterone concentration increase within at least about 10 minutes following nasal administration to a subject;

(d) a plasma testosterone concentration of at least about 0.4 ng/ml, wherein the increase is achieved and maintained for at least about 6 hours immediately following nasal administration to a subject;

(e) a plasma testosterone level of at least about 0.3 ng/ml is achieved and maintained for at least about 13 hours immediately following nasal administration to a subject; and/or (f) a plasma testosterone concentration of at least about 0.7 ng/ml is achieved within about 100 minutes immediately following nasal administration to a subject (see FIG. 1).

Thus, as exemplified in FIG. 1, the present invention overcomes certain of the limitations associated with the treatment of anorgasmia and/or HSDD using currently available therapies, for example, Intrinsa®, and addresses current medical needs for (1) a pharmaceutical formulation that is conveniently, easily and unobtrusively administered; (2) a rapidly acting formulation that improves female sexual dysfunction in a timely manner; (3) a decrease in the incidence of application site reactions; (4) a formulation that has reduced side effects; and (5) a formulation that can be used either according to a prescribed treatment regimen or on demand; to treat anorgasmia and/or HSDD.

A safety study was also conducted in accordance with the present invention, as reported in Example 11, wherein women were treated intranasally with a 0.72% testosterone gel (about 1200 mcg/dose administration) of the present invention t.i.d. for two consecutive days and qd on the third consecutive day resulting in a total daily dose of testosterone of about 3600 mcg/day for the first two days and about 1200 mcg on the third consecutive day. As shown in Example 11, the intranasal testosterone gels of the present invention are believed to be safe and well tolerated.

The salient elements of the novel intranasal testosterone gels according to the present invention comprise (a) testosterone in a therapeutically effective amount, (b) a solvent, (c) a wetting agent, and (d) a viscosity increasing agent. The improved lower dosage strength testosterone gel formulations of the present invention may be formulated with testosterone in amounts by weight of between about 0.10% to about 1.5%, e.g., about 0.15%, 0.24%, 0.45%, 0.48%, 0.6% and 0.72%, and more preferably between about 0.24% and 0.72%. Exemplary nasally administered testosterone gel formulations contemplated by the present invention include:

(a) 0.15% testosterone, 91.85% castor oil, 4.0% oleoyl polyoxylglycerides, and 4% colloidal silicon dioxide;

(b) 0.24% testosterone, 91.76% castor oil, 4.0% oleoyl polyoxylglycerides, and 4% colloidal silicon dioxide (c) 0.45% testosterone, 91.55% castor oil, 4.0% oleoyl polyoxylglycerides, and 4% colloidal silicon dioxide;

(d) 0.48% testosterone, 91.52% castor oil, 4.0% oleoyl polyoxylglycerides, and 4% colloidal silicon dioxide (e) 0.6% testosterone, 91.4% castor oil, 4.0% oleoyl polyoxylglycerides, and 4% colloidal silicon dioxide; and (f) 0.72% testosterone, 91.28% castor oil, 4.0% oleoyl polyoxylglycerides, and 4% colloidal silicon dioxide.

Thus, the improved testosterone gel formulations for nasal administration of the invention may further comprise any pharmaceutically acceptable vehicle, excipient and/or other active ingredient.

In addition, the present invention contemplates testosterone gel formulations for nasal administration that are pharmaceutically equivalent, therapeutically equivalent, bioequivalent and/or interchangeable, regardless of the method selected to demonstrate equivalents or bioequivalence, such as pharmacokinetic methodologies, microdialysis, in vitro and in vivo methods and/or clinical endpoints described herein.

Thus, the present invention contemplates testosterone gel formulations for nasal administration that are bioequivalent, pharmaceutically equivalent and/or therapeutically equivalent, especially testosterone gel formulations for nasal administration that are 0.15% testosterone by weight of the gel formulation, 0.24% testosterone by weight of the gel formulation, 0.45% testosterone by weight of the gel formulation, 0.48% testosterone by weight of the gel formulation, 0.6% testosterone by weight of the gel formulation and 0.72% testosterone by weight of the gel formulation, when used in accordance with the therapy of the present invention to treat anorgasmia and/or HSDD by intranasal administration. Thus, the present invention contemplates: (a) pharmaceutically equivalent testosterone gel formulations for nasal administration which contain the same amount of testosterone in the same dosage form; (b) bioequivalent testosterone gel formulations for nasal administration which are chemically equivalent and which, when administered to the same individuals in the same dosage regimens, result in comparable bioavailabilities; (c) therapeutic equivalent testosterone gel formulations for nasal administration which, when administered to the same individuals in the same dosage regimens, provide essentially the same efficacy and/or toxicity; and (d) interchangeable testosterone gel formulations for nasal administration of the present invention which are pharmaceutically equivalent, bioequivalent and therapeutically equivalent.

While the intranasal testosterone gels of the present invention are preferred pharmaceutical preparations when practicing the novel methods of the present invention, it should be understood that the novel topical intranasal gel formulations and methods of the present invention also contemplate the pernasal administration of any suitable active ingredient, either alone or in combination with testosterone or other active ingredients, such as neurosteroids or sexual hormones (e.g., androgens and progestins, like testosterone, estradiol, estrogen, oestrone, progesterone, etc.), neurotransmitters, (e.g., acetylcholine, epinephrine, norepinephrine, dopamine, serotonin, melatonin, histamine, glutamate, gamma aminobutyric acid, aspartate, glycine, adenosine, ATP, GTP, oxytocin, vasopressin, endorphin, nitric oxide, pregnenolone, etc.), prostaglandin, benzodiazepines like diazepam, midazolam, lorazepam, etc., and PDEF inhibitors like sildenafil, tadalafil, vardenafil, etc., in any suitable pharmaceutical preparation, such as a liquid, cream, ointment, salve or gel. Examples of additional topical formulations for practice in accordance with the novel methods of the present invention include the topical pernasal formulations disclosed in, for example, U.S. Pat. Nos. 5,578,588, 5,756,071 and 5,756,071 and U.S. Patent Publication Nos. 2005/0100564, 2007/0149454 and 2009/0227550, all of which are incorporated herein by reference in their entireties.

The present invention is also directed to packaged pharmaceuticals comprising the novel and improved testosterone gel formulations for nasal administration of the invention. For example, the present invention contemplates pre-filled, single or multi-dose applicator systems for pernasal administration to strategically and uniquely deposit the nasal testosterone gels at the preferred locations within the nasal cavity for practicing the novel methods and teachings of the present invention. Generally, speaking the applicator systems of the present invention are, e.g., airless fluid, dip-tube fluid dispensing systems, pumps, syringes or any other system suitable for practicing the methods of the present invention. The applicator systems or pumps include, for example, a chamber, pre-filled with a single dose or multiple doses of an intranasal testosterone gel of the present invention, that is closed by an actuator nozzle or cap. The actuator nozzle may comprise an outlet channel and tip, wherein the actuator nozzle is shaped to conform to the interior surface of a user's nostril for (a) consistent delivery of uniform dose amounts of an intranasal testosterone gel of the present invention during pernasal application within the nasal cavity, and (b) deposition at the instructed location within each nostril of a patient as contemplated by the novel methods and teachings of the present invention. Examples of pre-filled, multi-dose applicator systems include, e.g., (a) the COMOD system available from Ursatec, Verpackung-GmbH, Schillerstr. 4, 66606 St. Wendel, Germany, (b) the Albion or Digital airless applicator systems available from Airlessystems, RD 149 27380 Charleval, France or 250 North Route 303 Congers, N.Y. 10950 (See, for example, FIG. 39), (c) the nasal applicators from Neopac, The Tube, Hoffmann Neopac AG, Burgdorfstrasse 22, Postfach, 3672 Oberdiessbach, Switzerland, or (d) the syringes described in the Examples herein below.

It should be understood by those versed in this art that the amount of testosterone in a lower dosage strength intranasal testosterone gel of the present invention that will be therapeutically effective in a specific situation will depend upon such things as the dosing regimen, the application site, the particular gel formulation, dose longevity and the condition being treated. As such, it is generally not practical to identify specific administration amounts herein; however, it is believed that those skilled in the art will be able to determine appropriate therapeutically effective amounts based on the guidance provided herein, information available in the art pertaining to testosterone replacement therapy, and routine testing.

It should be further understood that the above summary of the present invention is not intended to describe each disclosed embodiment or every implementation of the present invention. The description further exemplifies illustrative embodiments. In several places throughout the specification, guidance is provided through examples, which examples can be used in various combinations. In each instance, the examples serve only as representative groups and should not be interpreted as exclusive examples.

BRIEF DESCRIPTION OF THE DRAWINGS

The foregoing and other objects, advantages and features of the present invention, and the manner in which the same are accomplished, will become more readily apparent upon consideration of the following detailed description of the invention taken in conjunction with the accompanying figures and examples, which illustrate embodiments, wherein:

FIG. 6 is comparative data from treatment study for HSDD for the 0.6% testosterone gel and Intrinsa® from days 1 and 3;

FIG. 9 shows the accumulation effect effects of a testosterone nasal gel formulation of the invention (0.15, 0.45 and 0.6% testosterone by weight of the gel formulation) before each bi-daily dose of testosterone gel on the plasma testosterone levels at time (0) in subjects diagnosed with HSDD or anorgasmia;

FIG. 10 (same as 12 but table on AUC Cavg and Cmax) vs Intrinsa® (note—because Intrinsa® is not approved for Anorgasmia, it was not assessed in the study);

FIG. 11 presents trough data for subjects diagnosed with anorgasmia or HSDD and treated with testosterone nasal gel formulations of the invention (0.15%, 0.45% or 0.6% testosterone by weight of the gel formulation) or placebo (anorgasmia) or Intrinsa® (HSDD);

FIG. 13 presents scores on the AFSDQ 30 minutes (left) and 4.5 hours (right) after dosing. White bars=start of session; solid bars=end of session. Groups left to right: ANOR placebo, ANOR low, ANOR medium, ANOR high, HSDD Intrinsa patch (at 30 min. only), HSDD low, HSDD medium, HSDD high;

As illustrated in FIG. 14, the testosterone serum levels are compared for the three different testosterone bio-adhesive gel formulations of the invention (0.15%-, 0.45% and 0.6% testosterone by weight of the gel formulation, as reported in Examples 1-5), during 2 hours following a single application of each TBS-2 formulation or a placebo to each of the 12 women. The total testosterone dosage strength that is adminstered is either 1.2 mg (0.6%—0.6 mg/100 µl/nostril), 0.9 mg (0.45%—0.45 mg/100 µl/nostril) or 0.3 mg (0.15%—0.15 mg/100 µl/nostril). Following administration, the testosterone serum level is measured and compared. As shown in FIG. 14, the $C_{max}$ and $C_{avg}$ for testosterone following single dose administration for each of the three dosage strengths do not exceed the normal testosterone serum level in women (3-80 ng/dL);

DETAILED DESCRIPTION

Figure 1:
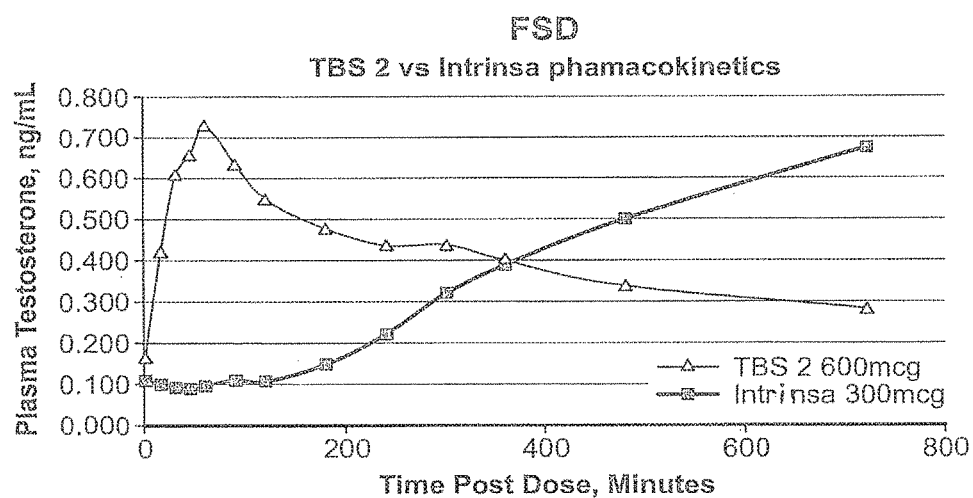
FIG. 1 shows the effects of a single dose testosterone nasal gel formulation of the invention (0.6% testosterone by weight of the gel formulation) as compared to Intrinsa® on the plasma testosterone levels in subjects diagnosed with HSDD (triangles-100 microliters 0.6% testosterone nasal gel formulation of the invention in each nostril; squares—Intrinsa®)
Figure 2:
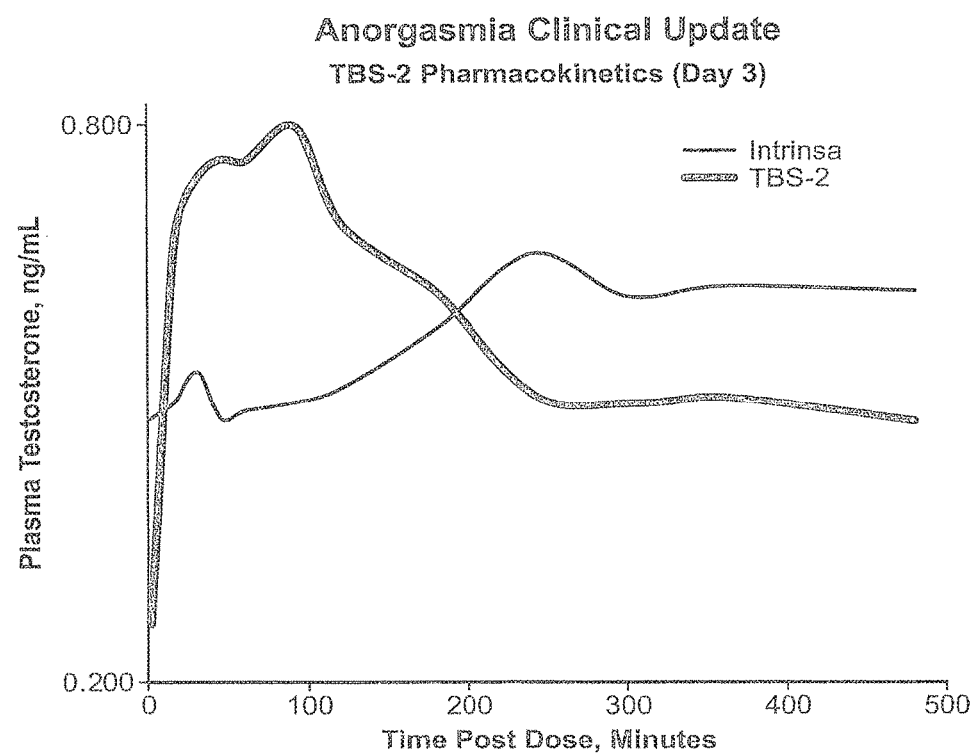
FIG. 2 shows the effects of a testosterone nasal gel formulation of the invention after the fifth 12 hourly dose (0.6% testosterone by weight of the gel formulation) as compared to Intrinsa® on the plasma testosterone levels in subjects diagnosed with anorgasmia (TBS-2 line-0.6% testosterone nasal gel formulation of the invention (100 mcl*2); solid line—Intrinsa®)
Figure 3:
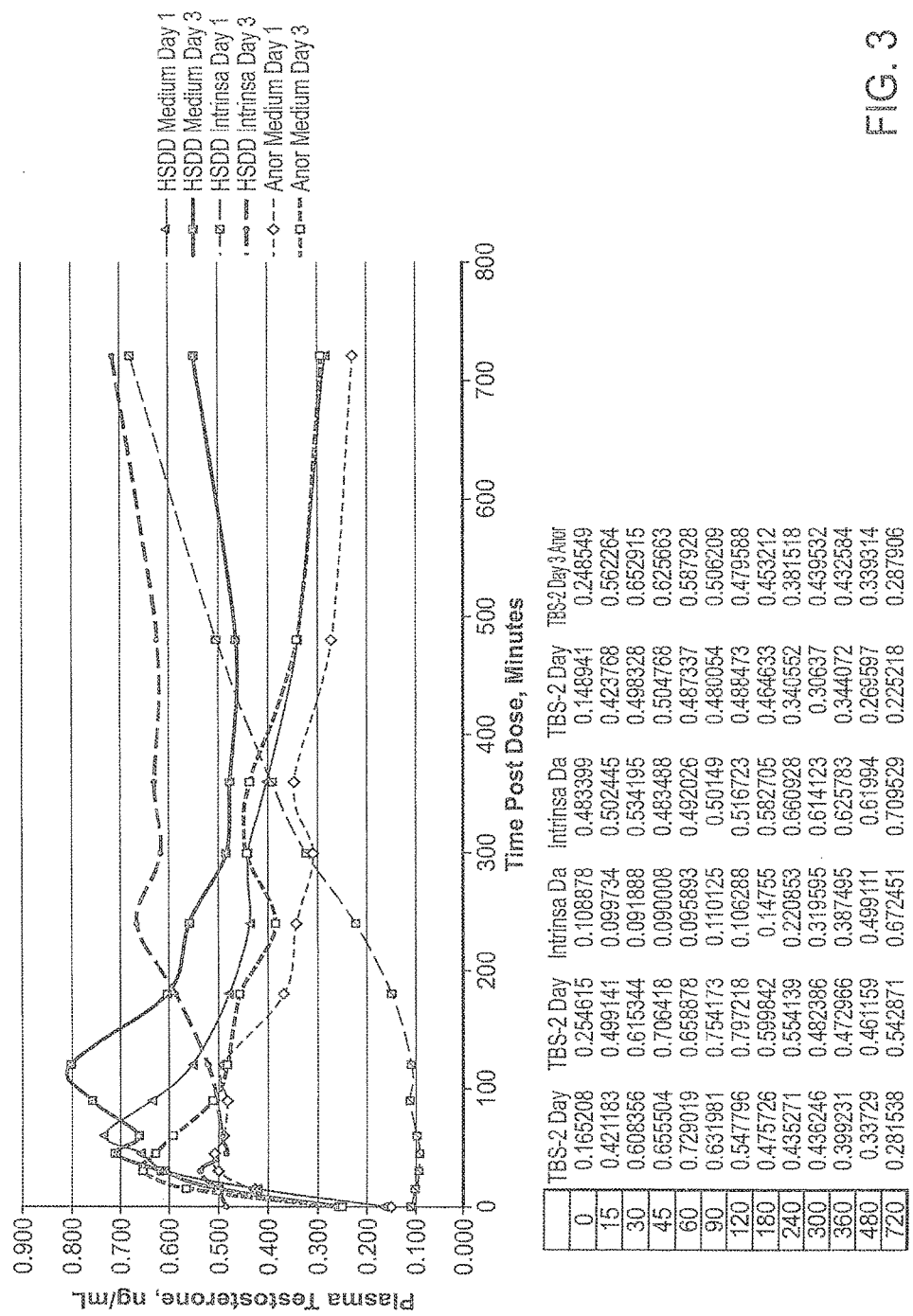
FIG. 3 shows the effects of a testosterone nasal gel formulation of the invention (0.15, 0.45 and 0.6% testosterone by weight of the gel formulation) after the first and the 5th 12 hourly dose as compared to Intrinsa® single dose on the plasma testosterone levels in subjects diagnosed with HSDD.
Figure 4:
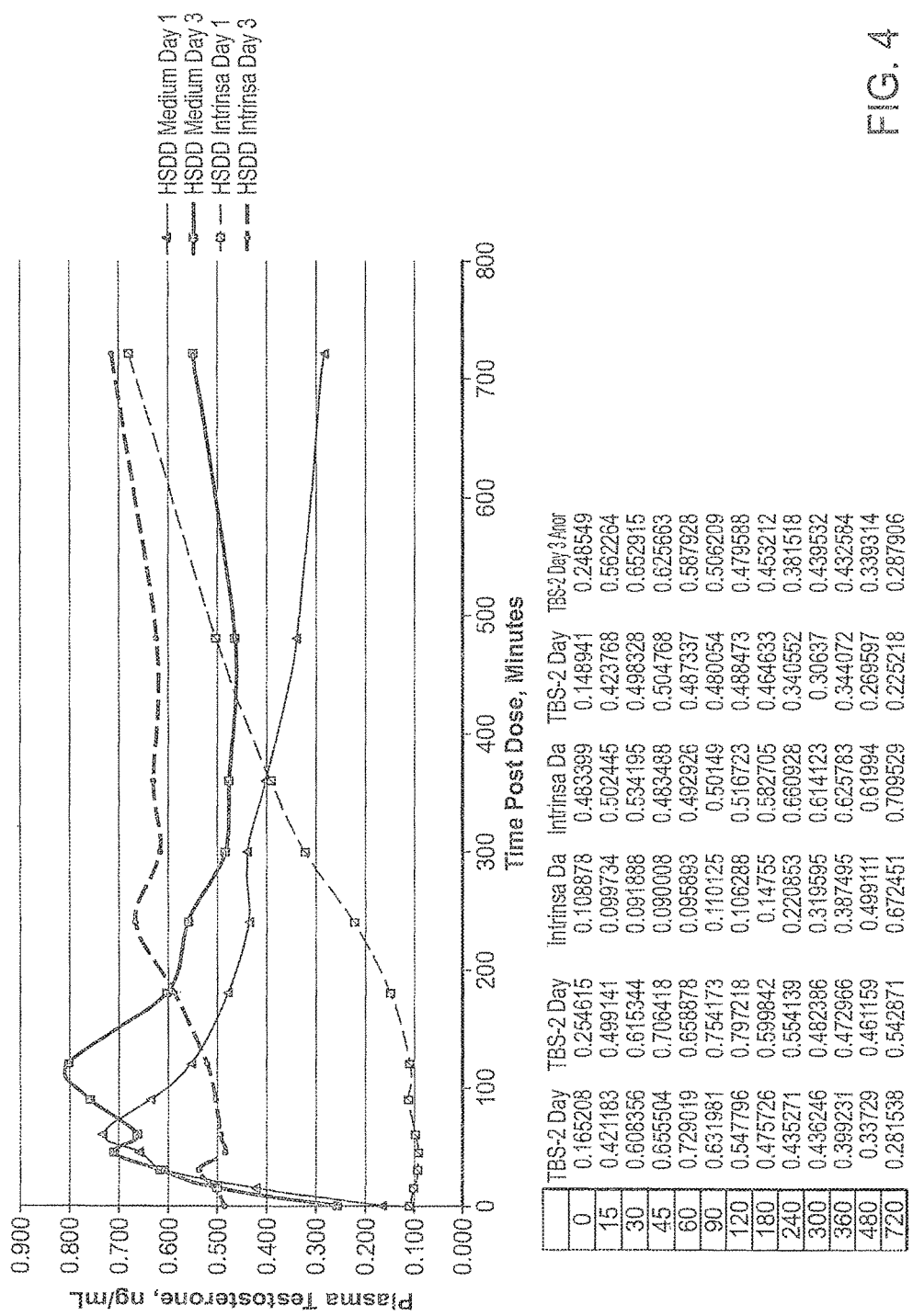
FIG. 4 shows the effects of a testosterone nasal gel formulation of the invention at day zero (open triangles) and day 3 (dose 5—closed square—of 0.6% testosterone by weight of the gel formulation) as compared to Intrinsa® on the plasma testosterone levels in subjects diagnosed with HSDD (open squares day 0—lines day 3 of 0.6% squares—Intrinsa®.
Figure 5:
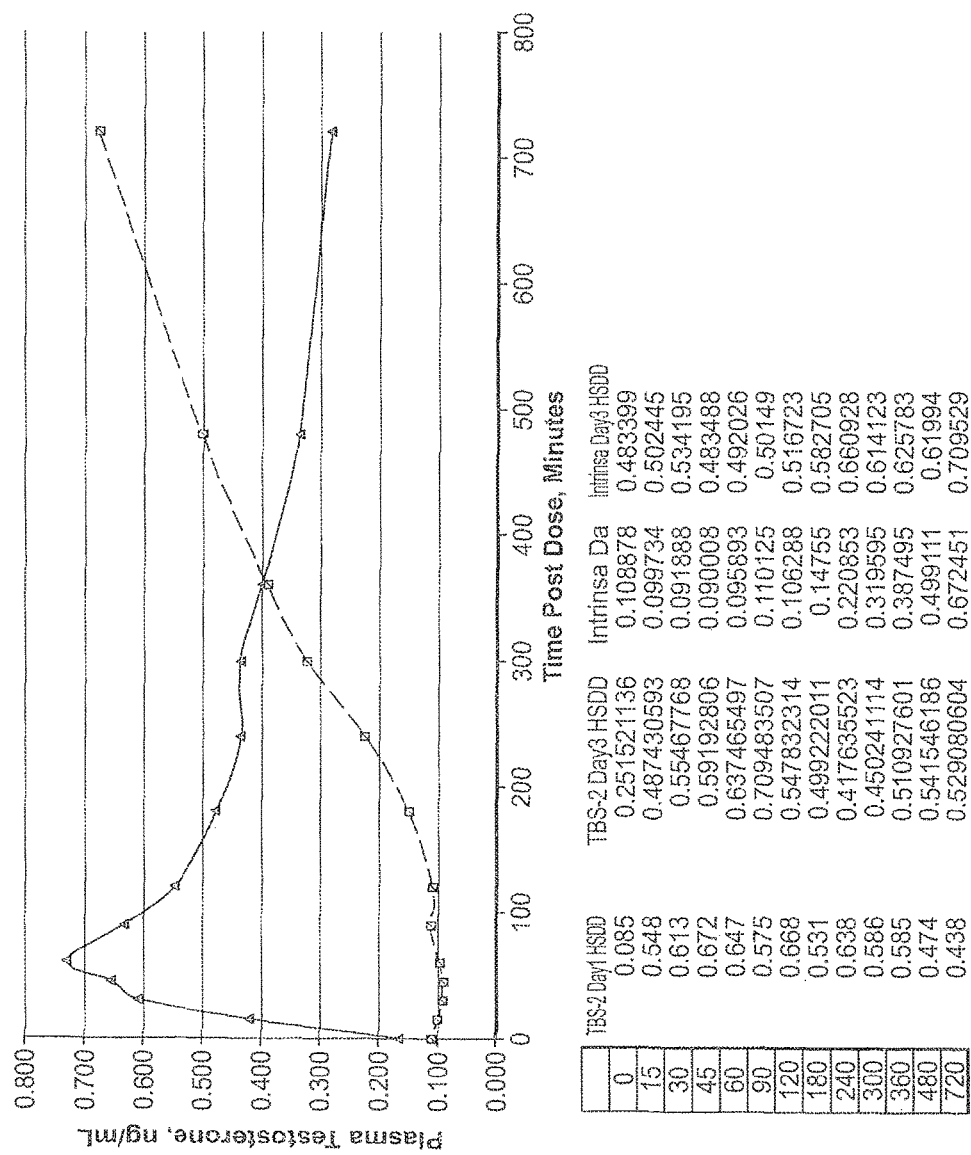
FIG. 5 is a copy of FIG. 1, but with comparative data for the 0.6% testosterone gel and Intrinsa® from days 1 and 3.
Figure 7:
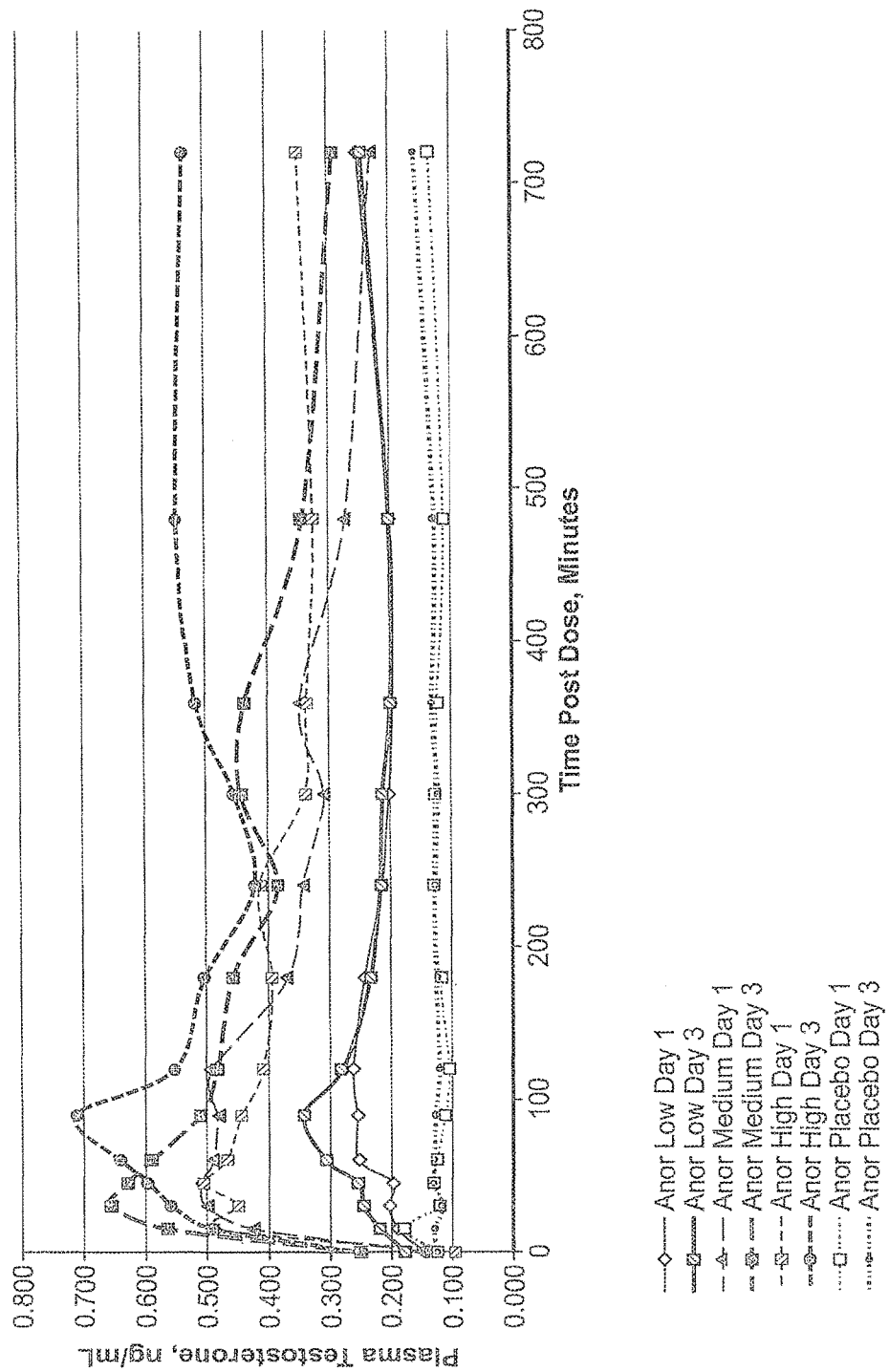
FIG. 7 shows the effects of a testosterone nasal gel formulation of the invention (0.15, 0.45 and 0.6% testosterone by weight of the gel formulation) after the first and the 5th 12 hourly dose as compared to Intrinsa® single dose on the plasma testosterone levels in subjects diagnosed with anorgasmia.
Figure 8:
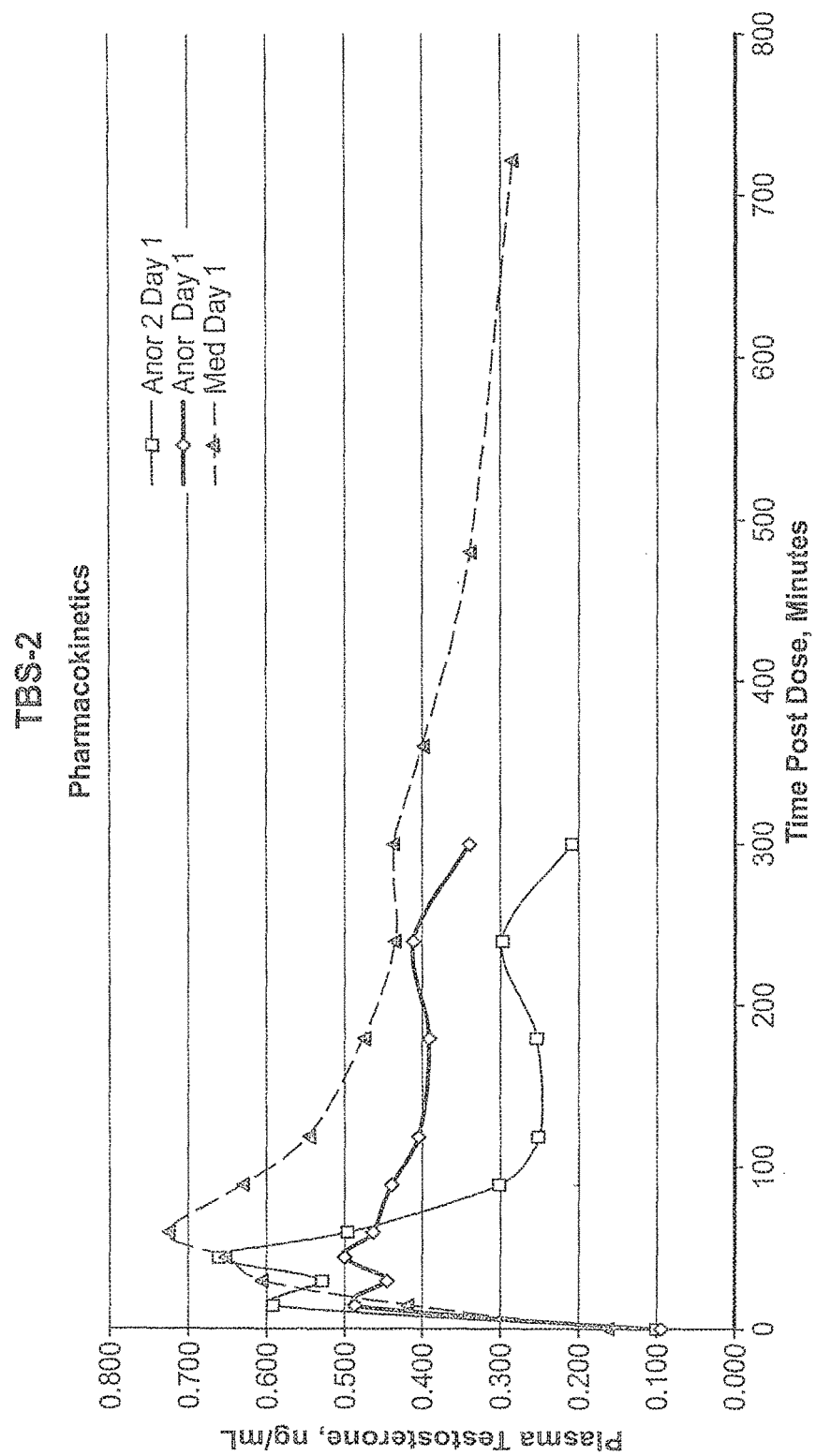
FIG. 8 shows the effects of a testosterone nasal gel formulation of the invention (0.45% day 3 (Med Day 1) and 0.6% day zero and Day 3 (ANOR) testosterone by weight of the gel formulation) after the first and the $5^{th}$ 12 hourly dose.
Figure 12:
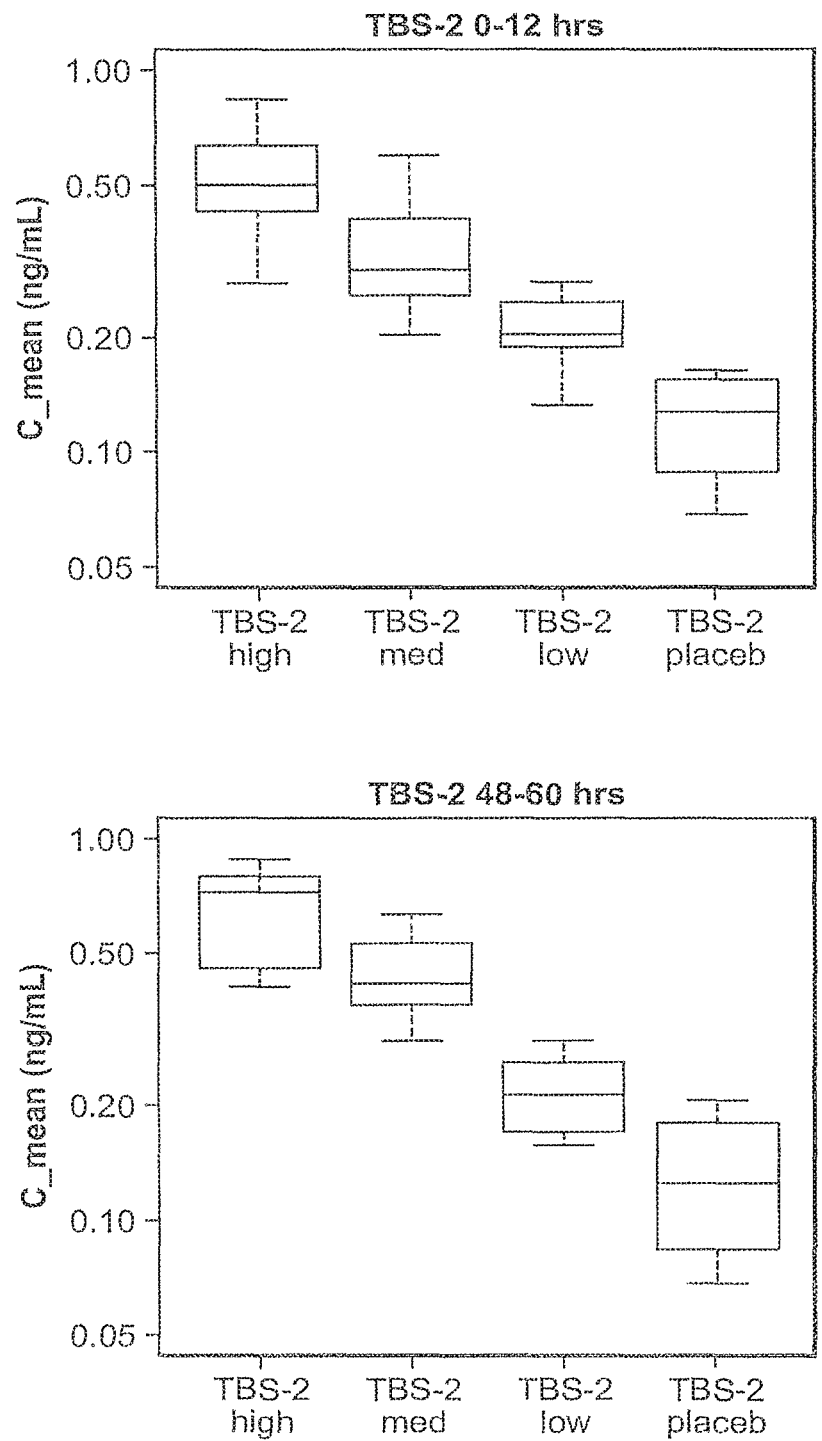
FIG. 12 presents distribution of testosterone mean concentration for TBS-2 treatments for the first (AUC_0-12) and the last dose (AUC_48-60). The boxplots show the median (thick solid line), the inter-quartile range (box) and the extreme values (whiskers). The horizontal solid grey line indicates the median C_mean during treatment with Intrinsa from 48 to 60 hrs, and the horizontal dotted lines indicate the minimum and maximum C_mean during treatment with Intrinsa from 48-60 hrs.

By way of illustrating and providing a more complete appreciation of the present invention and many of the attendant advantages thereof, the following detailed description and examples are given concerning the novel lower dosage strength intranasal testosterone gels, application devices and methods of the present invention.

I. Definitions

As used in the description of the invention and the appended claims, the singular forms "a", "an" and "the" are used interchangeably and intended to include the plural forms as well and fall within each meaning, unless the context clearly indicates otherwise. Also, as used herein, "and/or" refers to and encompasses any and all possible combinations of one or more of the listed items, as well as the lack of combinations when interpreted in the alternative ("or").

As used herein, "at least one" is intended to mean "one or more" of the listed elements.

Singular word forms are intended to include plural word forms and are likewise used herein interchangeably where appropriate and fall within each meaning, unless expressly stated otherwise.

Except where noted otherwise, capitalized and non-capitalized forms of all terms fall within each meaning.

Unless otherwise indicated, it is to be understood that all numbers expressing quantities, ratios, and numerical properties of ingredients, reaction conditions, and so forth used in the specification and claims are contemplated to be able to be modified in all instances by the term "about".

All parts, percentages, ratios, etc. herein are by weight unless indicated otherwise.

As used herein, "bioequivalence" or "bioequivalent", refers to nasally administered testosterone gel formulations or drug products which are pharmaceutically equivalent and their bioavailabilities (rate and extent of absorption) after administration in the same molar dosage or amount are similar to such a degree that their therapeutic effects, as to safety and efficacy, are essentially the same. In other words, bioequivalence or bioequivalent means the absence of a significant difference in the rate and extent to which testosterone becomes available from such formulations at the site of testosterone action when administered at the same molar dose under similar conditions, e.g., the rate at which testosterone can leave such a formulation and the rate at which testosterone can be absorbed and/or become available at the site of action to affect anorgasmia and/or HSDD. In other words, there is a high degree of similarity in the bioavailabilities of two testosterone gel formulation pharmaceutical products for nasal administration (of the same galenic form) from the same molar dose, that are unlikely to produce clinically relevant differences in therapeutic effects, or adverse reactions, or both. The terms "bioequivalence", as well as "pharmaceutical equivalence" and "therapeutic equivalence" are also used herein as defined and/or used by (a) the FDA, (b) the Code of Federal Regulations ("C.F.R."), Title 21, (c) Health Canada, (d) European Medicines Agency (EMEA), and/or (e) the Japanese Ministry of Health and Welfare. Thus, it should be understood that the present invention contemplates testosterone gel formulations for nasal administration or drug products that may be bioequivalent to other testosterone gel formulations for nasal administration or drug products of the present invention. By way of example, a first testosterone gel formulation for nasal administration or drug product is bioequivalent to a second testosterone gel formulation for nasal administration or drug product, in accordance with the present invention, when the measurement of at least one pharmacokinetic parameter(s), such as a Cmax, Tmax, AUC, etc., of the first testosterone gel formulation for nasal administration or drug product varies by no more than about ±25%, when compared to the measurement of the same pharmacokinetic parameter for the second testosterone gel formulation for nasal administration or drug product of the present invention.

As used herein, "bioavailability" or "bioavailable", means generally the rate and extent of absorption of testosterone into the systemic circulation and, more specifically, the rate or measurements intended to reflect the rate and extent to which testosterone becomes available at the site of action or is absorbed from a drug product and becomes available at the site of action. In other words, and by way of example, the extent and rate of testosterone absorption from a lower dosage strength gel formulation for nasal administration of the present invention as reflected by a time-concentration curve of testosterone in systemic circulation.

As used herein, the terms "pharmaceutical equivalence" or "pharmaceutically equivalent", refer to testosterone gel formulations for nasal administration or drug products of the present invention that contain the same amount of testosterone, in the same dosage forms, but not necessarily containing the same inactive ingredients, for the same route of administration and meeting the same or comparable compendial or other applicable standards of identity, strength, quality, and purity, including potency and, where applicable, content uniformity and/or stability. Thus, it should be understood that the present invention contemplates testosterone gel formulations for nasal administration or drug products that may be pharmaceutically equivalent to other testosterone gel formulations for nasal administration or drug products used in accordance with the present invention.

As used herein, "therapeutic equivalence" or "therapeutically equivalent", means those testosterone gel formulations for nasal administration or drug products which (a) will produce the same clinical effect and safety profile when utilizing testosterone drug product to treat anorgasmia or HSDD in accordance with the present invention and (b) are pharmaceutical equivalents, e.g., they contain testosterone in the same dosage form, they have the same route of administration; and they have the same testosterone strength. In other words, therapeutic equivalence means that a chemical equivalent of a lower dosage strength testosterone formulation of the present invention (i.e., containing the same amount of testosterone in the same dosage form when administered to the same individuals in the same dosage regimen) will provide essentially the same efficacy and toxicity.

As used herein a "testosterone gel formulation for nasal administration" means a formulation comprising testosterone in combination with a solvent, a wetting agent, and a viscosity increasing agent.

As used herein, "increases" as it refers to the plasma testosterone level, also means that the plasma testosterone level is 1, 2, 3, 4, 5, 10, 15, 20, 25, 30, 35, 40, 45, 50, 100, 500, 1000 or 10,000-fold or more greater in a subject that has been treated with a testosterone gel formulation for nasal administration of the invention as compared to the plasma testosterone level in the subject prior to treatment.

As used herein, "plasma testosterone level" means the level of testosterone in the plasma of a subject. The plasma testosterone level is determined by methods known in the art.

"Diagnosis" or "prognosis," as used herein, refers to the use of information (e.g., biological or chemical information from biological samples, signs and symptoms, physical exam findings, psychological exam findings, etc.) to anticipate the most likely outcomes, timeframes, and/or responses to a particular treatment for a given disease, disorder, or condition, based on comparisons with a plurality of individuals sharing symptoms, signs, family histories, or other data relevant to consideration of a patient's health status, or the confirmation of a subject's affliction, e.g., with anorgasmia and/or HSDD.

A "subject" according to some embodiments is an individual whose signs and symptoms, physical exams findings and/or psychological exam findings are to be determined and recorded in conjunction with the individual's condition (i.e., disease or disorder status) and/or response to a candidate drug or treatment.

"Subject," as used herein, is preferably, but not necessarily limited to, a human subject. The subject may be male or female, and is preferably female, and may be of any race or ethnicity, including, but not limited to, Caucasian, African-American, African, Asian, Hispanic, Indian, etc. Subject as used herein may also include an animal, particularly a mammal such as a canine, feline, bovine, caprine, equine, ovine, porcine, rodent (e.g., a rat and mouse), a lagomorph, a primate (including non-human primate), etc., that may be treated in accordance with the methods of the present invention or screened for veterinary medicine or pharmaceutical drug development purposes. A subject according to some embodiments of the present invention include a patient, human or otherwise, in need of therapeutic treatment for anorgasmia and/or HSDD.

"Treatment," as used herein, includes any drug, drug product, method, procedure, lifestyle change, or other adjustment introduced in attempt to effect a change in a particular aspect of a subject's health (i.e., directed to a particular disease, disorder, or condition).

"Drug" or "drug substance," as used herein, refers to an active ingredient, such as a chemical entity or biological entity, or combinations of chemical entities and/or biological entities, suitable to be administered to a subject to (a) treat anorgasmia and/or (b) treat HSDD. In accordance with the present invention, the drug or drug substance is testosterone or a pharmaceutically acceptable salt or ester thereof.

The term "drug product," as used herein, is synonymous with the terms "medicine," "medicament," "therapeutic intervention," or "pharmaceutical product." Most preferably, a drug product is approved by a government agency for use in accordance with the methods of the present invention. A drug product, in accordance with the present invention, is an intranasal gel formulated with a drug substance, i.e., testosterone.

"Disease," "disorder," and "condition" are commonly recognized in the art and designate the presence of signs and/or symptoms in an individual or patient that are generally recognized as abnormal and/or undesirable. Diseases or conditions may be diagnosed and categorized based on pathological changes. The disease or condition may be selected from the types of diseases listed in standard texts, such as Harrison's Principles of Internal Medicine, 1997, or Robbins Pathologic Basis of Disease, 1998.

As used herein, "diagnosing" or "identifying a patient or subject having anorgasmia or HSDD" refers to a process of determining if an individual is afflicted with anorgasmia or HSDD.

As used herein, "control subject" means a subject that has not been diagnosed with anorgasmia and/or HSDD and/or does not exhibit any detectable symptoms associated with these diseases. A "control subject" also means a subject that is not at risk of developing anorgasmia and/or HSDD, as defined herein.

II. Diseases

Anorgasmia

Anorgasmia is a type of sexual dysfunction in which a person cannot regularly achieve orgasm, even with adequate stimulation. In males the condition is often related to delayed ejaculation. Anorgasmia can often cause sexual frustration. Anorgasmia is far more common in females than in males and is especially rare in younger men. Anorgasmia is a very common occurrence in women, affecting 1 in 5 women worldwide.

The condition is sometimes classified as a psychiatric disorder. However, it can also be caused by medical problems such as diabetic neuropathy, multiple sclerosis, genital mutilation, complications from genital surgery, pelvic trauma (such as from a straddle injury caused by falling on the bars of a climbing frame, bicycle or gymnastics beam), hormonal imbalances, total hysterectomy, spinal cord injury, cauda equina syndrome, uterine embolisation, childbirth trauma (vaginal tearing through the use of forceps or suction or a large or unclosed episiotomy), vulvodynia and cardiovascular disease.

A comprehensive definition of female orgasm, as Meston et al. proposed, is as follows:

"[A] variable, transient peak sensation of intense pleasure creating an altered state of consciousness, usually accompanied by involuntary, rhythmic contractions of the pelvic striated circumvaginal musculature, often with concomitant uterine and anal contractions and myotonia that resolves the sexually-induced vasocongestion (sometimes only partially), usually with an induction of well-being and contentment."

The Diagnostic and Statistical Manual of Mental Disorders, 4th Edition, Text Revision (DSM-IV-TR) defines female orgasmic disorder (FOD, formerly inhibited female orgasm) as a persistent or recurrent delay in, or absence of, orgasm following a normal sexual excitement phase.

The type or intensity of stimulation that triggers female orgasm varies widely among women. Therefore, the diagnosis of female orgasmic disorder, according to the DSM-IV-TR, is based on these 3 criteria:

Criterion A: A clinician must judge that a woman's orgasmic capacity is less than what is reasonable for her age, sexual experience, and the adequacy of sexual stimulation she receives.

Criterion B: The disturbance must cause marked distress or interpersonal difficulty.

Criterion C: Another axis I disorder (except another sexual dysfunction) does not account for the orgasmic dysfunction better than female orgasmic disorder does, and the orgasmic dysfunction is not exclusively due to the direct physiologic effects of a substance (e.g., drug of abuse, medication) or a general medical condition.

In the DSM-IV-TR, female orgasmic disorder specifiers include the following:
Lifelong or acquired
Generalized or situational
Due to psychological or combined factors The presence of a normal sexual excitement phase is a prerequisite for female orgasmic disorder. In other words, if the absence of orgasm follows a time of decreased desire for sexual activity, an aversion to genital sexual contact, or a decreased lubrication-swelling response, diagnoses such as hypoactive sexual desire disorder, sexual aversion disorder, or female sexual arousal disorder, respectively, might be more appropriate, even if anorgasmia is the common final outcome.

A wide range of physical and psychological causes of anorgasmia have been identified.

They include the following:
A history of sexual abuse or rape
Boredom and monotony in sexual activity
Certain prescription drugs, including fluoxetine (Prozac), paroxetine (Paxil), and sertraline (Zoloft)
Hormonal disorders, hormonal changes due to menopause, and chronic illnesses that affect general health and sexual interest
Medical conditions that affect the nerve supply to the pelvis (such as multiple sclerosis, diabetic neuropathy, and spinal cord injury)
Negative attitudes toward sex (usually learned in childhood or adolescence)
Shyness or embarrassment about asking for whatever type of stimulation works best
Strife or lack of emotional closeness within the relationship Physical Causes A wide range of illnesses, physical changes and medications can interfere with orgasm:

Medical diseases. Any illness can affect this part of an individual's sexuality, including diabetes and neurological diseases, such as multiple sclerosis. Orgasm may also be affected by gynecologic surgeries, such as hysterectomy or cancer surgeries. In addition, lack of orgasm often goes hand in hand with other sexual problems, such as painful intercourse.

Medications. Many prescription and over-the-counter medications can interfere with orgasm. This includes blood pressure medications, antihistamines and antidepressants—particularly selective serotonin reuptake inhibitors (SSRIs). In men, SSRIs can actually result in both anorgasmia and inability to obtain an adequate erection for satisfactory sexual activity (erectile dysfunction).

Alcohol and drum. A glass of wine may make you feel amorous, but too much alcohol can cramp your ability to climax; the same is true of street drugs.

The aging process. As you age, normal changes in your anatomy, hormones, neurological system and circulatory system can affect your sexuality. The drop in estrogen that occurs during the transition to menopause can be a particularly notable foe of orgasm. Lower levels of this female hormone can decrease sensations in the clitoris, nipples and skin and impede blood flow to the vagina and clitoris, which can delay or stop orgasm entirely. Still, anorgasmia isn't limited to older women. And many women say sex becomes more satisfying with age.

Psychological Causes

Many psychological factors play a role in your ability to orgasm, including:
Mental health problems, such as anxiety or depression
Performance anxiety
Stress and financial pressures
Cultural and religious beliefs
Fear of pregnancy or sexually transmitted diseases
Embarrassment
Guilt about enjoying sexual experiences Relationship Issues Many couples who are experiencing problems outside of the bedroom will also experience problems in the bedroom. These overarching issues may include:
Lack of connection with your partner
Unresolved conflicts or fights
Poor communication of sexual needs and preferences
Infidelity or breach of trust A common cause of situational anorgasmia, in both men and women, is the use of anti-depressants, particularly selective serotonin reuptake inhibitors (SSRIs). Post-SSRI sexual dysfunction (PSSD) is a name given to a reported iatrogenic sexual dysfunction caused by the previous use of SSRI antidepressants. Though reporting of anorgasmia as a side effect of SSRIs is not precise, it is estimated that 15-50% of users of such medications are affected by this condition. The chemical amantadine has been shown to relieve SSRI-induced anorgasmia in some, but not all, people.

Another cause of anorgasmia is opiate addiction, particularly to heroin.

About 15% of women report difficulties with orgasm, and as many as 10% of women in the United States have never climaxed. Many women who orgasm regularly only climax about 50-70% of the time.

The major symptoms of anorgasmia are inability to experience orgasm or long delays in reaching orgasm. Different types of anorgasmia have been identified.

Primary Anorgasmia

Primary anorgasmia is a condition where one has never experienced an orgasm. This is significantly more common in women, although it can occur in men who lack the gladipudendal (bulbocavernosus) reflex.

Women with this condition can sometimes achieve a relatively low level of sexual excitement. Frustration, restlessness, and pelvic pain or a heavy pelvic sensation may occur because of vascular engorgement.

On occasion, there may be no obvious reason why orgasm is unobtainable. In such cases, women report that they are unable to orgasm even if they have a caring, skilled partner, adequate time and privacy, and an absence of medical issues which would affect sexual satisfaction. It should be noted that the attention and skill of one's partner are not inextricably linked to woman's internal, implicit comfort level. Thus, anorgasmia in a woman whose partner is adequately attentive and skilled should not be regarded as a clinical mystery.

Some social theorists believe that inability to orgasm may be related to residual psychosocial perceptions that female sexual desire is somehow 'wrong,' and that this stems from the age of Victorian repression. It is thought that this view may impede some women—perhaps those raised in a more repressed environment—from being able to experience natural and healthy sexual feeling. While such proposals may have a place in academic social theory, they have not been established scientifically. Therefore, an idea such as this may be a component of treatment as one consideration among many, but responsible clinical practice should not be guided, based on, or informed by it.

Primary male anorgasmia is more common among circumsized men than intact men. As many men age, they lose the ability to orgasm even if they still ejaculate. The pleasure of orgasm may diminish in older men.

Secondary Anorgasmia

Secondary anorgasmia is the loss of the ability to have orgasms. Particularly, you used to have orgasms, but now experience difficulty reaching climax. The cause may be alcoholism, depression, grief, pelvic surgery (such as total hysterectomy) or injuries, certain medications, illness, estrogen deprivation associated with menopause or an event that has violated the patient's sexual value system.

Secondary anorgasmia is close to 50% among males undergoing prostatectomy; 80% among radical prostatectomies. This is a serious adverse result because radical prostatectomies are usually given to younger males who are expected to live more than 10 years. At more advanced ages, the prostate is more unlikely to grow during that person's remaining lifetime. This is generally caused by damage to the primary nerves serving the penile area, which pass near the prostate gland. Removal of the prostate frequently damages or even completely removes these nerves, making sexual response unreasonably difficult.

Due to the existence of these nerves in the prostate, surgeons performing sex reassignment surgery on transsexual male to female patients avoid removing the prostate. This leaves the nerves that will then lead to the newly-formed clitoris, and decreases the chances that the patient will not respond to clitoral stimulation after surgery. Additionally, by leaving the prostate in the patient, the surgeon allows it to be situated close to the wall of the newly-formed vagina, which may potentially increase stimulation during vaginal intercourse after the procedure.

Situational Anorgasmia

People who are orgasmic in some situations may not be in others. This means that you are able to orgasm only during certain circumstances, such as during oral sex or masturbation. This is very common in women. In fact, about 80% of women experience orgasm from stimulation of the clitoris.

A person may have an orgasm from one type of stimulation but not from another, a person may achieve orgasm with one partner but not another, or have an orgasm only under certain conditions or only with a certain type or amount of foreplay. These common variations are within the range of normal sexual expression and should not be considered problematic.

Factors that may affect whether or not an individual is orgasmic, include fatigue, emotional concerns, feeling pressured to have sex when he or she is not interested, or a partner's sexual dysfunction. In the relatively common case of female situational anorgasmia during penile-vaginal intercourse, some sex therapists recommend that couples incorporate manual or vibrator stimulation during intercourse, or using the female-above position as it may allow for greater stimulation of the clitoris by the penis or pubic symphysis or both, and it allows the woman better control of movement.

General Anorgasmia

This means an individual cannot orgasm in any situation with any partner.

Random Anorgasmia

Some people are orgasmic but not in enough instances to satisfy their sense of what is appropriate or desirable.

Prevention

A healthy attitude toward sex, and education about sexual stimulation and response will minimize problems.

Couples who clearly communicate their sexual needs and desires, verbally or nonverbally, will experience orgasmic dysfunction less frequently.

It is also important to realize that sexual response is a complex coordination of the mind and the body, and both need to be functioning well for orgasms to happen.

Symptoms

The symptom of orgasmic dysfunction is being unable to reach orgasm, taking longer than you want to reach orgasm, or having only unsatisfying orgasms.

Signs and Tests

A complete medical history and physical examination needs to be done, but results are almost always normal. If the problem began after starting a medication, this should be discussed with the doctor who prescribed the drug. A qualified specialist in sex therapy may be helpful.

Treatment

Treatment can involve education, cognitive behavioral therapy, teaching orgasm by focusing on pleasurable stimulation, and directed masturbation.

Most women require clitoral stimulation to reach an orgasm. Incorporating this into sexual activity may be all that is necessary. If this doesn't solve the problem, then teaching the woman to masturbate may help her understand what she needs to become sexually excited.

A series of couple exercises to practice communication, more effective stimulation, and playfulness can help. If relationship difficulties play a role, treatment may include communication training and relationship enhancement work.

Medical problems, new medications, or untreated depression may need evaluation and treatment in order for orgasmic dysfunction to improve.

If other sexual dysfunctions (such as lack of interest and pain during intercourse) are happening at the same time, these need to be addressed as part of the treatment plan.

HSDD

Hypoactive sexual desire disorder (HSDD), is considered as a sexual dysfunction and is listed under the Sexual and Gender Identity Disorders of the DSM-IV. It was first included in the DSM-III under the name Inhibited Sexual Desire Disorder, but the name was changed in the DSM-III-R.

HSDD is characterized as a lack or absence of sexual fantasies and desire for sexual activity for some period of time. For this to be regarded as a disorder, it must cause marked distress or interpersonal difficulties and not be better accounted for by another mental disorder (i.e. depression), a drug (legal or illegal), or some other medical condition.

There are various subtypes. HSDD can be general (general lack of sexual desire) or situational (still has sexual desire, but lacks sexual desire for current partner), and it can be acquired (HSDD started after a period of normal sexual functioning) or life-long (the person has always had no/low sexual desire.)

In the early versions of the DSM, there were only two sexual dysfunctions listed: frigidity (for women) and impotence (for men).

In 1970, Masters and Johnson published their book Human Sexual Inadequacy describing sexual dysfunctions, though these included only dysfunctions dealing with the function of genitals such as premature ejaculation and impotence for men, and anorgasmia and vaginismus for women. Prior to Masters and Johnson's research, female orgasm was assumed to originate primarily from vaginal, rather than clitoral, stimulation. Consequently, feminists have argued that "frigidity" was "defined by men as the failure of women to have vaginal orgasms".

Following this book, sex therapy increased throughout the 1970s. Reports from sex-therapists about people with low sexual desire are reported from at least 1972, but labeling this as a specific disorder did not occur until 1977. In that year, sex therapists Helen Singer Kaplan and Harold Lief independently of each other proposed creating a specific category for people with low or no sexual desire. Lief named it "Inhibited Sexual Desire," and Kaplan named it "Hypoactive Sexual Desire." The primary motivation for this was that previous models for sex therapy assumed certain levels of sexual interest in one's partner and that problems were only caused by abnormal functioning/non-functioning of the genitals or performance anxiety but that therapies based on those problems were ineffective for people who did not sexually desire their partner. The following year, 1978, Lief and Kaplan together made a proposal to the APA's taskforce for sexual disorders for the DSM III, of which Kaplan and Lief were both members. The diagnosis of Inhibited Sexual Desire (ISD) was added to the DSM when the 3rd edition was published in 1980.

For understanding this diagnosis, it is important to recognize the social context in which it was created. In some cultures, low sexual desire may be considered normal and high sexual desire is problematic. In others, this may be reversed. Some cultures try hard to restrain sexual desire. Others try to excite it. Concepts of "normal" levels of sexual desire are culturally dependent and rarely value-neutral. In the 1970s, there were strong cultural messages that sex is good for you and "the more the better." Within this context, people who were habitually uninterested in sex, who in previous times may not have seen this as a problem, were more likely to feel that this was a situation that needed to be fixed. They may have felt alienated by dominant messages about sexuality and increasingly people went to sex-therapists complaining of low sexual desire. It was within this context that the diagnosis of ISD was created.

In the revision of the DSM-III, published in 1987 (DSM-III-R), ISD was subdivided into two categories: Hypoactive Sexual Desire Disorder and Sexual Aversion Disorder (SAD). The former is a lack of interest in sex and the latter is a phobic aversion to sex. In addition to this subdivision, one reason for the change is that the committee involved in revising the psychosexual disorders for the DMS-III-R thought that term "inhibited" suggests psychodynamic etiology (i.e. that the conditions for sexual desire are present, but the person is, for some reason, inhibiting their own sexual interest.) The term "hypoactive sexual desire" is more awkward, but more neutral with respect to the cause. The DSM-III-R estimated that about 20% of the population had HSDD. In the DSM-IV (1994), the criterion that the diagnosis requires "marked distress or interpersonal difficulty" was added.

Causes

Low sexual desire is not equivalent to HSDD because of the requirement that the low sexual desire causes marked distress and interpersonal difficulty and because of the requirement that the low desire is not better accounted for by another disorder in the DSM or by a general medical problem, so it is difficult to say exactly what causes HSDD. It is easier to describe, instead, what causes low sexual desire.

In men, there are theoretically more types of HSDD/low sexual desire, typically men are only diagnosed with one of three subtypes.

Lifelong/Generalized:

The man has little or no desire for sexual stimulation (with a partner or alone) and never has.

Acquired/Situational:

The man was previously sexually interested in his present partner but now lacks sexual interest in them but has desire for sexual stimulation (i.e. alone or with someone other than his present partner.)

Acquired/generalized:

The man previously had sexual interest in his present partner, but lacks interest in sexual activity, partnered or solitary.

Though it can sometimes be difficult to distinguish between these types, they do not necessarily have the same etiology. The cause of lifelong/generalized HSDD is unknown. In the case of acquired/generalized low sexual desire, possible causes include various medical/health problems, psychiatric problems, low levels of testosterone or high levels of prolactin. One theory suggests that sexual desire is controlled by a balance between inhibitory and excitatory factors. This is thought to be expressed via neurotransmitters in selective brain areas. A decrease in sexual desire may therefore be due to an imbalance between neurotransmitters with excitatory activity like dopamine and norepinephrine and neurotransmitters with inhibitory activity, like serotonin. Low sexual desire can also be a side effect of various medications. In the case of acquired/situational HSDD, possible causes include intimacy difficulty, relationship problems, sexual addiction, and chronic illness of the man's partner. The evidence for these is somewhat in question. Some claimed causes of low sexual desire are based on empirical evidence. However, some are based merely on clinical observation. In many cases, the cause of HSDD is simply unknown.

There are some factors that are believed to be possible causes of HSDD in women. As with men, various medical problems, psychiatric problems (such as mood disorders), or increased amounts of prolactin can cause HSDD. Other hormones are believed to be involved as well. Additionally, factors such as relationship problems or stress are believed to be possible causes of reduced sexual desire in women.

III. Testosterone

The steroid hormone testosterone is the active ingredient in the testosterone gel formulations of the invention. The manufacture of the drug substance presents no potential risk for humans; the synthesis route is well-characterized.

TABLE 1

| Nomenclature Testosterone | |
|---|---|
| INN name | Testosterone |
| Compendial name | Testosterone |
| Chemical name | 17β-Hydroxyandrost-4-en-3-one |
| Other non-proprietary names | Androst-4-en-3-one, 17-hydroxy-, (17β)-<br>Trans-testosterone<br>Δ4-androsten-17β-ol-3-one |
| CAS registry number | 58-22-0 |
| Proquina code | 8139 |

Structural Formula

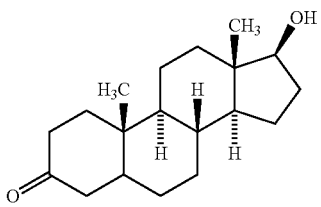

C₁₉H₂₈O₂            Molecular Formula

Relative Molecular Mass
288.4

The physical chemical properties of testosterone are listed in Table 2.

TABLE 2

General Properties of Testosterone

| | |
|---|---|
| Appearance | White or slightly creamy white crystals or crystalline powder. It is odourless, and stable in air. |
| Solubility | Practically insoluble in water (0.024 g/L), freely soluble in dehydrated alcohol, chloroform and in methylene chloride, soluble in dioxane and in vegetable oils; slightly soluble in ether. |
| Melting range | 153° C. to 157° C. |
| Specific rotation | +101° to +105° (dioxane) |
| Loss on drying | Not more than 1.0% |
| UV max | 238 nm |
| Storage | Protected from light |

Testosterone, for testosterone gel formulations of the invention, appears as white or slightly creamy white crystals or crystalline powder. It is freely soluble in methanol and ethanol, soluble in acetone and isopropanol and insoluble in n-heptane. It can also be considered as insoluble in water ($S_{20° C.}$=2.41×10⁻² g/L±0.04×10⁻² g/L); its n-Octanol/Water partition coefficient (log $P_{OW}$ determined by HPLC) is 2.84. The solubility of testosterone in oils was determined to be 0.8% in isopropylmyristate, 0.5% in peanut oil, 0.6% in soybean oil, 0.5% in corn oil, 0.7% in cottonseed oil and up to 4% in castor oil.

Because testosterone is fully dissolved within the formulations of the present invention, physical characteristics of the drug substance do not influence the performance of the drug product, testosterone gel formulations of the invention. The manufacturability of testosterone gel formulations of the invention, however is influenced by the particle size of testosterone. When using a particle size of 50%≤25 microns, 90%≤50 microns the solubility of the drug substance in the matrix is especially favorable.

In accordance with the present invention, the testosterone drug can be in, for instance, crystalline, amorphous, micronized, non-micronized, powder, small particle or large particle form when formulating to intranasal testosterone gels of the present invention. An Exemplary range of testosterone particle sizes include from about 0.5 microns to about 200 microns. Preferably, the testosterone particle size is in a range of from about 5 microns to about 100 microns, and the testosterone is in crystalline or amorphous and non-micronized or micronized form. Preferably, the testosterone is in crystalline or amorphous micronized form.

The molecular structure of testosterone contains no functional groups that can be protonated or deprotonated in the physiological pH-range. Therefore testosterone is to be considered as a neutral molecule with no pKa value in the range 1-14. Because it is neutral, testosterone is compatible with excipients.

Drug Product

The testosterone gel formulations of the invention are viscous and thixotropic, oil-based formulations containing a solution of testosterone intended for intranasal application. The non-irritating formulation is designed to adhere to the inner nose. In addition, it acts as a controlling matrix, thus allowing sustained drug delivery through the nasal mucosa.

Other pharmacologically inactive ingredients in the testosterone intranasal gel are castor oil USP, oleoyl macrogolglycerides EP and colloidal silicon dioxide NF. None of these excipients are of human or animal origin. All excipients are well-known and listed in the "Inactive Ingredient" list for Approved Drug Products issued by the FDA.

According to the "Handbook of Pharmaceutical Additives" oleoyl polyoxylglycerides are used as hydrophilic oil for topicals, injectables and nasals. In FDA-approved medicinal products it is used as co-emulsifier in topical emulsions/lotions/creams and in vaginal emulsions/creams. In France this excipient is approved for nasal preparations such as "Rhino-Sulforgan" (Laboratoire Jolly-Jatel, France; containing 10% oleoyl polyoxylglycerides) and "Huile Gomenolee 2% ("Laboratoire Goménol, France; containing 10% oleoyl polyoxylglycerides). Hence, like for castor oil it can be deduced that oleoyl polyoxylglycerides is suitable for an application route where safety and tolerability are of highest importance (e.g. injectables and nasal or vaginal preparations).

Oleoyl macrogolglycerides are also referred to as Labrafil M 1944 CS, apricot kernel oil PEG-6 esters, Peglicol-5-oleate, mixture of glycerides and polyethylene esters. The castor oil, which is used as a solvent for testosterone gel formulations of the invention is a fixed oil. Such oils have the advantage of being non-volatile or spreading (in contrast to essential oils or liquid paraffin), but have the disadvantage of being hydrophobic. The nasal mucosa contains 95-97% water. Without the oleoyl macrogol-glycerides, the castor oil containing the active ingredient would form a non-interactive layer on the mucous membrane. In order to achieve adequate contact between the castor oil layer and the mucous membrane, the hydrophilic oleoyl macrogol-glycerides oil is added to the formulation to form an emulsion between the castor oil and the mucosa fluid.

Oleoyl macrogol-glycerides are used in semi-solids at concentrations ranging from about 3 to 20%, depending on the application. The amount of oleoyl macrogol-glycerides in testosterone gel formulations of the invention is high enough to allow for a better contact of the carrier oil with the mucous membrane and low enough to have minimal impact on the amount of testosterone that can be incorporated into the carrier oil. A favourable concentration of oleoyl microgol-glycerides in testosterone gel formulations of the invention is found to be 4% of the formulation.

According to the "Handbook of Pharmaceutical Additives" colloidal silicon dioxide is used as an oil adsorbent, thermal stabilizer and gellant. In FDA-approved medicinal products it is used in dental gels, sublingual tablets, endocervical gel, suppositories, vaginal emulsions/creams/tablets/tampons and capsules for inhalation. Furthermore, it is used as an excipient in "Testoderm with adhesives" (Alza Corporation, approved in 1996) a testosterone transdermal patch. Hence, it can be deduced that colloidal silicon dioxide is suitable for an application route where safety and tolerability are of highest importance (e.g. inhalations, endocervical, vaginal or rectal preparations).

For clinical trial supplies, testosterone intranasal gel is supplied in unit-dose syringes consisting of a syringe body made from polypropylene, a plunger molded from polyethylene and a syringe cap made from high density polyethylene. The syringes are wrapped in aluminum foil as secondary packaging. The content of a syringe (125 mg) amounts to 0.10 to 1.5 mg of testosterone.

The oil in testosterone gel formulations of the invention is thickened with colloidal silicon dioxide, which acts as a gel-forming agent. This compound is used commonly for stiffening oleogels.

The intended dosage form for testosterone gel formulations of the invention is a semi-solid, not a liquid. The formulation is thickened with colloidal silicon dioxide. It is believed that colloidal silicon dioxide contributes to the thixotropic properties of the gel, simplifying drug delivery to the nostril.

Colloidal silicon dioxide is generally an inert material which is well tolerated as an excipient in mucosal applications such as suppositories. Colloidal silicon dioxide is typically used in these preparations at concentrations ranging from about 0.5 to 10%. The concentration of colloidal silicon dioxide in testosterone gel formulations of the invention is high enough to achieve gel formation but at a level that has minimal impact on testosterone incorporation into the carrier oil.

Preferably, the intranasal testosterone gels of the present invention have in general, a viscosity in the range of between about 3,000 cps and about 27,000 cps. It should nevertheless be understood by those versed in this art that, while the above-mentioned viscosity range is believed to be a preferred viscosity range, any suitable viscosities or viscosity ranges that do not defeat the objectives of the present invention are contemplated.

A detailed description of batches of a testosterone gel formulation of the invention is shown in Table 3.

TABLE 3

Composition of a testosterone gel formulation of the invention

| Component | Amount (% w/w) 0.15% | Amount (% w/w) 0.24% | Amount (% w/w) 0.45% | Amount (% w/w) 0.48% | Amount (% w/w) 0.60% | Amount (% w/w) 0.72% |
|---|---|---|---|---|---|---|
| Testosterone | 0.15% | 0.15% | 0.45% | 0.48% | 0.60% | 0.72% |
| Castor oil | 91.85% | 91.76% | 91.55% | 91.52% | 91.4% | 91.28% |
| Oleoyl macrogol-glycerides | 4.0% | 4.0% | 4.0% | 4.0% | 4.0% | 4.0% |
| Colloidal silicon dioxide | 4.0% | 4.0% | 4.0% | 4.0% | 4.0% | 4.0% |

The testosterone gel formulations of the invention are stored at room temperature (20-25° C. or 68 to 77° F.). See also Example 11. Temperature excursions from 15 to 30° C. or 59 to 86° F. are permissible for the testosterone gel formulations of the inventions. The stability data available to date are conclusive to support a 24-month shelf life. Unit dose syringes are chosen for the primary packaging of the clinical materials for this clinical trial to allow for ease of dosing, ability to generate multiple doses by varying the fill volume and consistency of dose delivered. The syringe consists of a syringe body, a plunger and a syringe cap. The syringes body is molded from polypropylene, the plunger is molded from polyethylene and the cap is HDPE. These syringes are designed and manufactured to deliver sterile and non-sterile solutions, liquids and gels at low volumes. For additional protection from the environment (i.e., exposure to dirt, light, humidity and oxygen), the syringes are packed in a foil-laminate overwrap pouch.

Figure 39:
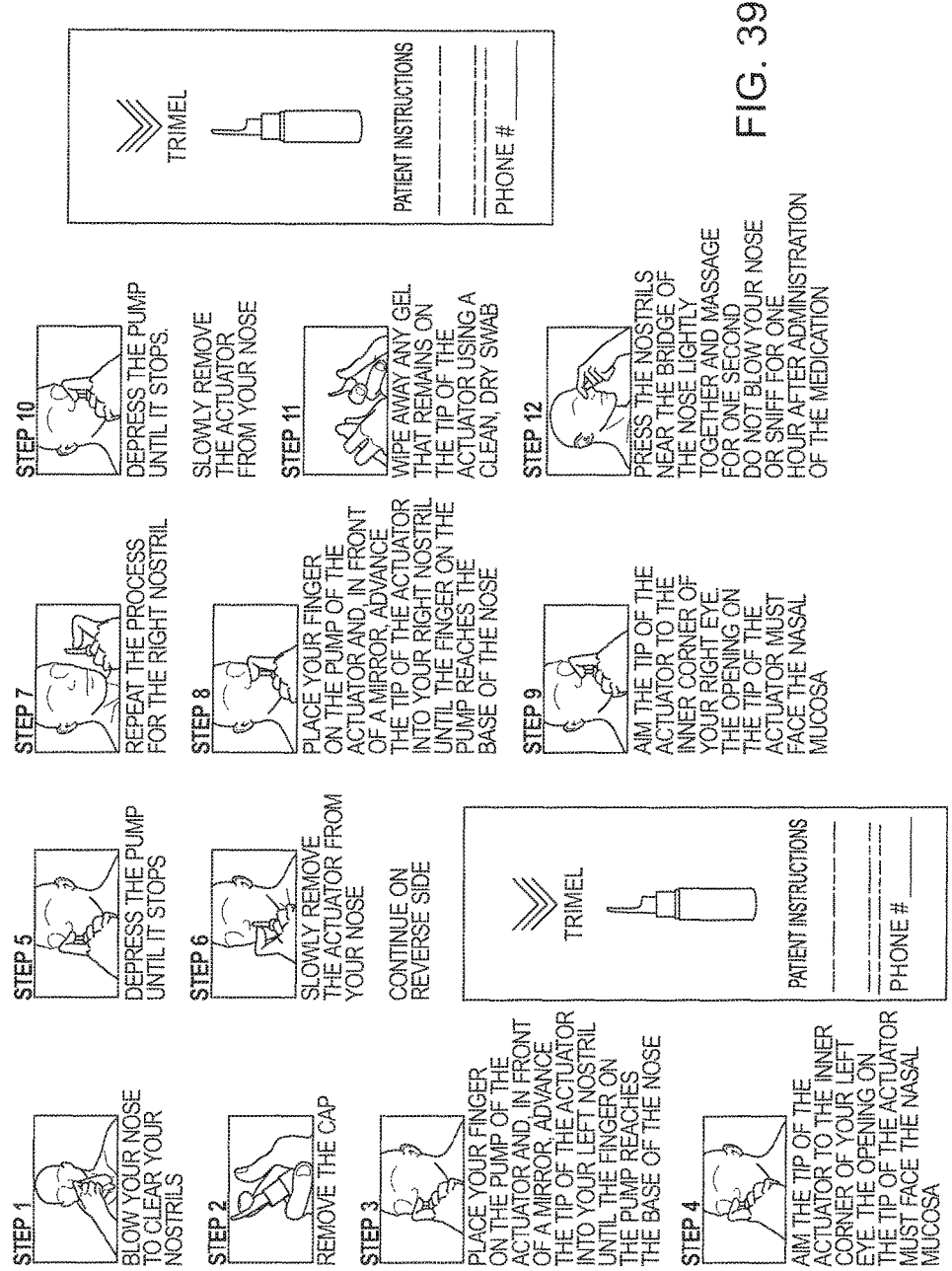
FIG. 39 depicts an intranasal applicator contemplated by and used in accordance with the present invention.

The syringes and caps are designed for use in a clinical setting and meet the requirements of the EU Medical Devices Directive 93/42/EEC of Jun. 14, 1993 and as amended. As this container closure is only intended for use in this portion of the clinical program, no additional studies are performed on the syringe and syringe components. See also Example 11 and FIG. 39.

For a further element of protection, two syringes are contained in secondary packaging consisting of an aluminium foil pouch. Two syringes are packaged in the aluminium foil pouch and each pouch is sealed.

The pouch consists of a flexible, 3-layered-foil-laminate of a) polyester 12 micron, b) aluminum 12 micron and c) a polyethylene 75 micron. It is manufactured by Floeter Flexibles GmbH, and supplied under the name "CLIMA-PAC II 12-12-75".

Intrinsa®

Procter & Gamble developed a transdermal therapeutic system containing testosterone as active substance for the treatment of HSDD (SD Intrinsa®). Four controlled clinical studies were performed (2 in Phase II b, 2 in Phase III). The 300 µg testosterone transdermal system is effective in the treatment of HSDD in surgically menopausal women on concomitant estrogen therapy. The women who received testosterone experienced increased frequency of satisfying sexual activity, increased sexual desire, and decreased distress compared with women who received placebo. Improvements were also seen in all other efficacy endpoints (i.e., arousal, pleasure, orgasm, responsiveness, self-image, concerns). The testosterone serum levels were increased to the physiological range of premenopausal women, but did not exceed this range.

Overall, treatment benefits were seen as early as 4 weeks with maximal effects in total satisfying episodes and sexual desire seen by approximately 12 weeks. Beneficial effects were maintained for the remainder of the 24-week efficacy period. At week 24, trial results showed that Intrinsa® significantly increased the frequency of total satisfying episodes compared to placebo ($p<0.05$) and also experienced a significantly greater increase in sexual desire domain of PSFS (profile of female sexual function) and a significantly greater decrease in personal distress ($p<0.05$) in patients on placebo. Intrinsa® is approved for the treatment of HSDD in bilaterally oophorectomised and hysterectomised women receiving concomitant estrogen therapy in the European Union.

Libigel®

Biosante developed a testosterone gel designed to be quickly absorbed through the skin after a once-daily application on the upper arm, delivering testosterone to the bloodstream evenly over time for the treatment of HSDD. One Phase II study has been performed and 2 Phase III studies are ongoing.

The Phase II trial results showed LibiGel significantly increased the number of satisfying sexual events by 238% versus baseline ($p<0.0001$); this increase also was significant versus placebo ($p<0.05$). In this study, the effective dose of LibiGel produced testosterone blood levels within the normal range for pre-menopausal women and had a safety profile similar to that observed in the placebo group. In addition, no serious adverse events and no discontinuations due to adverse events occurred in any subject receiving LibiGel.

IV. Dosages and Modes of Administration

The invention provides for gel formulations of testosterone to be administered intranasally, wherein the dosage of the formulation is from about 0.15% testosterone by weight of said gel formulation to about 0.6% testosterone by weight of said gel formulation, for example, 0.15% testosterone by weight of the gel formulation, 0.45% testosterone by weight of said gel formulation and 0.6% by weight of the gel formulation.

V. Uses

The methods of the invention are used to treat anorgasmia and/or HSDD in a diagnosed with one or both of these conditions. The invention also provides for intranasal testosterone gel formulations that can be used to treat anorgasmia or HSDD in a patient diagnosed with one or both of these conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Having now generally described the invention, the same will be more readily understood through reference to the following Examples which are provided by way of illustration, and are not intended to be limiting of the present invention, unless specified.

The following examples are put forth for illustrative purposes only and are not intended to limit the scope of what the inventors regard as their invention.

Example 1

Description and Composition of Testosterone Gel Formulations of the Invention

The compositions of three different concentrations of the drug product to be administered in this clinical trial are provided in the tables below.

Description of Dosage Form

The testosterone gel formulations of the invention are viscous and thixotropic, oil-based formulations containing solubilized testosterone intended for intranasal application. The drug product is formulated with the compendial inactive ingredients: castor oil, oleoyl polyoxyl-glycerides and colloidal silicon dioxide.

Three different doses of the testosterone gel formulations of the invention are intranasally administered: 0.15% w/w, 0.45% w/w and 0.6% w/w. An overage is added to each syringe to account for the gel that is retained in the syringe after dosing. This overage remains consistent at 23 µl, regardless of volume of gel in the syringe.

Lower Dosage Strength Intranasal Testosterone Compositions

TABLE 4

Components, Quantity, Quality Standards and Function - 0.15% testosterone gel formulation of the invention

| Component | Amount (% w/w) | Amount per Syringe (mg) | Amount Delivered per Dose (mg) | Function | Quality Standard |
|---|---|---|---|---|---|
| Testosterone | 0.15% | 0.18 | 0.15 | Active ingredient | USP |
| Castor oil | 91.85% | 112.98 | 91.85 | Solvent | USP |
| Oleoyl polyoxylglycerides | 4.0% | 4.92 | 4.0 | Wetting agent (hydrophilic oil) | Ph. Eur./NF |
| Colloidal silicon dioxide | 4.0% | 4.92 | 4.0 | Viscosity increasing agent | NF |
| Total | 100% | 123 mg | 100 mg | | |

TABLE 5

Components, Quantity, Quality Standards and Function - 0.45% testosterone gel formulation of the invention

| Component | Amount (% w/w) | Amount per Syringe (mg) | Amount Delivered per Dose (mg) | Function | Quality Standard |
|---|---|---|---|---|---|
| Testosterone | 0.45% | 0.55 | 0.45 | Active ingredient | USP |

TABLE 5-continued

Components, Quantity, Quality Standards and Function - 0.45% testosterone gel formulation of the invention

| Component | Amount (% w/w) | Amount per Syringe (mg) | Amount Delivered per Dose (mg) | Function | Quality Standard |
|---|---|---|---|---|---|
| Castor oil | 91.55% | 112.61 | 91.55 | Solvent | USP |
| Oleoyl polyoxylglycerides | 4.0% | 4.92 | 4.0 | Wetting agent (hydrophilic oil) | Ph. Eur./NF |
| Colloidal silicon dioxide | 4.0% | 4.92 | 4.0 | Viscosity increasing agent | NF |
| Total | 100% | 123 mg | 100 mg | | |

TABLE 6

Components, Quantity, Quality Standards and Function - 0.6% testosterone gel formulation of the invention

| Component | Amount (% w/w) | Amount per Syringe (mg) | Amount Delivered per Dose (mg) | Function | Quality Standard |
|---|---|---|---|---|---|
| Testosterone | 0.6% | 0.74 | 0.6 | Active ingredient | USP |
| Castor oil | 91.4% | 112.42 | 91.4 | Solvent | USP |
| Oleoyl polyoxylglycerides | 4.0% | 4.92 | 4.0 | Wetting agent (hydrophilic oil) | Ph. Eur/NF. |
| Colloidal silicon dioxide | 4.0% | 4.92 | 4.0 | Viscosity increasing agent | NF |
| Total | 100% | 123 mg | 100 mg | | |

Container

Testosterone gel formulations of the invention are supplied in unit-dose polypropylene syringes. Two syringes of each dosage are packaged in a protective aluminium foil pouch.

Example 2

Intranasal Testosterone Gel Formulations

The testosterone gel formulations of the invention, are formulations of testosterone in an intranasal gel proposed for assessing the pharmacokinetic and pharmacodynamics of three different doses of testosterone gel formulations of the invention, compared to Intrinsa® and placebo for testosterone gel formulations of the invention in women with hypoactive sexual desire disorder (HSDD) and secondary anorgasmia (SA).

The active ingredient, testosterone, is sourced from Bayer Schering. Challenges for nasal delivery include:
- requirements for larger particles than pulmonary administration (i.e., only particles >10 μm are sufficiently heavy to avoid entering the respiratory tract);
- concentrations must be higher due to the smaller volumes that can be administered;
- rapid clearance of the therapeutic agent from the site of deposition results in a shorter time available for absorption;
- potential for local tissue irritation; and
- limited formulation manipulation possibilities to alter drug delivery profiles.

Testosterone is indicated for the treatment of HSDD in bilaterally oophorectomised and hysterectomised (surgically induced menopausal) women receiving concomitant estrogen therapy. It is also indicated for the treatment of hormone replacement therapy in the treatment of hypogonadism in men. The currently available options for administration of testosterone are oral, buccal, injectable, implantable and transdermal.

An intranasal testosterone (3.2%) gel, TBS-1 gel, is developed for the treatment of hypogonadism in men and has been administered to hypogonadal men in several clinical trials (Mattern, C. et al., 2008 The Aging Male 11(4): 171-178 (December 2008), which is incorporated herein by reference in its entirety). The intranasal testosterone gel for women, testosterone gel formulations of the present invention, are developed at concentrations ranging from about 0.15% to about 0.6% testosterone.

Example 3

Overages

Testosterone Gel Formulations of the Invention

No overage is added to the formulation. An overage is added to each syringe to account for the gel that is retained in the syringe after dosing. This overage remains consistent at 23 μl, regardless of volume of gel in the syringe. The theoretical fill and dispensed amounts for testosterone gel formulations of the invention are provided below.

| Syringe Dosage | Theoretical Fill Volume (μl) | Theoretical Dispensed Volume (μl) |
|---|---|---|
| 0.15% Testosterone Gel formulation of the Invention | 123 | 100 |
| 0.45% Testosterone Gel formulation of the Invention | 123 | 100 |
| 0.6% Testosterone Gel formulation of the Invention | 123 | 100 |

Example 4

Physicochemical and Biological Properties [Testosterone Gel Formulations of the Invention]

The testosterone gel formulations of the invention has a viscosity in the range of 3,000 to 10,000 mPa×sec. The viscosity is important because it facilitates maintenance of the gel in the nasal cavity in contact with the nasal mucosa. When the viscosity is less than approximately 3,000 mPa×sec (i.e., 3,000 centipoise), the gel tends to be drawn by gravity out of the nasal cavity.

Example 5

Batch Formula [Testosterone Gel Formulations of the Invention]

Three different concentrations of testosterone gel formulations of the invention, 0.15%, 0.45% and 0.6%, are manufactured for the proposed clinical trial. The batch formulae for these batches are presented in Table 5 below.

TABLE 5

Batch Formulae for 0.15%, 0.45% and 0.6% testosterone gel formulations of the invention at the 8 kg Batch Size

| | Quantity per Batch (g) | | |
|---|---|---|---|
| Components | 0.15% | 0.45% | 0.6% |
| Testosterone, USP | 12 | 36 | 48 |
| Castor oil, USP | 7348 | 7324 | 7312 |
| Oleoyl polyoxylglycerides, Ph. Eur./NF | 320 | 320 | 320 |
| Colloidal silicon dioxide, NF | 320 | 320 | 320 |

Figure 40:
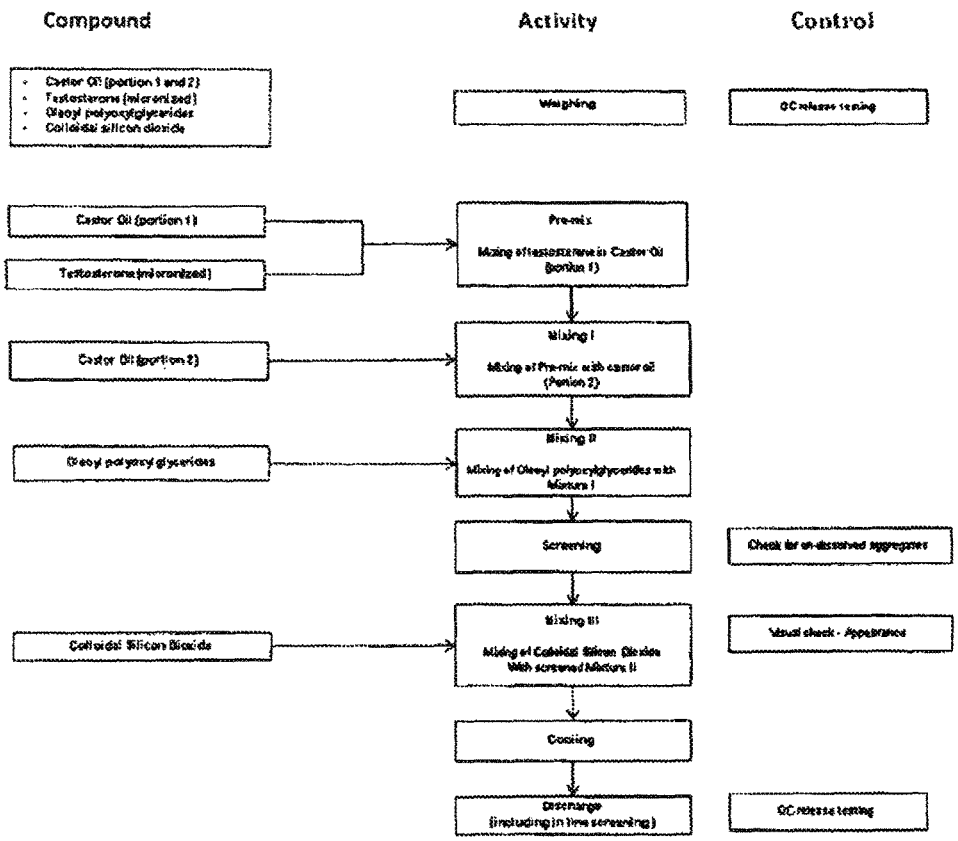
FIG. 40 is a schematic diagram of a manufacturing process in accordance with one embodiment of the invention.

As seen in FIG. 40, the PreMix prepared by mixing, with a propeller mixer, the full amount of Testosterone with portion 1 of the castor oil for 10 minutes.

Mixture I is prepared by adding the Pre-Mix to the remaining castor oil and mixing for 60 minutes. The product temperature is maintained below 50° C. for the entire mixing process.

The oleoyl polyoxylglycerides are pre-heated to 40-50° C. and mixed for 10 minutes before being added to Mixture I. This is identified as Mixture II. It is mixed for 45 minutes while maintaining product temperature below 50° C. Mixture II is then screened through a sieve to remove any un-dissolved Testosterone aggregates.

Mixture III is prepared by adding the colloidal silicon dioxide to Mixture II and mixing for 15 minutes while maintaining product temperature below 50° C. A visual check is conducted after this step, to ensure that the gel is clear.

At the completion of mixing the gel is stirred and cooled to a product temperature below 30° C. The product is then discharged into stainless steel drums and the bulk gel sample is taken for analytical testing.

Filling and Packaging—Clinical Supplies

After release of the final gel mixture by the quality control laboratory, the filling and packaging process is carried out by filling a pre-determined volume into the syringe followed by the application of the syringe cap. Two syringes are packaged into a foil pouch.

The syringes are filled using a pipette with the gel taken from a holding tank. The tip of the pipette is discarded after the syringe is filled and the syringe cap is applied. Each syringe is individually labelled.

Following the application of the label, two syringes are packaged in a pre-formed foil pouch and the pouch is sealed. Each pouch is labeled.

Example 7

Evaluation of Testosterone Gel Formulations of the Invention in Women with Anorgasmia The pharmacokinetics and pharmacodynamic efficacy of testosterone gel formulations of the invention are evaluated in studies of women with anorgasmia. The effect of testosterone gel formulations of the invention on sexual stimuli in women with anorgasmia is also determined.

Patient Population

Otherwise healthy females, aged 18 to 65 years, presenting with anorgasmia are evaluated. Sixteen (16) subjects are recruited.

Dosing

Three doses of testosterone gel formulations of the invention are investigated: 150 μg, 450 μg and 600 μg per nostril. A total of 5 doses of a testosterone gel formulation of the invention is administered BID intranasally to women. Placebo testosterone gel formulation of the invention is administered as a control.

Treatment Duration

Test subjects receive 5 doses of a testosterone gel formulation of the invention over a three day period.

Endpoints

Primary End-Point

The plasma concentrations of total testosterone and dihydrotestosterone are measured using validated LC/MS/MS. The following pharmacokinetic parameters are determined for all subjects:

Cmin, Cmax, tmax, PTF and PTS are determined, for each dosing interval $AUC_{0-\tau}$, and Cavg, are calculated for each dosing interval.

The percentage of time within, below, and above the physiological reference range for plasma testosterone and dihydrotestosterone.

Secondary End-Points:

Efficacy is determined by a battery of computer and psychophysiological tests.

Safety is monitored according to the following parameters:

Complete blood counts at Baseline and the Close-Out Visit.

Clinical chemistry and urinalysis testing at Baseline and Close-Out assesses selected endocrine parameters, renal function, liver function, skeletal/heart muscle damage, lipid abnormalities, and changes in calcium homeostasis.

Measurement of plasma testosterone, dihydrotestosterone and various hormones at Baseline, study days and Close-Out.

Adverse Events.

Randomization

Subjects in the ANOR cohort are randomized to receive either a testosterone gel formulation of the invention (3 dose levels) or placebo. Randomization is according to the design allocation below.

| ANOR Cohort (Pre- and Post-menopausal) | Testosterone Gel Formulation of the invention LD BID | Testosterone Gel Formulation of the invention MD BID | Testosterone Gel Formulation of the invention HD BID | Placebo BID |
|---|---|---|---|---|

LD (0.15%)—low dose;
MD (0.45%)—mid dose;
HD (0.6%)—high dose

Blinding

The analysis is both a double-blind and open label study, depending on the treatment cohort. For subjects in the ANOR group, the study is placebo-controlled and double-blinded.

Dosage and Dosage Regimen

All subjects are administered a testosterone gel formulation of the invention (0.15%, 0.45% or 0.6%) or testosterone gel formulation of the invention placebo on five (5) occasions during the study: Day 1 at 2000 hours, Day 2 at 800 and 2000 hours, and Day 3 at 800 and 2000 hours. The intranasal gel is administered to both nostrils (1 syringe (100 µl volume) per nostril).

Package and Labelling

Study medication consists of a testosterone gel formulation of the invention and placebo gel and is packed in single use syringes designed to expel 100 µl of gel. Two syringes are packaged in a foil pouch.

Treatment Schedule

Subjects are randomized into the dosing regimen that is administered during a four day (three night) in-patient treatment period and receive either an intranasal testosterone gel formulation of the invention (3 dose levels) or placebo (ANOR) according to the design allocation:

| ANOR Cohort | Testosterone Gel Formulation of the invention LD BID | Testosterone Gel Formulation of the invention MD BID | Testosterone Gel Formulation of the invention HD BID | Placebo BID |
|---|---|---|---|---|

The randomization scheme is created for each study center and will consist of blocks of four treatments per cohort.

The study is a four day study. The study starts with Study Drug dosing between 2000 and 2100 hours on Day 1 (Baseline). Blood samples for plasma testosterone and dihydrotestosterone profiles are drawn at −60, 0, 15, 30, 45, 60, 90, 120, 180, 240, 300, 360 and 480 minutes following the evening dose on Days 1 and 3 and at 0 and 60 minutes post administration following the morning/evening doses on Day 2 and morning dose on Day 3.

For subjects allocated to the three testosterone gel formulation of the invention arms or the placebo gel, PD testing takes place on Day 2, 30 minutes and 4.5 hours after the morning dose (psychophysiological testing) and Day 3, 30 minutes after the morning dose (computer testing). Subjects undergo a practice psychophysiological session before the first dosing.

Because subjects are expected to not sleep well during their first overnight stay with repeated nightly blood draws, the order of psychophysiological testing and computer testing is not counterbalanced. Computer testing is expected to be more negatively affected by sleep deprivation than psychophysiological testing. Therefore, on Day 2 psychophysiological testing takes place, and computer testing occurs on Day 3.

Adverse events are assessed and reported.

Patient Selection and Withdrawal

The subjects in this study are women with ANOR. Subjects are recruited from the medical practice or the general population through advertisements in local newspapers with additional information available on a website. Before scheduling the screening visit, subjects are asked a series of standardized questions by telephone to assess whether they are likely to be suitable for the study.

Inclusion Criteria

Women aged 18-65 years.

Diagnosis of Female Orgasmic Disorder (Anorgasmia) according to the DSM-IV criteria. The current episode must be at least 24 weeks in duration by the Screening Visit. Subtype should be generalized and not due to etiological factors that would prohibit treatment response (e.g., depression, alcoholism, surgery, injury). HSDD as a co-morbid disorder is allowed only if it began after the anorgasmia.

BMI≤35.

Women must have a score of >11 on the FSDS-R at the Screen Visit together with a score of <26.55 on the FSFI.

Women in a steady relationship of at least 12 months or single women who use masturbation as the primary way to attempt to reach orgasm.

Pre- and post-menopausal women—for physiological and surgical post-menopausal women—estrogen/progestagen substitution (low dose combined ET/P) for at least three (3) months before study entry or post-menopausal women naïve to ET/P substitution.

Premenopausal heterosexual women will need to be on a reliable birth control method (i.e., OCPs or partner must use condoms).

Normal thyroid function, physiological prolactin concentration.

Normal otorhinolaryngologic examination.

Provide written informed consent.

Exclusion Criteria

History of any other clinically relevant psychiatric disorders that could impact sexual function, risks patient's safety, or may impact compliance are as assessed. This includes bipolar disorders, psychotic disorders, severe anxiety, eating disorders, antisocial personality disorders, etc.

History of Major Depressive Disorder within six (6) months prior the Screening Visit or a score of ≥14 on the Beck Depression Inventory II.

Subjects who meet DSM-IV criteria (APA) for Sexual Aversion Disorder,

Substance-Induced Sexual Dysfunction, Dyspareunia (not caused by inadequate foreplay stimulation or alleviated by lubricants), Vaginismus, Gender Identity Disorder, Paraphilia, or for Sexual Dysfunction Due to a General Medical Condition.

- Subjects experiencing relational discord as indicated by a score of ≥20 on the MMQ.
- Subjects with known active pelvic inflammatory disease, urinary tract or vaginal infection/vaginitis, cervicitis, interstitial cystitis, vulvodynia, or significant vaginal atrophy.
- Subjects who are breast feeding or have breast fed within the last six (6) months prior to the Baseline Visit.
- Subjects who are pregnant (by serum pregnancy test at the Screen Visit) or have been pregnant within the last 12 months prior to the Baseline Visit.
- Treatment with systemic glucocorticoids.
- Treatment with sex steroid hormones such as androgens, estrogens other than in low dose combined ET/P, or gestagens (e.g. anabolic steroids, DHEA, Premarin® (conjugated equine estrogens)).
- Treatment with thyroid hormones (only for stable replacement therapy).
- Significant intercurrent disease of any type, in particular liver, kidney, or heart disease, any form of diabetes mellitus (subjects using antacids or with treated hyperlipidaemia or treated hypothyroidism will not be excluded provided they have been stable on their drug dose for at least six (6) months).
- History of nasal disorders (e.g., seasonal or perennial allergic rhinitis, atrophic rhinitis, polyposis, abuse of nasal decongestants, clinically relevant nasal septum deviation, recurrent epistaxis) or sleep apnea.
- Subjects with a history of dementia or other neurodegenerative diseases, organic brain disease, stroke, transient ischemic attacks, brain surgery, significant brain trauma, multiple sclerosis, spinal cord injury, peripheral neuropathy, and epilepsy (febrile seizures limited to childhood do not exclude subjects).
- History of cancer, excluding basal cell carcinoma.
- History of severe or multiple allergies, severe adverse drug reaction or leucopenia.
- History of abnormal bleeding tendencies or thrombophlebitis unrelated to venepuncture or intravenous cannulation.
- History of DVT.
- History of Hepatitis B, a positive test for Hepatitis B surface antigen, a history of Hepatitis C, a positive test for Hepatitis C antibody, a history of HIV infection or demonstration of HIV antibodies.
- Recent history of significant sleeping problems. Shift-worker need to have adequate day-night rhythms for three weeks before study entry.
- Regular drinkers of more than three (3) units of alcohol daily (1 unit=300 ml beer, 1 glass wine, 1 measure spirit).
- History of, or current evidence of, abuse of alcohol or any drug substance, licit or illicit; or positive urine drug and alcohol screen for drugs of abuse and alcohol.
- Difficulty in abstaining from OTC medication (except occasional paracetamol/aspirin) for the duration of the study.
- Poor compliers or subjects unlikely to attend study visits.
- Receipt of any drug as part of a research study within 30 days of initial dose administration in this study.
- Blood donation (usually 550 ml) within the 12 week period before the initial study dose.

Treatment of Subjects

Study Visits

Visit 1 (Day-15)—Screening Subjects for Inclusion and Exclusion Criteria:

- Pre-study screening is carried out within two (2) weeks prior to the start of the treatment. Subjects, after having voluntarily signed the Informed Consent Form, and before enrolment, are interviewed by the Clinical Investigator or his/her designee physician who will take the medical, sexual and physical history, record demographic data, and perform a routine physical examination including vital signs (blood pressure, resting heart rate, body weight, and height).
- FSFI and FSDS-R are administered, as well as MMQ, BDI-II, ISS, SIDI-II, SESII-W.
- The otolaryngologic examination is done by an ENT specialist.
- Venous blood is collected, after an overnight fast, for a CBC (hemoglobin, hemoglobin A1c, hematocrit, MCV, MCHC, RBC, WBC & differential), Clinical Chemistry profile (Na/K, glucose, urea, creatinine, total bilirubin, albumin, calcium, phosphate, uric acid, LDL, HDL, triglycerides, AST, ALT, ALP, GGT and CK).
- Venous blood samples for estradiol, free testosterone, free testosterone (percent), follicle stimulating hormone, luteinizing hormone, prolactin, progesterone, sex hormone binding globulin, total testosterone, and dehydroepiandrosterone sulfate are collected.
- A blood sample for TSH, total and free tri-iodothyronine, total and free thyroxine is obtained.
- Urine is collected for measuring specific gravity, glucose, ketones, bilirubin, pH, urobilinogen, leukocytes, nitrites.
- Subjects undergo Hepatitis B, C and HIV testing (Hepatitis B surface antigen, Hepatitis C antibody, HIV antibodies in plasma).
- A urine drug screen is performed for amphetamines, benzodiazepines, cannabinoids, cocaine, opiates, MDMA. Subjects with positive test are not enrolled.
- Ethanol will be screened for by breathalyzer.

Visit 2 (Day 1)—Start of Baseline, Randomization, PK Blood Sampling and PD Testing:

- Subjects are admitted to the clinic in the afternoon for three overnights stays.
- A check-in examination is conducted to check for disallowed medications (OTC and prescription), drugs, alcohol or cigarettes. Subjects are requested to abstain from alcohol for 48 hours prior to admission to the clinic. Alcohol consumption is strictly forbidden at any time during the overnight stay in the clinic. There are no restrictions with respect to food intake during the blood collections for the PK profile.
- Urine tests for the same drugs of abuse as at Screening are repeated.
- Pregnancy is excluded using a urine test (if applicable).
- Vital signs (blood pressure, resting heart rate, and body weight) are checked.
- Blood is drawn for a CBC, chemistry profile, hormone profile, and pregnancy testing.
- Urine for urinalysis and urine drug screen is collected along with performing an alcohol breath test.
- Before dosing and blood sampling, subjects undergo a psychophysiological familiarization test in which neutral and erotic films are shown and VPA is recorded to get acquainted with the experimental procedures and being exposed to explicit erotic stimuli. The data obtained is not be used for analysis.

A venous cannula will be placed in a forearm vein, and blood sampling starts one hour before the evening administration of the Study Drug.

Subjects are dosed between 2000 and 2100 hours.

Blood samples are drawn for plasma testosterone and dihydrotestosterone levels at −60, 0, 15, 30, 45, 60, 90, 120, 180, 240, 300, 360, and 480 minutes post administration.

Randomization to the treatment schemes is done at this visit.

Safety assessment is recorded.

Subjects remain in the clinic overnight.

Visit 3 (Day 2)—PK Blood Sampling:

Vital signs are obtained.

A hormone profile is collected.

Subjects are dosed with Study Drug between 800 and 900 and between 2000 and 2100 hours (unless on Intrinsa®). Blood samples are drawn for plasma testosterone and dihydrotestosterone levels at times 0 and 60 minutes post administration.

For subjects allocated to the three testosterone gel formulation of the invention-arms or the placebo gel, psychophysiological testing is performed 30 minutes and 4.5 hours post-dosing in the morning Safety assessment is recorded.

Subjects remain in the clinic overnight.

Visit 4 (Day 3)—PK Blood Sampling and PD Testing:

Vital signs are obtained.

A hormone profile is collected.

Subjects are dosed with Study Drug at 800 and 900 and between 2000 and 2100 hours. Blood samples are drawn for plasma testosterone and dihydrotestosterone levels at times 0 and 60 minutes following administration of the morning dose and at 0, 15, 30, 45, 60, 90, 120, 180, 240, 300, 360, and 480 minutes following administration of the evening dose.

For subjects allocated to the three testosterone gel formulation of the invention-arms or the placebo gel, computer testing is performed 30 minutes post-dosing in the morning.

Safety assessment is recorded.

Visit 5 (Day 4)—Discharge-Close Out:

Physical examination including vital signs.

Venous blood is collected, after an overnight fast, for a CBC (hemoglobin, hemoglobin A1c, hematocrit, MCV, MCHC, RBC, WBC & differential), clinical chemistry profile (Na/K, glucose, urea, creatinine, total bilirubin, albumin, calcium, phosphate, uric acid, LDL, HDL, triglycerides, AST, ALT, ALP, GGT and CK).

Appropriate blood samples for estradiol, free testosterone, free testosterone (percent), follicle stimulating hormone, luteinizing hormone, prolactin, progesterone, sex hormone binding globulin, total testosterone, and dehydroepiandrosterone sulfate are collected.

Urine is collected for measuring specific gravity, glucose, ketones, bilirubin, pH, urobilinogen, leukocytes, nitrites.

Safety assessment is recorded.

Clinical Assessments

Screening and Covariate Questionnaires are used for clinical assessments.

BDI

To index the current level of depressive symptoms, the 21-item BDI-II is administered (Beck, Steer, & Brown. 1996), Dutch adaptation (Van der Does, 2002). The range for the BDI total score is 0-63, with higher scores indicating more depressive symptoms.

MMQ

The Maudsley Marital Questionnaire (MMQ; Crowe, 1978) is a 20-item self-report instrument measuring dissatisfaction with the general relationship, with the sexual relationship, and with life in general. The MMQ has shown good reliability and validity. The psychometric qualities of the Dutch version of the MMQ were also found to be satisfactory (Arrindell, Boelens, & Lambert. 1983). Higher scores represent larger dissatisfaction.

FSFI

The level of the woman's sexual functioning is assessed by the Female Sexual Function Index (FSFI; Rosen, Brown, Heiman, et al. 2000). The FSFI© is a self-administered questionnaire that consists of 19 questions. The scale contains six domains: desire; arousal, lubrication, orgasm, satisfaction, and pain. The range for the total score is 2-36, with lower scores representing worse sexual function. The psychometric quality of the FSFI is satisfactory (Wiegel, Meston, & Rosen. 2005). Based on a Dutch sample consisting of approximately 350 women with and without sexual complaints, the internal consistency and stability of the FSFI were found to be satisfactory-to-good. The FSFI's ability to discriminate between sexually functional and dysfunctional women was excellent as was the ability to predict the presence or absence of sexual complaints (ter Kuile, Brauer, & Laan, 2006).

FSDS-R

The woman's level of personal distress due to sexual dysfunction is assessed by the Female Sexual Distress Scale-Revised (FSDS-R©; Derogatis, Clayton, Lewis-D'Agostino, et al. 2008).

The items inquire about negative feelings and problems that are bothersome or cause distress during the past 30 days. Reliability and validity of the FSDS© (12-item version) has been evaluated in different samples of sexually functional and dysfunctional women. For the FSDS©, results indicated a unidimensional factor structure, a high degree of internal consistency, and test-retest reliability. The FSDS© showed a high degree of discrimination between sexually dysfunctional and functional women in each of its three validation studies. Results in a Dutch sample supported the unidimensional structure of the FSDS and its reliability and psychometric validity (ter Kuile, Brauer, & Laan, 2006). An additional question (question 13) has been added to the validated FSDS©. This question is about distress specifically related to sexual desire. The maximum total score of the FSDS-R© indicating the maximum level of sexual distress is '52'. Both the FSDS-R© total score and the Question 13 score alone will be analyzed.

Covariate Questionnaires

Index of Sexual Satisfaction (ISS)

The woman's level of sexual satisfaction as assessed by the Index of Sexual Satisfaction (ISS; Hudson, Harrison, & Crosscup. 1981). This 25-item questionnaire asks subjects to evaluate various aspects of their sexual relationship, leading to a sum score that can range between 0 and 100. Higher scores correspond to greater sexual satisfaction. This measure has been shown to have good face, convergent, and discriminant validity with various samples. Example items are "I feel that my partner enjoys our sex life," "I think that sex is wonderful," and "My partner is sexually very exciting." For the purpose of the present study, the ISS is translated into Dutch.

SDI-II

The level of the woman's sexual desire is assessed by the Sexual Desire Inventory-II (SDI-II; Spector, Carey, & Steinberg. 1996). The SDI-II consists of two seven-item self-report scales: the Dyadic Sexual Desire scale, which measures an individual's desire for sexual activity with a partner, and the Solitary Sexual Desire scale, which measures an individual's desire for autoerotic sexual activity. The two subscales were internally consistent (Cronbach's α: Dyadic scale=0.86; Solitary scale=0.96).

Sexual Excitation/Sexual Inhibition (SESII-W)

The Sexual Inhibition/Excitation Inventory for women (SESII-W; Graham, Sanders, & Milhausen. 2006) is used to assess individuals' propensity for sexual excitation and sexual inhibition. It consists of 36 items, referring to stimulus situations that could affect sexual inhibition and sexual excitation or to general statements about arousability and inhibition. The instructions ask women to report what would be the most typical reaction now or how they think they would respond if the item does not apply to them. Items are rated on a 4-point Likert-rating scale, from "strongly disagree" to "strongly agree." The SESII-W has eight lower-order factors, which in turn load on two higher-order factors, Sexual Excitation and Sexual Inhibition. The questionnaire shows good test-retest reliability and convergent and discriminant validity and Sexual Excitation and Sexual Inhibition appear to be relatively independent factors. The list is already in use in the Netherlands, but psychometric properties have not been investigated yet.

Efficacy Pharmacodynamic Testing

Computer Testing

Single Target Implicit Association Task (StIAT):

Conform Wigboldus et al. (2005), the stIAT used in this study is designed to assess subjects' affective associations with sexual stimuli (Brauer, van Leeuwen, Janssen, et al. submitted). Subjects are instructed to classify pictures portraying sexual acts (i.e., target stimuli) and words representing "positive" or "negative" meanings (i.e., attribute stimuli) to the appropriate superordinate category (i.e., "sex", "positive", "negative") as quickly as possible by pressing only a left or right response key on a keyboard. These labels used for these categories (sex, positive, negative) are continuously visible on the computer screen. The stIAT consists of a combination of practice and experimental blocks (see Greenwald, McGhee & Schwartz. 1998 for detailed methodology). The experimental blocks consist of one 'incongruent' and one 'congruent' block of trials. In the incongruent block, "sex" and "negative" are mapped on a single key and "positive" on the other, while in the congruent block, "sex" and "positive" are mapped on the same key and "negative" on the other. The difference in reaction times between the two experimental blocks is assumed to reflect whether sex is associated more strongly with either positive or negative. Faster responses in the congruent block (compared to the other block) reflect stronger associations between positive and sex, and faster responses in the incongruent block reflect stronger associations between negative and sex. The target-attribute combinations that share response keys (i.e., block order), and left or right key response requirements are counterbalanced. Each critical block consists of 40 trials of which responses were divided equally over the two response keys. The target category consists of 5 exemplar stimuli of sexual images from the International Affective Picture System (ZAPS; Center for the Study of Emotion and Attention, 1995), with the following numbers: 4800, 4652, 4658, 4659, and 4672. The attribute categories consists of 20 generally positive and 20 generally negative words (Dotsch & Wigboldus, 2008; Dotsch, Wigboldus, Langner et al. 2008), thus reflecting more global affective associations with sex: These words were controlled for length and frequency. With respect to the validity, the stIAT's strength lies in high effect sizes due to double opposing categories often leading to slower reaction times (the categorization decision requires effort as there are several possibilities to consider).

Picture Association Task (PAT)

This task, developed by van Leeuwen and Macrae (2004), is based on the Affective Priming Task (e.g., Bargh, Chaiken, Govender, et al. 1992; Fazio, Sanbonmatsu, Powell, et al. 1986; Hermans, De Houwer, & Eelen, 1994) where target words are preceded by another word or image that influences the categorisation speed of the target word. In the PAT, however, target words and images appear simultaneously. In the PAT used in this study, subjects are presented with positive or negative words superimposed on either sexual or neutral pictures (Brauer, van Leeuwen, Janssen, et al. submitted). They are instructed to categorize the words as fast as possible as either positive or negative by pressing one of two computer keys. Subjects are further instructed to focus on the words that appeared on the screen and not to attend to the background images as these are of no importance for the task and the categories to which the pictorial stimuli belong (sex, neutral) are not explained. Thus, the PAT captures the unintentional influence of the affective value of the pictorial background stimuli on task performance. The time to select the correct response to the words (positive or negative) is influenced by the match between the valence of the word and the valence of the background image (sex or neutral), thereby revealing indirectly the valence of the picture for the subjects. The word categories consist of 10 positive words and 10 negative words. Whereas for the stIAT general positive and negative words are selected (e.g., peace, respect, war, hate), the PAT consists of positive and negative words that are applicable to a sexual situation, but that do not exclusively refer to sexual experiences (e.g., enjoyable, wonderful, dirty, disgusting) in order to create a conceptual overlap between the content of the words and the content triggered by the sexual pictures. These words are taken from a pilot study in the Netherlands in which female subjects (N=20) were asked to indicate on a 7-point Likert scale for each positive and negative word how well it described a positive or a negative sexual situation, respectively (Brauer & Laan, 2008). The words appear at one of four randomized locations on the picture to avoid expectation-related responses and to make sure subjects would move their eyes over the image. The sexual pictures were taken from another study on implicit associations with sexual stimuli in women with dyspareunia (Brauer, de Jong, Huijding et al., 2009). These pictures display a variety of sexual acts (e.g., kissing, cunnilingus, fellatio, coitus). Based on each sexual picture, a control picture was created by scrambling the sexual image, leaving a neutral stimulus. All pictures are standardized to 600×480 pixels and matched for brightness and contrast. Each stimulus remains on the screen until subjects make a decision or until 3,000 ms has elapsed. After 10 practice trials, 80 experimental trials are presented. Each word is paired randomly with a sexual picture and a neutral picture, resulting in four different combinations each presented 20 times: positive words and sexual images, negative words and sexual images, positive words and neutral images, negative words and neutral images. The order of presentation of the trials is counterbalanced within, and response key mappings (i.e., positive/negative or negative/positive) are counterbalanced across subjects. The computer records the accuracy and latency of each response. With respect to validity, the strength of the PAT is that it is not sensitive to a possible interpretation bias due to the need to attend to the different stimulus categories at the same time, as is the case in the stIAT.

Dot Probe Task (DOT)

The dot-probe task (DOT) assesses attentional preference for sexual and neutral visual stimuli. In this task, subjects are shown two images side by side on a computer screen for 500 ms. When the two images disappear, a target stimulus represented by a small dot appears in the place of one of the images. Subjects are asked to indicate the location (side) of the dot. Mean RTs are calculated for three categories: 1) neutral neutral 2) neutral sex with the dot under neutral 3) neutral sex with the dot under sex. If reaction times are faster when the dot appears in the place of a certain class of stimuli this indicates an attentional bias towards this class of stimuli.

Psychophysiological Testing

Genital Response (VPA)

Psychophysiological testing consists of assessment of genital response (vaginal pulse amplitude) and subjective sexual arousal during sexual to self-induced erotic fantasy (3 min), a low-intensity erotic film clip (5 min), and a high-intensity erotic film clip (5 min) (Laan et al., in preparation). The erotic conditions are separated by variable interstimulus intervals during which subjects complete a concentration task (simple arithmetic problems) to allow for return-to-baseline. The erotic stimulus testing is preceded by a 8 min neutral film to establish baseline levels. VPA is measured using a vaginal photoplethysmograph developed by Bert Molenkamp (Technical Support, Department of Psychology, University of Amsterdam) based on instruments initially developed by Sintchak and Geer (1975). The light source (3 mm LED, $\lambda$=620 nm) and optical sensor (Texas Instruments TSL250) are produced in batches of 100, resulting in all photoplethysmographs used in this study having nearly equal electronic characteristics. A signal-conditioning amplifier separates the VPA from the direct current component using a 12 dB/octave, 0.7-Hz filter. Additional filtering for VPA is 24 dB/octave, 0.4 Hz high-pass. The VPA signal is digitalized at 100 Hz with a Keithley KPCI3107 A/D converter, running on a Windows 2000 PC system. Depth of the probe and orientation of the light source is controlled by a device (a 9-×2-cm FDA-approved perspex plate) attached to the cable within 5 cm of the optical sensor. Subjects are instructed to insert the probe until the plate touched their labia. The probe and plate are sterilized according to standard department protocol.

Sexual Feelings and Affect (SAQ).

Prior to and immediately after erotic stimulus subjects fill out a questionnaire measuring sexual feelings and affect during sexual stimulation, consisting of 5 scales: sexual arousal (Cronbach's $\alpha$=0.87); genital sensations (Cronbach's $\alpha$=0.96); sensuality (Cronbach's $\alpha$=0.73); positive affect (Cronbach's $\alpha$=0.93); and negative affect (Cronbach's $\alpha$=0.65). Each question is preceded by the sentence: "During the film, I felt:" after which a positive, negative, physical or sexual experience is described, for instance, pleasant; worried; genital pulsing or throbbing; sexually aroused. The items are measured on a 1 (not at all) to 7 (intensely) scale.

Acute Female Sexual Desire (AFSDQ)

Prior to and following psychophysiological testing subjects fill out the Acute Female Sexual Desire Questionnaire (Laan, Heiman, unpublished). This questionnaire assesses sexual interest in erotic stimuli and has shown to discriminate between women with acquired HSDD and sexually functional controls (Laan et al., in preparation)

Statistical Methodology

Calculation of Pharmacokinetic Parameters $C_{min}$, $C_{max}$, and $t_{max}$ are taken from the actual measured values. Values are determined relative to the testosterone administration time in treated subjects.

Area under the concentration curve (AUC) are estimated for the 0 to 24 hour time interval, as well as the BID dosing intervals, using the trapezoidal rule.

PK evaluations after Day 1 evening dose for testosterone gel formulation of the invention and placebo and Day 3 evening dose for testosterone gel formulation of the invention, placebo and Intrinsa® patch (which was applied on Day 1)—AUC, concentrations of total and free testosterone, DHT, estradiol, SHBG. Analyses of $C_{avg}$, $C_{min}$, $C_{max}$, $C_{max}$, $t_{max}$, $AUC_{0-t}$, PTF, and PTS. $C_{avg}$ are calculated for the 12 hour period as well as r when appropriate. For subjects on Intrinsa®, a 24 hour calculation is performed.

The average concentration in the dosing interval ($C_{avg}$) is calculated from the AUC using the following formula: $C_{avg}=AUC_{0-\tau}/\tau$, with $\tau$=dosing interval time.

Peak Trough Fluctuation (PTF) and Peak Trough Swing (PTS) are calculated as follows:

PTF=$(C_{max}-C_{min})/C_{avg}$

PTS=$(C_{max}-C_{min})/C_{min}$

Percent time that the plasma testosterone concentration is above, within, and below the reference range of 10 to 70 ng/dl, is calculated.

Statistical Analysis of Pharmacodynamic Data stIAT:

Incorrect responses are excluded from analyses. In addition, RTs shorter than 300 ms or longer than 3000 ms are excluded from analyses. With respect to the stIAT data, Wigboldus, Holland & van Knippenberg (2005) is followed in that, for each subject, the median response latency of the correct responses to the attribute items in congruent and incongruent blocks is used. Following this, median reaction times of the two experimental blocks are subtracted from one another to obtain a stIAT effect (i.e., stIAT effect=median (Sex/Negative)−median (Sex/Positive)). Negative stIAT effects indicate relatively stronger negative associations with sexual stimuli.

The stIAT effect is analyzed with an analysis of variance with fixed factor treatment, group (HSDD and SA) and the interaction treatment by group. The contrasts are calculated within the model.

PAT:

Median response latencies of the correct responses are calculated, following van Leeuwen and Macrae (2004). To correct for baseline reactions to positive and negative words, difference scores are calculated by subtracting RTs for neutral words superimposed on sexual pictures from positive words superimposed on sexual pictures. The same is done for negative words superimposed on sexual and neutral pictures (i.e., Sex/+=RT (sex/positive words)−RT (neutral/positive words) and Sex/−=RT (sex/negative words)−RT (neutral/negative words. Sex/+<Sex/−=automatic positive associations with sex).

The two PAT variables (RT positive and RT negative) are analyzed with an analysis of variance with fixed factors treatment, group (ANOR) and group by treatment. The contrasts will be calculated within the model.

DOT:

For each subject the difference between mean RT for the category neutral sex with the dot under sex and the mean RT for the category neutral sex with the dot under neutral is calculated to obtain a DOT effect (i.e., DOT effect=mean neutral sex with dot under neutral−mean neutral sex with dot under sex). Higher DOT scores indicate relatively stronger attention for sexual stimuli.

The DOT effect is analyzed with an analysis of variance with fixed factor treatment, group (ANOR) and the interaction treatment by group. The contrasts are calculated within the model.

VPA:

After VPA artefact deletion, done by a computer program developed Bert Molenkamp (Technical Support, Department of Psychology, University of Amsterdam), peak-to-trough amplitude is calculated for each remaining pulse. VPA is averaged every 30 seconds during several conditions: neutral film (8 min), self induced erotic fantasy (3 min), low intensity erotic film clip (5 min) and high intensity erotic film clip (5 min). All conditions are offered twice: once 0.5 hours after application of the nasal gel and once 4.5 hours after application of the nasal gel.

VPA during the erotic fantasy, the low intensity film and the high intensity film are analyzed separately and the different moments (0.5 hours after and 4.5 hours after dosing) are also be analyzed separately, resulting in 6 analyses. VPA during a condition and a moment is analyzed with a mixed model analysis of variance with fixed factors treatment, group (ANOR), time, group by treatment, treatment by time and random factor subject and the average VPA score during the neutral film as covariate. Contrasts are calculated within the model.

SAQ:

For each of the five SAQ scale mean response during a condition and a moment are analyzed with an analysis of variance with factors treatment, group (ANOR) and group by treatment, with the score prior to sexual stimuli as covariate. Contrasts are calculated within the model.

AFSDQ:

ASFDQ score after erotic stimulation during a moment is analyzed with an analysis of variance with factors treatment, group (ANOR), and group by treatment; and the score prior to sexual stimuli as covariate. Contrasts are calculated within the model.

If necessary to meet requirements for analysis of variance data is log-transformed. Results are back-transformed and reported as % change.

Graphs of least square means estimates over time by treatment are presented with error bars indicating the upper and lower 95% confidence interval for the highest and lowest profile respectively. Least square means of the contrasts are tabulated.

If analyses are not feasible according to the described models with the given data, analyses are adjusted. If considered useful extra exploratory analyses are conducted.

Statistical Analysis of Safety Data

Nasal Tolerance:

Nasal tolerance data is presented in summary tables. No statistical analysis will be performed.

Vital Signs and Clinical Laboratory Parameters: A table summarizing all laboratory test values and changes from Baseline is presented for each treatment group. In case parameters are ±20% of their reference range, the clinical significance of these findings are evaluated.

The results of this analysis are presented in FIGS. 1, and 4-6. The following FIGS. 3 and 9-11, compare the results between the effects of the lower dosage strength testosterone gel nasal formulations of the present invention in subjects diagnosed with anorgasmia or HSDD.

Example 8

Evaluation of a Testosterone Nasal Gel Formulation of the Invention in Women with HSDD The pharmacokinetics and pharmacodynamic efficacy of testosterone gel formulations of the invention are evaluated in studies of women with HSDD. The effect of testosterone gel formulations of the invention on sexual stimuli in women with HSDD is also determined.

Dosing

Three doses of a testosterone gel formulation of the invention are investigated: 150 μg, 450 μg and 600 μg per nostril. A total of 5 doses of a testosterone gel formulation of the invention is administered BID intranasally to women. The Intrinsa® patch (300 μg testosterone) is administered as a control in the HSDD cohort.

Patient Population

Otherwise healthy females, aged 18 to 65 years, presenting with HSDD are evaluated. Sixteen (16) subjects are be recruited to each indication.

Treatment Duration

Test subjects receive 5 doses of a testosterone gel formulation of the invention over a three day period.

Endpoints

Primary End-Point

The plasma concentrations of total testosterone and dihydrotestosterone are measured using validated LC/MS/MS. The following pharmacokinetic parameters are determined for all subjects:

Cmin, Cmax, tmax, PTF and PTS are determined, for each dosing interval

AUC0-τ, and Cavg, are calculated for each dosing interval.

The percentage of time within, below, and above the physiological reference range for plasma testosterone and dihydrotestosterone.

Secondary End-Points:

Efficacy is determined by a battery of computer and psychophysiological tests.

Safety is monitored according to the following parameters:

Complete blood counts at Baseline and the Close-Out Visit.

Clinical chemistry and urinalysis testing at Baseline and Close-Out assesses selected endocrine parameters, renal function, liver function, skeletal/heart muscle damage, lipid abnormalities, and changes in calcium homeostasis.

Measurement of plasma testosterone, dihydrotestosterone and various hormones at Baseline, study days and Close-Out.

Adverse Events.

Randomization

Subjects in the HSDD cohort are randomized to receive either a testosterone gel formulation of the invention (3 dose levels) or the Intrinsa® patch. Randomization is according to the design allocation below.

| HSDD Cohort (Post-menopausal) | Testosterone Gel Formulation of the invention LD BID | Testosterone Gel Formulations of the invention MD BID | Testosterone Gel Formulations of the invention HD BID | Intrinsa ® Patch (one patch in total) |
| --- | --- | --- | --- | --- |

LD (0.15%)—low dose;
MD (0.45%)—mid dose;
HD (0.6%)—high dose

Blinding

This is both a double-blind and open label study, depending on the treatment cohort. For the HSDD cohort, this is a partly open-label study, as blinding of intra-nasal dosing versus patch dosing is not feasible. The testosterone gel formulation of the invention dose in the HSDD cohort is blinded.

Dosage and Dosage Regimen

Three-quarters (75%) of the subjects in the HSDD cohort are administered a testosterone gel formulation of the invention (0.15%, 0.45% or 0.6%) on five (5) occasions during the study: Day 1 at 2000 hours, Day 2 at 800 and 2000 hours, and Day 3 at 800 and 2000 hours. The intranasal gel is administered to both nostrils (1 syringe (100 µl volume) per nostril). To the remaining one-quarter (25%) of the subjects is administered the Intrinsa® patch at 2000 hours on Day 1 which will remain on the subject's lower abdomen for the duration of the study. The patch is removed on Day 4 prior to discharging the subject from the clinic.

Package and Labelling

Study medication consists of testosterone gel formulations of the invention and testosterone gel formulations of the invention placebo gel and is packed in single use syringes designed to expel 100 µl of gel. Two syringes are packaged in a foil pouch. The active control for the HSDD cohort, Intrinsa®, remains in its original packaging from the manufacturer.

Treatment Schedule

Subjects are randomized into the dosing regimen that is administered during a four day (three night) in-patient treatment period and receive either intranasal testosterone gel formulation of the invention (3 dose levels) or Intrinsa® patch (HSDD) according to the design allocation:

| HSDD Cohort | Testosterone Gel Formulations of the invention LD BID | Testosterone Gel Formulations of the invention MD BID | Testosterone Gel Formulations of the invention HD BID | Intrinsa ® Patch (one patch in total) |
| --- | --- | --- | --- | --- |

The randomization scheme is created for each study center and consists of blocks of four treatments per cohort.

The study is a four day study. The study start with Study Drug dosing between 2000 and 2100 hours on Day 1 (Baseline). Blood samples for plasma testosterone and dihydrotestosterone profiles are drawn at −60, 0, 15, 30, 45, 60, 90, 120, 180, 240, 300, 360 and 480 minutes following the evening dose on Days 1 and 3 and at 0 and 60 minutes (except Intrinsa arm—no 60 minute on Day 2 and Day 3 morning draws) post administration following the morning/evening doses on Day 2 and morning dose on Day 3.

For subjects allocated to the three testosterone gel formulations of the invention arms or the placebo gel, PD testing will take place on Day 2, 30 minutes and 4.5 hours after the morning dose (psychophysiological testing) and Day 3, 30 minutes after the morning dose (computer testing). Subjects will have undergone a practice psychophysiological session before the first dosing.

Because subjects are expected to not sleep well during their first overnight stay with repeated nightly blood draws, the order of psychophysiological testing and computer testing is not counterbalanced. Computer testing is expected to be more negatively affected by sleep deprivation than psychophysiological testing. Therefore, on Day 2 psychophysiological testing takes place, and computer testing occurs on Day 3. For the subjects randomized to the Intrinsa® patch, psychophysiological testing take place on Day 3 between 800 and 900 hours and computer testing follows in the afternoon of Day 3 between 1600 and 1700 hours.

Adverse events are assessed and reported.

Patient Selection and Withdrawal

The subjects in this study are women with HSDD. Subjects are recruited from the medical practice or the general population through advertisements in local newspapers with additional information available on a website. Before scheduling the screening visit, subjects are asked a series of standardized questions by telephone to assess whether they are likely to be suitable for the study.

Inclusion Criteria

Women up to 65 years.

Postmenopausal women with the primary diagnosis of HSDD, generalized acquired type, according to DSM-IV criteria at the Screening Visit. The current episode must be at least 24 weeks in duration by the Screening Visit. Secondary Female Sexual Arousal Disorder and/or Female Orgasmic Disorder are allowed if co-morbid. This inclusion criterion is met only if the HSDD began prior to Female Sexual Arousal Disorder and/or Female Orgasmic Disorder and the HSDD is of more importance to the subject, in the investigators' judgment.

BMI≤35.

Women must have a score of >11 on the FSDS-R at the Screen Visit together with a score of <26.55 on the FSFI.

Women in a steady relationship of at least 12 months

Physiological and surgical post-menopausal women—estrogen/progesterone substitution (low dose combined ET/P) for at least three (3) months before study entry or post-menopausal women naïve to ET/P substitution.

Normal thyroid function, physiological prolactin concentration.

Normal otorhinolaryngologic examination.

Provide written informed consent.

Exclusion Criteria—HSDD

History of any other clinically relevant psychiatric disorders that could impact sexual function, risk patient's safety, or may impact compliance, as assessed by the MINI. This includes bipolar disorders, psychotic disorders, severe anxiety, eating disorders, antisocial personality disorders, etc.

History of Major Depressive Disorder within six (6) months prior to Screening Visit or a score of on the Beck Depression Inventory II.

Subjects who meet DSM-IV criteria (APA) for Sexual Aversion Disorder, Substance-Induced Sexual Dysfunction, Dyspareunia (not caused by inadequate foreplay stimulation or alleviated by lubricants), Vaginismus, Gender Identity Disorder, Paraphilia, or for Sexual Dysfunction Due to a General Medical Condition.

Subjects with known active pelvic inflammatory disease, urinary tract or vaginal infection/vaginitis, cervicitis, interstitial cystitis, vulvodynia, or significant vaginal atrophy.

Women with relationship discord as indicated by a score of ≥20 on the MMQ.

Treatment with systemic glucocorticoids.

Treatment with sex steroid hormones such as androgens, estrogens other than in low dose combined ET/P, or gestagens (e.g. anabolic steroids, DHEA, Premarin® (conjugated equine estrogens)).

Treatment with thyroid hormones (only for stable replacement therapy).

Significant intercurrent disease of any type, in particular liver, kidney, or heart disease, or any form of diabetes mellitus (subjects using antacids or with treated hyperlipidaemia or treated hypothyroidism will not be excluded provided they have been stable on their drug dose for at least six months).

History of nasal disorders (e.g., seasonal or perennial allergic rhinitis, atrophic rhinitis, polyposis, abuse of nasal decongestants, clinically relevant nasal septum deviation, recurrent epistaxis) or sleep apnea.

Subjects with a history of dementia or other neurodegenerative diseases, organic brain disease, stroke, transient ischemic attacks, brain surgery, significant brain trauma, multiple sclerosis, spinal cord injury, peripheral neuropathy, and epilepsy (febrile seizures limited to childhood do not exclude subjects)

History of cancer, excluding basal cell carcinoma

History of severe or multiple allergies, severe adverse drug reaction or leucopenia.

History of abnormal bleeding tendencies or thrombophlebitis unrelated to venepuncture or intravenous cannulation.

History of DVT.

History of Hepatitis B, a positive test for Hepatitis B surface antigen, a history of Hepatitis C, a positive test for Hepatitis C antibody, a history of HIV infection or demonstration of HIV antibodies.

Recent history of significant sleeping problems. shift-workers need to have adequate day-night rhythms for three weeks before study entry.

Regular drinkers of more than three (3) units of alcohol daily (1 unit=300 ml beer, 1 glass wine, 1 measure spirit).

History of, or current evidence of, abuse of alcohol or any drug substance, licit or illicit; or positive urine drug and alcohol screen for drugs of abuse and alcohol.

Difficulty in abstaining from OTC medication (except occasional paracetamol/aspirin) for the duration of the study.

Poor compliers or subjects unlikely to attend study visits.

Receipt of any drug as part of a research study within 30 days of initial dose administration in this study.

Blood donation (usually 550 ml) within the 12 week period before the initial study dose.

Treatment of Subjects
Study Visits
Visit 1 (Day-15)—Screening Subjects for Inclusion and Exclusion Criteria:

Pre-study screening is carried out within two (2) weeks prior to the start of the treatment. Subjects, after having voluntarily signed the Informed Consent Form, and before enrolment, are interviewed by the Clinical Investigator or his/her designee physician who takes the medical, sexual and physical history, record demographic data, and performs a routine physical examination including vital signs (blood pressure, resting heart rate, body weight, and height).

FSFI and FSDS-R are administered, as well as MMQ, BDI-II, ISS, SIDI-II, SESII-W.

The otolaryngologic examination is done by an ENT specialist.

Venous blood is collected, after an overnight fast, for a CBC (hemoglobin, hemoglobin A1c, hematocrit, MCV, MCHC, RBC, WBC & differential), Clinical Chemistry profile (Na/K, glucose, urea, creatinine, total bilirubin, albumin, calcium, phosphate, uric acid, LDL, HDL, triglycerides, AST, ALT, ALP, GGT and CK).

Venous blood samples for estradiol, free testosterone, free testosterone (percent), follicle stimulating hormone, luteinizing hormone, prolactin, progesterone, sex hormone binding globulin, total testosterone, and dehydroepiandrosterone sulfate are collected.

A blood sample for TSH, total and free tri-iodothyronine, total and free thyroxine is obtained.

Urine is collected for measuring specific gravity, glucose, ketones, bilirubin, pH, urobilinogen, leukocytes, nitrites.

Subjects also undergo Hepatitis B, C and HIV testing (Hepatitis B surface antigen, Hepatitis C antibody, HIV antibodies in plasma).

A urine drug screen is performed for amphetamines, benzodiazepines, cannabinoids, cocaine, opiates, MDMA. Subjects with positive test are not enrolled.

Ethanol is screened for by breathalyzer.

Visit 2 (Day 1)—Start of Baseline, Randomization, PK Blood Sampling and PD Testing:

Subjects are admitted to the clinic in the afternoon for three overnights stays.

A check-in examination is conducted to check for disallowed medications (OTC and prescription), drugs, alcohol or cigarettes. Subjects are requested to abstain from alcohol for 48 hours prior to admission to the clinic. Alcohol consumption is strictly forbidden at any time during the overnight stay in the clinic. There are no restrictions with respect to food intake during the blood collections for the PK profile.

Urine tests for the same drugs of abuse as at Screening are repeated.

Pregnancy is excluded using a urine test (if applicable).

Vital signs (blood pressure, resting heart rate, and body weight) are checked.

Blood is drawn for a CBC, chemistry profile, hormone profile, and pregnancy testing.

Urine for urinalysis and urine drug screen is collected along with performing an alcohol breath test.

Before dosing and blood sampling, subjects undergo a psychophysiological familiarization test in which neutral and erotic films are shown and VPA is recorded to get acquainted with the experimental procedures and being exposed to explicit erotic stimuli. The data obtained is not used for analysis.

A venous cannula is placed in a forearm vein, and blood sampling starts one hour before the evening administration of the Study Drug.

Subjects are dosed between 2000 and 2100 hours.

Blood samples are drawn for plasma testosterone and dihydrotestosterone levels at −60, 0, 15, 30, 45, 60, 90, 120, 180, 240, 300, 360, and 480 minutes post administration.

Randomization to the treatment schemes is done at this visit.

Safety assessment is recorded.

Subjects remain in the clinic overnight.

Visit 3 (Day 2)—PK Blood Sampling:

Vital signs are obtained.

A hormone profile is collected.

Subjects are dosed with Study Drug between 800 and 900 and between 2000 and 2100 hours (unless on Intrinsa®). Blood samples are drawn for plasma testosterone and dihydrotestosterone levels at times 0 and 60 minutes post administration. For subjects on Intrinsa®, a time 0 draw between 800-900 and 2000-2100 hours is obtained.

For subjects allocated to the three testosterone gel formulations of the invention-arms or the placebo gel, psychophysiological testing is performed 30 minutes and 4.5 hours post-dosing in the morning Safety assessment is recorded.

Subjects remain in the clinic overnight.

Visit 4 (Day 3)—PK Blood Sampling and PD Testing:

Vital signs are obtained.

A hormone profile is collected.

Subjects are dosed with Study Drug at 800 and 900 and between 2000 and 2100 hours (unless on Intrinsa®). Blood samples are drawn for plasma testosterone and dihydrotestosterone levels at times 0 and 60 minutes following administration of the morning dose and at 0, 15, 30, 45, 60, 90, 120, 180, 240, 300, 360, and 480 minutes following administration of the evening dose. Subjects receiving Intrinsa® have the time 0 draw for the morning dose and all times in the evening as if they received a new dose.

For subjects allocated to the three testosterone gel formulations of the invention-arms or the placebo gel, computer testing is performed 30 minutes post-dosing in the morning. For the women randomized to the Intrinsa® patch, psychophysiological testing takes place on Day 3 between 800 and 900 hours. Computer testing follows in the afternoon of Day 3 between 1600 and 1700 hours.

Safety assessment is recorded.

Visit 5 (Day 4)—Discharge-Close Out:

Physical examination including vital signs.

Venous blood is collected, after an overnight fast, for a CBC (hemoglobin, hemoglobin A1c, hematocrit, MCV, MCHC, RBC, WBC & differential), clinical chemistry profile (Na/K, glucose, urea, creatinine, total bilirubin, albumin, calcium, phosphate, uric acid, LDL, HDL, triglycerides, AST, ALT, ALP, GGT and CK).

Appropriate blood samples for estradiol, free testosterone, free testosterone (percent), follicle stimulating hormone, luteinizing hormone, prolactin, progesterone, sex hormone binding globulin, total testosterone, and dehydroepiandrosterone sulfate are collected.

Urine is collected for measuring specific gravity, glucose, ketones, bilirubin, pH, urobilinogen, leukocytes, nitrites.

The Intrinsa® patch is removed (as appropriate).

Safety assessment is recorded.

Clinical Assessments

Screening and Covariate Questionnaires are used for clinical assessments.

BDI

To index the current level of depressive symptoms, the 21-item BDI-II is administered (Beck, Steer, & Brown. 1996), Dutch adaptation (Van der Does, 2002). The range for the BDI total score is 0-63, with higher scores indicating more depressive symptoms.

MMQ

The Maudsley Marital Questionnaire (MMQ; Crowe, 1978) is a 20-item self-report instrument measuring dissatisfaction with the general relationship, with the sexual relationship, and with life in general. The MMQ has shown good reliability and validity. The psychometric qualities of the Dutch version of the MMQ were also found to be satisfactory (Arrindell, Boelens, & Lambert. 1983). Higher scores represent larger dissatisfaction.

FSFI

The level of the woman's sexual functioning is assessed by the Female Sexual Function Index (FSFI; Rosen, Brown, Heiman, et al. 2000). The FSFI© is a self-administered questionnaire that consists of 19 questions. The scale contains six domains: desire, arousal, lubrication, orgasm, satisfaction, and pain. The range for the total score is 2-36, with lower scores representing worse sexual function. The psychometric quality of the FSFI is satisfactory (Wiegel, Meston, & Rosen. 2005). Based on a Dutch sample consisting of approximately 350 women with and without sexual complaints, the internal consistency and stability of the FSFI were found to be satisfactory-to-good. The FSFI's ability to discriminate between sexually functional and dysfunctional women was excellent as was the ability to predict the presence or absence of sexual complaints (ter Kuile, Brauer, & Laan, 2006).

FSDS-R

The woman's level of personal distress due to sexual dysfunction is assessed by the Female Sexual Distress Scale-Revised (FSDS-R©; Derogatis, Clayton, Lewis-D'Agostino, et al. 2008).

The items inquire about negative feelings and problems that are bothersome or cause distress during the past 30 days. Reliability and validity of the FSDS© (12-item version) has been evaluated in different samples of sexually functional and dysfunctional women. For the FSDS©, results indicated a unidimensional factor structure, a high degree of internal consistency, and test-retest reliability. The FSDS© showed a high degree of discrimination between sexually dysfunctional and functional women in each of its three validation studies. Results in a Dutch sample supported the unidimensional structure of the FSDS and its reliability and psychometric validity (ter Kuile, Brauer, & Laan, 2006). An additional question (question 13) has been added to the validated FSDS©. This question is about distress specifically related to sexual desire. The maximum total score of the FSDS-R© indicating the maximum level of sexual distress is '52'. Both the FSDS-R© total score and the Question 13 score alone will be analyzed.

Index of Sexual Satisfaction (ISS)

The woman's level of sexual satisfaction as assessed by the Index of Sexual Satisfaction (ISS; Hudson, Harrison, & Crosscup. 1981). This 25-item questionnaire asks subjects to evaluate various aspects of their sexual relationship, leading to a sum score that can range between 0 and 100. Higher scores correspond to greater sexual satisfaction. This measure has been shown to have good face, convergent, and discriminant validity with various samples. Example items are "I feel that my partner enjoys our sex life," "I think that sex is wonderful," and "My partner is sexually very exciting." For the purpose of the present study, the ISS is translated into Dutch.

SDI-II

The level of the woman's sexual desire is assessed by the Sexual Desire Inventory-II (SDI-II; Spector, Carey, & Steinberg. 1996). The SDI-II consists of two seven-item self-report scales: the Dyadic Sexual Desire scale, which measures an individual's desire for sexual activity with a partner, and the Solitary Sexual Desire scale, which measures an individual's desire for autoerotic sexual activity. The two subscales were internally consistent (Cronbach's α: Dyadic scale=0.86; Solitary scale=0.96).

Sexual Excitation/Sexual Inhibition (SESII-W)

The Sexual Inhibition/Excitation Inventory for women (SESII-W; Graham, Sanders, & Milhausen. 2006) is used to assess individuals' propensity for sexual excitation and sexual inhibition. It consists of 36 items, referring to stimulus situations that could affect sexual inhibition and sexual excitation or to general statements about arousability and inhibition. The instructions ask women to report what would be the most typical reaction now or how they think they would respond if the item does not apply to them. Items are rated on a 4-point Likert-rating scale, from "strongly disagree" to "strongly agree." The SESII-W has eight lower-order factors, which in turn load on two higher-order factors, Sexual Excitation and Sexual Inhibition. The questionnaire shows good test-retest reliability and convergent and discriminant validity and Sexual Excitation and Sexual Inhibition appear to be relatively independent factors. The list is already in use in the Netherlands, but psychometric properties have not been investigated yet.

Efficacy Pharmacodynamic Testing

Computer Testing

Single Target Implicit Association Task (StIAT):

Conform Wigboldus et al. (2005), the stIAT used in this study is designed to assess subjects' affective associations with sexual stimuli (Brauer, van Leeuwen, Janssen, et al. submitted). Subjects are instructed to classify pictures portraying sexual acts (i.e., target stimuli) and words representing "positive" or "negative" meanings (i.e., attribute stimuli) to the appropriate superordinate category (i.e., "sex", "positive", "negative") as quickly as possible by pressing only a left or right response key on a keyboard. These labels used for these categories (sex, positive, negative) are continuously visible on the computer screen. The stIAT consists of a combination of practice and experimental blocks (see Greenwald, McGhee & Schwartz. 1998 for detailed methodology). The experimental blocks consist of one 'incongruent' and one 'congruent' block of trials. In the incongruent block, "sex" and "negative" are mapped on a single key and "positive" on the other, while in the congruent block, "sex" and "positive" are mapped on the same key and "negative" on the other. The difference in reaction times between the two experimental blocks is assumed to reflect whether sex is associated more strongly with either positive or negative. Faster responses in the congruent block (compared to the other block) reflect stronger associations between positive and sex, and faster responses in the incongruent block reflect stronger associations between negative and sex. The target-attribute combinations that share response keys (i.e., block order), and left or right key response requirements are counterbalanced. Each critical block consists of 40 trials of which responses were divided equally over the two response keys. The target category consists of 5 exemplar stimuli of sexual images from the International Affective Picture System (ZAPS; Center for the Study of Emotion and Attention, 1995), with the following numbers: 4800, 4652, 4658, 4659, and 4672. The attribute categories consists of 20 generally positive and 20 generally negative words (Dotsch & Wigboldus, 2008; Dotsch, Wigboldus, Langner et al. 2008), thus reflecting more global affective associations with sex. These words were controlled for length and frequency. With respect to the validity, the stIAT's strength lies in high effect sizes due to double opposing categories often leading to slower reaction times (the categorization decision requires effort as there are several possibilities to consider).

Picture Association Task (PAT)

This task, developed by van Leeuwen and Macrae (2004), is based on the Affective Priming Task (e.g., Bargh, Chaiken, Govender, et al. 1992; Fazio, Sanbonmatsu, Powell, et al. 1986; Hermans, De Houwer, & Eelen, 1994) where target words are preceded by another word or image that influences the categorisation speed of the target word. In the PAT, however, target words and images appear simultaneously. In the PAT used in this study, subjects are presented with positive or negative words superimposed on either sexual or neutral pictures (Brauer, van Leeuwen, Janssen, et al. submitted). They are instructed to categorize the words as fast as possible as either positive or negative by pressing one of two computer keys. Subjects are further instructed to focus on the words that appeared on the screen and not to attend to the background images as these are of no importance for the task and the categories to which the pictorial stimuli belong (sex, neutral) are not explained. Thus, the PAT captures the unintentional influence of the affective value of the pictorial background stimuli on task performance. The time to select the correct response to the words (positive or negative) is influenced by the match between the valence of the word and the valence of the background image (sex or neutral), thereby revealing indirectly the valence of the picture for the subjects. The word categories consist of 10 positive words and 10 negative words. Whereas for the stIAT general positive and negative words are selected (e.g., peace, respect, war, hate), the PAT consists of positive and negative words that are applicable to a sexual situation, but that do not exclusively refer to sexual experiences (e.g., enjoyable, wonderful, dirty, disgusting) in order to create a conceptual overlap between the content of the words and the content triggered by the sexual pictures. These words are taken from a pilot study in the Netherlands in which female subjects (N=20) were asked to indicate on a 7-point Likert scale for each positive and negative word how well it described a positive or a negative sexual situation, respectively (Brauer & Laan, 2008). The words appear at one of four randomized locations on the picture to avoid expectation-related responses and to make sure subjects would move their eyes over the image. The sexual pictures were taken from another study on implicit associations with sexual stimuli in women with dyspareunia (Brauer, de Jong, Huijding et al., 2009). These pictures display a variety of sexual acts (e.g., kissing, cunnilingus, fellatio, coitus). Based on each sexual picture, a control picture was created by scrambling the sexual image, leaving a neutral stimulus. All pictures are standardized to 600×480 pixels and matched for brightness and contrast. Each stimulus remains on the screen until subjects make a decision or until 3,000 ms has elapsed. After 10 practice trials, 80 experimental trials are presented. Each word is paired randomly with a sexual picture and a neutral picture, resulting in four different combinations each presented 20 times: positive words and sexual images, negative words and sexual images, positive words and neutral images, negative words and neutral images. The order of presentation of the trials is counterbalanced within, and response key mappings (i.e., positive/negative or negative/positive) are counterbalanced across subjects. The computer records the accuracy and latency of each response. With respect to validity, the strength of the PAT is that it is not sensitive to a possible interpretation bias due to the need to attend to the different stimulus categories at the same time, as is the case in the stIAT.

Dot Probe Task (DOT)

The dot-probe task (DOT) assesses attentional preference for sexual and neutral visual stimuli. In this task, subjects are shown two images side by side on a computer screen for 500 ms. When the two images disappear, a target stimulus represented by a small dot appears in the place of one of the images. Subjects are asked to indicate the location (side) of the dot. Mean RTs are calculated for three categories: 1) neutral neutral 2) neutral sex with the dot under neutral 3)

neutral sex with the dot under sex. If reaction times are faster when the dot appears in the place of a certain class of stimuli this indicates an attentional bias towards this class of stimuli.

Psychophysiological Testing

Genital Response (VPA)

Psychophysiological testing consists of assessment of genital response (vaginal pulse amplitude) and subjective sexual arousal during sexual to self-induced erotic fantasy (3 min), a low-intensity erotic film clip (5 min), and a high-intensity erotic film clip (5 min) (Laan et al., in preparation). The erotic conditions are separated by variable interstimulus intervals during which subjects complete a concentration task (simple arithmetic problems) to allow for return-to-baseline. The erotic stimulus testing is preceded by a 8 min neutral film to establish baseline levels. VPA is measured using a vaginal photoplethysmograph developed by Bert Molenkamp (Technical Support, Department of Psychology, University of Amsterdam) based on instruments initially developed by Sintchak and Geer (1975). The light source (3 mm LED, $\lambda$=620 nm) and optical sensor (Texas Instruments TSL250) are produced in batches of 100, resulting in all photoplethysmographs used in this study having nearly equal electronic characteristics. A signal-conditioning amplifier separates the VPA from the direct current component using a 12 dB/octave, 0.7-Hz filter. Additional filtering for VPA is 24 dB/octave, 0.4 Hz high-pass. The VPA signal is digitalized at 100 Hz with a Keithley KPCI3107 A/D converter, running on a Windows 2000 PC system. Depth of the probe and orientation of the light source is controlled by a device (a 9-×2-cm FDA-approved perspex plate) attached to the cable within 5 cm of the optical sensor. Subjects are instructed to insert the probe until the plate touched their labia. The probe and plate are sterilized according to standard department protocol.

Sexual Feelings and Affect (SAO).

Prior to and immediately after erotic stimulus subjects fill out a questionnaire measuring sexual feelings and affect during sexual stimulation, consisting of 5 scales: sexual arousal (Cronbach's $\alpha$=0.87); genital sensations (Cronbach's $\alpha$=0.96); sensuality (Cronbach's $\alpha$=0.73); positive affect (Cronbach's $\alpha$=0.93); and negative affect (Cronbach's $\alpha$=0.65). Each question is preceded by the sentence: "During the film, I felt:" after which a positive, negative, physical or sexual experience is described, for instance, pleasant; worried; genital pulsing or throbbing; sexually aroused. The items are measured on a 1 (not at all) to 7 (intensely) scale.

Acute Female Sexual Desire (AFSDQ)

Prior to and following psychophysiological testing subjects fill out the Acute Female Sexual Desire Questionnaire (Laan, Heiman, unpublished). This questionnaire assesses sexual interest in erotic stimuli and has shown to discriminate between women with acquired HSDD and sexually functional controls (Laan et al., in preparation).

Statistical Methodology

Calculation of Pharmacokinetic Parameters $C_{min}$, $C_{max}$, and $t_{max}$ are taken from the actual measured values. Values are determined relative to the testosterone administration time in treated subjects.

Area under the concentration curve (AUC) are estimated for the 0 to 24 hour time interval, as well as the BID dosing intervals, using the trapezoidal rule.

PK evaluations after Day 1 evening dose for testosterone gel formulations of the invention and placebo and Day 3 evening dose for testosterone gel formulations of the invention, placebo and Intrinsa® patch (which was applied on Day 1)—AUC, concentrations of total and free testosterone, DHT, estradiol, SHBG. Analyses of $C_{avg}$, $C_{min}$, $C_{max}$, $t_{max}$, $AUC_{0-\tau}$, PTF, and PTS. $C_{avg}$ are calculated for the 12 hour period as well as $\tau$ when appropriate. For subjects on Intrinsa®, a 24 hour calculation is performed.

The average concentration in the dosing interval ($C_{avg}$) is calculated from the AUC using the following formula: $C_{avg}=AUC_{0-\tau}/\tau$, with $\tau$=dosing interval time.

Peak Trough Fluctuation (PTF) and Peak Trough Swing (PTS) are calculated as follows:

$$PTF=(C_{max}-C_{min})/C_{avg}$$

$$PTS=(C_{max}-C_{min})/C_{min}$$

Percent time that the plasma testosterone concentration is above, within, and below the reference range of 10 to 70 ng/dl, is calculated.

Statistical Analysis of Pharmacodynamic Data stIAT:

Incorrect responses are excluded from analyses. In addition, RTs shorter than 300 ms or longer than 3000 ms are excluded from analyses. With respect to the stIAT data, Wigboldus, Holland & van Knippenberg (2005) is followed in that, for each subject, the median response latency of the correct responses to the attribute items in congruent and incongruent blocks is used. Following this, median reaction times of the two experimental blocks are subtracted from one another to obtain a stIAT effect (i.e., stIAT effect=median (Sex/Negative)–median (Sex/Positive)). Negative stIAT effects indicate relatively stronger negative associations with sexual stimuli.

The stIAT effect is analyzed with an analysis of variance with fixed factor treatment, group (HSDD and SA) and the interaction treatment by group. The contrasts are calculated within the model.

PAT:

Median response latencies of the correct responses are calculated, following van Leeuwen and Macrae (2004). To correct for baseline reactions to positive and negative words, difference scores are calculated by subtracting RTs for neutral words superimposed on sexual pictures from positive words superimposed on sexual pictures. The same is done for negative words superimposed on sexual and neutral pictures (i.e., Sex/+=RT (sex/positive words)–RT (neutral/positive words) and Sex/–=RT (sex/negative words)–RT (neutral/negative words. Sex/+<Sex/–=automatic positive associations with sex).

The two PAT variables (RT positive and RT negative) are analyzed with an analysis of variance with fixed factors treatment, group (ANOR) and group by treatment. The contrasts will be calculated within the model.

DOT:

For each subject the difference between mean RT for the category neutral sex with the dot under sex and the mean RT for the category neutral sex with the dot under neutral is calculated to obtain a DOT effect (i.e., DOT effect=mean neutral sex with dot under neutral–mean neutral sex with dot under sex). Higher DOT scores indicate relatively stronger attention for sexual stimuli.

The DOT effect is analyzed with ah analysis of variance with fixed factor treatment, group (ANOR) and the interaction treatment by group. The contrasts are calculated within the model.

VPA:

After VPA artefact deletion, done by a computer program developed Bert Molenkamp (Technical Support, Department of Psychology, University of Amsterdam), peak-to-trough amplitude is calculated for each remaining pulse.

VPA is averaged every 30 seconds during several conditions: neutral film (8 min), self induced erotic fantasy (3 min), low intensity erotic film clip (5 min) and high intensity erotic film clip (5 min). All conditions are offered twice: once 0.5 hours after application of the nasal gel and once 4.5 hours after application of the nasal gel.

VPA during the erotic fantasy, the low intensity film and the high intensity film are analyzed separately and the different moments (0.5 hours after and 4.5 hours after dosing) are also be analyzed separately, resulting in 6 analyses. VPA during a condition and a moment is analyzed with a mixed model analysis of variance with fixed factors treatment, group (ANOR), time, group by treatment, treatment by time and random factor subject and the average VPA score during the neutral film as covariate. Contrasts are calculated within the model.

SAQ:

For each of the five SAQ scale mean response during a condition and a moment are analyzed with an analysis of variance with factors treatment, group (ANOR) and group by treatment, with the score prior to sexual stimuli as covariate. Contrasts are calculated within the model.

AFSDQ:

ASFDQ score after erotic stimulation during a moment is analyzed with an analysis of variance with factors treatment, group (ANOR), and group by treatment; and the score prior to sexual stimuli as covariate. Contrasts are calculated within the model.

If necessary to meet requirements for analysis of variance data is log-transformed. Results are back-transformed and reported as % change.

Graphs of least square means estimates over time by treatment are presented with error bars indicating the upper and lower 95% confidence interval for the highest and lowest profile respectively. Least square means of the contrasts are tabulated.

If analyses are not feasible according to the described models with the given data, analyses are adjusted. If considered useful extra exploratory analyses are conducted.

Statistical Analysis of Safety Data

Nasal Tolerance:

Nasal tolerance data is presented in summary tables. No statistical analysis will be performed.

Vital Signs and Clinical Laboratory Parameters:

A table summarizing all laboratory test values and changes from Baseline is presented for each treatment group. In case parameters are ±20% of their reference range, the clinical significance of these findings are evaluated.

The results of this analysis is presented in FIGS. 2, 3 and 7-8. FIGS. 3, 9-11 show or compare the results between the effects of the testosterone gel nasal formulations of the invention on subjects diagnosed with anorgasmia or HSDD.

Example 9

Pharmacokinetic ("PK") and Pharmacodynamic ("PD") Study Concerning 53 Anorgasmia Women and the Three Different Testosterone Bio-Adhesive Gel Formulations of the Invention (0.15%-, 0.45% and 0.6% Testosterone by Weight of the Gel Formulation, as Reported in Examples 1-5)

Figure 14:
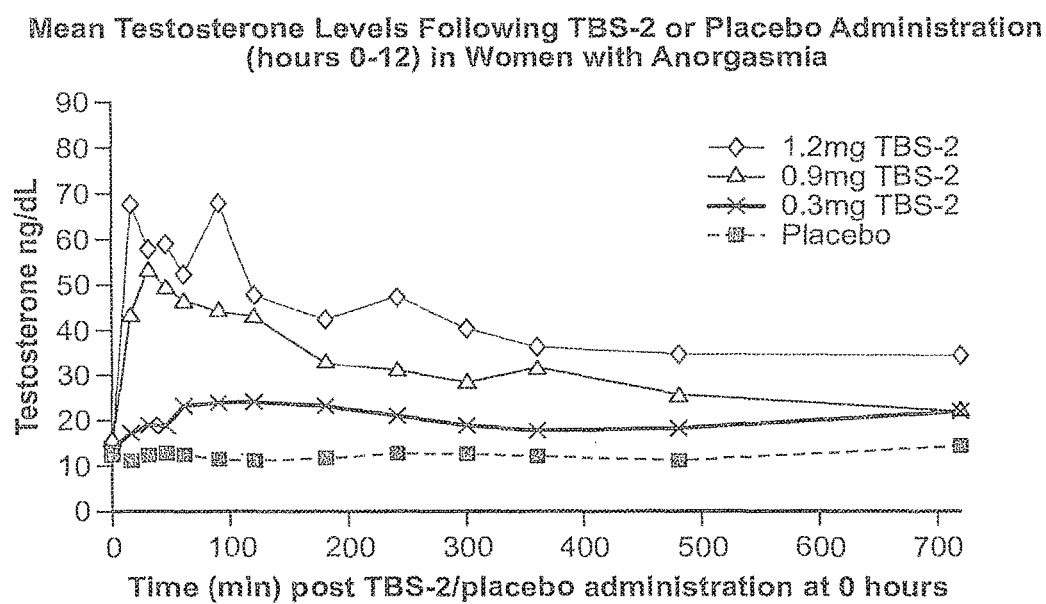
FIG. 14 concerns mean testisterone levels following TBS-2 high, TBS-2 medium and TBS-2 low dose administration or placebo administration (hours 0-12) in women with anorgasmia. In this pharmacokinetic study, as described in Example 9, three different dosage strengths of TBS-2 testosterone bio-adhesive gel formulations of the invention are adminstered intranasally to a hybrid group of 12 healthy and anorgasmic women.

Objective:

As shown in FIG. 14, this PK and PD study is to assess the serum testosterone pharmacokinetic profile and the pharmacodynamic response measuring Vaginal Pulse Amplitude ("VPA") following a single dose administration of each of the testosterone bio-adhesive gel formulations of the invention (0.15%-, 0.45% and 0.6% testosterone by weight of the gel formulation, as reported in Examples 1-5), as compared to placebo, in women with anorgasmia.

Method:

A total of 12 women with anorgasmia (n=12) are included in this placebo and active comparator PK and PD study. Each women receives four different single intranasal doses of 100 µl per nostril administered via a unit-dose syringe on four different days (that is, each of the 12 women in this study receives a TBS-2 high dose (1.2 mg—0.6% by weight testosterone—0.6 mg/100 µl/nostril), a TBS-2 medium dose (0.9 mg—0.45% by weight testosterone—0.45 mg/100 µl/nostril) or a TBS-2 low dose (0.3 mg—0.15% by weight testosterone—0.15 mg/100 µl/nostril), and placebo TBS-2 (anorgasmia cohort). Frequent PK serum samples are collected from each woman during the first 12 hours after intranasal dose administration. Initial pharmacodynamic efficacy is explored using vaginal pulse amplitude (VPA). VPA is a measure of blood flow to the vagina (engorgement). Safety is monitored throughout the PK and PD study.

Results:

The PK results show that there is an increase in plasma testosterone levels with increasing dose levels. See FIG. 14. Mean concentrations of plasma testosterone 0-12 hours after dosing are: (a) TBS-2 high dose (1.2 mg—0.6% by weight testosterone—0.6 mg/100 µl/nostril)—about 70 ng/dL after about the first 100 minutes of administration, about 50 ng/dL after about the first 250 minutes of administration, and about 40 ng/dL after about 350 minutes following administration and thereafter; (b) TBS-2 medium dose (0.9 mg—0.45% by weight testosterone—0.45 mg/100 µl/nostril)—about 55 ng/dL after about the first 25 minutes of administration, about 35 ng/dL after about the first 250 minutes of administration, and about 35-30 ng/dL after about 350 minutes following administration and thereafter; and (c) TBS-2 low dose (0.3 mg—0.15% by weight testosterone—0.15 mg/100 µl/nostril)—about 28 ng/dL after about the first 100 minutes of administration, about 23 ng/dL after about the first 250 minutes of administration, and about 20 ng/dL after about 350 minutes following administration and thereafter.

The testosterone $C_{max}$ and $C_{avg}$ for testosterone following single dose administration for each of the three TBS-2 dosage strengths do not exceed the normal testosterone serum level in women (3-80 ng/dL).

For all TBS-2 dosage strengths, the testosterone level returns to baseline following administration of the single dose.

As to the PD aspect of the study, there are favorable statistically significant differences in VPA response in the women for each of the TBS-2 dosage strengths vs. placebo at 0.5 hours and at 4.5 hours post-dose.

Conclusion:

It is presently believed that the TBS-2 nasally applied testosterone bio-adhesive gels of the preset invention (i) may be uniquely taken on a prn basis, i.e., on demand, (ii) have an ideal safety profile, i.e., there appears to be no androgen-related side effects, there is a low testosterone drug load, and (iii) present no risk of testosterone transference.

Example 10

Vibrotactile Stimulation Study ("VTS") of 56 Women with Anorgasmia

Objective:

To evaluate the effect of a single dose of high dose TBS-2 (1.2 mg—0.6% by weight testosterone—0.6 mg/100 µl/nostril, as reported in Examples 1-5) on orgasm at 0.5, 2.0 4.0 and 8.0 hours post-dose administration in 56 women with anorgasmia. Another objective of this study is to evaluate the time to orgasm and the quality of the orgasm following TBS-2 intranasal administration. Further, an objective of this VTS study is to determine the effect of high dose TBS-2 on arousal, sensuality and genital stimulation and to assess safety. See FIG. 15.

Method:

This VTS study is a single-center, randomized, single-blind, placebo-controlled, five-arm parallel group study using vibrotactile stimulation that is combined with visual sexual stimulation (n=56). See FIG. 15.

In accordance with this VTS study protocol, each women is administered an intranasal single high-dose of TBS-2 (1.2 mg—0.6% by weight testosterone—0.6 mg/100 µl/nostril).

Figure 15:
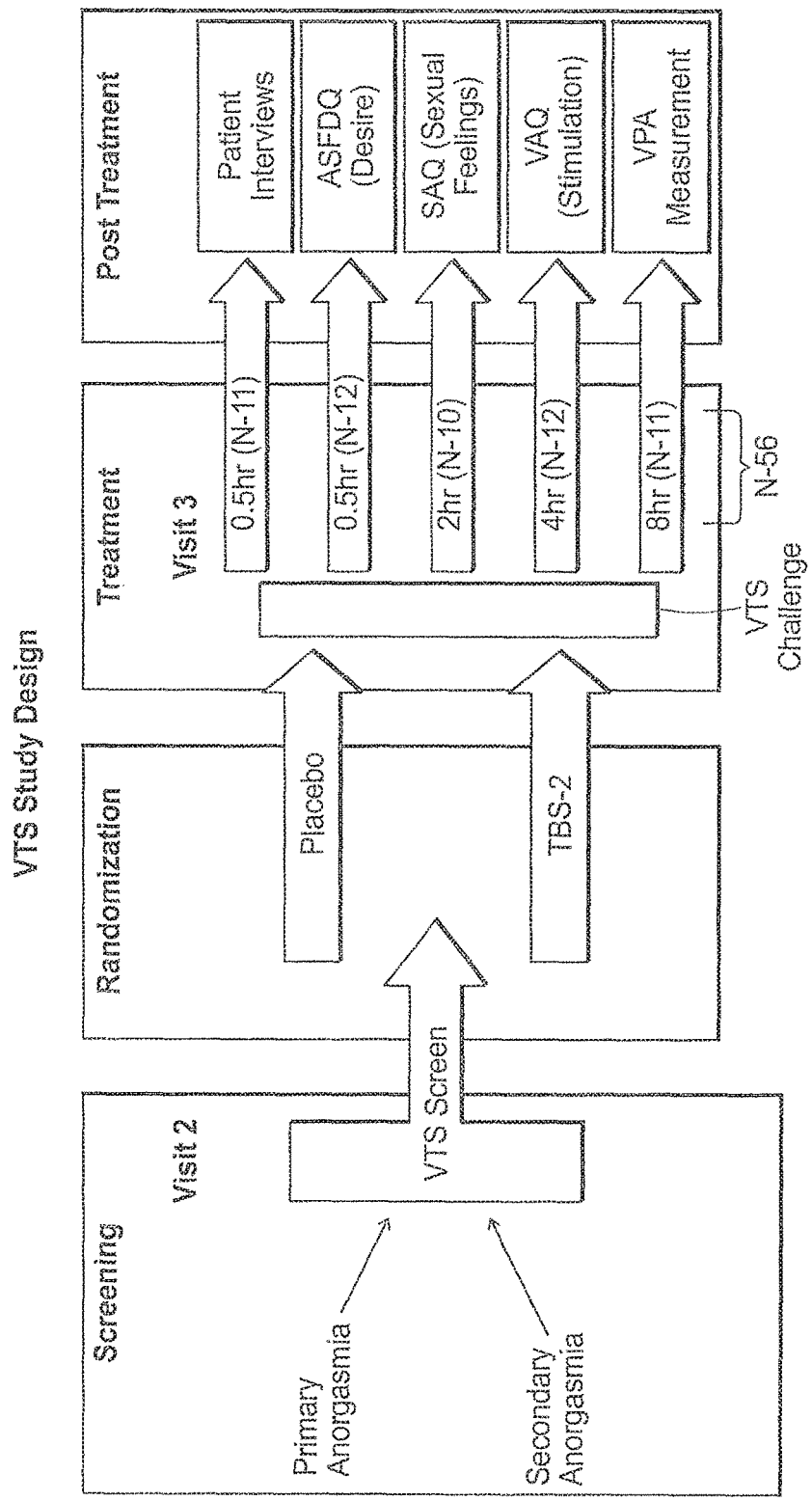
FIG. 15 depicts a study design (Example 10), in which 56 anorgasmic women are enrolled for a Vibrotactile Stimulation Study (VTS) that concerns the three different testosterone bio-adhesive gel formulations of the invention, i.e., the 0.15%-, 0.45% and 0.6% testosterone by weight of the gel formulation, as reported in Examples 1-5.

The demographics for this VTS study are, see FIG. 15:
59 women randomized, 56 completed the study
All 3 drop-outs due to protocol violations
Average age 27.8 years
87.5% Primary Anorgasmia, 12.5% Secondary Anorgasmia
All randomized subjects met entrance criteria for Martial Quality and Depression
3% of patients (3 out of 97) excluded due to orgasm at Visit 2

Figure 16:
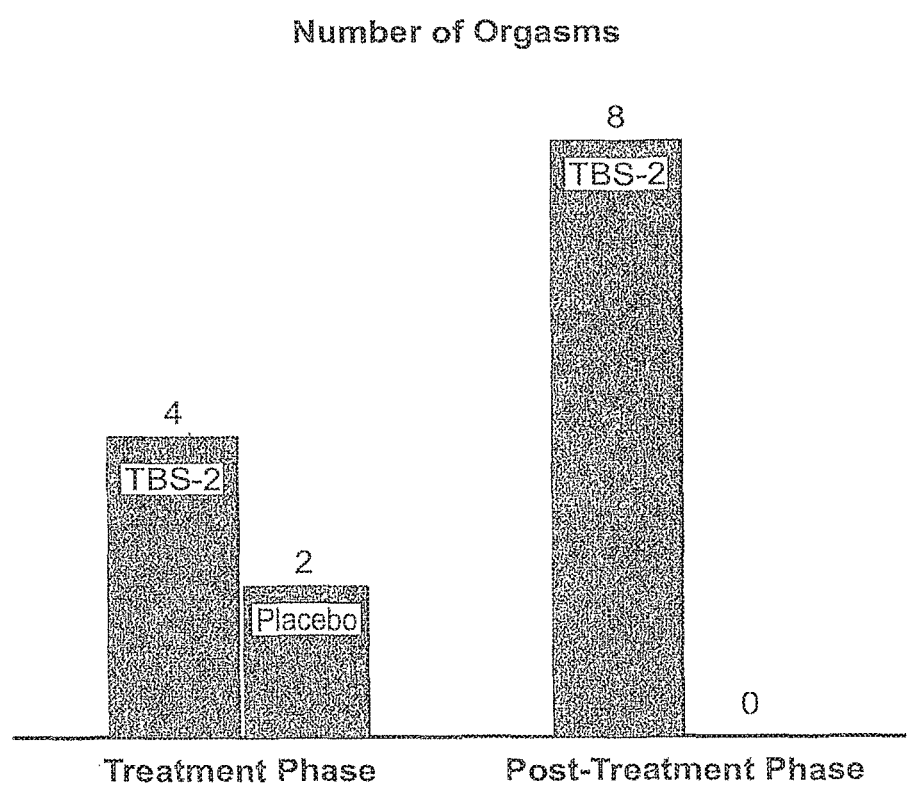
FIG. 16 depicts orgasm result of the VTS study of Example 10, wherein the number of orgasms achieved during the treatment phase and the post-treatment phase are compared.

Results:

As shown in FIG. 16, more women report, treated with high dose TBS-2, report orgasms, as compared to placebo. In fact, during the 4 weeks post-treatment phase, women who are treated with high dose TBS-2 8 report a total of 8 orgasms, as compared to no orgasms for those women who receive placebo. With respect to the treatment phase, women who are treated with high dose TBS-2 8 report a total of 4 orgasms, as compared to 2 orgasms for those women who receive placebo. See FIG. 16.

Figure 17:
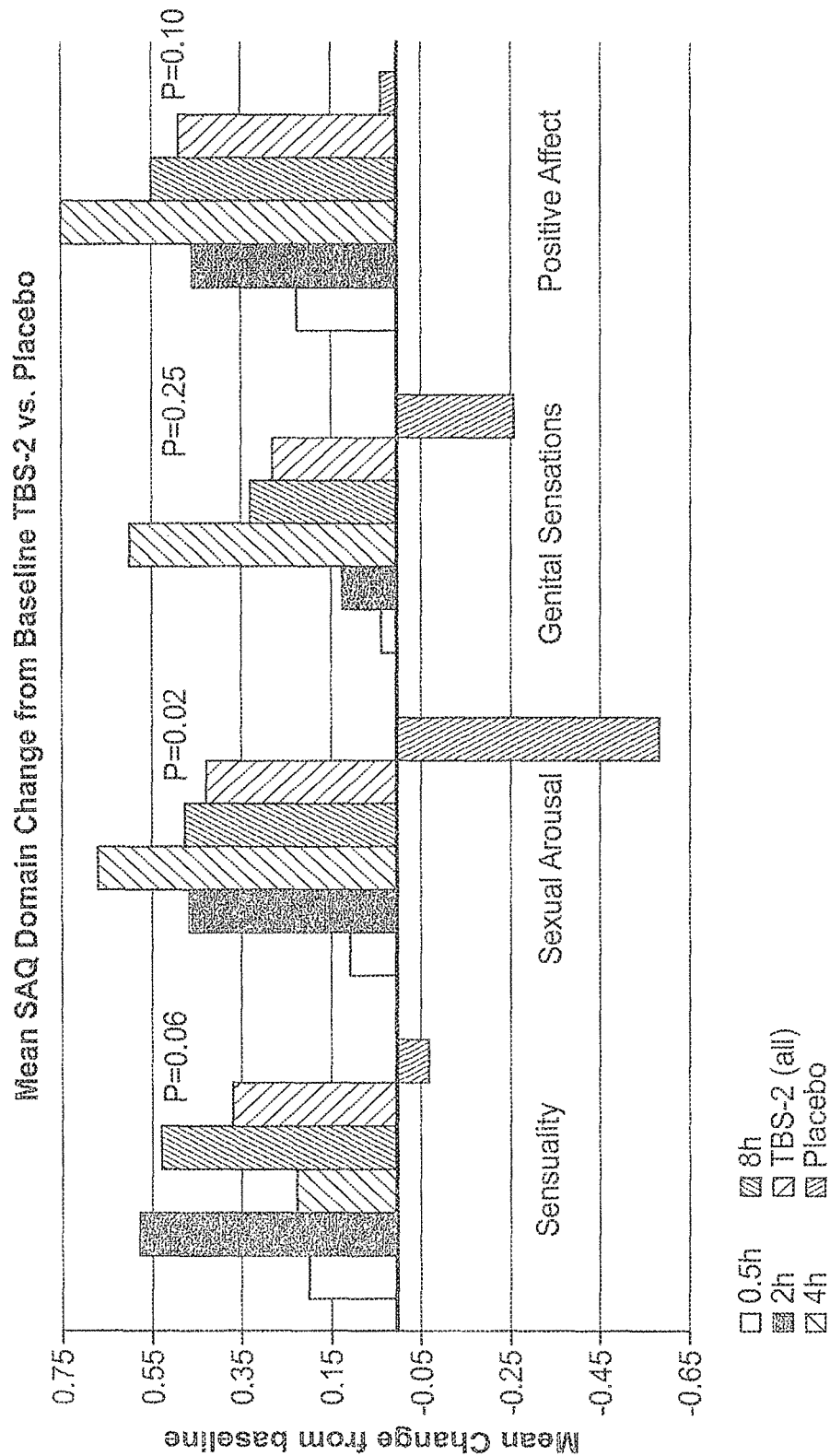
FIG. 17 depicts sexual response results of the VTS study of Example 10 for the three different testosterone bio-adhesive gel formulations of the invention, i.e., the 0.15%-, 0.45% and 0.6% testosterone by weight of the gel formulation, as reported in Examples 1-5, as compared to placebo.
Figure 18:
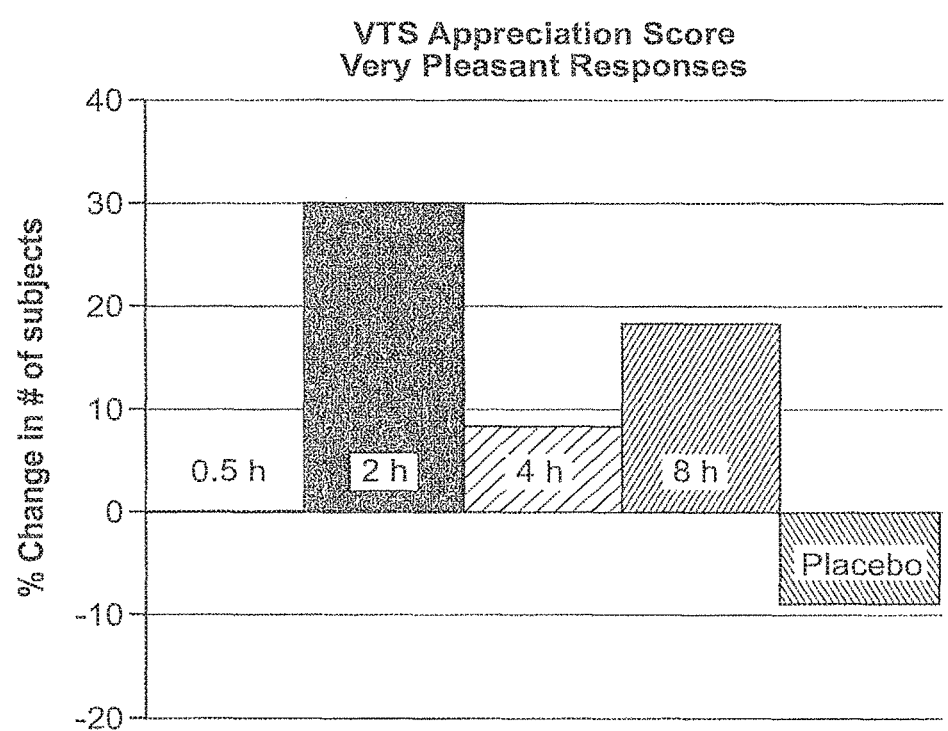
FIG. 18 depicts the VTS appreciation score of the VTS study of Example 10 for the three different testosterone bio-adhesive gel formulations of the invention, i.e., the 0.15%, 0.45% and 0.6% testosterone by weight of the gel formulation, as reported in Examples 1-5, as compared to placebo.

Additional VTS study results and findings include:
The time to orgasm ranges from 12.17 minutes to 18.22 minutes following high dose TBS-2 administration;
The orgasms by women, who are administered TBS-2, are reported as more pleasant and more intense as compared to the orgasms by those women who are administered placebo;
More TBS-2 women report high arousal compared to Placebo (83.3% vs. 16.7%). See FIGS. 17 and 18;
TBS-2 women report more sexual desire (AFSDQ Scores). See also FIGS. 17 and 18;
Positive response to stimulation more pronounced for TBS-2. See FIG. 18;
As reported in Example 9, there is statistically significant differences in VPA between TBS-2 high, medium and low dose and Placebo (mean change from baseline);
Total testosterone levels are increased to upper end of normal (mean about 66.7 ng/dL);
Mean free testosterone levels are about 6.35 µg/mL (chronic treatments achieve about 3.1-4.0 µg/mL);
Other Findings—Patient Feedback
(a) Women prefer home setting
(i) thoughts about hospital setting, experimenter, are distracting
(ii) still a little tense, because of the setting
(iii) home is a better setting
(iv) at home, more relaxed
(v) a little limited in movement due to position
(b) Partner Involvement Important to some women
(i) with real life partner, it would be better
(ii) felt guilty he is (partner) is not here
(iii) nicer with a man Safety:
No Serious Adverse Events
Total of 18 Adverse Events reported
(i) mild and resolved by end of study
(ii) 5 Not Related to study medication
(iii) 3 of unknown etiology (Possibly Related)
(iv) no association with active treatment and adverse events
(v) placebo had 50% of women report adverse events vs. 19.1% for TBS-2
No difference in endorcinology results (SHBG, Albumin, Hemogolobin)

Conclusion
Adequate clitoral stimulation alone is not sufficient to treat anorgasmia
The data from Examples 10 and 11 point to the success of TBS-2 pharmaceutical intervention in addition to effective stimulation
TBS-2 data indicates a positive response between 2 and 8 hours post-dose
TBS-2, when administered prn, is believed to elicit and enhance sexual response in women
TBS-2 is believed to maintain total and free testosterone levels in the normal range
TBS-2 is believed to be safe and none of the adverse events commonly observed with chronic testosterone treatments are observed
Comfortable environment (home setting) and partner interaction may play a role in achievement of orgasm Example 11

1. TITLE

An Open-Label, Single and Multiple-Application of Intranasal Testosterone Gel (TBS-2) in Healthy Pre-Menopausal Female Subjects at Three Dose Levels

2. SYNOPSIS

The primary objective is to assess the bioavailability of total testosterone through pharmacokinetic (PK) profiles obtained following single administration of an intranasal application of TBS-2 at doses of 600 µg, 1200 µg, and 1800 µg, and multiple administration of 1200 µg of TBS-2 given three times a day (t.i.d.) for 3 days. TBS-2 is a bioadhesive intranasal testosterone gel.

The secondary objectives are to assess the bioavailability of free testosterone, dihydrotestosterone, sex hormone-binding globulin (SHBG), and estradiol through PK profiles obtained following single administration of an intranasal application of TBS-2 at doses of 600 µg (0.24%), 1200 µg (0.48%), and 1800 µg (0.72%), and multiple administration of 1200 µg (0.72%) TBS-2 given for 3 days (t.i.d. for the first 2 days, and once in the morning of the third day) and to assess the safety of TBS-2

A. Methodology

This was a phase 1, single-center, randomized, open-label parallel-group study designed to evaluate the safety, tolerability, and PK of TBS-2 in healthy, normal-cycling adult women. Subjects were randomly assigned on a 1:1:1 basis to 1 of 3 treatment groups (Cohort 1, Cohort 2, or Cohort 3) during Period 1 and were administered a single dose of an intranasal application of TBS-2 at doses of 600 µg, 1200 µg, or 1800 µg (single doses of 300 µg, 600 µg, and 900 µg per nostril). At the end of Period 1, a total of 8 subjects sampled from these 3 cohorts, who were willing and able to continue with the multiple-dose portion of the study were selected to participate in Period 2. During Period 2, subjects were administered 1200 µg TBS-2 (600 µg per nostril) t.i.d. for 2 days and once on the morning of the third day. Subjects were screened (Visit 1) for eligibility up to 3 weeks prior to dosing in Period 1, and were admitted to the Clinical Research Unit (CRU) at 0700 hours on the day prior to dosing (Visit 2, Day 1). On Day 2, subjects were administered a single dose of TBS-2 and remained in the CRU for 72 hours post-dose (Day 4) for safety monitoring and PK assessments. During Period 2, subjects were admitted to the CRU at 0700 hours on the day of dosing (Visit 3, Day 1). On Days 1 and 2, subjects were administered TBS-2 at 0800 hours (±30 minutes), 1600 hours (±30 minutes), and 2400 hours (±30 minutes). On Day 3, subjects were administered TBS-2 at 0800 hours (±30 minutes).

During Period 1, blood samples for determination of baseline testosterone (free and total), SHBG, dihydrotestosterone (DHT), and estradiol concentration were collected on Day 1 at 0745 hours and then at 15, 30, and 45 minutes and at 1, 1.5, 2, 4, 6, 8, 12, 16, 20, and 23.5 hours relative to an 0800 hour clock time. Blood samples for determination of testosterone (free and total), SHBG, dihydrotestosterone, and estradiol plasma concentration were collected on Day 2 (15, 30, and 45 minutes and 1, 1.5, 2, 4, 6, 8, 12, 16, and 20 hours post-dose) and Day 3 (24, 32, 40, and 48 hours post-dose) during the confinement period.

During Period 2, a blood sample for baseline testosterone (free and total), SHBG, DHT, and estradiol concentration was collected at 0745 hours (i.e., 15 minutes prior to study drug administration). Blood samples for determination of testosterone (free and total), SHBG, dihydrotestosterone, and estradiol concentration were collected on Day 1 (pre-dose [15 minutes prior to dosing] and at 1545 and 2345 hours), Day 2 (1545 and 2345 hours), Day 3 (15, 30, and 45 minutes and 1, 1.5, 2, 4, 6, 8, 12, 16, and 20 hours), and Day 4 (24, 32, 40, and 48 hours) during the confinement period.

Other assessments performed during the study included the monitoring of adverse events (AEs), clinical laboratory evaluations (chemistry [including hormone profile], hematology, and urinalysis), vital signs assessments (systolic and diastolic blood pressure [BP], heart rate [HR], respiratory rate [RR], and body temperature), and physical examinations. In addition, otorhinolaryngological examination findings, 12-lead electrocardiogram (ECG) readings, medical history, and concomitant medication use were recorded.

B. Number of Subjects (Planned and Analyzed)

Planned: A total of 24 subjects were planned to be enrolled.

Enrolled: A total of 24 subjects were enrolled and randomly assigned to treatment in Period 1: 8 subjects in Cohort 1, 8 subjects in Cohort 2, 8 subjects in Cohort 3. A total of 8 subjects sampled from these 3 cohorts, who were willing and able to continue with the multiple-dose portion of the study, were selected to participate in Period 2.

Analyzed: All 24 subjects were included in the safety analyses and 24 subjects were included in the PK analyses.

C. Diagnosis and Main Criteria for Inclusion

Healthy, normal-cycling women between the ages of 18 and 40 years (inclusive) who were premenopausal, had a body mass index (BMI) of 18.5 to 35 kg/m$^2$ (inclusive), met all of the inclusion and none of the exclusion criteria, and provided informed consent were included in the study.

D. Test Product, Dose and Mode of Administration, Batch Number

The TBS-2 used in this study was an intranasal testosterone gel supplied in prefilled dispensers with 0.24% testosterone gel to deliver a single intranasal dose of 300 µg of Testosterone per nostril (Cohort 1), 0.48% testosterone gel to deliver a single intranasal dose of 600 µg of testosterone per nostril (Cohort 2 [single-dose] and Multidose group), and 0.72% testosterone gel to deliver a single intranasal dose of 900 µg of testosterone per nostril (Cohort 3). The lot numbers of TBS-2 drug substance used in this study were IMP11008, IMP11009 and IMP11010.

The compositions of the three different concentrations of the drug product to be used in this clinical trial are provided in the CMC Section below and in Tables 3.2.P.1-1-3.

E. Duration of Treatment

The study involved 1 period for Cohorts 1, 2, and 3 and the duration of individual subject participation from the start of screening until the post-study visit, was approximately 25 days. This study involved 2 periods totaling 30 to 36 days for the Multi-dose group.

F. Criteria for Evaluation

Safety: Safety was assessed throughout the study and included the monitoring of AEs, clinical laboratory evaluations (chemistry [including hormone profile], hematology, and urinalysis), vital signs, and 12-lead ECGs. Physical and otorhinolaryngological examinations were performed and medical history and concomitant medication use were recorded.

Pharmacokinetics: Whole blood samples for determination of plasma concentrations of testosterone (free and total), SHBG, DHT, and estradiol were collected at specified time points. Actual sampling time points were recorded and used for PK calculations. Pharmacokinetic parameters for testosterone (free and total), SHBG, DHT, and estradiol were calculated by standard non-compartmental methods for all subjects as data permitted. The PK parameters evaluated for plasma concentrations of testosterone (free and total), SHBG, dihydrotestosterone, and estradiol following the single-dose cohorts (Cohorts 1, 2, and 3) included area under the plasma concentration time curve from time zero to the last measurable concentration time point ($AUC_{0-t}$), area under the plasma concentration time curve from time zero to infinity ($AUC_{0-\infty}$), maximum concentration observed after dosing ($C_{max}$), time of observed $C_{max}$ relative to the time of dosing ($t_{max}$), terminal elimination rate constant ($\lambda_z$), and elimination half-life ($t_{1/2}$). The PK parameters evaluated for plasma testosterone (free and total), SHBG, dihydrotestosterone, and estradiol concentrations following the multiple-dose cohort included area under the concentration-time curve from time zero to the dosing interval ($AUC_{0-\tau}$, where $\tau$=8 hours), $C_{max}$, $t_{max}$, minimum concentration over a dosing interval during multiple dosing ($C_{min}$), pre-dose concentration determined immediately before a dose at steady state ($C_{pd}$), average steady-state concentration ($C_{avg}$), % peak to trough fluctuation (PTF), and % peak to trough swing (PTS).

G. Statistical Methods

This study evaluated the PK properties as well as the safety and tolerability of TBS-2. Power calculations were not performed. The sample size for this study was not determined on the basis of statistical hypothesis testing. Based on typical, early-stage PK studies, groups of 8 subjects per cohort provided adequate clinical information to satisfy the objectives of the study. Data were summarized by using descriptive statistics (sample size, mean, median, standard deviation [SD], minimum, and maximum) for each of the safety variables by treatment group and overall. Data from all visits during the study were displayed in the data listings.

Concentration-time data for 5 analytes (testosterone [total and free], SHBG, dihydrotestosterone, and estradiol) were determined by a validated assay method and PK parameters were calculated. Actual sampling time points were recorded and used in calculation of the actual elapsed time from dose to sample for PK calculations. As each administration was to each of the nostrils, the time of dosing was the time of the first nostril administration. Baseline analyte concentrations from the 24-hour pre-dose profile were subtracted from the time-matched analyte concentrations following dose administration before calculation of the PK parameters.

Individual PK parameters were estimated for each subject's profile in the PK population by using WinNonlin (Pharsight Corporation) and were displayed in the data listings. Data were summarized by using descriptive statistics (mean, SD, % coefficient of variation [CV], confidence interval (CI), median, minimum, and maximum) and are presented by treatment group. Geometric means were included for AUC and $C_{max}$ estimations and were included for some other PK parameters. By using Generalized Linear Model (GLM) procedure in SAS®, an analysis of variance (ANOVA) was performed on natural logarithmic (ln) transformed parameters $AUC_{0-t}$, $AUC_{0-\infty}$, $AUC_{0-\tau}$, $C_{avg}$, and $C_{max}$ and on untransformed parameters $t_{1/2}$, and $\lambda_z$ at the significance level of 0.05. The intrasubject CV was calculated for $AUC_{0-t}$, $AUC_{0-\infty}$, $AUC_{0-\tau}$, and $C_{max}$ by using the ANOVA residual error.

Dose linearity following single-dose administration (Period 1) was assessed after natural-log transformation for the $AUC_{0-t}$, $AUC_{0-\infty}$, and $C_{max}$.

The following Period 1 comparisons for PK parameters were made:

Comparison 1: 600 μg (0.24%) TBS-2 versus 1200 μg 0.48% TBS-2;
Comparison 2: 600 μg (0.24%) TBS-2 versus 1800 μg 0.72% TBS-2;
Comparison 3: 1200 μg (0.48%) TBS-2 versus 1800 μg 0.72% TBS-2.

3. LIST OF TABLES AND FIGURES

Figure 29:
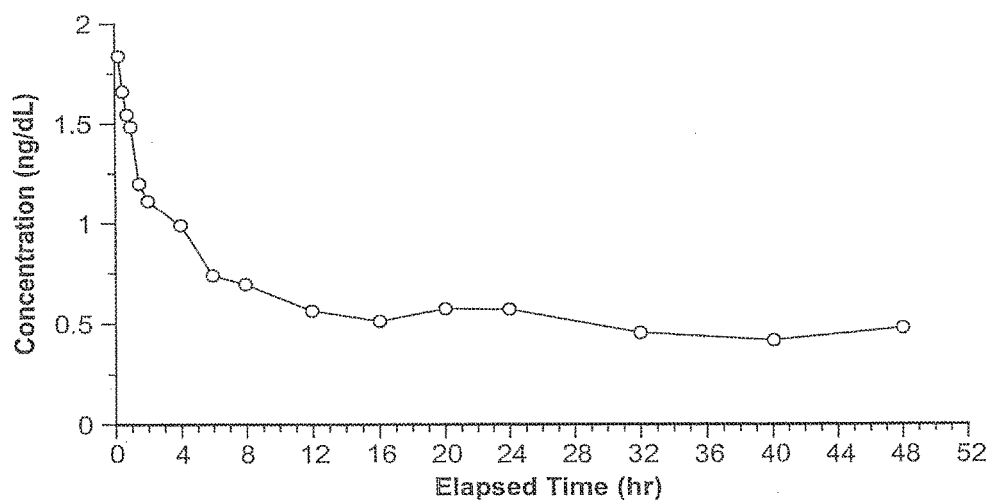
FIG. 29 depicts Mean Free Testosterone Plasma Concentrations (Multi-Dose Population)
Figure 30:
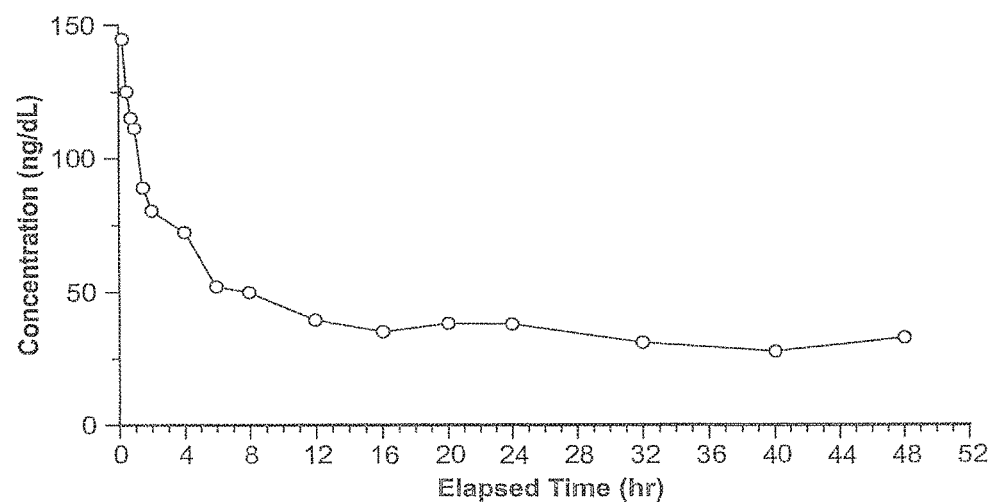
FIG. 30 depicts Mean Total Testosterone Plasma Concentrations (Multi-Dose Population)
Figure 31:
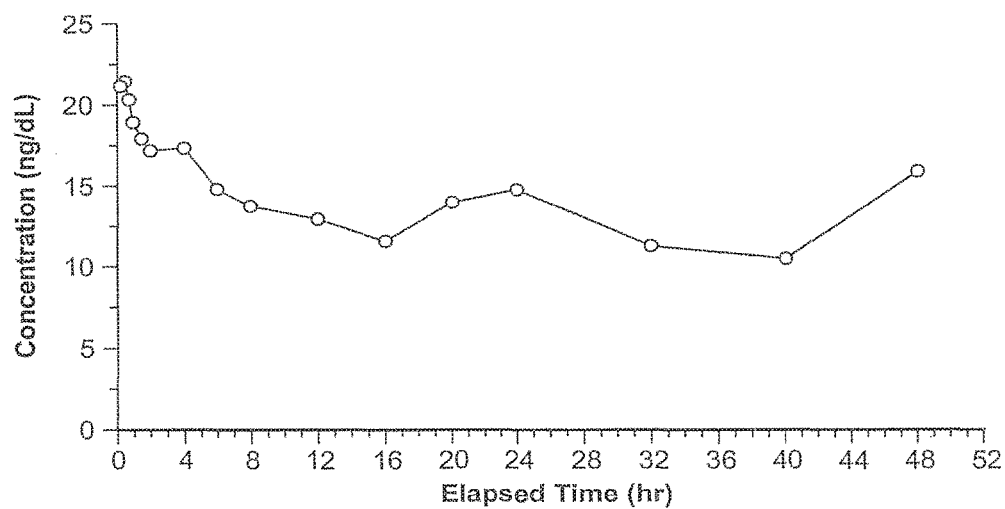
FIG. 31 depicts Mean Dihydrotestosterone Plasma Concentrations (Multi-Dose Population)

Table 9 1: Study Schedule
Table 9 2: Schedule of Pharmacokinetic Sample Collection
Table 11 1: Medical History (Single-Dose Population)
FIG. 19: Mean Corrected Free Testosterone Concentrations (Single-Dose Population)
FIG. 20: Mean Corrected Total Testosterone Concentrations (Single-Dose Population)
FIG. 21: Mean Corrected Dihydrotestosterone Concentrations (Single-Dose Population)
FIG. 22: Mean Corrected Estradiol Concentrations (Single-Dose Population)
FIG. 23: Mean Corrected SHBG Concentrations (Single-Dose Population)
FIG. 24: Mean Observed Free Testosterone Concentrations (Single-Dose Population)
FIG. 25: Mean Observed Total Testosterone Concentrations (Single-Dose Population)
FIG. 26: Mean Observed Dihydrotestosterone Concentrations (Single-Dose Population)
FIG. 27: Mean Observed Estradiol Concentrations (Single-Dose Population)
FIG. 28: Mean Observed SHBG Concentrations (Single-Dose Population)
FIG. 29: Mean Free Testosterone Plasma Concentrations (Multi-Dose Population)
FIG. 30: Mean Total Testosterone Plasma Concentrations (Multi-Dose Population)
FIG. 31: Mean Dihydrotestosterone Plasma Concentrations (Multi-Dose Population)
FIG. 32: Mean Estradiol Plasma Concentrations (Multi-Dose Population)
FIG. 33: Mean SHBG Plasma Concentrations (Multi-Dose Population)
FIG. 34: Spaghetti Concentration Plots with Mean for Free Testosterone Plasma Concentrations (Multi-Dose Population)
FIG. 35: Spaghetti Concentration Plots with Mean for Total Testosterone Plasma Concentrations (Multi-Dose Population)
FIG. 36: Spaghetti Concentration Plots with Mean for Dihydrotestosterone Plasma Concentrations (Multi-Dose Population)
FIG. 37: Spaghetti Concentration Plots with Mean for Estradiol Plasma Concentrations (Multi-Dose Population)
FIG. 38: Spaghetti Concentration Plots with Mean for SHBG Plasma Concentrations (Multi-Dose Population)
Table 11 22: Free Testosterone Summary (Single-Dose Population)
Table 11 23: Total Testosterone Summary (Single-Dose Population)
Table 11 24: Dihydrotestosterone Summary (Single-Dose Population)
Table 11 25: Estradiol Summary (Single-Dose Population)
Table 11 26: SHBG Summary (Single-Dose Population)
Table 11 27: Free Testosterone Summary for Multiple Dose Profile (Multi-Dose Population)
Table 11 28: Free Testosterone Concentration at Baseline (Single-Dose Population)
Table 11 29: Total Testosterone Summary for Multiple Dose Profile (Multi-Dose Population)
Table 11 30: Total Testosterone Concentration at Baseline (Single-Dose Population)
Table 11 31: Dihydrotestosterone Summary for Multiple Dose Profile (Multi-Dose Population)
Table 11 32: Dihydrotestosterone Concentration at Baseline (Single-Dose Population)
Table 11 33: Estradiol Summary for Multiple Dose Profile (Multi-Dose Population)
Table 11 34: Estradiol Concentration at Baseline (Single-Dose Population)
Table 11 35: SHBG Summary for Multiple Dose Profile (Multi-Dose Population)
Table 11 36: SHBG Concentration at Baseline (Single-Dose Population)
Table 11 37: Dose Proportionality Analysis (Single-Dose Population)
Table 11 38: Analysis of Variance for Some Pharmacokinetic Parameters (Single-Dose Population)
Table 11 39: Paired t-Test Results for Pharmacokinetic Parameters AUC0-8 and AUC0-24 for Subjects Who Had 1200 μg TBS-2 in Period 1 and Period 2
Table 12 1: Incidence of Treatment-Emergent Adverse Events by System Organ Class and Preferred Term (Single-Dose Population)
Table 12 2: Incidence of Treatment-Emergent Adverse Events by System Organ Class and Preferred Term (Multi-Dose Population)
Table 12 3: Subjects with Adverse Reactions (Single- and Multi-Dose Populations)

Table 12 4: Subjects with New Abnormal Hematology Laboratory Evaluation Results Post Dose (Single- and Multi-Dose Populations)

Table 12 5: Subjects with New Abnormal Chemistry Laboratory Evaluation Results Post Dose (Single- and Multi-Dose Populations)

Table 12 6: Subjects with New Abnormal Urinalysis Laboratory Evaluation Results Post Dose (Single- and Multi-Dose Populations)

Table 12 7: Subjects with Abnormal Basic Ear, Nose, and Throat Examination Results (Single- and Multi-Dose Populations)

4. GLOSSARY OF ABBREVIATIONS AND TERMS

AE adverse event
ALT alanine transaminase
ANOVA analysis of variance
AST aspartate transaminase
AUC area under the plasma concentration time curve
$AUC_{0-\infty}$ AUC from time zero to infinity
$AUC_{0-t}$ AUC from time zero to the last measurable concentration time point
$AUC_{0-\tau}$ AUC from time zero to the dosing interval (where $\tau=8$ hours) during multi-dose period
$AUC_{0-8}$ AUC from time zero to 8 hours during single-dose period
BMI body mass index
BP blood pressure
BUN blood urea nitrogen
Cavg average steady-state concentration
CFR Code of Federal Regulations
CI confidence interval
CK creatine kinase
CL Clearance
Cmax maximum concentration observed after dosing
Cmin minimum concentration over a dosing interval during multiple dosing
ConcBase baseline concentration
ConcBC baseline corrected concentration
ConcBLQ Active dose concentrations corrected for BLQ
Cpd pre-dose concentration determined immediately before a dose at steady state
CRF case report form
CRU clinical research unit
CS clinically significant
CV coefficient of variation
DHT Dihydrotestosterone
ECG Electrocardiogram
eCRF electronic case report form
FDA Food and Drug Administration
FSD female sexual dysfunction
GCP good clinical practice
GGT gamma-glutamyl transferase
GLM Generalized Linear Model
HbsAg hepatitis B surface antigen
HCV hepatitis C virus
HIV human immunodeficiency virus
HR heart rate
ICF informed consent form
IRB institutional review board
ln Logarithmic
MedDRA Medical Dictionary for Regulatory Activities
NCS not clinically significant
OTC over-the-counter
PD Pharmacodynamic
PI Principal Investigator
PK Pharmacokinetic
PTF % peak to trough fluctuation
PTS % peak to trough swing
RR respiratory rate
SAP statistical analysis plan
SD standard deviation
SHBG sex hormone-binding globulin
t½ elimination half-life
tmax time of observed Cmax relative to the time of dosing
VPA vaginal pulse amplitude
$\lambda z$ terminal elimination rate constant

5. ETHICS

A. Institutional Review Board (IRB)

The study and any amendments were reviewed by the Institutional Review Board (IRB) for each center. Any subsequent protocol amendments or informed consent revisions were approved by the IRB before any changes were initiated.

B. Ethical Conduct of the Study

This study was conducted in accordance with the ethical principles originating from the Declaration of Helsinki and current good clinical practice (GCP) and in compliance with local regulatory requirements and 21 CFR 312.

C. Subject Information and Consent

The format and content of the subject information sheet and informed consent form (ICF) were agreed upon by the Principal Investigator (PI), the IRB, and Trimel Pharmaceuticals Corp. (hereafter referred to as Trimel). Each subject's written informed consent to participate in the study was obtained before any study specific procedures were performed. The PI or a medically qualified member of the study team provided the subject with a full explanation of the study drugs and manner of treatment allocation, the possible risks and benefits, and the compensation or treatment available in the event of study-related injury.

Subjects who agreed to participate in the study signed and dated an ICF. The ICF was also signed and dated by designated site personnel. The original and all amended signed and dated ICFs were retained at the study site, and copies of these forms were provided to the subject.

6. INVESTIGATORS AND STUDY ADMINISTRATIVE STRUCTURE

This study was conducted at 1 investigative site in the United States. The PI at the investigative site was responsible for the validity and accuracy of the data supplied on the case report form (CRF). Delegation of authority for completion of the CRF was permitted, but the PI was responsible for its accurate completion and was required to sign the completed CRF that it was a true and accurate reflection of the subject's participation in the study.

The PI at the investigative site signed the protocol signature page. By signing this page, the PI agreed to conduct the study in accordance with the study protocol and also to comply with the requirements regarding the obligations of clinical investigators and all other pertinent requirements of applicable regulatory agencies.

7. INTRODUCTION

TBS-2 is developed for the treatment of anorgasmia.

A. Background

Anorgasmia is the second most frequently reported women's sexual problem after hypoactive sexual desire disorder. The Global Survey of Sexual Attitudes and Behaviors assessed sexual problems in 9000 women aged 40 to 80 years (inclusive) in 29 countries. The prevalence of inability to reach orgasm ranged from 17.7% (in Northern Europe) to 41.2% (in Southeast Asia). In the PRESIDE survey of over 31,000 women, approximately 10% reported low desire with distress and almost 5% report difficulty reaching orgasm with distress. Anorgasmia is considered to be the persistent or recurrent delay in, or absence of, orgasm following a normal sexual excitement phase, causing marked distress or interpersonal difficulty. When a woman has sexual activity that is not accompanied by good quality orgasmic release, sexual activity may become a chore or a duty rather than a mutually satisfying, intimate experience. This may also lead to secondary loss of sexual interest and/or interpersonal difficulties.

Testosterone, the primary circulating androgen in women, is a naturally occurring steroid secreted by the ovaries and the adrenal glands. Contrary to the sudden drop in estrogen during menopause, serum levels of androgens fall gradually as women age primarily due to a decrease in the production of adrenal androgen precursors. Testosterone plays a role in regulation of mood, body composition, and bone mineral density, and has central and peripheral effects on sexual function. In the periphery, testosterone is required for nitric oxide to stimulate vasocongestion for the engorgement of clitoral tissue and vaginal lubrication during sexual arousal. Testosterone stimulates dopamine release in various brain structures implicated in motivation and reward systems, including sexual desire. Testosterone was found to stimulate dopamine release in the medial preoptic area of the anterior hypothalamus under basal conditions and with sexual stimulation in rats.

The use of androgens to increase women's sexual desire was first reported in 1940 by Loeser. Salmon observed that a number of young married women who formerly considered themselves "frigid" were able to experience "a marked increase in coital gratification, culminating in an orgasm" after testosterone propionate injections, with the effects wearing off within several weeks after the discontinuation of the injections. In the 1980s, the role of androgens in maintaining sexual functioning was studied in oophorectomized women. In this 3-month, prospective open-label study of 44 women, monthly injections of estrogen and testosterone increased rates of sexual desire, sexual arousal, and number of fantasies. Furthermore, rates of intercourse and orgasm were higher in women treated with androgens and estrogen compared to the controls. Over the two past decades, over 80 studies have been conducted in women with hypoactive sexual desire disorder by using exogenous testosterone through the oral, transdermal, sublingual or parenteral route of administration with or without concomitant estrogen therapy, resulting in an increase in sexual desire, orgasm, arousal, frequency of satisfactory sexual activity, pleasure and responsiveness.

Trimel has developed an intranasal testosterone gel containing 0.24% to 0.72% testosterone with castor oil, oleoyl polyoxylglycerides, and colloidal silicon dioxide as excipients. TBS-2 is administered as a dose applied equally into each nostril. The formulation has many advantageous features including rapid absorption into systemic circulation and rapid clearance, the lack of first-pass metabolism, the avoidance of transference from one person to another, and ease of use. It is a logical next step in a research program dedicated to investigating the role of testosterone, to investigate whether TBS-2, in the absence of other FSDs, has a direct effect on sexual function in general and anorgasmia in particular.

Two pharmacokinetic (PK)/pharmacodynamic (PD) studies have been performed to evaluate the effect of testosterone on the amygdala reactivity and PD endpoints associated with sexual stimulation. The first PD study (CMO-nr: 2004/144) investigated whether the age-related decline in androgen levels was associated with reduced amygdala activity, and whether exogenous testosterone could restore amygdala activity. The enhanced testosterone levels correlated positively with superior frontal cortex responses and negatively with orbitofrontal cortex responses across individuals, which may reflect testosterone-induced changes in amygdala regulation. These results support the modulatory role of testosterone on emotional cues suggesting testosterone helps to enhance sensation that is necessary to trigger orgasm.

The second study (TBS-2-2010-01) evaluated the PK of 3 dose levels of TBS-2 and sexual function PD compared to a testosterone patch and placebo. The PK results demonstrated a linear increase in plasma testosterone levels with increasing dose levels. During the first PK series, the mean plasma testosterone concentration and area under the plasma concentration-time curve (AUC) in the TBS-2 high-dose group reached the same level as the mean concentration and AUC of the testosterone patch at steady state. During the second PK series, the mean plasma testosterone concentration and AUC in the TBS-2 high-dose group reached levels higher than the mean plasma testosterone concentration and AUC in the testosterone patch group, but still within the upper limit of the normal physiological range. Sexual function PD efficacy was explored by assessing the role of testosterone on vaginal pulse amplitude (VPA), subjective arousal questionnaires, and validated computer tasks. Significant differences were observed in VPA response following testosterone administration in women in the anorgasmia cohort. Women who received TBS-2 (see Examples 9 and 10 above) had greater responsiveness in genital response and subjective sexual measurement compared to women receiving the testosterone patch.

The product under investigation in this study, TBS-2 at 0.24%, 0.48% and 0.72% strengths, is a bioadhesive intranasal testosterone gel. Contrary to the transdermal administration (Intrinsa, a testosterone transdermal patch that has been approved in the European Union for the treatment of hypoactive sexual desire disorder (HSDD) in bilaterally oophorectomized and hysterectomized [surgically induced menopausal] women receiving concomitant estrogen therapy), administration of the bioadhesive TBS-2 through the nasal mucosa allows for rapid absorption into the systemic circulation. The rapid onset and higher peak concentration are hypothesized to be more effective in enhancing sexual desire and orgasm with lower total concentrations of testosterone needed, thus increasing efficacy and decreasing side effects. In addition, TBS-2 may prove effective in alleviating anorgasmia in an "as needed" way, thus avoiding chronic exposure to testosterone.

8. STUDY OBJECTIVES

A. Primary Objective

The primary objective of this study was to assess the bioavailability of total testosterone through PK profiles obtained following single administration of an intranasal application of TBS-2 at doses of 600 µg, 1200 µg, and 1800 µg, and multiple administration of 1200 µg TBS-2 given 3 times daily (t.i.d) for the first 2 days and once on the morning of the third day.

B. Secondary Objectives

The secondary objectives of this study were:

To assess the bioavailability of free testosterone, sex hormone-binding globulin (SHBG), dihydrotestosterone (DHT), and estradiol through PK profiles obtained following single administration of an intranasal application of TBS-2 at doses of 600 µg, 1200 µg, and 1800 µg, and multiple administration of 1200 µg TBS-2 given for 3 days (t.i.d. for the first 2 days and once on the morning of the third day).

To evaluate the safety of TBS-2.

9. INVESTIGATIONAL PLAN

A. Overall Design and Plan Description

This was a phase 1, single-center, randomized, open-label parallel-group study in healthy, normal-cycling adult women. Approximately 24 healthy adult women were to be enrolled. Subjects were randomly assigned on a 1:1:1 basis to 1 of 3 treatment groups (Cohort 1, Cohort 2, or Cohort 3) during Period 1 and were administered a single dose of an intranasal application of TBS-2 at doses of 600 µg, 1200 µg, or 1800 µg (single doses of 300 µg, 600 µg, and 900 µg per nostril). At the end of Period 1, a total of 8 subjects sampled from these 3 cohorts, who were willing and able to continue with the multiple-dose portion of the study were selected to participate in Period 2. During Period 2, subjects were administered 1200 µg TBS-2 (600 µg per nostril) t.i.d. for 2 days and once on the morning of the third day.

Subjects were screened (Visit 1) for eligibility up to 3 weeks prior to dosing in Period 1, and were admitted to the Clinical Research Unit (CRU) at 0700 hours on the day prior to dosing (Visit 2, Day 1) for baseline testosterone measurement. On Day 2, subjects were administered a single dose of TBS-2 and remained in the CRU for 72 hours post-dose (Day 4) for safety monitoring and PK assessments. Subjects were discharged from the clinic on Day 4, and subjects who did not continue into Period 2 also underwent close-out assessments. Depending on their cycle, subjects selected to participate in Period 2 returned to the CRU approximately 26 to 32 days following the conclusion of Period 1 for Visit 3 (Period 2). During Period 2, subjects were admitted to the CRU at 0700 hours on the day of dosing (Visit 3, Day 1). On Days 1 and 2, subjects were administered TBS-2 at 0800 hours (±30 minutes), 1600 hours (±30 minutes), and 2400 hours (±30 minutes). On Day 3, subjects were administered TBS-2 at 0800 hours. Subjects remained in the CRU for 48 hours following dosing on Day 3 for safety monitoring and PK assessments. Subjects were discharged from the clinic on Day 5.

During Period 1, blood samples for determination of baseline testosterone (free and total), SHBG, dihydrotestosterone (DHT), and estradiol concentration were collected on Day 1 at 0745 hours and then at 15, 30, and 45 minutes and at 1, 1.5, 2, 4, 6, 8, 12, 16, 20, and 23.5 hours relative to an 0800 hour clock time. Blood samples for determination of testosterone (free and total), SHBG, dihydrotestosterone, and estradiol concentration were collected on Day 2 (15, 30, and 45 minutes and at 1, 1.5, 2, 4, 6, 8, 12, 16, and 20 hours post-dose) and Day 3 (24, 32, 40, and 48 hours post-dose) during the confinement period. During Period 2, a blood sample for a baseline serum testosterone concentration was collected at 0745 hours (ie, 15 minutes prior to study drug administration). Blood samples for determination of testosterone (free and total), SHBG, dihydrotestosterone, and estradiol plasma concentration were collected on Day 1 (pre-dosepre-dose [15 minutes prior to dosing] and at 1545 and 2345 hours), Day 2 (1545 and 2345 hours), Day 3 (15, 30, and 45 minutes and at, 1, 1.5, 2, 4, 6, 8, 12, 16, and 20 hours), and Day 4 (24, 32, 40, and 48 hours) during the confinement period.

Other assessments performed during the study included the monitoring of adverse events (AEs), clinical laboratory evaluations (chemistry [including hormone profile], hematology, and urinalysis), vital signs assessments (systolic and diastolic blood pressure [BP], heart rate [HR], respiratory rate [RR], and body temperature), and physical examinations. In addition, otorhinolaryngological examination findings, 12-lead electrocardiogram (ECG) readings, medical history, and concomitant medication use were recorded.

B. Discussion of Study Design and Choice of Control Groups

This was a phase 1, single-center, randomized, open-label parallel-group study of TBS-2 in 3 cohorts of subjects (Cohorts 1, 2, and 3) in Period 1 (single-dose) and a multiple-dose cohort in Period 2. Approximately 24 healthy women were to receive a single intranasal dose of 600 µg, 1200 µg, or 1800 µg TBS-2 to evaluate the safety, tolerability, and PK of TBS-2. Subjects were confined in a CRU for 4 days during Period 1 and 5 days during Period 2.

C. Selection of Study Population

Inclusion Criteria

Subjects were eligible for study inclusion if they met all of the following inclusion criteria:

1. Female subjects between 18 and 40 years of age.
2. Subjects with regular menstrual cycles between 26 and 32 days.
3. Women of childbearing potential must have agreed to use 1 of the following reliable birth control methods prior to the study, during the study, and up until 1 month after the end of the study:
   a. Surgically sterile (tubal ligation).
   b. Intrauterine device in place for at least 3 months prior to study initiation.
   c. Barrier method (condom with spermicidal agent use by partner).
   d. Abstinence.
4. Subjects negative for drugs of abuse, hepatitis B-surface antigen (HbsAg), hepatitis C, human immunodeficiency virus (HIV), and pregnancy (serum B-HCG).
5. Subjects with a Body Mass Index (BMI) between 18.5 kg/m$^2$ and 35 kg/m$^2$ (inclusive).
6. Subjects with a normal ear, nose, throat (ENT) examination.
7. Subjects with normal thyroid-stimulating hormone (TSH) values.
8. Subjects with no clinically significant findings in the physical examination, 12-lead ECG, and vital signs.
9. Subjects with normal thyroid function. Physiological prolactin concentration.
10. Subjects with no clinical laboratory values outside of the acceptable range, unless the PI decided that they were not clinically significant.
11. Subjects who were able to understand and provide written informed consent.
12. Subjects who were available for the entire study period and were willing to adhere to protocol requirements, as evidenced by a signed ICE.

Exclusion Criteria

Subjects were excluded from study participation if they met any of the following exclusion criteria:

1. Known history of hypersensitivity to testosterone (eg, Intrinsa patch) and/or related drugs.
2. Known history of polycystic ovarian syndrome.

3. Known history or presence of cardiac, pulmonary, gastrointestinal, endocrine, musculoskeletal, neurological, psychiatric, hematological, reproductive, liver, or kidney disease, unless judged not clinically significant by the PI or medical designate.
4. Presence of or known history of estrogen-responsive tumors such as breast cancer and/or history of any cancer, excluding basal cell carcinoma.
5. Known history of frequent clinically significant acne.
6. Known history of hirsutism.
7. History of nasal surgery, specifically turbinoplasty, septoplasty, rhinoplasty, "nose job," or sinus surgery.
8. Prior nasal fractures.
9. Active allergies, such as rhinitis, rhinorrhea, and nasal congestion.
10. Mucosal inflammatory disorders, specifically pemphigus and Sjogren's syndrome.
11. Sinus disease, specifically acute sinusitis, chronic sinusitis, or allergic fungal sinusitis.
12. History of nasal disorders (eg, polyposis, recurrent epistaxis [>1 nose bleed per month], abuse of nasal decongestants) or sleep apnea.
13. Use of any form of intranasal medication delivery, specifically nasal corticosteroids and oxymetazoline containing nasal sprays (eg, Dristan 12-Hour Nasal Spray).
14. History of hepatitis B, a positive test for HbsAg, a history of hepatitis C, a positive test for hepatitis C antibody, a history of HIV infection, or demonstration of HIV antibodies.
15. Any history of severe allergic reaction including drugs, food, insect bites, environmental allergens, or any condition known to interfere with the absorption, distribution, metabolism, or excretion of drugs.
16. Any history of drug abuse or alcohol abuse as per the Diagnostic and Statistical Manual of Mental Disorders (fourth edition) criteria within 6 months of study drug administration.
17. Current treatment with any hormonal therapy within previous 12 months, treatment with drugs that interfere with metabolism of testosterone within 30 days of study drug administration and/or any other prescription medications. Difficulty in abstaining from over-the-counter (OTC) medication use for the duration of study.
18. Use of oral, transdermal, and implant contraceptives within 30 days prior to study drug administration or a depot contraceptives injection within 1 year prior to study drug administration.
19. Evidence of pregnancy or lactation.
20. Subjects who were breast feeding or had breast fed within 6 months prior to the screening visit.
21. Administration of another investigational drug within 30 days prior to study drug administration.
22. Blood donation within 56 days prior to study drug administration.
23. Any participation as a plasma donor in a plasmapheresis program within 7 days preceding this study.
24. Intolerance to venipuncture.
25. History of abnormal bleeding tendencies or thrombophlebitis unrelated to venipuncture or intravenous cannulation.
26. History of deep venous thrombosis or coagulation disorders.

Removal of Subjects from Therapy or Assessment

Subjects withdrawn from the study after receiving study drug were not replaced, regardless of the reason for withdrawal.

A subject may have been prematurely discontinued from the study for any of the following reasons:
  Significant noncompliance with the study protocol and procedures.
  Intercurrent illness that interfered with the progress of the study.
  Intolerable AE, including clinically significant abnormal laboratory findings, which in the opinion of the PI could have interfered with the subject's safety.
  Principal Investigator's decision that the withdrawal from the study was in the best interest of the subject.

D. Treatments

Treatments Administered

Subjects were randomly assigned on a 1:1:1 basis to 1 of 3 treatment groups (Cohort 1, Cohort 2, or Cohort 3) during Period 1 and were administered a single dose of an intranasal application of TBS-2 at doses of 600 µg, 1200 µg, or 1800 µg (single doses of 300 µg, 600 µg, and 900 µg per nostril). At the end of Period 1, a total of 8 subjects sampled from these 3 cohorts, who were willing and able to continue with the multiple-dose portion of the study were selected to participate in Period 2. During Period 2, subjects were administered 1200 µg TBS-2 (600 µg per nostril) t.i.d. for 2 days and once on the morning of the third day.

Treatment 1: TBS-2 dispensers prefilled with 0.24% testosterone gel to deliver a single dose of 300 µg of testosterone per nostril, for a total dose of 600 µg given at 0800 hours (±30 minutes) on Day 2 of Period 1 for Cohort 1.

Treatment 2: TBS-2 dispensers prefilled with 0.48% testosterone gel to deliver a single dose of 600 µg of testosterone per nostril, for a total dose of 1200 µg given at 0800 hours (±30 minutes) on Day 2 of Period 1 for Cohort 2.

Treatment 3: TBS-2 dispensers prefilled with 0.72% testosterone gel to deliver a single dose of 900 µg of testosterone per nostril, for a total dose of 1800 µg given at 0800 hours (±30 minutes) on Day 2 of Period 1 for Cohort 3.

Treatment 4: TBS-2 dispensers prefilled with 0.48% testosterone gel to deliver a single dose of 600 µg of testosterone per nostril, for a total dose of 1200 µg given t.i.d. daily at 0800 hours (±30 minutes), 1600 hours (±30 minutes), and 2400 hours (±30 minutes) on Days 1 and 2 of Period 2, and once in the morning at 0800 hours (±30 minutes) on Day 3 of Period 2 (Multidose group).

Subjects were instructed on the proper procedure for applying the TBS-2 gel intranasally by using the prefilled dispensers. Study drug was self-administered at 0800 hours on Day 2 of Period 1 and on Days 1, 2, and 3 of Period 2. Self-administration of TBS-2 was monitored by study personnel. Subjects were instructed to not blow their nose or sniff immediately, and for the first hour following study drug administration.

Identity of Investigational Products

Active study drug was supplied in prefilled dispensers containing 0.24%, 0.48%, or 0.72% TBS-2.

The TBS-2 gels were packaged in prefilled dispensers. A multidose dispenser was used for gel deposition into the nasal cavity. The dispenser was a finger actuated dispensing system designed to dispense 125 µL of TBS-2 gel per actuation from a non-pressurized container into the nasal cavity. The key components of the multiple-dose dispenser included a barrel, base, pump, and actuator, which were composed of polypropylene and a piston, which was composed of polyethylene. See FIG. 39 and CMC Section below.

All study drug boxes and dispensers were labeled and supplied according to applicable regulatory requirements. Qualified licensed study personnel prepared the unit doses for the study as per the randomization schedule. Study drug was provided to the subjects in appropriate unit-dose foil pouches, clearly labeled as to the amount of drug being given.

Study drug was stored in a secure location at a controlled room temperature of 15° C. to 25° C. (59° F. to 77° F.). The storage location was a locked room with limited access, available to appropriate study personnel only.

The PI, or an approved representative, (eg, co-investigator), ensured that all study drug was stored in a secured area, under recommended storage conditions, and in accordance with applicable regulatory requirements.

Upon the completion or termination of the study, and upon written authorization from Trimel, all unused and/or partially used study drug was returned or destroyed at the investigational site, as specified by Trimel.

Method of Assigning Subjects to Treatment Groups

A randomization schedule was prepared by Premier Research and was provided to the PI at the CRU prior to the start of the study.

Subjects who met the enrollment criteria were randomly assigned on a 1:1:1 basis to 1 of 3 treatment groups.

Selection of Doses in the Study

The doses of 600 μg, 1200 μg, and 1800 μg were selected for this study based on clinical pharmacology data and are appropriate for a phase 1 study. The animal toxicology studies completed to date do not suggest any unusual or unexpected toxicities related to TBS-2 exposure. Subjects were not expected to experience side effects with TBS-2.

Selection and Timing of Dose for Each Subject

Study drug was administered on Day 2 of Period 1 (single-dose). During Period 2 (multi-dose), study drug was administered t.i.d. on Days 1 and 2 and on the morning of Day 3. Subjects were confined in a CRU for 4 days during Period 1 and 5 days during Period 2.

Blinding

This was an open-label study; subjects were not blinded to treatment assignments.

Prior and Concomitant Therapy

The use of any prescription or nonprescription medication or treatment with drugs that interfere with the metabolism of testosterone was prohibited within 30 days of study drug administration and until the final study visit. The use of any form of intranasal medication delivery, specifically nasal corticosteroids and oxymetazoline-containing nasal sprays (eg, Dristan 12-Hour Nasal Spray) was prohibited until the final study visit. Current treatment with any hormonal therapy was prohibited 12 months prior to study drug administration and until the final study visit. Also prohibited was the use of oral, transdermal, or implant contraceptives within 30 days prior to drug administration or a depot contraceptives injection within 1 year prior to study drug administration. In addition, the administration of another investigational drug was prohibited within 30 days prior to study drug administration. The use of illegal drugs was not permitted while the subjects were enrolled in this study.

Throughout the study, the PI could prescribe any concomitant therapy deemed necessary to provide adequate supportive care. The PI was to notify the sponsor of any subject using medications within 30 days prior to Day 1 or if concomitant medications were required during the study. The decision to allow the subject to be enrolled into the study or take medications during the study was made jointly by the sponsor and PI and was based on their opinion that the use of the medication was unlikely to compromise the safety of the subject or the interpretation of the study data. All medications taken within 30 days prior to dosing and all concomitant therapy were recorded on the appropriate section of the CRF.

Treatment Compliance

Subjects who received doses of study drug were monitored by study personnel for 1 hour post-dose to assure conformity to the TBS-2 instructions. Subjects were confined in a CRU for 4 days during Period 1 and 5 days during Period 2 and were closely monitored. A drug dispensing, log was maintained. Pharmacokinetic results were available to confirm compliance.

Study drug was administered on Day 2 of Period 1 (single-dose). During Period 2 (multi-dose), study drug was administered t.i.d. on Days 1 and 2 and on the morning of Day 3. Subjects were confined in a CRU for 4 days during Period 1 and 5 days during Period 2.

E. Pharmacokinetic and Safety Variables

Pharmacokinetic and Safety Measurements Assessed and Flow Chart

The Study Schedule is presented in Table 9-1.

TABLE 9-1

Study Schedule

| PROCEDURE | Screening Visit 1 | Period 1 Visit 2 (Cohorts 1, 2, and 3) | | | | Post-Study | Period 2 Visit 3[a] | | | | Post-Study |
|---|---|---|---|---|---|---|---|---|---|---|---|
| | Day −21 to −1 | 1 | 2 | 3 | 4 | 4 | 1 | 2 | 3 | 4 | 5 |
| Informed Consent | X | | | | | | | | | | |
| Inclusion/Exclusion | X | | | | | | | | | | |
| Confinement | | X | X | X | | | X | X | X | X | |
| Vital Signs[b] | X | X | X | X | X | X | X | X | X | X | X |
| ECG | X | | | | | | | | | | |
| Urine Drug Screen | X | X | | | | | X | | | | |
| Breath Alcohol Testing | X | X | | | | | X | | | | |
| ENT (otorhinolaryngological) Nasal Endoscopic Examination | X | | | | | | | | | | |
| Basic ENT (Otorhinolaryngological) Examination | | X[c] | | | | X[c] | X | | | | X[c] |
| Medical History | X | | | | | | | | | | |
| Physical Examination | X | | | | | X | | X | | | X |
| Serum Pregnancy Test | X | X | | | | X | X | | | | X |
| Height/Weight | X | | | | | | | | | | |
| Clinical Laboratory Tests[d] | X | | | | | X | | | | | X |

TABLE 9-1-continued

Study Schedule

| PROCEDURE | Screening Visit 1 Day −21 to −1 | Period 1 Visit 2 (Cohorts 1, 2, and 3) | | | Post-Study 4 | Period 2 Visit 3[a] | | | | Post-Study 5 |
|---|---|---|---|---|---|---|---|---|---|---|
| | | 1 | 2 | 3 | 4 | 1 | 2 | 3 | 4 | |
| Serology (HIV, HbsAg, hepatitis C antibody) | X | | | | | | | | | |
| Hormone Profile[e] | X | | | | X | | | | | X |
| Dosing | | | X[f] | | | X[g] | X[g] | X[h] | | |
| PK Sampling | | X[i] | X[j] | X[j] | X[j] | X[k] | X[l] | X[m] | X[m] | |
| Adverse Events | | X | X | X | X | X | X | X | | X |
| Concomitant Medications | X | X | X | X | X | X | X | X | X | X |

Abbreviations:
AE = adverse event;
CBC = complete blood count;
DHT = dihydrotestosterone;
ECG = electrocardiogram;
ENT = ear, nose, throat;
FSH = follicle-stimulating hormone;
HbsAg = hepatitis B surface antigen;
HIV = human immunodeficiency virus;
LH = luteinizing hormone;
PK = pharmacokinetic;
SHBG = sex hormone-binding globulin;
TSH = thyroid-stimulating hormone.
[a]A total of 8 subjects who were willing and able to continue on to the multiple dose portion of the study were selected from Cohorts 1, 2, and 3 and comprised the Multi-Dose group.
[b]Vital signs (heart rate, blood pressure, temperature, and respiratory rate).
[c]The site physician examined subjects and identified any clinically significant changes to the nasal mucosa at follow-up.
[d]Chemistry, hematology, urinalysis.
[e]Hormone profile: TSH, total and free tri-iodothyronine, total and free thyroxine, FSH, prolactin, and progesterone.
[f]Study drug administered at 0800 hours (±30 minutes).
[g]Study drug administered at 0800 hours (±30 minutes), 1600 hours (±30 minutes), and 2400 hours (±30 minutes).
[h]Study drug a administered at 0800 hours (±30 minutes).
[i]Blood samples for the 24-hour baseline profile (total and free testosterone, SHBG, DHT, and estradiol) were collected at 0745 hours and then at 15, 30, and 45 minutes and at 1, 1.5, 2, 4, 6, 8, 12, 16, 20, and 23.5 hours relative to an 0800 hour clock time.
[j]Blood samples for the 48-hour PK profile (total and free testosterone, SHBG, DHT, and estradiol) were collected at 15, 30, and 45 minutes and at 1, 1.5, 2, 4, 6, 8, 12, 16, 20, 24, 32, 40, and 48 hours.
[k]A baseline serum testosterone blood sample was collected at 0745 hour (ie, 15 minutes prior to dosing).
[l]PK sampling for trough level measurement was done prior to dosing at 0800, 1600, and 2400 hours.
[m]The 48-hour PK profile blood samples were collected pre-dose at 0745 hours and at 15, 30, and 45 minutes and at 1, 1.5, 2, 4, 6, 8, 12, 16, 20, 24, 32, 40, and 48 hours.

Appropriateness of Measurements

The measurements included in this study were typical for a phase I single- and multiple-dose study.

Pharmacokinetic Drug Concentration Measurements

Whole blood samples for determination of testosterone (free and total), SHBG, dihydrotestosterone, and estradiol concentration were collected at each time point indicated in Table 9-2 Table 9-2. The date and time of collection were recorded on the CRF to the nearest minute. Whole blood samples were obtained through direct venipuncture; the use of a heparin lock or IV indwelling catheter was allowed for early time point PK sample collections. The volume of plasma samples collected for PK analysis for each subject was approximately 120 mL during Period 1 and 92 mL duilng Period 2.

TABLE 9-2

Schedule of Pharmacokinetic Sample Collection

| Visit/Day | Treatment | PK Sample Collection |
|---|---|---|
| Visit 1/Day 1 | None; Baseline measurement | Blood samples for 24-hour baseline profile (total and free testosterone, SHBG, DHT, and estradiol) were collected at 0745 hours and then at 15, 30, and 45 minutes and at 1, 1.5, 2, 4, 6, 8, 12, 16, 20, and 23.5 hours relative to an 0800 hour clock time. |
| Visit 2/Days 2-4 | Single-dose (Cohorts 1, 2, and 3) | Blood samples for the 48-hour PK profile (total and free testosterone, SHBG, DHT, and estradiol) were collected at 15, 30, and 45 minutes and at 1, 1.5, 2, 4, 6, 8, 12, 16, 20, 24, 32, 40, and 48 hours. |
| Visit 3/Day 1 | Multiple-dose | A baseline serum blood sample was collected at 0745 hour (ie, 15 minutes prior to dosing). |

TABLE 9-2-continued

Schedule of Pharmacokinetic Sample Collection

| Visit/Day | Treatment | PK Sample Collection |
|---|---|---|
| Visit 3/Days 1-2 | Multiple-dose | PK sampling for trough level measurement was done prior to dosing at 0800, 1600, and 2400 hours. |
| Visit 3/Days 3-5 | Multiple-dose | The 48-hour PK profile blood samples were collected pre-dose at 0745 hours (pre-dose) and at 15, 30, and 45 minutes and at 1, 1.5, 2, 4, 6, 8, 12, 16, 20, 24, 32, 40, and 48 hours. |

Abbreviations:
DHT = dihydrotestosterone;
PK = pharmacokinetic;
SHBG—sex hormone-binding globulin;
t.i.d. = three times daily
Note:
During Period 1 dosing occurred on the morning of Day 2.
During Period 2, dosing occurred t.i.d. on Days 1 and 2, and once on the morning of Day 3.

Pharmacokinetic Parameter Estimates

Concentration-time data for 5 analytes [testosterone (Total and Free), SHBG, dihydrotestosterone and estradiol] were determined and PK parameters were calculated from them. Actual sampling time points were recorded and used in calculation of the actual elapsed time from dose to sample for PK calculations. As each administration was made to each of the nostrils, the time of dosing was the time of the first nostril administration. The units of concentration for each of the 5 different analytes may have differed so the final units of concentration reflected the bioanalytical laboratory data reported on the concentrations. Units of PK parameters were derived from the analyte concentration units. Baseline analyte concentrations from the 24-hour pre-dose profile were subtracted from the reported analyte concentrations before calculation of the PK parameters.

The following PK parameters were calculated following single-dose (Cohorts 1, 2, and 3) for PK characterization. Profile intervals were from the start of the first dosing and continued to the last sample collected on the dosing day. PK parameters were estimated by standard methods used by the WinNonlin program and short descriptions are given below. The determination of the terminal elimination phase was more fully described in the WinNonlin documentation. Note that $C_{min}$, $C_{max}$, and $t_{max}$ were taken from the actual measured values but after baseline correction for $C_{min}$ and $C_{max}$.

| Parameter | Description and Calculation |
|---|---|
| $AUC_{0-t}$ | Area under the plasma concentration time curve from time zero to the last measurable concentration time point, calculated by using the combination of the linear nd log trapezoid rules. The linear trapezoidal rule would be used from the time of dose to $t_{max}$ and the log trapezoidal rule would be used following $t_{max}$. |
| $AUC_{0-8}$ | Area under the plasma concentration time curve from time zero to 8 hours. |
| $AUC_{0-24}$ | Area under the plasma concentration time curve from time zero to 24 hours. |
| $AUC_{0-\infty}$ | Area under the plasma concentration time curve from time zero to infinity, calculated as $AUC_{0-\infty} = AUC_{0-t} + \frac{C_{last}}{\lambda_z}$, where $C_{last}$ is the last measurable concentration, and $\lambda_z$ is the terminal elimination rate constant calculated from the log-linear terminal phase. |
| $C_{max}$ | Maximum concentration observed after dosing. |
| $C_0$ | Concentration at pre-dose. |
| $C_{24}$ | Concentration at 24 hours. |
| $t_{max}$ | Time of observed maximum concentration ($C_{max}$) relative to the time of dosing. |
| $\lambda z$ | Terminal elimination rate constant. |
| $t_{1/2}$ | Elimination half-life calculated as $\frac{\ln(2)}{\lambda_z}$. |

The following PK parameters were calculated following multiple-dose (Multi-Dose group):

| Parameter | Description and Calculation |
|---|---|
| $AUC_{0-\tau}$ | Area under the concentration-time curve from time zero to the dosing interval ($\tau$ = 8 hours). |
| $AUC_{0-8}$ | Area under the plasma concentration time curve from time zero to 8 hours. |
| $AUC_{0-24}$ | Area under the plasma concentration time curve from time zero to 24 hours. |
| $C_{max}$ | Maximum concentration observed after dosing. |
| $t_{max}$ | Time of observed maximum concentration ($C_{max}$) relative to the time of dosing. |
| $C_{min}$ | Minimum concentration over a dosing interval during multiple dosing. |
| $C_{pd}$ | Pre-dose concentration determined immediately before a dose at steady state |
| $C_0$ | Concentration at pre-dose. |
| $C_{24}$ | Concentration at 24 hours. |
| $C_{avg}$ | Average steady-state concentration, calculated as $\frac{AUC_{0-\tau}}{\tau}$, where $\tau$ = 8 hours. |
| % PTF | % Peak to Trough Fluctuation $\frac{(C_{max} - C_{min}) = 100}{C_{avg}}$ |
| % PTS | % Peak to Trough Swing is the degree of concentration swing at a steady state: $\frac{(C_{max} - C_{min}) = 100}{C_{min}}$ |

Additional exploratory analyses of PK parameters may have been performed as necessary.

Safety Measurements

Safety measurements included the monitoring of AEs, clinical laboratory evaluations (chemistry [including hormone profile], hematology, and urinalysis), vital signs, and 12-lead ECGs. In addition, physical and otorhinolaryngological examinations were performed and medical history and concomitant medication use were recorded. Safety measurements were performed at the times specified in Table 9-1. The PI followed all clinically-significant abnormal findings after study drug treatment until resolution or return to baseline.

Adverse Events

An AE is any untoward, undesired, unplanned clinical event in the form of signs, symptoms, disease, or laboratory or physiological observations occurring in a human participating in a clinical study with a Trimel product, regardless of causal relationship. A pre-existing condition is one that is present prior to study drug administration and is reported as part of the subject's medical history. Pre-existing conditions were reported as an AE only if the frequency, intensity, or character of the pre-existing condition worsened during the course of the study.

Laboratory abnormalities were not considered AEs unless they were associated with clinical signs or symptoms, or required medical intervention. However, a laboratory abnormality (eg, a clinically significant change detected in clinical chemistry [including hormone profile], hematology, urinalysis) that was independent from the underlying medical condition and that required medical or surgical intervention, or led to study drug interruption or discontinuation, was considered an AE.

All AEs judged to be clinically significant, including clinically-significant laboratory abnormalities, were followed until resolution or return to baseline.

F. Severity Rating

All AEs or SAEs were assessed for severity, by using the following grading scale:

Mild An event easily tolerated by the subject; transient or mild discomfort (usually <48 hours); no medical intervention/therapy required.

Moderate An event that may interfere with normal, everyday activities; some assistance may be needed; no or minimal medical intervention/therapy required.

Severe An event that prevented the subject from performing their normal, everyday activities; some assistance usually required; medical intervention/therapy required, hospitalizations possible.

When changes in the severity of an AE occurred more frequently than once a day, the maximum severity for the experience that day was noted. If the severity category changed over a number of days, then those changes were recorded separately (with distinct onset dates). The severity of the AE was recorded in the appropriate section of the AE page of the CRF. The evaluation of severity was distinguished from the evaluation of "seriousness." A severe event might not have met the criteria for seriousness and a serious event might have been evaluated as mild.

G. Causality Rating

For each reported adverse reaction, the PI made an assessment of the relationship of the event to the study drug by using the following scale:

Definite There is a plausible temporal relationship with drug administration and withdrawal, and reappears after drug restart.

Probable There is a plausible temporal relationship with drug administration.

Possible There is a plausible temporal relationship with drug administration but can reasonably be associated to other factors.

Unlikely There is no plausible temporal relationship with drug administration.

Unknown There are no sufficient elements to establish a correlation with drug intake.

Not Related Cannot be correlated to study drug administration.

H. Serious Adverse Events

The PI classified each AE as either serious or not serious. A serious adverse event (SAE) was defined as any AE occurring at any dose that resulted in any of the following outcomes:

Death$^a$

Was life-threatening$^b$

Required inpatient hospitalization or prolongation of existing hospitalization

Resulted in a persistent or significant disability/incapacity$^b$

Resulted in a congenital anomaly/birth defect

Additionally, important medical events that may not have resulted in death, been life-threatening, or required hospitalization may be considered an SAE when, based upon appropriate medical judgment, they may jeopardize the subject and may require medical or surgical intervention to prevent one of the outcomes listed above. Example: allergic bronchospasm requiring intensive treatment in an emergency room or at home.

Notes:

a. Death was an outcome and was NOT the AE. In the event of death, the cause of death was recorded as the AE. The only exception was "sudden death" when the cause was unknown.

b. Life-threatening AEs included any adverse drug experience, which, in the view of the PI, placed the subject at immediate risk of death from the reaction as it occurred. It did not include a reaction that, had it occurred in a more serious form, might have caused death.

c. Disability was defined as a substantial disruption in a person's ability to conduct normal life functions.

All SAEs that resulted in death or were life-threatening, regardless of causal relationship, were reported to Trimel (or designee) within 24 hours of the site's knowledge of the event. A copy of the initial SAE report was to have been received within 1 business day. All other SAEs or other events reportable to Trimel were forwarded to Trimel (or designee) within 1 business day. If there was any doubt whether the information constituted an SAE, the information was treated as an SAE for the purposes of this study.

Clinical Laboratory Tests

Clinical laboratory tests were performed according to the schedule provided in Table 9-1.

Serum chemistry evaluations included sodium, potassium, chloride, glucose, urea, creatinine, calcium, phosphate, uric acid, total bilirubin, albumin, aspartate transaminase (AST), alanine transaminase (ALT), alkaline phosphatase, gamma-glutamyl transferase (GGT), creatine kinase (CK), and cholesterol, and hormone profiles.

Hormone profiles included TSH, total and free tri-iodothyronine, total and free thyroxine, FSH, prolactin, and progesterone.

Hematology evaluations included white blood count, hemoglobin, and hematocrit.

Urinalysis included glucose, bilirubin, ketones, specific gravity, blood, pH, protein, urobilinogen, nitrites, leukocytes and, if necessary, microscopic examination.

At Screening and on admission to the CRU, a urine specimen was obtained to test for drugs of abuse (marijuana, cocaine, opiates, amphetamines, phencyclidine, benzodiazepines, and barbiturates) and alcohol was tested for by use of an alcohol breath test.

Testing for HbsAg, antiHCV, and HIV were performed at Screening (Visit 1) only.

Samples were analyzed by MEDTOX Laboratories, Inc.

Vital Signs

Vital sign measurements included systolic and diastolic BP and HR, body temperature, and RR. Vital signs assessments were performed at the times specified in Table 9-1.

12-Lead Electrocardiogram

A standard 12-lead ECG was assessed at Screening (Visit 1) only.

Other Safety Measurements

Physical examinations were performed at the times specified in Table 9-1

An ENT (otorhinolaryngological) nasal endoscopic examination was performed at Screening. Basic ENT (otorhinolaryngological) examinations were performed at the times specified in Table 9-1; the site physician examined subjects and identified any clinically significant changes to the nasal mucosa at follow-up.

Concomitant medications were monitored throughout the study.

I. Data Quality Assurance

This study was monitored by trained experienced personnel in accordance with GCPs. The clinical study monitor reviewed study records to verify adherence to the protocol, accuracy, completeness, and consistency of the data; and adherence to local regulations on the conduct of clinical research. The clinical monitor maintained regular contact with the site and had access to subject medical records and other study-related records needed to verify the entries on the CRFs.

Electronic CRFs (eCRFs) were used for this study and included only the subject's initials, date of birth, and an assigned subject number on the eCRFs as identifiers. The PI ensured the availability and reliability of source documents from which the information on the eCRF was derived, and was required to comply with document retention procedures as outlined in the protocol. Case report forms were reviewed for accuracy and signed and dated by the PI.

J. Statistical Methods and Determination of Sample Size

Statistical and Analytical Plans

The statistical methods presented in the study protocol were superseded by those described in the statistical analysis plan (SAP). This study evaluated the PK properties as well as the safety and tolerability of TBS-2. Power calculations were not performed. Data were summarized by using descriptive statistics (sample size, mean, median, standard deviation [SD], minimum, and maximum) for each of the safety variables by treatment group and overall. Data from all visits during the study were displayed in the data listings.

Concentration-time data for 5 analytes (testosterone [total and free], SHBG, dihydrotestosterone, and estradiol) were determined by a validated assay method and PK parameters were calculated. Actual sampling time points were recorded and used in calculation of the actual elapsed time from dose to sample for PK calculations. As each administration was to each of the nostrils, the time of dosing was the time of the first nostril administration. Baseline analyte concentrations from the 24-hour pre-dose profile were subtracted from the time-matched analyte concentrations following dose administration before calculation of the PK parameters.

The plasma TBS-2 concentration-time data were analyzed by using Phoenix WinNonlin (Pharsight Corporation). The PK parameters (refer to Pharmacokinetic Parameter Estimates) for testosterone (free and total), SHBG, DHT, and estradiol were calculated by standard noncompartmental methods for all subjects as data permitted. Individual PK parameters estimated for each subject's profile in the PK population were displayed in the data listings. Data were summarized by using descriptive statistics (mean, SD, % coefficient of variation [CV], confidence interval (CI), median, minimum, and maximum) and are presented by treatment group.

Geometric means were included for AUC and $C_{max}$ estimations and were included for some other PK parameters. By using Generalized Linear Model (GLM) procedure in SAS®, an analysis of variance (ANOVA) was performed on natural logarithmic (ln) transformed parameters $AUC_{0-t}$, $AUC_{0-\infty}$, $AUC_{0-\tau}$, $C_{avg}$, and $C_{max}$ and on untransformed parameters $t_{1/2}$, and $\lambda_z$ at the significance level of 0.05. The intrasubject CV was calculated for $AUC_{0-t}$, $AUC_{0-\infty}$, $AUC_{0-\tau}$, and $C_{max}$ by using the ANOVA residual error.

Dose linearity following single-dose administration (Period 1) was assessed after normalizing the $AUC_{0-t}$, $AUC_{0-\infty}$, and $C_{max}$ to the dose administered.

The following Period 1 comparisons for PK parameters were made:

Comparison 1: 600 μg 0.24% TBS-2 versus 1200 μg 0.48% TBS-2;

Comparison 2: 600 μg 0.24% TBS-2 versus 1800 μg 0.72% TBS-2;

Comparison 3: 1200 μg 0.48% TBS-2 versus 1800 μg 0.72% TBS-2.

Determination of Sample Size

The sample size for this study was not determined on the basis of statistical hypothesis testing. Based on typical, early-stage PK studies, groups of 8 subjects per cohort were sufficient to provide adequate clinical information to satisfy the objectives of the study.

Interim Analysis

No formal interim analysis was performed in this study. However, when the concentration data were received from the bioanalytical laboratory following Period 1 and again following Period 2, all PK TLFs were provided to the limit of data available by using scheduled sampling times rather than the actual scheduled sampling times. Multiple-dose data were made available after Period 2. No quality control testing of the preliminary PK analysis or the preliminary tables, listings, and figures were completed for the interim analysis and no testing of the interim PK parameters were completed for the interim analysis.

K. Changes in the Conduct of the Study or Planned Analyses

There were changes to the SAP detailing the planned PK analysis of the data after the first draft analysis was conducted. These fell under the category of additional exploratory analyse's of PK parameters as provided for in the SAP.

The first analysis followed the SAP (corrected tau=8 hours) but found that the elimination half-life could not be adequately estimated during the entire 48 hours of the collection period.

Pharmacokinetic consultants directed the PK analysis and made changes to the PK analysis plans to best present the PK results. In the final analysis a number of additional PK parameters were added to the analysis and additional tests were performed.

The first round of consultant comments requested these additions to the PK analysis:

1. Individual figures of the 3 subjects who received the 1200 µg dose in both periods. Data include plots of the BLQ-corrected raw data from the Bioanalyst for free, total and dihydro-testosterone. Total of 9 figures with 3 for each of the 3 analytes.
2. Recalculate the $AUC_{0-8}$ and $AUC_{0-24}$ on the BLQ-corrected data from the Bioanalyst (ConcBLQ). These parameters were compared by ANOVA between Period 1 and Period 2 in a new table. There were only 3 subjects who received the 1200 µg dose in Period 1 (single-dose) and Period 2 (multi-dose). The ANOVA requested was on the 3 subjects who received the 1200 µg dose and also on all 8 subjects' data.

The second round of consultant comments requested the following. Both consultants reviewed the PK section of the SAP and had the following comments.

1. The AUC was requested for either $AUC_{0-8}$ or $AUC_{0-24}$ using baseline corrected for single dose and not baseline corrected for multiple dose. Both were supplied.
2. $AUC_{0-\infty}$ was requested to be limited to the 24 hours that was baseline corrected for single dose.
3. Concentration at $C_{24}$ was to be reported as a PK parameter for single-dose.
4. The error in the SAP was noted where tau was incorrectly given as 12 hours when it was 8 hours.
5. Requested $C_0$ and $C_{24}$ from the multiple-dose to be added to the PK parameters
6. Noted that the $C_{avg}$ was to be based on an 8 hour dosing interval (tau).

10. STUDY SUBJECTS

A. Disposition of Subjects

A total of 24 subjects were enrolled in Period 1; 8 subjects each were randomized into Cohort 1, Cohort 2, and Cohort 3. All 24 subjects completed Period 1.

Following Period 1, a total of 8 subjects continued to Period 2. All 8 subjects completed Period 2.

B. Protocol Deviations

The protocol deviations reported during the study were minor and were not expected to affect the outcome of the study. A total of 6 of 24 subjects (25.0%) had protocol deviations of vital signs assessments missed or PK blood draws out of window by 2 or 3 minutes.

11. PHARMACOKINETICS EVALUATION

A. Data Sets Analyzed

Single-Dose Population: All subjects who were randomized and received at least 1 dose of TBS-2 during the study; 24 subjects (100%) were included in this population. (Section 14.1, Table 14.1.1a)

Multi-Dose Population: All subjects in the Single-Dose Population who were selected to continue in study Period 2; 8 subjects (100%) were included in this population. (Section 14.1, Table 14.1.1b)

B. Demographic and Other Baseline Characteristics

Demographic Data

Most subjects in Period 1 were white (19 of 24 subjects [79.2%]), followed in percentage by subjects who were black (4 of 24 subjects [16.7%]) and those who were American Indian or Alaskan Native/white (1 of 24 subjects [4.2%]). A similar number of subjects were not Hispanic or Latino (13 of 24 subjects [54.2%]) and Hispanic or Latino (11 of 24 subjects [45.8%]). Mean (SD) age was 29.8 (5.86) years. Mean (SD) height was 161.02 (6.667) cm, weight was 66.36 (11.378) kg, and BMI was 25.61 (4.079) kg/m². Most subjects had a normal BMI (13 of 24 subjects [54.2%]), followed in percentage by subjects who were overweight (7 of 24 subjects [29.2%]) and subjects who were obese (4 of 24 subjects [16.7%]).

Most subjects in Period 2 were white (5 of 8 subjects [62.5%]), followed in percentage by those who were black (2 of 8 subjects [25.0%]) and those who were American Indian or Alaskan Native/white (1 of 8 subjects [12.5%]). A similar number of subjects were not Hispanic or Latino (5 of 8 subjects [62.5%]) and Hispanic or Latino (3 of 8 subjects [37.5%]). Mean (SD) age was 30.3 (6.48) years. Mean (SD) height was 160.8 (3.99) cm, weight was 61.13 (9.815) kg, and BMI was 23.65 (3.454) kg/m². Most subjects had a normal BMI (6 of 8 subjects [75.0%]), followed in percentage by those who were overweight (2 of 8 subjects [25.0%]).

Baseline Characteristics

Medical History

Subject medical history reported at Screening is summarized by body system in Table 11.1.

Currently active non-exclusionary medical history conditions were reported by at least 10% of subjects overall in the following body systems: nervous system (15 of 24 subjects [62.5%]), genitourinary system (7 of 24 subjects [29.2%]), integumentary system (4 of 24 subjects [16.7%]), and allergic conditions (4 of 24 subjects [16.7%]).

TABLE 11-1

Medical History (Single-Dose Population)

| Body System | Cohort 1 (600 µg) (n = 8) Any History | Cohort 1 Currently Active | Cohort 2 (1200 µg) (n = 8) Any History | Cohort 2 Currently Active | Cohort 3 (1800 µg) (n = 8) Any History | Cohort 3 Currently Active | Total (n = 24) Any History | Total Currently Active |
|---|---|---|---|---|---|---|---|---|
| HEENT | 1 (12.5%) | 0 | 1 (12.5%) | 0 | 2 (25.0%) | 0 | 4 (16.7%) | 0 |
| Respiratory System | 0 | 0 | 1 (12.5%) | 0 | 3 (37.5%) | 0 | 4 (16.7%) | 0 |
| Musculoskeletal System | 3 (37.5%) | 0 | 2 (25.0%) | 0 | 2 (25.0%) | 1 (12.5%) | 7 (29.2%) | 1 (4.2%) |
| Integumentary System (skin, hair, nails) | 0 | 0 | 2 (25.0%) | 2 (25.0%) | 2 (25.0%) | 2 (25.0%) | 4 (16.7%) | 4 (16.7%) |
| Gastrointestinal System | 2 (25.0%) | 1 (12.5%) | 1 (12.5%) | 0 | 1 (12.5%) | 1 (12.5%) | 4 (16.7%) | 2 (8.3%) |

TABLE 11-1-continued

Medical History (Single-Dose Population)

| Body System | Cohort 1 (600 µg) (n = 8) | | Cohort 2 (1200 µg) (n = 8) | | Cohort 3 (1800 µg) (n = 8) | | Total (n = 24) | |
|---|---|---|---|---|---|---|---|---|
| | Any History | Currently Active | Any History | Currently Active | Any History | Currently Active | Any History | Currently Active |
| Genitourinary System | 2 (25.0%) | 0 | 4 (50.0%) | 4 (50.0%) | 3 (37.5%) | 3 (37.5%) | 9 (37.5%) | 7 (29.2%) |
| Nervous System | 5 (62.5%) | 5 (62.5%) | 6 (75.0%) | 6 (75.0%) | 4 (50.0%) | 4 (50.0%) | 15 (62.5%) | 15 (62.5%) |
| Endocrine System | 1 (12.5%) | 0 | 0 | 0 | 0 | 0 | 1 (4.2%) | 0 |
| Lymphatic System | 0 | 0 | 0 | 0 | 0 | 0 | 0 | 0 |
| Immunological System | 0 | 0 | 0 | 0 | 0 | 0 | 0 | 0 |
| Circulatory System | 0 | 0 | 0 | 0 | 0 | 0 | 0 | 0 |
| Psychiatric/ Neurological System | 1 (12.5%) | 0 | 0 | 0 | 1 (12.5%) | 0 | 2 (8.3%) | 0 |
| Allergic Conditions | 1 (12.5%) | 1 (12.5%) | 0 | 0 | 4 (50.0%) | 3 (37.5%) | 5 (20.8%) | 4 (16.7%) |

HEENT = head, eyes, ears, nose, and throat

D. Prior and Concomitant Medications

No concomitant medications were reported during the study.

Overall, 10 subjects reported prior medications. Most reported prior medications were over-the-counter analgesic or anti-inflammatory medications and multivitamins.

E. Measurement of Treatment Compliance

All subjects were observed during dosing at the study site and were compliant with the study drug administration.

F. Tabulations of Individual Subject Data

Analysis of Pharmacokinetics

There were 3 doses profiled pharmacokinetically in this study: 3 doses were profiled for the single-dose period and 1 dose was profiled for the multi-dose period. The single-dose profile included doses of 600, 1200, and 1800 µg testosterone in separate cohorts while the multi-dose period included only the 1200 µg testosterone dose. Each dose was profiled for free and total testosterone, dihydrotestosterone, estradiol, and SHBG. There were 8 subjects in each dose group.

The results are presented first for the concentrations and then for the PK parameters.

G. Concentration Results

Period 1: Single Dose Profile

Figure 19:
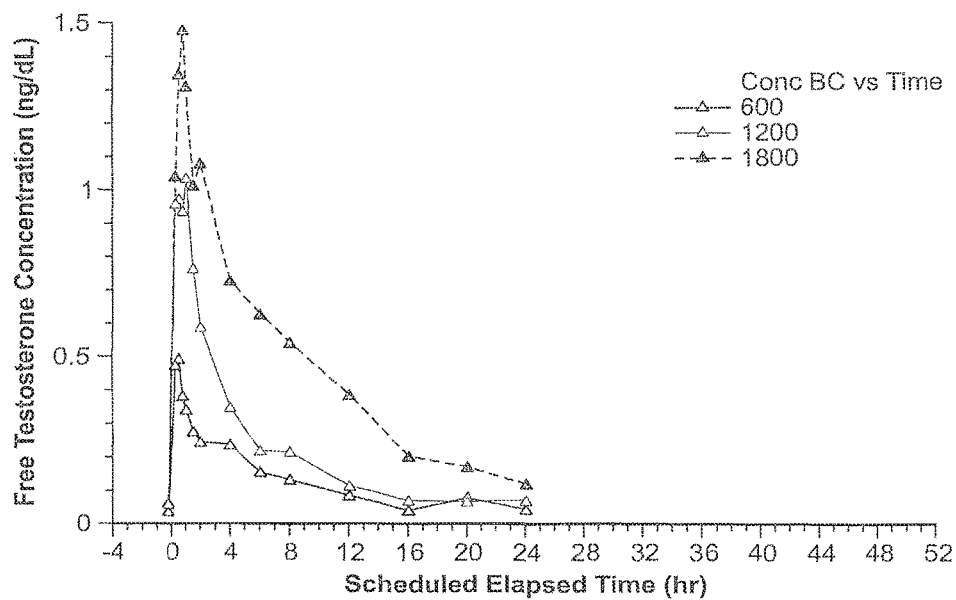
FIG. 19 depicts Mean Corrected Free Testosterone Concentrations (Single-Dose Population)
Figure 20:
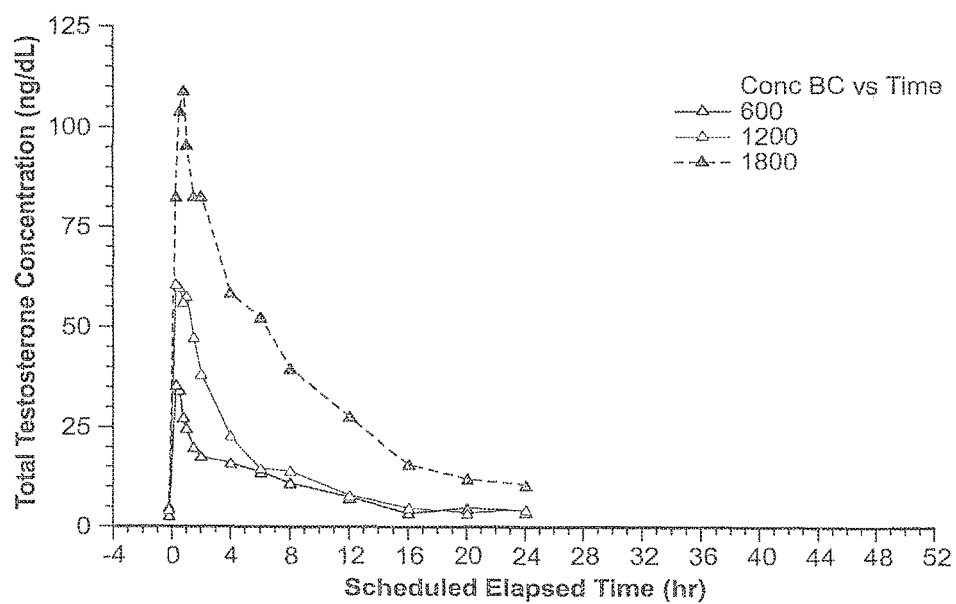
FIG. 20 depicts Mean Corrected Total Testosterone Concentrations (Single-Dose Population)
Figure 21:
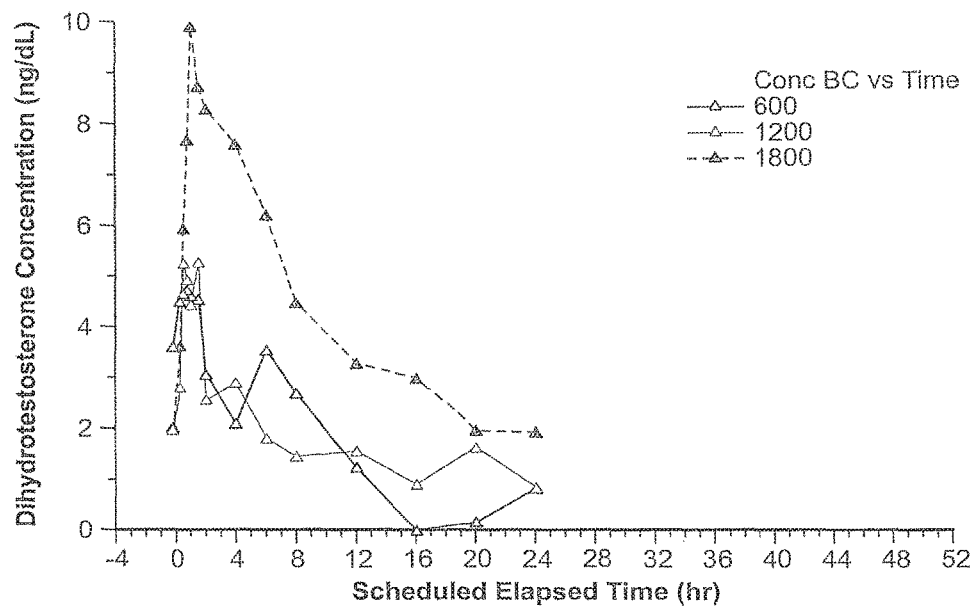
FIG. 21 depicts Mean Corrected Dihydrotestosterone Concentrations (Single-Dose Population)
Figure 22:
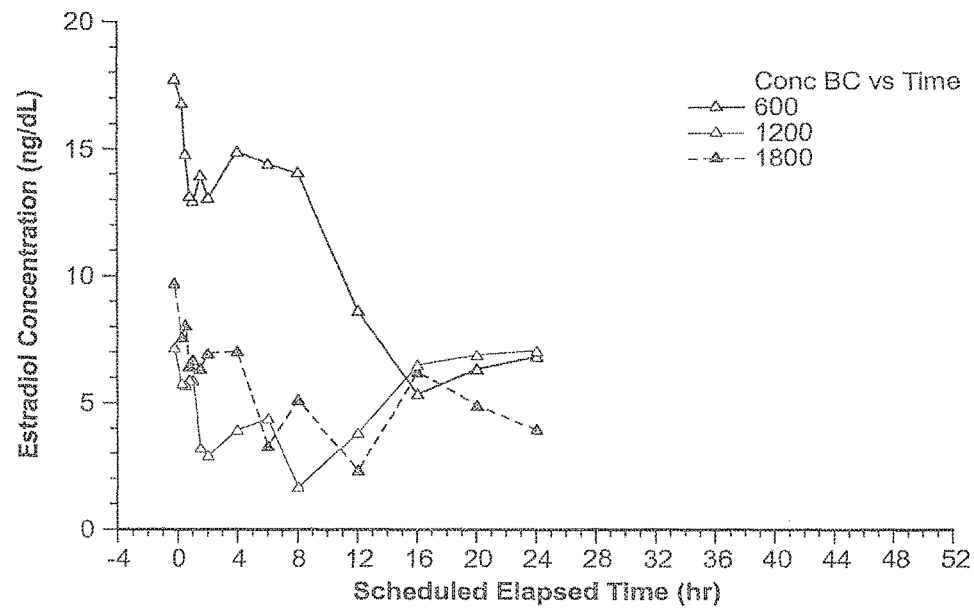
FIG. 22 depicts Mean Corrected Estradiol Concentrations (Single-Dose Population)
Figure 23:
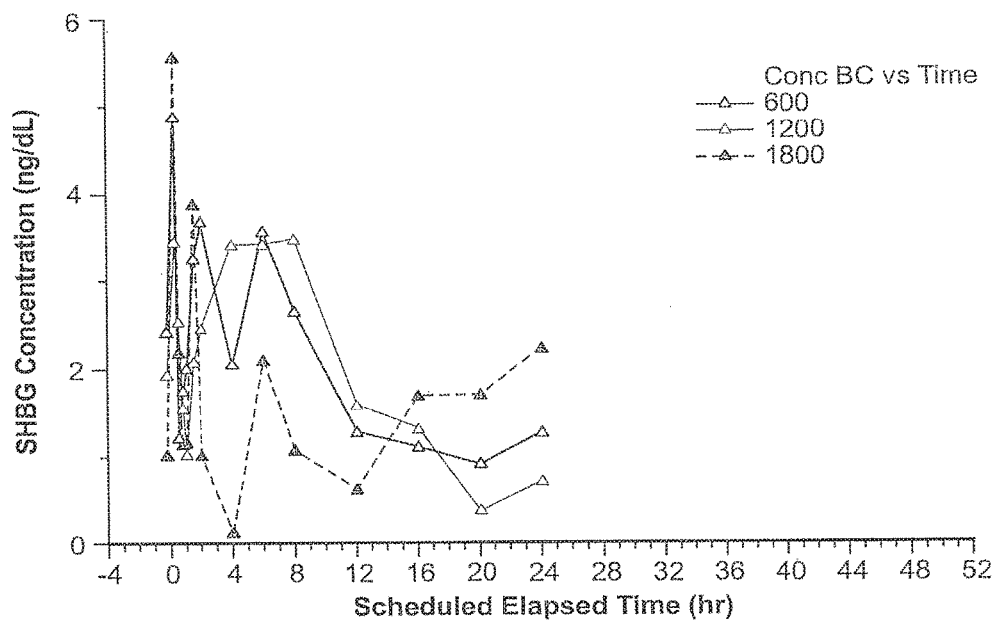
FIG. 23 depicts Mean Corrected SHBG Concentrations (Single-Dose Population)

The mean concentration profiles are presented in the following figures for each of the 5 analytes after baseline correction. The free testosterone and total testosterone concentration figures present the clearest relationship of concentration to increasing testosterone dose (FIG. 19 and FIG. 20, respectively). The dihydrotestosterone analyte provides a clear distinction between the 1800 µg dose compared with the lower doses which are not clearly differentiated from each other (FIG. 21). The obverse is observed in the estradiol concentrations where it is the lowest dose of 600 µg, which is clearly distinct from the two higher doses, which are not clearly differentiated from each other (FIG. 22). The SHBG concentrations are not clearly distinguished between administered testosterone doses (FIG. 23).

Figure 24:
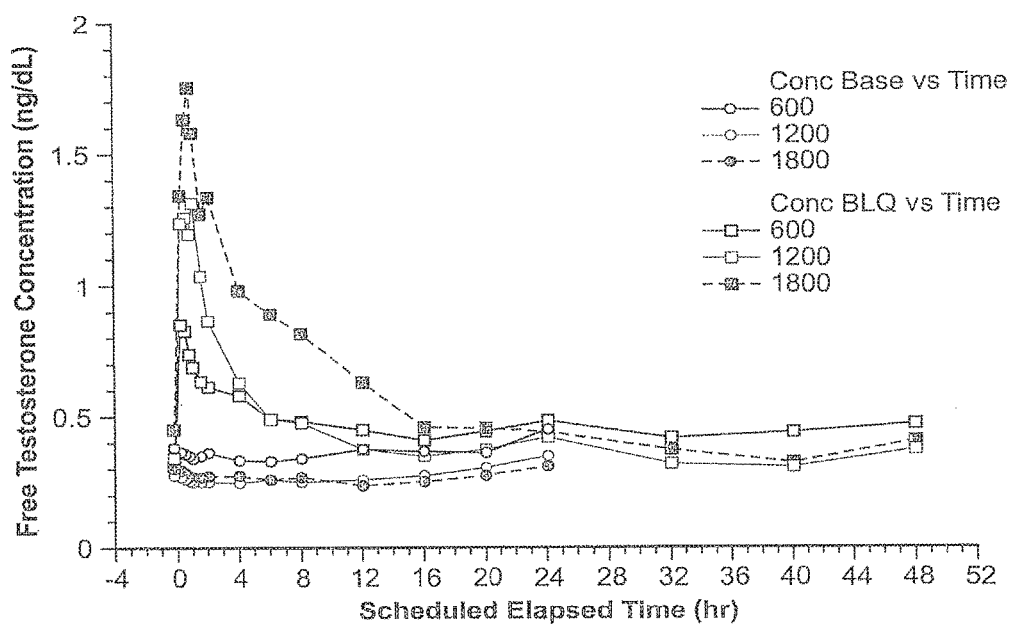
FIG. 24 depicts Mean Observed Free Testosterone Concentrations (Single-Dose Population)
Figure 25:
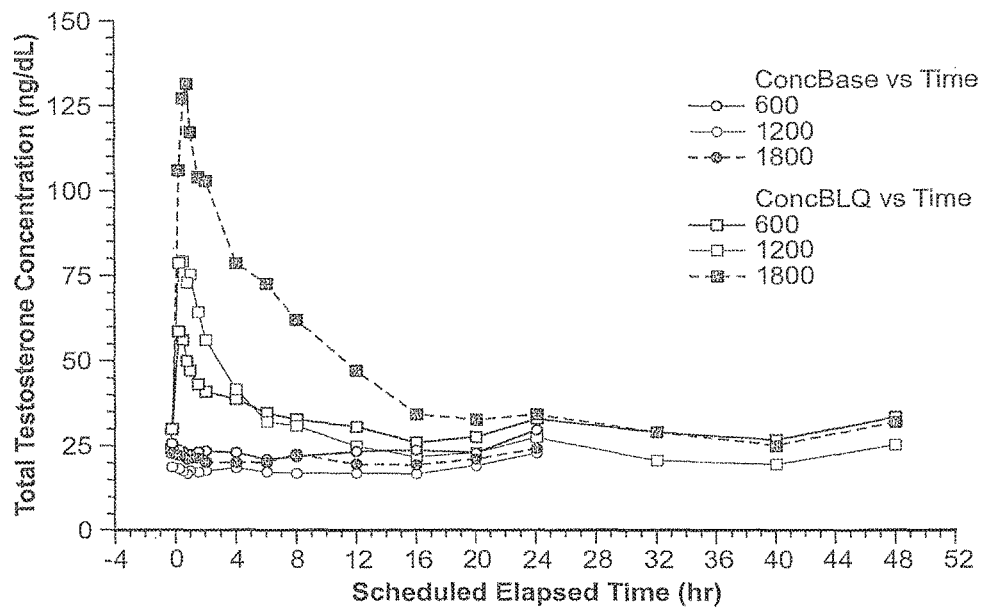
FIG. 25 depicts Mean Observed Total Testosterone Concentrations (Single-Dose Population)
Figure 26:
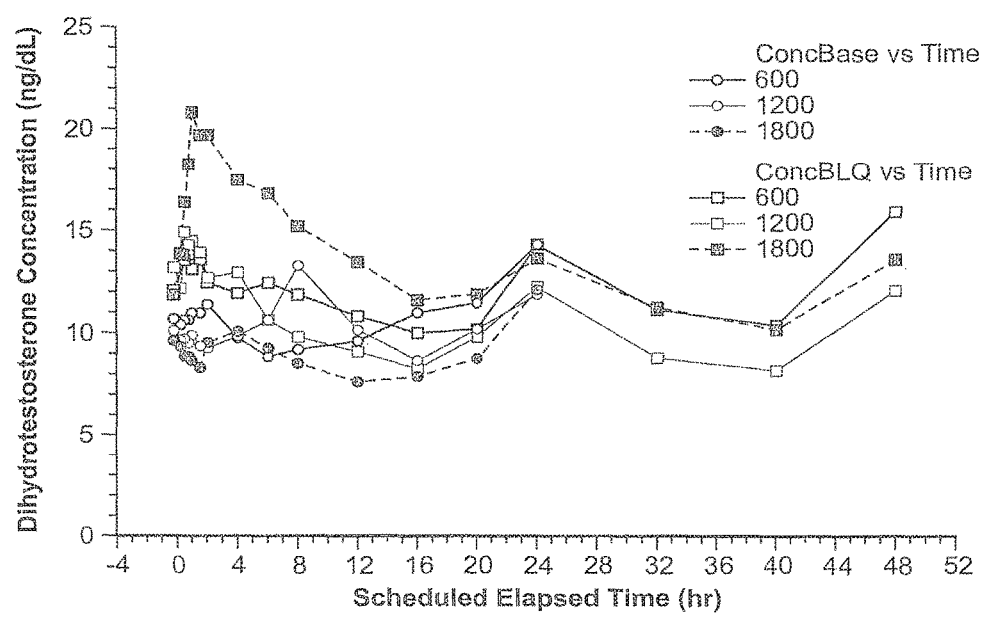
FIG. 26 depicts Mean Observed Dihydrotestosterone Concentrations (Single-Dose Population)
Figure 27:
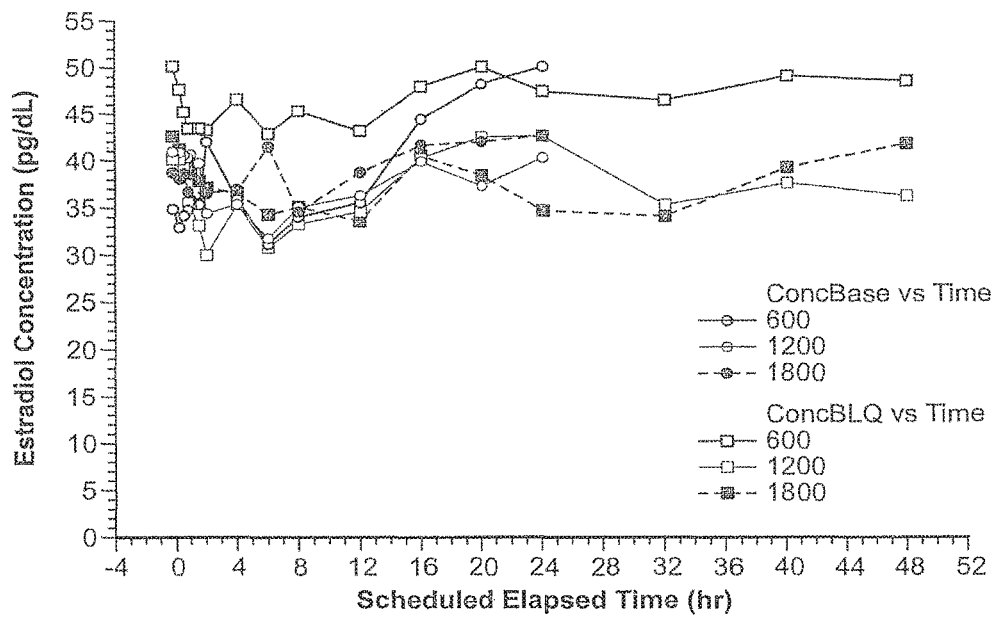
FIG. 27 depicts Mean Observed Estradiol Concentrations (Single-Dose Population)
Figure 28:
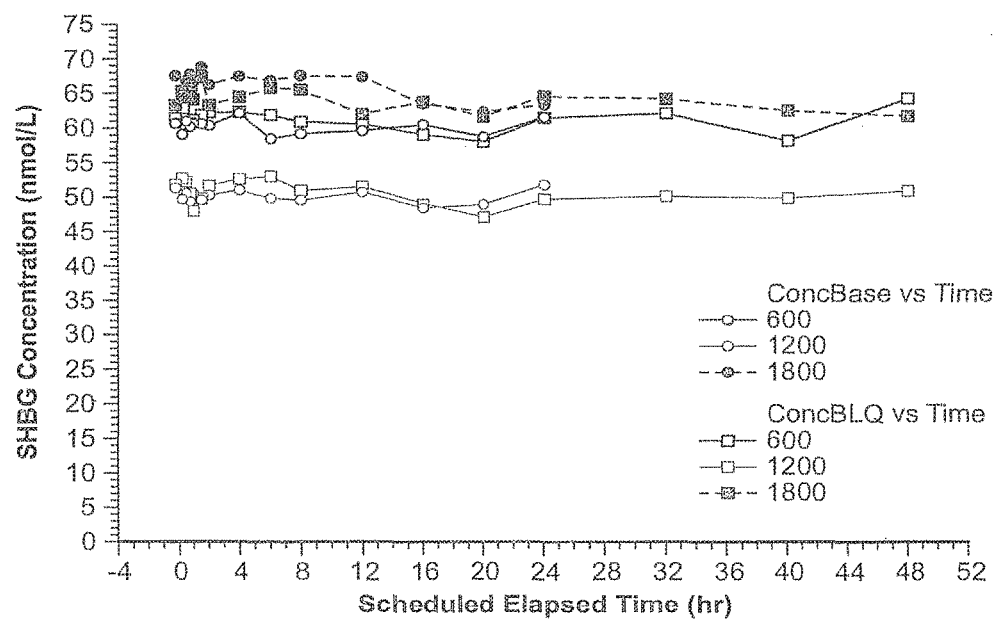
FIG. 28 depicts Mean Observed SHBG Concentrations (Single-Dose Population)

The free and total testosterone and to a lesser extent the dihydrotestosterone concentrations are more clearly differentiated between the baseline and the active dose (FIG. 24, FIG. 25, and FIG. 26, respectively). The estradiol and SHBG concentrations have post-dose curves that overlap with the baseline concentrations in the same doses (FIG. 27 and FIG. 28, respectively).

Period 2: Multiple Dose Profiles

Figure 32:
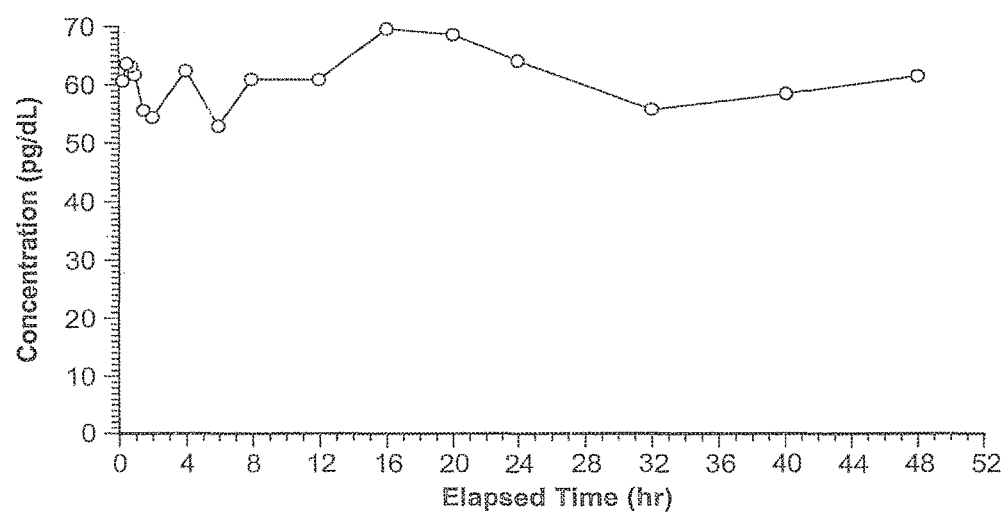
FIG. 32 depicts Mean Estradiol Plasma Concentrations (Multi-Dose Population)
Figure 33:
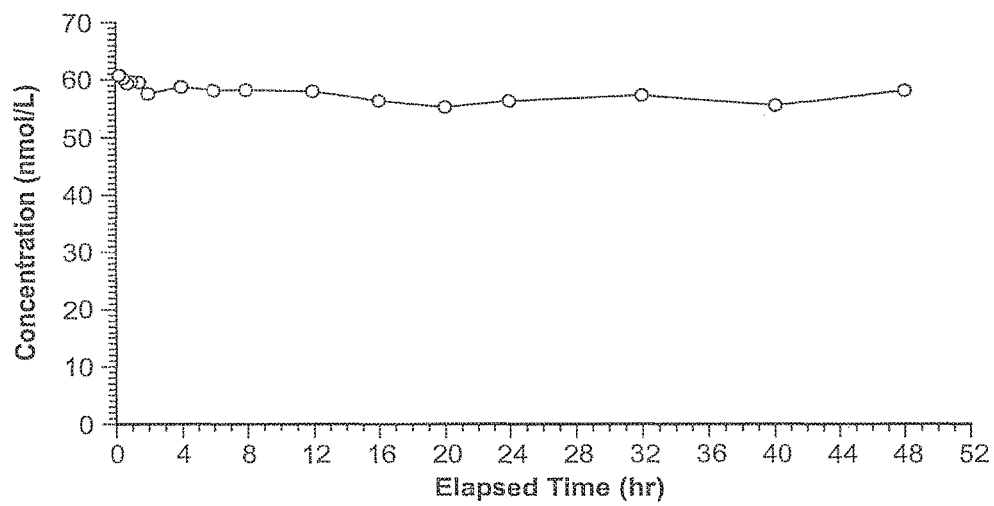
FIG. 33 depicts Mean SHBG Plasma Concentrations (Multi-Dose Population)

The free testosterone and total testosterone mean figures present the clearest dose effect with the highest concentrations at the time of dose and decreasing to a plateau at about 12-16 hours. The concentrations seem to get back to baseline levels after 10 hours post dose. These two plots track so closely that they seem to be superimposableonce the scale is adjusted (FIG. 19 and FIG. 20, respectively). The dihydrotestosterone concentrations also indicate a peak at the time of dose but it is not as clear as with the free and total testosterone (FIG. 21). Little difference in estradiol and SHBG concentrations can been seen over the observation period of the multi-dose profile that can be attributed to the absence of a spike in concentration when the dose was administered. (FIG. 32 and FIG. 33, respectively).

Figure 34:
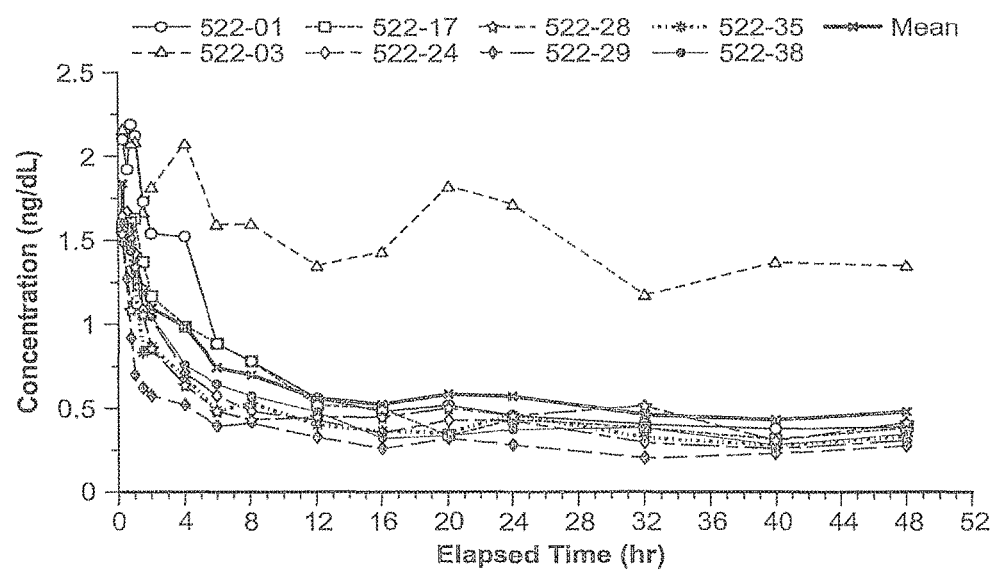
FIG. 34 depicts Spaghetti Concentration Plots with Mean for Free Testosterone Plasma Concentrations (Multi-Dose Population)
Figure 35:
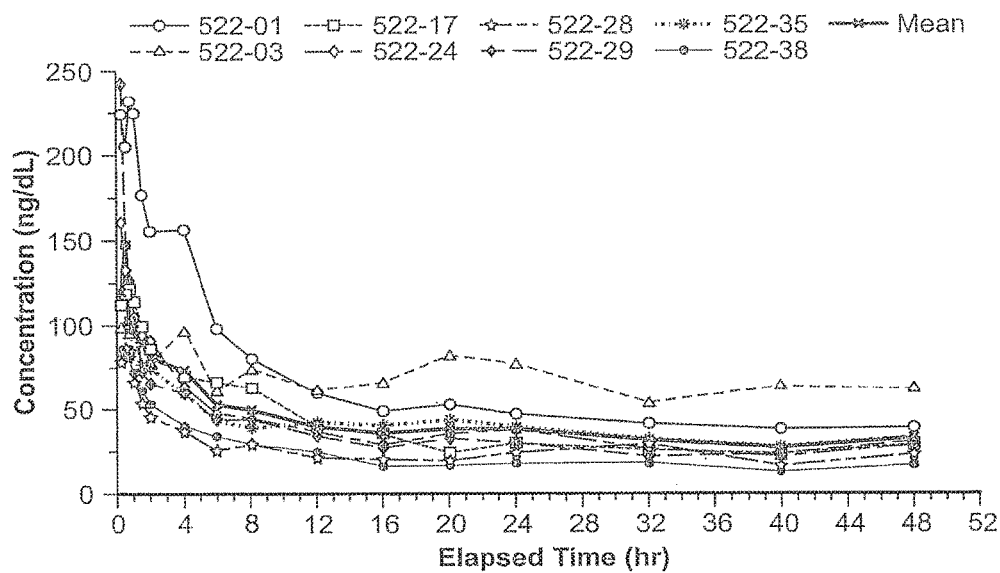
FIG. 35 depicts Spaghetti Concentration Plots with Mean for Total Testosterone Plasma Concentrations (Multi-Dose Population)
Figure 36:
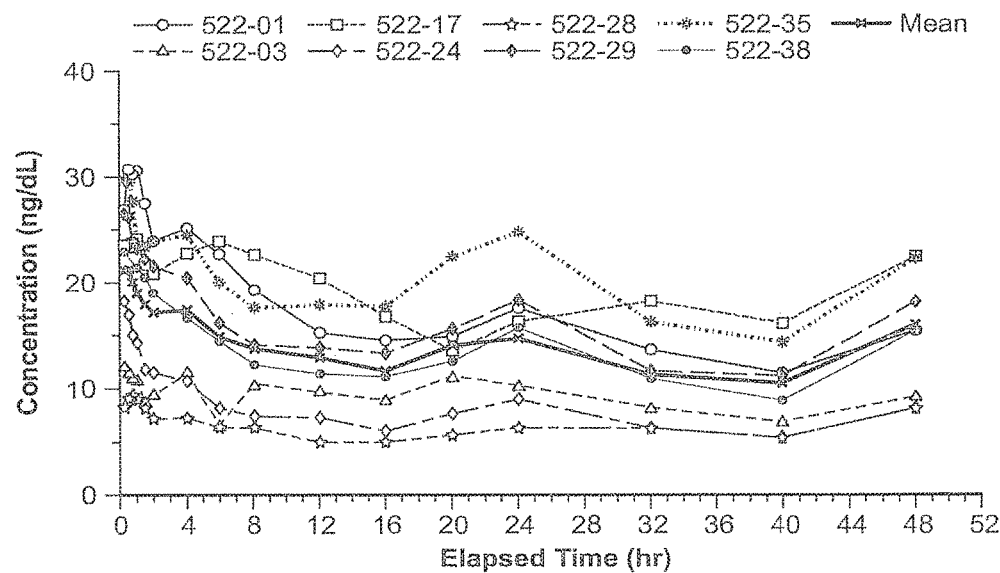
FIG. 36 depicts Spaghetti Concentration Plots with Mean for Dihydrotestosterone Plasma Concentrations (Multi-Dose Population)
Figure 37:
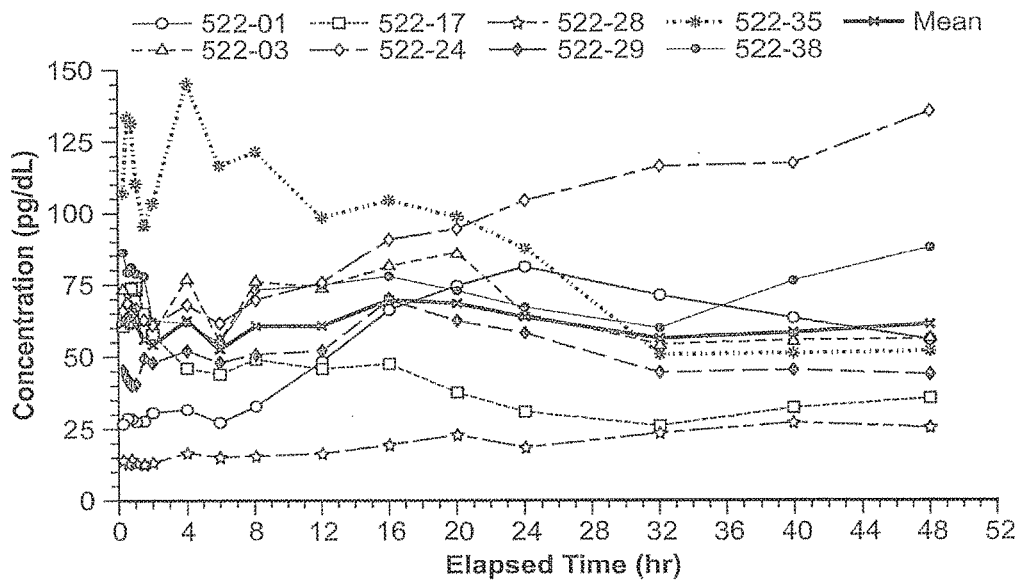
FIG. 37 depicts Spaghetti Concentration Plots with Mean for Estradiol Plasma Concentrations (Multi-Dose Population)
Figure 38:
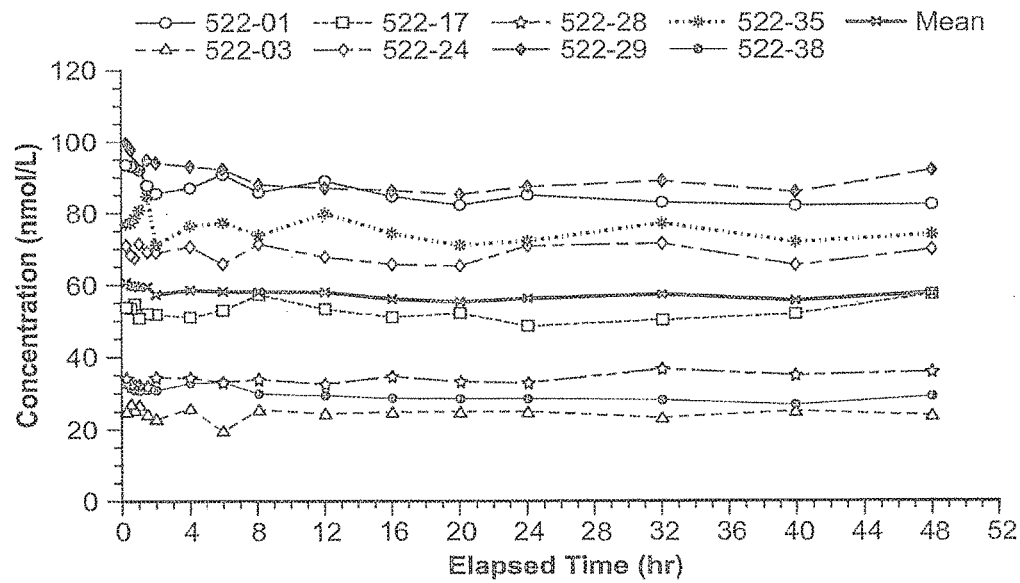
FIG. 38 depicts Spaghetti Concentration Plots with Mean for SHBG Plasma Concentrations (Multi-Dose Population)

Subject 522-03 had free testosterone concentrations that didn't show a similar decrease as compared to the other 7 subjects 12 hours after the final dose (FIG. 34). The free testosterone concentrations for Subject 522-03 were also the highest concentrations after 12 hours but not as different from the other 7 subjects as were the free testosterone concentrations (FIG. 35). Relationship to dose is increasingly harder to find for the dihydrotestosterone, estradiol, and SHBG in that order with SHBG concentrations essentially constant for each subject but at different concentrations (FIG. 36, FIG. 37, and FIG. 38, respectively).

H. Pharmacokinetic Parameter Estimates

Pharmacokinetic parameters were estimated by using Phoenix WinNonlin Version 6.2.

Period 1: Single Dose Pharmacokinetic Parameter Estimates

All PK parameter estimates were performed on the first 24 hours with the baseline-corrected concentrations. The PK parameters estimated from the single-dose profiles for each individual are presented in Appendix 16.2, Listing 16.2.5.1.2a and summarized in Section 14.2, Table 14.4.2a. The following table (Table 11-22) presents the data for the single-dose PK parameters but the SD and median have been omitted.

All 24 subjects had profiles that estimated the λz (terminal elimination rate) for free and total testosterone. Only 12 subjects had profiles that estimated the λz for dihydrotestosterone, 11 for estradiol, and 9 for SHBG. Without λz, the elimination half-life, $t_{1/2}$, and $AUC_{0-\infty}$, could not be calculated.

Free Testosterone

For free testosterone, the mean $C_{max}$ closely tracked the administered dose suggesting proportionality to dose. The mean $AUC_{0-8}$ was proportional from the 600 μg dose to the 1200 μg dose (1.94 ratio compared to 2.00 dose ratio) but was somewhat lower for the 1800 μg dose (3.55 ratio compared to 3.00 dose ratio). Other measures of AUC were less clearly related to dose and did not suggest a proportional relationship to dose as strongly as the $AUC_{0-8}$. This was probably due to the increase in concentration from the dose being most prominent in the first 8 hours as seen in the figures. The λz values were similar across doses.

TABLE 11-22

Free Testosterone Summary (Single-Dose Population)

| Dose (μg) | | $C_{max}$ (ng/dL) | $t_{max}$ (hr) | $AUC_{0-8}$ (hr * ng/dL) | $AUC_{0-24}$ (hr * ng/dL) | $AUC_{0-t}$ (hr * ng/dL) | $AUC_{0-\infty}$ (hr * ng/dL) | $\lambda_z$ (1/hr) | $t_{1/2}$ (hr) | $C_{24}$ ConcBase (ng/dL) | $C_{24}$ ConcBLQ (ng/dL) | $C_{24}$ ConcBC (ng/dL) |
|---|---|---|---|---|---|---|---|---|---|---|---|---|
| 600 | N | 8 | 8 | 8 | 8 | 8 | 8 | 8 | 8 | 8 | 8 | 8 |
| | Mean | 0.56 | 0.438 | 1.85 | 3.104 | 3.006 | 4.489 | 0.101 | 10.291 | 0.448 | 0.481 | 0.052 |
| | CV | 74.2 | 59.1 | 61.5 | 58.1 | 55.2 | 63.8 | 90.5 | 48.9 | 91.9 | 75 | 107.2 |
| | Min | 0.16 | 0.25 | 0.94 | 1.45 | 1.41 | 1.47 | 0.04 | 2.21 | 0.18 | 0.2 | 0 |
| | Max | 1.45 | 1 | 4.32 | 6.18 | 5.51 | 8.76 | 0.31 | 15.7 | 1.44 | 1.3 | 0.16 |
| | GeoMean | 0.442 | | 1.622 | 2.711 | 2.652 | 3.758 | 0.079 | 8.784 | 0.357 | 0.401 | |
| 1200 | N | 8 | 8 | 8 | 8 | 8 | 8 | 8 | 8 | 8 | 8 | 8 |
| | Mean | 1.274 | 0.656 | 3.598 | 5.265 | 5.265 | 6.099 | 0.104 | 7.289 | 0.346 | 0.423 | 0.077 |
| | CV | 63.8 | 73.2 | 60.8 | 54.8 | 54.8 | 49.3 | 36.8 | 27.8 | 39.7 | 35.9 | 42.1 |
| | Min | 0.32 | 0.25 | 0.87 | 1.28 | 1.28 | 1.64 | 0.07 | 3.79 | 0.2 | 0.24 | 0.04 |
| | Max | 2.51 | 1.5 | 8.16 | 10.61 | 10.61 | 11.42 | 0.18 | 9.59 | 0.53 | 0.63 | 0.12 |
| | GeoMean | 1.017 | | 3.021 | 4.488 | 4.488 | 5.354 | 0.099 | 6.995 | 0.322 | 0.4 | 0.071 |
| 1800 | N | 8 | 8 | 8 | 8 | 8 | 8 | 8 | 8 | 8 | 8 | 8 |
| | Mean | 1.708 | 1.406 | 6.562 | 10.958 | 10.926 | 12.314 | 0.123 | 6.411 | 0.314 | 0.436 | 0.125 |
| | CV | 44.2 | 137.4 | 36.8 | 50.1 | 50.5 | 51.1 | 43.3 | 34.4 | 24 | 25.5 | 79.5 |
| | Min | 0.41 | 0.25 | 2.36 | 3.68 | 3.68 | 4.04 | 0.07 | 2.9 | 0.19 | 0.28 | 0 |
| | Max | 2.53 | 6 | 9.46 | 21.22 | 21.22 | 23.23 | 0.24 | 10.32 | 0.41 | 0.62 | 0.28 |
| | GeoMean | 1.5 | | 6.053 | 9.615 | 9.561 | 10.689 | 0.115 | 6.049 | 0.306 | 0.423 | |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{24}$ ConcBase = baseline concentration;
$C_{24}$ ConcBLQ = concentration of active dose;
$C_{24}$ ConcBC = baseline-corrected concentration;
$C_{max}$ = maximum concentration observed after dosing;
CV = % coefficient of variation;
GeoMean = geometric mean;
$\lambda_z$ = terminal elimination rate constant;
$t_{1/2}$ = elimination half-life;
$t_{max}$ = time of observed maximum concentration relative to the time of dosing
Note:
The geometric mean is not normally reported for $t_{max}$.
Note:
The geometric mean cannot be calculated if Min = 0.

Total Testosterone

Total testosterone $C_{max}$ parameters increased with increasing dose as did all of the AUC measures. The $\lambda_z$ measures were similar across doses. (Table 11-23).

TABLE 11-23

Total Testosterone Summary (Single-Dose Population)

| Dose (μg) | | $C_{max}$ (ng/dL) | $t_{max}$ (hr) | $AUC_{0-8}$ (hr * ng/dL) | $AUC_{0-24}$ (hr * ng/dL) | $AUC_{0-t}$ (hr * ng/dL) | $AUC_{0-\infty}$ (hr * ng/dL) | $\lambda_z$ (1/hr) | $t_{1/2}$ (hr) | $C_{24}$ ConcBase (ng/dL) | $C_{24}$ ConcBLQ (ng/dL) | $C_{24}$ ConcBC (ng/dL) |
|---|---|---|---|---|---|---|---|---|---|---|---|---|
| 600 | N | 8 | 8 | 8 | 8 | 8 | 8 | 8 | 8 | 8 | 8 | 8 |
| | Mean | 40.625 | 0.438 | 135.313 | 229.095 | 223.981 | 327.448 | 0.108 | 9.434 | 30.138 | 33.138 | 4.175 |
| | CV | 61.1 | 59.1 | 31.6 | 38.3 | 39 | 45.1 | 91.2 | 48.6 | 44.7 | 36.6 | 98.9 |
| | Min | 15.8 | 0.25 | 84.58 | 127.73 | 127.79 | 157.01 | 0.04 | 2.03 | 17.1 | 16 | 0 |
| | Max | 86.7 | 1 | 195.66 | 396.56 | 396.56 | 553.97 | 0.34 | 16.5 | 58 | 50.7 | 10.4 |
| | GeoMean | 34.058 | | 129.311 | 215.781 | 210.961 | 296.981 | 0.086 | 8.106 | 27.873 | 31.141 | |

TABLE 11-23-continued

Total Testosterone Summary (Single-Dose Population)

| Dose (μg) | | $C_{max}$ (ng/dL) | $t_{max}$ (hr) | $AUC_{0-8}$ (hr * ng/dL) | $AUC_{0-24}$ (hr * ng/dL) | $AUC_{0-t}$ (hr * ng/dL) | $AUC_{0-\infty}$ (hr * ng/dL) | $\lambda_z$ (1/hr) | $t_{1/2}$ (hr) | $C_{24}$ ConcBase (ng/dL) | $C_{24}$ ConcBLQ (ng/dL) | $C_{24}$ ConcBC (ng/dL) |
|---|---|---|---|---|---|---|---|---|---|---|---|---|
| 1200 | N | 8 | 8 | 8 | 8 | 8 | 8 | 8 | 8 | 8 | 8 | 8 |
| | Mean | 71.063 | 0.688 | 225.758 | 328.002 | 328.002 | 372.176 | 0.118 | 6.472 | 23.538 | 28.013 | 4.475 |
| | CV | 48.6 | 66.6 | 41.9 | 35.8 | 35.8 | 27.5 | 39.5 | 28.5 | 43.3 | 35.2 | 67.3 |
| | Min | 21.9 | 0.25 | 65.78 | 102.59 | 102.59 | 161.89 | 0.07 | 3.09 | 13.3 | 17.2 | 1.4 |
| | Max | 133 | 1.5 | 377.85 | 448.61 | 448.61 | 487.25 | 0.22 | 9.34 | 41.1 | 44.6 | 11.4 |
| | GeoMean | 62.88 | | 203.648 | 301.821 | 301.821 | 355.747 | 0.112 | 6.199 | 21.791 | 26.582 | 3.809 |
| 1800 | N | 8 | 8 | 8 | 8 | 8 | 8 | 8 | 8 | 8 | 8 | 8 |
| | Mean | 130.863 | 1.031 | 515.848 | 837.083 | 834.391 | 947.786 | 0.133 | 6.143 | 24.35 | 34.55 | 10.625 |
| | CV | 44.3 | 118.4 | 44.6 | 49.3 | 49.7 | 54.5 | 52.1 | 34.7 | 28.8 | 32.1 | 100.1 |
| | Min | 27.2 | 0.25 | 169.05 | 273.14 | 273.14 | 315.07 | 0.09 | 2.57 | 17 | 25 | 0 |
| | Max | 194 | 4 | 899.74 | 1593.93 | 1593.93 | 1989.73 | 0.27 | 8.07 | 38.8 | 59.8 | 34 |
| | GeoMean | 113.912 | | 464.728 | 742.547 | 739.181 | 830.493 | 0.121 | 5.716 | 23.552 | 33.314 | |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{24}$ ConcBase = baseline concentration;
$C_{24}$ ConcBLQ = concentration of active dose;
$C_{24}$ ConcBC = baseline-corrected concentration;
$C_{max}$ = maximum concentration observed after dosing;
CV = % coefficient of variation;
GeoMean = geometric mean;
$\lambda_z$ = terminal elimination rate constant;
$t_{1/2}$ = eimination half-life; t
$t_{max}$ = time of observed maximum concentration relative to the time of dosing
Note:
The geometric mean is not normally reported for $t_{max}$.
Note:
The geometric mean cannot be calculated if Min = 0.

Dihydrotestosterone

Dihydrotestosterone PK parameters were missing a number of parameter values and some entire profiles were missing after baseline correction; only 18 of the 24 profiles were present and λz could be estimated in only 12 of the 24 profiles. Mean $C_{max}$, $AUC_{0-8}$, and $AUC_{0-\infty}$ values decreased from the 600 μg dose to the 1200 μg dose but then increased for the 1800 μg dose. The other AUC measures demonstrated increasing exposure with increasing dose. The $\lambda_z$ values were roughly similar for each dose. (Table 11-24)

TABLE 11-24

Dihydrotestosterone Summary (Single-Dose Population)

| Dose (μg) | | $C_{max}$ (ng/dL) | $t_{max}$ (hr) | $AUC_{0-8}$ (hr * ng/dL) | $AUC_{0-24}$ (hr * ng/dL) | $AUC_{0-t}$ (hr * ng/dL) | $AUC_{0-\infty}$ (hr * ng/dL) | $\lambda_z$ (1/hr) | $t_{1/2}$ (hr) | $C_{24}$ ConcBase (ng/dL) | $C_{24}$ ConcBLQ (ng/dL) | $C_{24}$ ConcBC (ng/dL) |
|---|---|---|---|---|---|---|---|---|---|---|---|---|
| 600 | N | 6 | 6 | 5 | 5 | 6 | 4 | 4 | 4 | 5 | 5 | 5 |
| | Mean | 7.078 | 1.75 | 26.902 | 39.038 | 31.844 | 83.96 | 0.153 | 16.229 | 14.274 | 14.302 | 0.828 |
| | CV | 70.1 | 122.6 | 74.8 | 61.7 | 74.9 | 98.6 | 127.7 | 105.6 | 44.2 | 31.4 | 151.3 |
| | Min | 2.66 | 0.25 | 9.44 | 11.51 | 5.61 | 13.85 | 0.02 | 1.58 | 8.23 | 8.61 | 0 |
| | Max | 16.27 | 6 | 59.82 | 71.37 | 70.18 | 202.98 | 0.44 | 39.89 | 22.1 | 19 | 2.97 |
| | GeoMean | 5.888 | | 21.859 | 32.493 | 23.515 | 55.582 | 0.077 | 9.009 | 13.144 | 13.697 | |
| 1200 | N | 6 | 6 | 6 | 6 | 6 | 3 | 3 | 3 | 6 | 6 | 6 |
| | Mean | 6.23 | 5.083 | 23.909 | 45.617 | 43.261 | 72.971 | 0.057 | 12.43 | 12.048 | 12.203 | 0.867 |
| | CV | 43.6 | 182.4 | 48.4 | 52.4 | 49.1 | 22.2 | 19.6 | 20.6 | 54.9 | 39.7 | 116 |
| | Min | 2.27 | 1 | 8.32 | 16.9 | 16.9 | 54.27 | 0.05 | 10.22 | 8.03 | 8.32 | 0 |
| | Max | 9.62 | 24 | 37.33 | 79.02 | 69.98 | 82.43 | 0.07 | 15.24 | 25.3 | 21.8 | 2.27 |
| | GeoMean | 5.646 | | 20.858 | 39.952 | 38.457 | 71.647 | 0.057 | 12.259 | 11.004 | 11.589 | |
| 1800 | N | 6 | 6 | 6 | 6 | 6 | 5 | 5 | 5 | 6 | 6 | 6 |
| | Mean | 11.392 | 2.792 | 52.921 | 98.838 | 98.078 | 158.68 | 0.1 | 11.855 | 11.865 | 13.615 | 1.918 |
| | CV | 59.3 | 101.1 | 68.5 | 63.4 | 64.2 | 73.4 | 71.6 | 78 | 40 | 37.6 | 124.6 |
| | Min | 3.93 | 0.75 | 19.3 | 41.71 | 41.71 | 70.03 | 0.03 | 3.7 | 5.55 | 8.06 | 0 |

TABLE 11-24-continued

Dihydrotestosterone Summary (Single-Dose Population)

| Dose (μg) | | $C_{max}$ (ng/dL) | $t_{max}$ (hr) | $AUC_{0-8}$ (hr * ng/dL) | $AUC_{0-24}$ (hr * ng/dL) | $AUC_{0-t}$ (hr * ng/dL) | $AUC_{0-\infty}$ (hr * ng/dL) | $\lambda_z$ (1/hr) | $t_{1/2}$ (hr) | $C_{24}$ ConcBase (ng/dL) | $C_{24}$ ConcBLQ (ng/dL) | $C_{24}$ ConcBC (ng/dL) |
|---|---|---|---|---|---|---|---|---|---|---|---|---|
| | Max | 23.4 | 8 | 117.76 | 217.97 | 217.97 | 327.95 | 0.19 | 23.31 | 20 | 21.4 | 6.4 |
| | GeoMean | 9.82 | | 43.767 | 86.043 | 85.18 | 128.512 | 0.077 | 8.971 | 11.068 | 12.834 | |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{24}$ ConcBase = baseline concentration;
$C_{24}$ ConcBLQ = concentration of active dose;
$C_{24}$ ConcBC = baseline-corrected concentration;
$C_{max}$ = maximum concentration observed after dosing;
CV = % coefficient of variation;
GeoMean = geometric mean;
$\lambda_z$ = terminal elimination rate constant;
$t_{1/2}$ = eimination half-life;
$t_{max}$ = time of observed maximum concentration relative to the time of dosing
Note:
The geometric mean is not normally reported for $t_{max}$.
Note:
The geometric mean cannot be calculated if Min = 0.

Estradiol

Estradiol PK parameters for $C_{max}$ and AUC measures were similar for the 1200 μg and 1800 μg doses, but consistently less than the values from the 600 μg dose. For example the mean $C_{max}$ ratios were 0.61 and 0.64 for 600 μg dose compared to the 1200 μg and 1800 μg doses, respectively. Similar ratios for $AUC_{0-8}$ were 0.31 and 0.47, respectively, where ratios of 2.00 and 3.00 would indicate proportionality. Also note that the 600 μg dose had an N=8 while both the 1200 μg and 1800 μg doses had an N=7. The $\lambda_z$ values were similar. (Table 11-25)

TABLE 11-25

Estradiol Summary (Single-Dose Population)

| Dose (ug) | | $C_{max}$ (pg/mL) | $t_{max}$ (hr) | $AUC_{0-8}$ (hr * pg/mL) | $AUC_{0-24}$ (hr * pg/mL) | $AUC_{0-t}$ (hr * pg/mL) | $AUC_{0-\infty}$ (hr * pg/mL) | $\lambda_z$ (1/hr) | $t_{1/2}$ (hr) | $C_{24}$ ConcBase (pg/mL) | $C_{24}$ ConcBLQ (pg/mL) | $C_{24}$ ConcBC (pg/mL) |
|---|---|---|---|---|---|---|---|---|---|---|---|---|
| 600 | N | 8 | 8 | 8 | 8 | 8 | 5 | 5 | 5 | 8 | 8 | 8 |
| | Mean | 23.275 | 10.816 | 112.508 | 236.334 | 230.951 | 718.407 | 0.063 | 30.458 | 50.1 | 47.438 | 6.863 |
| | CV | 128.4 | 90.3 | 159 | 120.4 | 118.7 | 69 | 106.8 | 119.5 | 65.4 | 41.4 | 81.1 |
| | Min | 3.4 | 0.25 | 0 | 10 | 10 | 194.98 | 0.01 | 3.88 | 22.9 | 27.9 | 0 |
| | Max | 92.8 | 24 | 528.41 | 723 | 679.81 | 1351.44 | 0.18 | 93.63 | 122 | 90.6 | 18 |
| | GeoMean | 13.468 | | | 106.562 | 105.763 | 553.278 | 0.039 | 17.818 | 43.319 | 44.477 | |
| 1200 | N | 7 | 7 | 7 | 7 | 7 | 2 | 2 | 2 | 8 | 8 | 8 |
| | Mean | 14.186 | 9.854 | 34.928 | 134.419 | 133.848 | 383.708 | 0.067 | 21.96 | 40.288 | 42.6 | 7.1 |
| | CV | 33.9 | 100.7 | 110.2 | 81.3 | 82.2 | 51.7 | 102.7 | 102.7 | 40.9 | 33.1 | 106.4 |
| | Min | 7.8 | 1 | 0 | 9.3 | 7.3 | 243.46 | 0.02 | 6.02 | 22.5 | 26.6 | 0 |
| | Max | 22.2 | 24 | 101.1 | 322.73 | 322.73 | 523.95 | 0.12 | 37.9 | 75 | 70.2 | 19.9 |
| | GeoMean | 13.474 | | | 80.078 | 75.97 | 357.16 | 0.046 | 15.104 | 37.815 | 40.76 | |
| 1800 | N | 7 | 7 | 7 | 7 | 7 | 4 | 4 | 4 | 8 | 8 | 8 |
| | Mean | 14.843 | 7.176 | 52.593 | 134.952 | 132.894 | 323.544 | 0.166 | 7.886 | 42.55 | 34.713 | 4.038 |
| | CV | 92.3 | 143.1 | 177.8 | 192.4 | 197.9 | 166.1 | 109.4 | 63.3 | 38.3 | 65 | 213 |
| | Min | 5.4 | 0.25 | 1.88 | 9.74 | 8.11 | 22.4 | 0.06 | 1.59 | 23.3 | 16.5 | 0 |
| | Max | 44.5 | 24 | 262.18 | 722.27 | 727.84 | 1128.44 | 0.44 | 12.24 | 65.4 | 88.2 | 24.1 |
| | GeoMean | 11.47 | | 18.811 | 48.85 | 43.97 | 105.227 | 0.114 | 6.103 | 39.849 | 30.552 | |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{24}$ ConcBase = baseline concentration;
$C_{24}$ ConcBLQ = concentration of active dose;
$C_{24}$ ConcBC = baseline-corrected concentration;
$C_{max}$ = maximum concentration observed after dosing;
CV = % coefficient of variation;
GeoMean = geometric mean;
$\lambda_z$ = terminal elimination rate constant;
$t_{1/2}$ = eimination half-life;
$t_{max}$ = time of observed maximum concentration relative to the time of dosing
Note:
The geometric mean is not normally reported for $t_{max}$.
Note:
The geometric mean cannot be calculated if Min = 0.

SHBG

The SHBG $C_{max}$ and $AUC_{0-8}$, $AUC_{0-24}$, and $AUC_{0-t}$ values were similar for the 600 μg and the 1200 μg doses. The $\lambda_z$ was not characterized for the majority of these subjects. (Table 11-26)

TABLE 11-26

SHBG Summary (Single-Dose Population)

| Dose (μg) | | $C_{max}$ (nmol/L) | $t_{max}$ (hr) | $AUC_{0-8}$ (hr * nmol/L) | $AUC_{0-24}$ (hr * nmol/L) | $AUC_{0-t}$ (hr * nmol/L) | $AUC_{0-\infty}$ (hr * nmol/L) | $\lambda_z$ (1/hr) | $t_{1/2}$ (hr) | $C_{24}$ ConcBase (nmol/L) | $C_{24}$ ConcBLQ (nmol/L) | $C_{24}$ ConcBC (nmol/L) |
|---|---|---|---|---|---|---|---|---|---|---|---|---|
| 600 | N | 8 | 8 | 8 | 8 | 8 | 4 | 4 | 4 | 8 | 8 | 8 |
| | Mean | 7.138 | 4.25 | 22.987 | 44.1 | 40.805 | 195.593 | 0.126 | 20.766 | 61.413 | 61.25 | 1.275 |
| | CV | 53.9 | 84.3 | 66.7 | 63.1 | 72.5 | 121.3 | 129.1 | 93 | 36.3 | 37.9 | 258.4 |
| | Min | 2.6 | 0.25 | 8.74 | 13.63 | 8.02 | 35.66 | 0.02 | 1.92 | 18.7 | 17.6 | 0 |
| | Max | 14.3 | 8 | 48.46 | 92.06 | 92.06 | 548.32 | 0.36 | 40.79 | 97.2 | 93.7 | 9.4 |
| | GeoMean | 6.284 | | 19.12 | 37.116 | 31.916 | 117.278 | 0.06 | 11.53 | 56.534 | 55.893 | |
| 1200 | N | 8 | 8 | 8 | 8 | 8 | 2 | 2 | 2 | 8 | 8 | 8 |
| | Mean | 7.525 | 5.406 | 23.798 | 45.416 | 40.309 | 99.885 | 0.323 | 4.869 | 51.738 | 49.663 | 0.713 |
| | CV | 52.2 | 91.5 | 109 | 81.4 | 97.7 | 16.6 | 105.7 | 105.7 | 45.9 | 43.5 | 282.8 |
| | Min | 1.2 | 0.25 | 0.2 | 7.1 | 5.29 | 88.18 | 0.08 | 1.23 | 17.4 | 17.2 | 0 |
| | Max | 11.8 | 16 | 80.45 | 111.62 | 111.42 | 111.59 | 0.56 | 8.51 | 86.7 | 77 | 5.7 |
| | GeoMean | 6.155 | | 9.296 | 32.213 | 24.806 | 99.197 | 0.214 | 3.235 | 46.256 | 44.723 | |
| 1800 | N | 8 | 7 | 7 | 6 | 8 | 3 | 3 | 3 | 8 | 8 | 8 |
| | Mean | 10.888 | 9.013 | 13.161 | 34.62 | 32.988 | 205.537 | 0.053 | 29.135 | 63.388 | 64.513 | 2.25 |
| | CV | 101 | 114.8 | 76.4 | 82.5 | 89.6 | 65.7 | 117.5 | 71.6 | 52.8 | 47.1 | 112.9 |
| | Min | 0 | 0.25 | 0.54 | 7.33 | 0 | 63.1 | 0.02 | 5.54 | 27.9 | 31.1 | 0 |
| | Max | 29.3 | 24.07 | 26.82 | 71.26 | 71.26 | 331.45 | 0.13 | 45.09 | 116 | 109 | 7.3 |
| | GeoMean | | | 8.128 | 23.258 | | 166.844 | 0.033 | 20.941 | 56.059 | 58.42 | |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{24}$ ConcBase = baseline concentration;
$C_{24}$ ConcBLQ = concentration of active dose;
$C_{24}$ ConcBC = baseline-corrected concentration;
$C_{max}$ = maximum concentration observed after dosing;
CV = % coefficient of variation;
GeoMean = geometric mean;
$\lambda_z$ = terminal elimination rate constant;
$t_{1/2}$ = elimination half-life;
$t_{max}$ = time of observed maximum concentration relative to the time of dosing
Note:
The geometric mean is not normally reported for $t_{max}$.
Note:
The geometric mean cannot be calculated if Min = 0.

I. Period 2: Multiple Dose Pharmacokinetic Parameter Estimates

The PK parameters estimated from the multi-dose profiles for each individual are presented in Appendix 16.2, Listing 16.2.5.1.2b and summarized in Section 14.2, Table 14.4.2b. The following tables present the data summarized in Section 14.2, Table 14.4.2b for the multi-dose PK parameters but the SD and median have been omitted. All subjects received 7 doses of 1200 μg testosterone.

Free Testosterone

Since the doses of 1200 μg testosterone were used in both the single- and multi-dose periods of this study, it is would seem useful to compare their PK parameters. However, this would not be useful as the single-dose data is based on baseline-corrected data while the multi-dose data is not. However, the baseline concentration data from the single-dose period may be reviewed in comparison to the multi-dose data. Since the data in TableTable 11-28 are from baseline, the dose is not relevant as all concentrations are prior to dose.

The minimum and maximum values observed in the multi-dose period are greater than the minimum and maximum values observed in the baseline period for all 3 dose cohorts. This demonstrates that the testosterone multiple dosing are increasing both the minimum and the maximum free testosterone concentrations over the baseline values and provides the expected increase in free testosterone concentrations after multiple dosing. (Table 11-27) and (Table 11-28 Table).

The $AUC_{0-8}$ and the $AUC_{0-\tau}$ are identical as the dosing interval is 8 hours. The $AUC_{0-24}$ hours spans the last dose period of 8 hours but also includes the preceding 16 hours. The % PTF and % PTS indicate the percent difference between the $C_{max}$ and $C_{min}$ when divided by the $C_{avg}$ or $C_{min}$, respectively.

TABLE 11-27

Free Testosterone Summary for Multiple Dose Profile (Multi-Dose Population)

|  | $C_{max}$ (ng/dL) | $t_{max}$ (hr) | $C_0$ (ng/dL) | $C_{min}$ (ng/dL) | $C_{avg}$ (ng/dL) | $C_{24}$ (ng/dL) | $AUC_{0-8}$ (hr * ng/dL) | $AUC_{0-24}$ (hr * ng/dL) | $AUC_{0-\tau}$ (hr * ng/dL) | % PTF | % PTS |
|---|---|---|---|---|---|---|---|---|---|---|---|
| N | 8 | 8 | 8 | 8 | 8 | 8 | 8 | 8 | 8 | 8 | 8 |
| Mean | 1.886 | 0.378 | 1.155 | 0.704 | 1.006 | 0.578 | 8.046 | 17.259 | 8.046 | 140.636 | 214.058 |
| CV | 12.4 | 49.6 | 34.2 | 55.1 | 40.6 | 79.8 | 40.6 | 55.0 | 40.6 | 55.2 | 55.0 |
| Min | 1.65 | 0.25 | 0.77 | 0.40 | 0.59 | 0.28 | 4.69 | 9.74 | 4.69 | 30.60 | 35.00 |
| Max | 2.18 | 0.75 | 1.82 | 1.60 | 1.83 | 1.71 | 14.64 | 39.66 | 14.64 | 295.75 | 437.88 |
| GeoMean | 1.874 | 0.344 | 1.098 | 0.638 | 0.944 | 0.492 | 7.554 | 15.722 | 7.554 | 119.579 | 176.905 |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-\tau}$ = Area under the concentration-time curve from time zero to the dosing interval;
$C_{max}$ = maximum concentration observed after dosing;
$C_0$ = maximum concentration at baseline;
$C_{min}$ = Minimum concentration over a dosing interval during multiple dosing;
$C_{avg}$ = Average steady-state concentration;
$C_{24}$ = maximum concentration at 24 hours after dosing;
CV = % coefficient of variation;
GeoMean = geometric mean;
% PTF = percent peak to trough fluctuation;
% PTS = percent peak to trough swing;
$t_{max}$ = time of observed maximum concentration relative to the time of dosing.

TABLE 11-28

Free Testosterone Concentration at Baseline (Single-Dose Population)

|  |  | Dose Cohort (ug) | | |
|---|---|---|---|---|
| Analyte |  | 600 | 1200 | 1800 |
|  |  | ConcBase (ng/dL) | | |
| Free Testosterone | N | 112 | 112 | 112 |
|  | Min | 0.10 | 0.13 | 0.15 |
|  | Max | 1.44 | 0.53 | 0.45 |

ConcBase = baseline concentration

Total Testosterone

The total testosterone PK $C_{max}$ range of 85.80 to 242.00 ng/dL following multiple dosing compares to the maximum testosterone concentration range of 41.10 to 58.00 ng/dL observed at baseline. The $C_{min}$ range of 25.20 to 79.50 ng/dL total testosterone following multiple dosing compares to the 8.00 to 12.70 ng/dL range of minimum value of total testosterone observed at baseline. Both the $C_{max}$ and the $C_{min}$ indicate an effect of the testosterone dose administration; 2- to 4-fold effect on $C_{max}$ and a 3-fold effect on $C_{min}$. (Table 11-29 and Table 11-30), however, this accumulation disappears within 24 hours after the last administration.

TABLE 11-29

Total Testosterone Summary for Multiple Dose Profile (Multi-Dose Population)

|  | $C_{max}$ (ng/dL) | $t_{max}$ (hr) | $C_0$ (ng/dL) | $C_{min}$ (ng/dL) | $C_{avg}$ (ng/dL) | $C_{24}$ (ng/dL) | $AUC_{0-8}$ (hr * ng/dL) | $AUC_{0-24}$ (hr * ng/dL) | $AUC_{0-\tau}$ (hr * ng/dL) | % PTF | % PTS |
|---|---|---|---|---|---|---|---|---|---|---|---|
| N | 8 | 8 | 8 | 8 | 8 | 8 | 8 | 8 | 8 | 8 | 8 |
| Mean | 148.038 | 0.440 | 85.450 | 49.088 | 73.802 | 38.513 | 590.419 | 1224.571 | 590.419 | 141.760 | 216.089 |
| CV | 41.5 | 49.8 | 32.1 | 36.4 | 41.4 | 47.2 | 41.4 | 38.5 | 41.4 | 53.8 | 53.5 |
| Min | 85.80 | 0.25 | 40.50 | 25.20 | 41.12 | 18.70 | 329.00 | 679.18 | 329.00 | 48.83 | 64.47 |
| Max | 242.00 | 0.75 | 131.00 | 79.50 | 141.00 | 77.30 | 1127.99 | 2026.22 | 1127.99 | 301.43 | 447.51 |
| GeoMean | 137.555 | 0.395 | 81.313 | 46.136 | 69.166 | 35.360 | 553.325 | 1147.566 | 553.325 | 125.100 | 187.544 |

$AUC_{0-8}$ = Area under the plasma concentration time curve from time zero to 8 hours after dosing;

$AUC_{0-24}$ = Area under the plasma concentration time curve from time zero to 24 hours after dosing;

$AUC_{0-\tau}$ = Area under the concentration-time curve from time zero to the dosing interval;

$C_{max}$ = maximum concentration observed after dosing;

$C_0$ = maximum concentration at baseline;

$C_{min}$ = Minimum concentration over a dosing interval during multiple dosing;

$C_{avg}$ = Average steady-state concentration;

$C_{24}$ = maximum concentration at 24 hours after dosing;

CV = % coefficient of variation;

GeoMean = geometric mean;

% PTF = percent peak to trough fluctuation;

% PTS = percent peak to trough swing;

$t_{max}$ = time of observed maximum concentration relative to the time of dosing.

TABLE 11-30

Total Testosterone Concentration at Baseline (Single-Dose Population)

|  |  | Dose Cohort (ug) | | |
|---|---|---|---|---|
|  |  | 600 | 1200 | 1800 |
| Analyte |  | ConcBase (ng/dL) | | |
| Total Testosterone | N | 112 | 112 | 112 |
|  | Min | 8.00 | 7.41 | 12.70 |
|  | Max | 58.00 | 41.10 | 43.90 |

ConcBase = baseline concentration

Dihydrotestosterone

The dihydrotestosterone observations do not indicate much difference from the baseline observations. The maximum dihydrotestosterone $C_{max}$ from the multi-dose period of 30.50 ng/dL is comparable to with the 32.60 $C_{max}$ observed at baseline. The minimum $C_{min}$ from the multi-dose period of 6.32 ng/dL is comparable to the 5.02 ng/dL observed at baseline. No effect of the testosterone administration is seen in this comparison of dihydrotestosterone concentrations to baseline. (Table 11-31 and Table 11-32)

TABLE 11-31

Dihydrotestosterone Summary for Multiple Dose Profile (Multi-Dose Population)

|  | $C_{max}$ (ng/dL) | $t_{max}$ (hr) | $C_0$ (ng/dL) | $C_{min}$ (ng/dL) | $C_{avg}$ (ng/dL) | $C_{24}$ (ng/dL) | $AUC_{0-8}$ (hr * ng/dL) | $AUC_{0-24}$ (hr * ng/dL) | $AUC_{0-\tau}$ (hr * ng/dL) | % PTF | % PTS |
|---|---|---|---|---|---|---|---|---|---|---|---|
| N | 8 | 8 | 8 | 8 | 8 | 8 | 8 | 8 | 8 | 8 | 8 |
| Mean | 22.300 | 0.500 | 20.724 | 13.465 | 16.628 | 14.774 | 133.024 | 338.888 | 133.024 | 57.240 | 73.956 |
| CV | 35.9 | 53.5 | 39.3 | 44.9 | 40.0 | 40.1 | 40.0 | 38.6 | 40.0 | 44.1 | 48.7 |
| Min | 10.20 | 0.25 | 7.39 | 6.32 | 7.21 | 6.33 | 57.66 | 145.85 | 57.66 | 13.66 | 14.90 |
| Max | 30.50 | 1.00 | 31.70 | 20.80 | 24.30 | 24.70 | 194.43 | 494.97 | 194.43 | 96.25 | 125.53 |
| GeoMean | 20.792 | 0.442 | 18.927 | 12.192 | 15.274 | 13.637 | 122.194 | 313.198 | 122.194 | 50.641 | 63.444 |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-\tau}$ = Area under the concentration-time curve from time zero to the dosing interval;
$C_{max}$ = maximum concentration observed after dosing;
$C_0$ = maximum concentration at baseline;
$C_{min}$ = Minimum concentration over a dosing interval during multiple dosing;
$C_{avg}$ = Average steady-state concentration;
$C_{24}$ = maximum concentration at 24 hours after dosing;
CV = % coefficient of variation;
GeoMean = geometric mean;
% PTF = percent peak to trough fluctuation;
% PTS = percent peak to trough swing;
$t_{max}$ = time of observed maximum concentration relative to the time of dosing.

TABLE 11-32

Dihydrotestosterone Concentration at Baseline (Single-Dose Population)

|  |  | Dose Cohort (ug) | | |
|---|---|---|---|---|
|  |  | 600 | 1200 | 1800 |
| Analyte |  | ConcBase (ng/dL) | | |
| Dihydrotestosterone | N | 75 | 78 | 78 |
|  | Min | 5.29 | 5.04 | 5.02 |
|  | Max | 22.10 | 25.30 | 32.60 |

ConcBase = baseline concentration

Estradiol

The estradiol $C_{min}$ concentration observed over 24 hours during the baseline observation period was 17.00 μg/mL (17.00 to 20.90 μg/mL range of 24 subjects in the single-dose period) which compares to the 12.70 μg/mL (12.70 to 95.20 μg/mL range of 8 subjects) in the multi-dose period. The estradiol $C_{max}$ concentration was 122.00 during the baseline period and 145.00 during the multi-dose period. While there is some difference in these concentrations, they are similar. (Table 11-33 and Table 11-34).

TABLE 11-33

Estradiol Summary for Multiple Dose Profile (Multi-Dose Population)

|  | $C_{max}$ (pg/mL) | $t_{max}$ (hr) | $C_0$ (pg/mL) | $C_{min}$ (pg/mL) | $C_{avg}$ (pg/mL) | $C_{24}$ (pg/mL) | $AUC_{0-8}$ (hr * pg/mL) | $AUC_{0-24}$ (hr * pg/mL) | $AUC_{0-\tau}$ (hr * pg/mL) | % PTF | % PTS |
|---|---|---|---|---|---|---|---|---|---|---|---|
| N | 8 | 8 | 8 | 8 | 8 | 8 | 8 | 8 | 8 | 8 | 8 |
| Mean | 70.800 | 3.231 | 54.113 | 48.875 | 58.019 | 64.113 | 464.148 | 1759.342 | 464.148 | 35.465 | 42.164 |

TABLE 11-33-continued

Estradiol Summary for Multiple Dose Profile (Multi-Dose Population)

|   | $C_{max}$ (pg/mL) | $t_{max}$ (hr) | $C_0$ (pg/mL) | $C_{min}$ (pg/mL) | $C_{avg}$ (pg/mL) | $C_{24}$ (pg/mL) | $AUC_{0-8}$ (hr * pg/mL) | $AUC_{0-24}$ (hr * pg/mL) | $AUC_{0-\tau}$ (hr * pg/mL) | % PTF | % PTS |
|---|---|---|---|---|---|---|---|---|---|---|---|
| CV | 54.9 | 79.7 | 44.3 | 50.6 | 54.0 | 44.2 | 54.0 | 41.3 | 54.0 | 44.8 | 46.9 |
| Min | 16.60 | 0.27 | 16.30 | 12.70 | 14.96 | 18.60 | 119.67 | 503.91 | 119.67 | 20.16 | 22.22 |
| Max | 145.00 | 8.00 | 84.20 | 95.20 | 120.64 | 104.00 | 965.13 | 2895.80 | 965.13 | 66.76 | 79.82 |
| GeoMean | 60.034 | 2.024 | 48.062 | 42.569 | 50.033 | 56.820 | 400.264 | 1587.754 | 400.264 | 32.768 | 38.514 |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-\tau}$ = Area under the concentration-time curve from time zero to the dosing interval;
$C_{max}$ = maximum concentration observed after dosing;
$C_0$ = maximum concentration at baseline;
$C_{min}$ = Minimum concentration over a dosing interval during multiple dosing;
$C_{avg}$ = Average steady-state concentration;
$C_{24}$ = maximum concentration at 24 hours after dosing;
CV = % coefficient of variation;
GeoMean = geometric mean;
% PTF = percent peak to trough fluctuation;
% PTS = percent peak to trough swing;
$t_{max}$ = time of observed maximum concentration relative to the time of dosing.

TABLE 11-34

Estradiol Concentration at Baseline (Single-Dose Population)

|  |  | Dose Cohort (ug) | | |
|---|---|---|---|---|
|  |  | 600 | 1200 | 1800 |
| Analyte |  | ConcBase (pg/mL) | | |
| Estradiol | N | 112 | 112 | 112 |
|  | Min | 20.90 | 17.00 | 17.70 |
|  | Max | 122.00 | 119.00 | 97.40 |

ConcBase = baseline concentration

SHBG

The SHBG $C_{min}$ from the baseline observation period was 15.30 nmol/L while the $C_{min}$ from the multi-dose period was 19.90 nmol/L. The SHBG $C_{max}$ was 137.00 nmol/L while the $C_{max}$ from the multi-dose period was 100.00 nmol/L. No effect from the testosterone dosing on SHBG concentrations is obvious. (Table 11-35 and Table 11-36).

TABLE 11-36

SHBG Concentratio at Baseline (Single-Dose Population)

|  |  | Dose Cohort (ug) | | |
|---|---|---|---|---|
|  |  | 600 | 1200 | 1800 |
| Analyte |  | ConcBase (nmol/L) | | |
| SHBG | N | 112 | 112 | 112 |
|  | Min | 15.30 | 16.00 | 25.20 |
|  | Max | 102.00 | 86.70 | 137.00 |

ConcBase = baseline concentration

J. Pharmacokinetic Parameter Statistical Testing

Dose Proportionality Analysis on Single Dose

Section 14.2, Table 14.4.3 presents the analysis of dose proportionality. Table 11-37 is abstracted from this table to present the linear regression analysis of the log-transformed PK parameters.

TABLE 11-35

SHBG Summary for Multiple Dose Profile (Multi-Dose Population)

|   | $C_{max}$ (nmol/L) | $t_{max}$ (hr) | $C_0$ | $C_{min}$ | $C_{avg}$ (nmol/L) | $C_{24}$ | $AUC_{0-8}$ | $AUC_{0-24}$ (hr * nmol/L) | $AUC_{0-\tau}$ | % PTF | % PTS |
|---|---|---|---|---|---|---|---|---|---|---|---|
| N | 8 | 8 | 8 | 8 | 8 | 8 | 8 | 8 | 8 | 8 | 8 |
| Mean | 62.725 | 1.998 | 59.700 | 55.300 | 58.548 | 56.275 | 468.387 | 1375.463 | 468.387 | 13.778 | 15.114 |
| CV | 46.2 | 136.0 | 46.2 | 47.5 | 45.9 | 45.5 | 45.9 | 45.1 | 45.9 | 56.6 | 64.6 |
| Min | 27.40 | 0.25 | 25.40 | 19.90 | 23.91 | 25.10 | 191.29 | 591.69 | 191.29 | 8.10 | 8.48 |
| Max | 100.00 | 7.98 | 93.90 | 87.90 | 92.65 | 87.30 | 741.16 | 2125.93 | 741.16 | 31.37 | 37.69 |
| GeoMean | 56.270 | 0.964 | 53.530 | 49.024 | 52.530 | 50.636 | 420.236 | 1239.069 | 420.236 | 12.392 | 13.279 |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-\tau}$ = Area under the concentration-time curve from time zero to the dosing interval;
$C_{max}$ = maximum concentration observed after dosing;
$C_0$ = maximum concentration at baseline;
$C_{min}$ = Minimum concentration over a dosing interval during multiple dosing;
$C_{avg}$ = Average steady-state concentration;
$C_{24}$ = maximum concentration at 24 hours after dosing;
CV = % coefficient of variation;
GeoMean = geometric mean;
% PTF = percent peak to trough fluctuation;
% PTS = percent peak to trough swing;
$t_{max}$ = time of observed maximum concentration relative to the time of dosing.

Dose proportionality occurs when increases in the administered dose are accompanied by proportional increases in a measure of exposure (PK parameter). The linear regression model is fitted to each of the interested PK parameters by using dose (600, 1200, and 1800 µg) as the predictor variable:

PK=Slope*Dose+Intercept.

A dose proportionality hypothesis cannot be rejected if the intercept's 95% confidence limit includes 0.

Dose proportionality was not rejected for only $AUC_{0-24}$, $AUC_{0-8}$, and $AUC_{0-t}$ for free testosterone.

TABLE 11-37

Dose Proportionality Analysis (Single-Dose Population)

| Analyte | PK Parameter | Log Transformed Regression | Estimate | Standard Error | 95% Confidence Limit for Estimate Lower Limit | Upper Limit | N/R-Square |
|---|---|---|---|---|---|---|---|
| Free Testosterone | $AUC_{0-24}$ | Intercept | 0.3211 | 0.3154 | −0.3331 | 0.9753 | 24 |
| | | Slope | 0.0011 | 0.0002 | 0.0006 | 0.0016 | 0.4607 |
| | $AUC_{0-8}$ | Intercept | −0.1868 | 0.2951 | −0.7988 | 0.4252 | 24 |
| | | Slope | 0.0011 | 0.0002 | 0.0006 | 0.0016 | 0.5136 |
| | $AUC_{0-\infty}$ | Intercept | 0.7450 | 0.3266 | 0.0676 | 1.4224 | 24 |
| | | Slope | 0.0009 | 0.0003 | 0.0003 | 0.0014 | 0.352 |
| | $AUC_{0-t}$ | Intercept | 0.2956 | 0.3134 | −0.3544 | 0.9456 | 24 |
| | | Slope | 0.0011 | 0.0002 | 0.0006 | 0.0016 | 0.4703 |
| | $C_{max}$ | Intercept | −1.3533 | 0.3811 | −2.1436 | −0.5630 | 24 |
| | | Slope | 0.0010 | 0.0003 | 0.0004 | 0.0016 | 0.3529 |
| Total Testosterone | $AUC_{0-24}$ | Intercept | 4.6622 | 0.2607 | 4.1216 | 5.2029 | 24 |
| | | Slope | 0.0010 | 0.0002 | 0.0006 | 0.0014 | 0.5437 |
| | $AUC_{0-8}$ | Intercept | 4.1608 | 0.2525 | 3.6371 | 4.6845 | 24 |
| | | Slope | 0.0011 | 0.0002 | 0.0007 | 0.0015 | 0.5765 |
| | $AUC_{0-\infty}$ | Intercept | 5.0683 | 0.2653 | 4.5181 | 5.6185 | 24 |
| | | Slope | 0.0009 | 0.0002 | 0.0004 | 0.0013 | 0.4435 |
| | $AUC_{0-t}$ | Intercept | 4.6351 | 0.2597 | 4.0965 | 5.1738 | 24 |
| | | Slope | 0.0010 | 0.0002 | 0.0006 | 0.0015 | 0.5528 |
| | $C_{max}$ | Intercept | 2.9275 | 0.3285 | 2.2463 | 3.6088 | 24 |
| | | Slope | 0.0010 | 0.0003 | 0.0005 | 0.0015 | 0.4174 |
| Dihydrotestosterone | $AUC_{0-24}$ | Intercept | 2.8766 | 0.4092 | 2.0043 | 3.7488 | 17 |
| | | Slope | 0.0008 | 0.0003 | 0.0002 | 0.0015 | 0.3234 |
| | $AUC_{0-8}$ | Intercept | 2.5722 | 0.4515 | 1.6098 | 3.5347 | 17 |
| | | Slope | 0.0006 | 0.0003 | −0.0001 | 0.0013 | 0.1713 |
| | $AUC_{0-\infty}$ | Intercept | 3.5478 | 0.5806 | 2.2542 | 4.8415 | 12 |
| | | Slope | 0.0007 | 0.0004 | −0.0003 | 0.0017 | 0.2131 |
| | $AUC_{0-t}$ | Intercept | 2.4635 | 0.4276 | 1.5571 | 3.3699 | 18 |
| | | Slope | 0.0011 | 0.0003 | 0.0004 | 0.0018 | 0.3979 |
| | $C_{max}$ | Intercept | 1.4180 | 0.3725 | 0.6283 | 2.2076 | 18 |
| | | Slope | 0.0004 | 0.0003 | −0.0002 | 0.0010 | 0.1209 |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{max}$ = maximum concentration observed after dosing.

Dose Pair-Wise Test Using Analysis of Variance

Table 11-38 presents pair-wise comparisons of single-dose PK parameters using ANOVA after dose normalizing. Results found that there were differences in the dose normalized values for all analytes for at least 1 of the 3 pair-wise comparisons except for free testosterone AUC measures for $AUC_{0-24}$, $AUC_{0-8}$, and $AUC_{0-t}$.

TABLE 11-38

Analysis of Variance for Some Pharmacokinetic Parameters (Single-Dose Population)

| Analyte | PK Parameter | Intra-subject Coefficient of Variation[a] | P-Value 600 µg vs. 1200 µg | 600 µg vs. 1800 µg | 1200 µg vs. 1800 µg |
|---|---|---|---|---|---|
| Free Testosterone | $AUC_{0-24}$ | 45.8505 | 0.2114 | 0.2182 | 0.9845 |
| | $AUC_{0-8}$ | 67.4794 | 0.7110 | 0.5338 | 0.7996 |
| | $AUC_{0-\infty}$ | 43.0039 | 0.0324 | 0.0197 | 0.8185 |
| | $AUC_{0-t}$ | 45.3344 | 0.2439 | 0.2477 | 0.9921 |
| | $C_{max}$ | −223.3208 | 0.0034 | 0.0010 | 0.6182 |
| | $\lambda z$ | 84.7568 | 0.0908 | 0.0406 | 0.6863 |
| | $t_{1/2}$ | 55.9189 | 0.0002 | <.0001 | 0.3257 |

TABLE 11-38-continued

Analysis of Variance for Some Pharmacokinetic Parameters (Single-Dose Population)

| Analyte | PK Parameter | Intra-subject Coefficient of Variation[a] | P-Value 600 µg vs. 1200 µg | 600 µg vs. 1800 µg | 1200 µg vs. 1800 µg |
|---|---|---|---|---|---|
| Total Testosterone | $AUC_{0-24}$ | 7.8951 | <.0001 | <.0001 | 0.0001 |
| | $AUC_{0-8}$ | 8.2332 | <.0001 | <.0001 | 0.0001 |

TABLE 11-38-continued

Analysis of Variance for Some Pharmacokinetic Parameters (Single-Dose Population)

| Analyte | PK Parameter | Intra-subject Coefficient of Variation[a] | P-Value | | |
|---|---|---|---|---|---|
| | | | 600 µg vs. 1200 µg | 600 µg vs. 1800 µg | 1200 µg vs. 1800 µg |
| | $AUC_{0-\infty}$ | 8.7190 | <.0001 | <.0001 | 0.0002 |
| | $AUC_{0-t}$ | 7.8792 | <.0001 | <.0001 | 0.0001 |
| | $C_{max}$ | 17.9163 | <.0001 | <.0001 | 0.0320 |
| | $\lambda z$ | 85.1223 | 0.1153 | 0.0454 | 0.6333 |
| | $t_{1/2}$ | 55.6641 | 0.0002 | <.0001 | 0.3940 |
| Dihydro- | $AUC_{0-24}$ | 19.8167 | <.0001 | <.0001 | 0.1756 |
| testosterone | $AUC_{0-8}$ | 23.5230 | <.0001 | <.0001 | 0.3291 |
| | $AUC_{0-\infty}$ | 26.0151 | 0.0048 | 0.0004 | 0.3131 |
| | $AUC_{0-t}$ | 26.5016 | 0.0011 | 0.0001 | 0.3144 |
| | $C_{max}$ | 37.3379 | 0.0021 | 0.0009 | 0.6763 |
| | $\lambda z$ | 158.0250 | 0.1869 | 0.1523 | 0.9553 |
| | $t_{1/2}$ | 117.5657 | 0.2274 | 0.1041 | 0.7665 |

$AUC_{0-8}$ = Area under the plasma concentration time curve from time zero to 8 hours after dosing;
$AUC_{0-24}$ = Area under the plasma concentration time curve from time zero to 24 hours after dosing;
$AUC_{0-t}$ = Area under the plasma concentration time curve from time zero to the last measurable concentration time point;
$AUC_{0-\infty}$ = Area under the plasma concentration time curve from time zero to infinity;
$C_{max}$ = maximum concentration observed after dosing;
$\lambda_z$ = terminal elimination rate constant;
$t_{1/2}$ = elimination half-life
[a]Coefficient of Variation = 100 × ANOVA residual error (Root Mean Square Error)/PK parameter mean. Pair-wise comparisons are from the ANOVA model with Dose as a class (categorical) variable and PK parameter estimate values as response.
Note:
$AUC_{0-8}$, $AUC_{0-\infty}$, $AUC_{0-t}$ and $C_{max}$ parameter values are natural logarithmic transformed.

Paired t-Test Comparison of $AUC_{0-8}$ and $AUC_{0-24}$ from Single to Multiple Dose There were 3 subjects who participated in both the single- and multi-dose periods at the 1200 µg dose. Uncorrected parameters for $AUC_{0-8}$ and $AUC_{0-24}$ were calculated from the free testosterone, total testosterone, and dihydrotestosterone analyte concentrations for comparison to uncorrected parameters from the multi-dose profile. Table 11-39 compares the $AUC_{0-8}$ and $AUC_{0-24}$ from these 3 subjects by using a paired t-test for free testosterone, total testosterone, and dihydrotestosterone. The results of the log transformed comparisons are provided.

TABLE 11-39

Paired t-Test Results for Pharmacokinetic Parameters $AUC_{0-8}$ and $AUC_{0-24}$ for Subjects Who Had 1200 µg TBS-2 in Period 1 and Period 2

| Analyte | Natural-logarithmic transformed PK Parameter Name | N | Mean of Difference | Standard Error of Difference | 95% Confidence Limit for Mean Difference | | P-Value |
|---|---|---|---|---|---|---|---|
| | | | | | Lower Limit | Upper Limit | |
| Free Testosterone | $AUC_{0-8}$ | 3 | 0.6041 | 0.4255 | −1.2267 | 2.4349 | 0.2915 |
| | $AUC_{0-24}$ | 3 | 0.9312 | 0.3853 | −0.7266 | 2.5890 | 0.1369 |
| Total Testosterone | $AUC_{0-8}$ | 3 | 0.5782 | 0.1780 | −0.1876 | 1.3440 | 0.0831 |
| | $AUC_{0-24}$ | 3 | 0.9058 | 0.1683 | 0.1815 | 1.6301 | 0.0328 |
| Dihydrotestosterone | $AUC_{0-8}$ | 3 | 2.1025 | 0.2060 | 1.2160 | 2.9889 | 0.0095 |
| | $AUC_{0-24}$ | 3 | 2.1709 | 0.4044 | 0.4311 | 3.9108 | 0.0330 |

$AUC_{0-8}$ = Area under the plasma concentration time curve from time zero to 8 hours;
$AUC_{0-24}$ = Area under the plasma concentration time curve from time zero to 24 hours;
PK = pharmacokinetic.

The free testosterone comparisons of 95% CI included zero in the difference for both AUC measures so equivalence between the single- and multi-dose AUC measures could not be rejected. Total testosterone 95% CIs included zero for the $AUC_{0-8}$ but not for the $AUC_{0-24}$ so equivalence could not be rejected for $AUC_{0-8}$ but was for $AUC_{0-24}$. In the analyte dihydrotestosterone, neither 95% CI included zero, so equivalence was rejected for both AUCs.

Statistical and Analytical Issues

K. Adjustments for Covariate

Not applicable.

L. Handling of Dropouts or Missing Data

To handle missing or partial AE and concomitant medication dates, the following rules were applied:

1. For partial AE and concomitant medication start dates, if the year was unknown, then a missing value was assigned. If the month was unknown and the year matches the year of the first dose date, then the month and day of the first dose date was imputed; otherwise January was assigned. If the day was unknown and the month and year matched the month and year of the first dose date, then the day of the first dose date was imputed; otherwise "01" was assigned.
2. For partial AE and concomitant medication end dates, if the year was unknown, then a missing value was assigned. If the month was unknown, then 'December' was assigned. If the day was unknown, then the last day of the month was assigned.

After implementing the rules above, to determine whether AEs (or medications) with missing start or stop dates are pretreatment or on/after treatment, the following strategy was used:

1. If the start date and stop date were both missing, then the most conservative approach was taken and the AE (or medication) was considered to be treatment-emergent (or concomitant).
2. If the start date was missing but the stop date was not missing and was after the day of study dose administration, then the most conservative approach was taken and the AE (or medication) was considered to be treatment-emergent (or concomitant).
3. If the start date was missing but the stop date was not missing and was on or before the day of study dose and after the date of signed informed consent, then the AE (or medication) was considered to be pretreatment (or prior).
4. If the start date was not missing but the stop date was missing, then the most conservative approach was taken and medication was considered to be concomitant while the AE was defined by start date.

The missing severity of an AE was imputed to the greatest severity; the missing study drug causality to an AE was imputed to "related."

M. Interim Analysis and Data Monitoring

Interim analyses are discussed in the Interim Analysis section above.

N. Multi-Center Studies

Not applicable

O. Multiple Comparison/Multiplicity

A few pair-wise comparisons were performed, but no Type 1 error rate was adjusted since they were exploratory analyses.

P. Use of a "Pharmacokinetics Subset" of Subjects

All subjects were included in the PK analyses.

Q. Active-Control Studies Intended to Show Equivalence

Not applicable.

R. Examination of Subgroups

Not applicable.

Tabulation of Individual Response Data

Not applicable.

Drug Dose, Drug Concentration, and Relationship to Response

Not applicable.

Drug-Drug and Drug-Disease Interactions

Not applicable.

By-Subject Displays

Not applicable.

Pharmacokinetics Conclusions

1. The single-dose baseline-corrected free and total testosterone concentrations have the clearest relationship of concentration to increasing testosterone dose. The dihydrotestosterone analyte concentrations provide a clear distinction between the 1800 µg dose compared with the lower doses, which are not clearly differentiated from each other. A slight change is observed in the estradiol concentrations where it is the lowest dose of 600 µg, which is clearly distinct from the two higher doses, which are not clearly differentiated from each other. The SHBG concentrations are not clearly distinguished between administered testosterone doses.
2. The multi-dose concentrations were not baseline corrected but have similar graphical evaluations. The free and total testosterone concentrations have the clearest demonstration of the concentration increase due to dose. A more modest increase in dihydrotestosterone concentration is observed at the time of dose, but little increase in concentration of estradiol and SHBG is seen at the time of dose. When given BID at these dose, Testosterone accumulates 2-4 fold, but returned to baseline after 12-15 hours
3. Pharmacokinetic parameters were listed individually and summarized for single-dose and multi-dose profiles. Formal statistical testing of dose proportionality was performed on the single-dose profiles.
4. Testing of the single-dose profiles using linear regression across all 3 doses indicated that the free testosterone PK parameters $AUC_{0-8}$, $AUC_{0-24}$, and $AUC_{0-t}$ were the only analyte parameters for which dose proportionality was not rejected.
5. Pair-wise testing of doses from the single-dose profile using ANOVA agreed with the linear regression and also indicated that the free testosterone $AUC_{0-8}$, $AUC_{0-24}$, and $AUC_{0-t}$ parameters were the only analyte parameters that indicated for which dose proportionality could not be rejected for at least one dose comparison.
6. The 3 subjects who participated in both the single- and multi-dose profiles at the same 1200 µg dose level were compared using a paired t-test for $AUC_{0-8}$ and $AUC_{0-24}$. Equivalence between the uncorrected single- and multi-dose profiles was rejected for both parameters for dihydrotestosterone, and for $AUC_{0-24}$ with total testosterone, but equivalence between the profiles was not rejected for either of the free testosterone parameters.

12. SAFETY EVALUATION

A. Extent of Exposure

Study drug administration was performed at the clinical site under study personnel supervision B. Adverse Events Summary of Treatment Emergent Adverse Events There were no deaths, SAEs, or AEs leading to discontinuation during the study. Most TEAEs were in the system organ classes of general disorders (nasal related events) and administration site conditions and respiratory, thoracic, and mediastinal disorders. Most TEAEs were mild in severity and were unlikely or not related to study medication.

Display of Treatment Emergent Adverse Events

The incidence of TEAEs is shown for Period 1 in Table 12-1 and Table 12-2.

TABLE 12-1

Incidence of Treatment-Emergent Adverse Events by System Organ Class and Preferred Term (Single-Dose Population)

| System Organ Class/<br>Preferred Term (MedDRA) | Cohort 1<br>(600 µg)<br>(n = 8) | Cohort 2<br>(1200 µg)<br>(n = 8) | Cohort 3<br>(1800 µg)<br>(n = 8) | Total<br>(N = 24) |
|---|---|---|---|---|
| Total Number of Subjects with at least 1 TEAE | 4 (50.0%) | 4 (50.0%) | 3 (37.5%) | 11 (45.8%) |
| Gastrointestinal disorders | 1 (12.5%) | 0 | 0 | 1 (4.2%) |
| Abdominal pain upper | 1 (12.5%) | 0 | 0 | 1 (4.2%) |
| General disorders and administration site conditions | 3 (37.5%) | 2 (25.0%) | 2 (25.0%) | 7 (29.2%) |
| Catheter site erythema | 1 (12.5%) | 1 (12.5%) | 1 (12.5%) | 3 (12.5%) |
| Catheter site hemorrhage | 0 | 0 | 2 (25.0%) | 2 (8.3%) |
| Catheter site inflammation | 2 (25.0%) | 0 | 0 | 2 (8.3%) |
| Catheter site pain | 0 | 1 (12.5%) | 0 | 1 (4.2%) |
| Infections and infestations | 1 (12.5%) | 0 | 0 | 1 (4.2%) |
| Vulvitis | 1 (12.5%) | 0 | 0 | 1 (4.2%) |
| Nervous system disorders | 0 | 1 (12.5%) | 1 (12.5%) | 2 (8.3%) |
| Dizziness | 0 | 1 (12.5%) | 1 (12.5%) | 2 (8.3%) |
| Headache | 0 | 1 (12.5%) | 0 | 1 (4.2%) |
| Respiratory, thoracic, and mediastinal disorders | 1 (12.5%) | 3 (37.5%) | 1 (12.5%) | 5 (20.8%) |
| Nasal congestion | 0 | 2 (25.0%) | 0 | 2 (8.3%) |
| Nasal mucosal disorder | 0 | 1 (12.5%) | 0 | 1 (4.2%) |
| Rhinalgia | 0 | 0 | 1 (12.5%) | 1 (4.2%) |
| Rhinorrhea | 1 (12.5%) | 0 | 0 | 1 (4.2%) |

MedDRA = Medical Dictionary for Regulatory Activities;
TEAE = treatment-emergent adverse event
Note:
Subjects reporting more than 1 TEAE in each level (system organ class or preferred term) were only counted once.

TABLE 12-2

Incidence of Treatment-Emergent Adverse Events by System Organ Class and Preferred Term (Multi-Dose Population)

| System Organ Class/<br>Preferred Term (MedDRA) | Total<br>(N = 8) |
|---|---|
| Total Number of Subjects with at least 1 TEAE | 4 (50.0%) |
| Gastrointestinal disorders | 1 (12.5%) |
| Dyspepsia | 1 (12.5%) |

TABLE 12-2-continued

Incidence of Treatment-Emergent Adverse Events by System
Organ Class and Preferred Term (Multi-Dose Population)

| System Organ Class/<br>Preferred Term (MedDRA) | Total<br>(N = 8) |
|---|---|
| General disorders and administration site conditions | 2 (25.0%) |
| Catheter site pain | 1 (12.5%) |
| Catheter site phlebitis | 1 (12.5%) |
| Nervous system disorders | 1 (12.5%) |
| Headache | 1 (12.5%) |
| Respiratory, thoracic, and mediastinal disorders | 1 (12.5%) |
| Rhinalgia | 1 (12.5%) |

MedDRA = Medical Dictionary for Regulatory Activities;
TEAE = treatment-emergent adverse event
Note:
Subjects reporting more than 1 TEAE in each level (system organ class or preferred term) were only counted once.

Analysis of Adverse Events
Adverse Events in Period 1

Overall, 11 of 24 subjects (45.8%) experienced at least one TEAE in Period 1. Most subjects experienced TEAEs of general disorders and administration site conditions (experienced by 7 of 24 subjects [29.2%]) and respiratory, thoracic, and mediastinal disorders (experienced by 5 of 24 subjects [20.8%]). TEAEs experienced by more than 1 subject were catheter site erythema (experienced by 3 of 24 subjects [12.5%]) and catheter site hemorrhage, catheter site inflammation, dizziness, and nasal congestion (each experienced by 2 of 24 subjects [8.3%]). (Table 12-1 Table).

The majority of TEAEs in Period 1 were of mild severity. A total of 10 of 24 subjects (41.7%) experienced mild TEAEs. Only 1 of 24 subjects (4.2%) experienced moderate TEAEs. Subject 522-53 (Cohort 2) experienced headache and dizziness of moderate severity on Day 1. Both TEAEs resolved without treatment the next day and were considered as unlikely to be related to the study drug.

Overall, 4 of 24 subjects (16.7%) experienced TEAEs that were considered possibly related to the study medication. A total of 3 of 24 subjects (12.5%) had TEAEs that were considered to be unlikely related to the study medication and 4 of 24 subjects (16.7%) had TEAEs that were considered not related to the study medication. Adverse Events in Period 2

Overall, 4 of 8 subjects (50.0%) experienced at least 1 TEAE in Period 2. General disorders and administration site conditions occurred in 2 of 8 subjects (25.0%). The TEAEs that were experienced by 1 of 8 subjects (12.5%) each were catheter site pain, catheter site phlebitis, dyspepsia, headache, and rhinalgia. (Table 12-2).

The majority of TEAEs in Period 2 were of mild severity. Overall, 3 of 8 subjects (37.5%) experienced mild TEAEs. Only 1 of 8 subjects (12.5%) experienced a moderate TEAE. Subject 522-29 experienced an increase in headache intensity of moderate severity on Day 2. The TEAE resolved without treatment 2 days later and was considered as possibly related to the study drug.

Overall, 2 of 8 subjects (25.0%) experienced TEAEs that were considered possibly related to the study medication and 2 of 8 subjects (25.0%) experienced TEAEs that were considered not related to the study medication.

Adverse Reactions in Period 1 and Period 2

Adverse reactions (defined as TEAEs considered possibly, probably, or definitely related to study medication) in Period 1 and Period 2 are shown in Table 12-3.

A total of 6 subjects experienced adverse reactions during the study: 4 of 24 subjects (16.7%) in Period 1 and 2 of 8 subjects (25.0%) in Period 2. All adverse reactions were considered possibly related to study medication. Subject 522-29 (Period 2) had 2 adverse reactions of headache that were each recorded as a TEAE: a mild headache that increased in severity to moderate.

TABLE 12-3

Subjects with Adverse Reactions (Single-and Multi-Dose Populations)

| Subject | Preferred Term (MedDRA) | Onset[a] | Severity[b] | Outcome |
|---|---|---|---|---|
| Period 1, 600 μg | | | | |
| 522-37 | Rhinorrhea | Day 2 | Mild | Resolved |
| Period 1, 1200 μg | | | | |
| 522-35 | Nasal congestion | Day 1 | Mild | Resolved |
| 522-51 | Nasal congestion | Day 1 | Mild | Resolved |
| 522-53 | Nasal mucosal disorder | Day 3 | Mild | Ongoing |
| Period 2 1200 μg | | | | |
| 522-29 | Headache | Day 2 | Mild | Resolved |
| | Headache (increase in intensity) | Day 2 | Moderate | Resolved |
| 522-24 | Rhinalgia | Day 2 | Mild | Resolved |

MedDRA = Medical Dictionary for Regulatory Activities;
TEAE = treatment-emergent adverse event
[a]The onset was calculated, respectively, as [Onset Date − Treatment Date of Period 1 + 1], if the onset was during Period 1, or [Onset Date − Treatment Date of Period 2 + 1], if the onset was during Period 2.
[b]Severity was rated by the Principal Investigator as mild, moderate, or severe.

Listing of Adverse Events by Subject

Adverse events are listed by subject in Appendix 16.2, Listing 16.2.7.1. Adverse reactions (defined as TEAEs considered possibly, probably, or definitely related to study medication) in Period 1 and Period 2 are listed by subject in Appendix 16.2, Listing 16.2.7.4.

C. Deaths, Other Serious Adverse Events, and Other Significant Adverse Events

There were no deaths, SAEs, or AEs leading to discontinuation during the study.

D. Clinical Laboratory Evaluations
Valuation of Each Laboratory Parameter
Laboratory Values Over Time Changes over time in laboratory values were not calculated.

Individual Subject Changes

Subjects with abnormal laboratory values that were not present at screening are shown in Table 12-4 (hematology), Table 12-5 (chemistry), and Table 12-26 (urinalysis).

TABLE 12-24

Subjects with New Abnormal Hematology Laboratory Evaluation
Results Post Dose (Sinle-and Multi-Dose Populations)

| Subject | Study Period | Study Day | Test (Normal Range) | Result | Low/High |
|---|---|---|---|---|---|
| Cohort 1, 600 μg | | | | | |
| 522-15 | 1 | 4 | Hematocrit (32.5%-46.9%) | 32.0% | Low |
| | 1 | 4 | Red Blood Cell Count (3.70-5.46 mil/mm$^3$) | 3.55 mil/mm$^3$ | Low |
| 522-40 | 1 | 4 | Lymphocytes (15.0%-50.0%) | 50.6% | High |
| 522-49 | 1 | 4 | Absolute Basophil Count (0-125 cells/mm$^3$) | 140 cells/mm$^3$ | High |
| Cohort 2, 1200 μg | | | | | |
| 522-28 | 2 | 5 | Absolute Basophil Count (0-125 cells/mm$^3$) | 160 cells/mm$^3$ | High |
| | 2 | 5 | Basophil Percentage (0.0-2.0%) | 2.6% | High |
| 522-38 | 2 | 5 | Absolute Basophil Count (0-125 cells/mm$^3$) | 160 cells/mm$^3$ | High |

TABLE 12-24-continued

Subjects with New Abnormal Hematology Laboratory Evaluation Results Post Dose (Sinle-and Multi-Dose Populations)

| Subject | Study Period | Study Day | Test (Normal Range) | Result | Low/High |
|---|---|---|---|---|---|
| Cohort 3, 1800 µg | | | | | |
| 522-24 | 1 | 4 | Eosinophils Percentage (0.0%-6.0%) | 7.0% | High |

TABLE 12-25

Subjects with New Abnormal Chemistry Laboratory Evaluation Results Post Dose (Single-and Multi-Dose Populations)

| Subject | Study Period | Study Day | Test (Normal Range) | Result | Low/High |
|---|---|---|---|---|---|
| Cohort 1, 600 µg | | | | | |
| 522-03 | 1 | 4 | Potassium (3.2-5.2 mmol/L) | 5.4 mmol/L | High |
| 522-29 | 1 | 4 | Prolactin (1.9-25.0 ng/mL) | 27.0 ng/mL | High |
| 522-40 | 1 | 4 | TSH (0.40-4.00 uIU/mL) | 4.34 uIU/mL | High |
| | 1 | 4 | Total T3 (84-172 ng/dL) | 83 ng/dL | Low |
| 522-43 | 1 | 4 | Prolactin (1.9-25.0 ng/mL) | 36.8 ng/mL | High |
| Cohort 2, 1200 µg | | | | | |
| 522-09 | 1 | 4 | Prolactin (1.9-25.0 ng/mL) | 31.7 ng/mL | High |
| 522-10 | 1 | 4 | Total T3 (84-172 ng/dL) | 72 ng/dL | Low |
| 522-28 | 1 | 4 | Total T3 (84-172 ng/dL) | 72 ng/dL | Low |
| | 2 | 5 | Prolactin (1.9-25.0 ng/mL) | 37.1 ng/mL | High |
| | 2 | 5 | Free T4 (0.89-1.76 ng/dL) | 0.83 ng/dL | Low |
| | 2 | 5 | Total T3 (84-172 ng/dL) | 78 ng/dL | Low |
| 522-34 | 1 | 4 | Prolactin (1.9-25.0 ng/mL) | 33.2 ng/mL | High |
| 522-38 | 1 | 4 | CK (33-211 U/L) | 32 U/L | Low |
| | 2 | 5 | Free T4 (0.89-1.76 ng/dL) | 0.76 ng/dL | Low |
| 522-51 | 1 | 4 | Fasting Glucose (70-99 mg/dL) | 101 mg/dL | High |
| 522-53 | 1 | 4 | Prolactin (1.9-25.0 ng/mL) | 56.3 ng/mL | High |
| Cohort 3, 1800 µg | | | | | |
| 522-01 | 1 | 4 | CK (33-211 U/L) | 26 U/L | Low |
| | 1 | 4 | Free T4 (0.89-1.76 ng/dL) | 0.82 ng/dL | Low |
| | 2 | 5 | CK (33-211 U/L) | 28 U/L | Low |
| | 2 | 5 | Total T3 (84-172 ng/dL) | 77 ng/dL | Low |
| 522-17 | 1 | 4 | Prolactin (1.9-25.0 ng/mL) | 30.4 ng/mL | High |
| | 2 | 5 | Prolactin (1.9-25.0 ng/mL) | 40.5 ng/mL | High |
| 522-18 | 1 | 4 | Prolactin (1.9-25.0 ng/mL) | 25.8 ng/mL | High |
| | 1 | 4 | Total T3 (84-172 ng/dL) | 73 ng/dL | Low |
| 522-42 | 1 | 4 | Prolactin (1.9-25.0 ng/mL) | 31.1 ng/mL | High |
| 522-44 | 1 | 4 | Prolactin (1.9-25.0 ng/mL) | 29.9 ng/mL | High |
| | 1 | 4 | TSH (0.40-4.00 uIU/mL) | 6.02 uIU/mL | High |
| 522-46 | 1 | 4 | Prolactin (1.9-25.0 ng/mL) | 45.0 ng/mL | High |
| | 1 | 4 | Total T3 (84-172 ng/dL) | 66 ng/dL | Low |
| 522-54 | 1 | 4 | Prolactin (1.9-25.0 ng/mL) | 57.2 ng/mL | High |
| | 1 | 4 | Free T4 (0.89-1.76 ng/dL) | 0.81 ng/dL | Low |

CK = creatine kinase;
TSH = thyroid-stimulating hormone

TABLE 12-26

Subjects with New Abnormal Urinalysis Laboratory Evaluation Results Post Dose (Single-and Multi-Dose Populations)

| Subject | Study Period | Study Day | Test (Normal Range) | Result | Low/High |
|---|---|---|---|---|---|
| Cohort 1, 600 µg | | | | | |
| 522-15 | 1 | 4 | Blood (Negative) | 1+ | High |
| 522-29 | 1 | 4 | Blood (Negative) | Trace | High |
| | 2 | 5 | Blood (Negative) | Trace | High |
| 522-52 | 1 | 4 | Blood (Negative) | Trace | High |
| Cohort 2, 1200 µg | | | | | |
| 522-28 | 1 | 4 | Blood (Negative) | 3+ | High |
| 522-35 | 2 | 5 | Protein (Negative or Trace) | 1+ | High |
| 522-38 | 2 | 5 | Blood (Negative) | Trace | High |
| 522-51 | 1 | 4 | Blood (Negative) | 1+ | High |
| | 1 | 4 | Leukocyte Esterase (Negative) | 3+ | High |
| Cohort 3, 1800 µg | | | | | |
| 522-17 | 1 | 4 | Blood (Negative) | 1+ | High |
| | 2 | 5 | Blood (Negative) | Trace | High |
| 522-18 | 1 | 4 | Blood (Negative) | Trace | High |
| 522-24 | 2 | 5 | Blood (Negative) | 1+ | High |

Individual Clinically Significant Abnormalities

No abnormal clinical laboratory results were recorded as TEAEs.

E. Vital Skins, Physical Examinations, and Other Observations Related to Safety

Vital Skins

No abnormal vital signs were reported by the PI or were recorded as a TEAE.

Physical Examination

Three subjects had abnormal physical examination results related to the PK blood sample venipuncture site. None of these results were considered clinically significant.

Subject 522-35 (1200 µg)—Period 2, Day 5: Slight phlebitis to left antecubital site Subject 522-38 (1200 µg)—Period 2, Day 5: Tenderness/soreness on left antecubital area Subject 522-51 (1200 µg)—Period 1, Day 4: Slight tenderness left AC IV site Except for those related to HEENT or the PK blood sample venipuncture site, no other abnormal physical examination results were reported.

Nasal Endoscopic Examination

No ENT nasal endoscopic examination findings were reported at Screening (Appendix 16.2, Listing 16.2.4.3.2).

Two subjects had ENT examination findings on Day 4 in Period 1 that were interpreted as clinically significant by the PI: Subject 522-37 (600 µg) had slight rhinorrhea and Subject 522-53 (1200 µg) had mild erythema to the left nostril mucosa.

All abnormal findings in basic ENT examinations are presented in Table 12-27.

TABLE 11-27

Subjects with Abnormal Basic Ear, Nose, and Throat Examination Results (Single-and Multi-Dose Populations)

| Subject | Study Period | Study Day | Test Comments | Investigator Interpretation |
|---|---|---|---|---|
| Cohort 1, 600 µg | | | | |
| 522-03 | 2 | 1 | Slight erythema | Abnormal NCS |
| 522-37 | 1 | 1 | Slight edema of turbinates | Abnormal NCS |
| | 1 | 4 | Slight rhinorrhea | Abnormal CS[a] |
| 522-43 | 1 | 1 | Slight erythema of turbinates. Nasal passages are patent. | Abnormal NCS |
| | 1 | 4 | Minimal less erythema than at check in | Abnormal NCS |
| 522-52 | 1 | 1 | Slight erythema | Abnormal NCS |

TABLE 11-27-continued

Subjects with Abnormal Basic Ear, Nose, and Throat Examination Results (Single-and Multi-Dose Populations)

| Subject | Study Period | Study Day | Test Comments | Investigator Interpretation |
|---|---|---|---|---|
| Cohort 2 1200 µg | | | | |
| 522-35 | 1 | 1 | Very slight edema left turbinates | Abnormal NCS |
| 522-38 | 2 | 1 | Slight erythema, probably temperature related | Abnormal NCS |
| 522-51 | 1 | 1 | Mild erythema to mucosa | Abnormal NCS |
|  | 1 | 4 | Very minimal erythema, no edema | Abnormal NCS |
| 522-53 | 1 | 4 | Erythema to left nostril slightly more than right, mucosa of left slightly erythemous relative to right, noticeable. | Abnormal CS[b] |
| Cohort 3, 1800 µg | | | | |
| 522-17 | 1 | 4 | Appears to be slight edema of right mucosa and turbinates relative to left. The nostril is patent so likely not clinically significant. | Abnormal NCS |
|  | 2 | 5 | Appears to be slight edema of right mucosa and turbinates relative to left. The nostril is patent so likely not clinically significant. | Abnormal NCS |
| 522-24 | 1 | 1 | Slight edema turbinates on right but minimal | Abnormal NCS |

CS = clinically significant;
ENT = ears, nose, and throat;
NCS = not clinically significant;
TEAE = treatment emergent adverse event
[a] A TEAE of rhinorrhea (mild, possibly related to study medication) was reported on Day 2 and resolved on Day 5.
[b] A TEAE of nasal mucosal disorder (mild, possibly related to study medication) was reported on Day 3 and was ongoing at study completion.

F. Safety Conclusions

There were no deaths, SAEs, or AEs leading to discontinuation during the study. Most TEAEs were in the system organ classes of general disorders and administration site conditions and respiratory, thoracic, and mediastinal disorders (nasal related events). Most TEAEs were mild in severity and were unlikely or not related to study medication.

In Period 1, a total of 11 of 24 subjects (45.8%) experienced at least 1 TEAE. Those experienced by more than 1 subject were catheter site erythema (experienced by 3 of 24 subjects [12.5%]) and catheter site hemorrhage, catheter site inflammation, dizziness, and nasal congestion (each experienced by 2 of 24 subjects [8.3%]).

The majority of TEAEs in Period 1 were of mild severity. A total of 10 of 24 subjects (41.7%) experienced mild TEAEs. Only 1 of 24 subjects (4.2%) experienced moderate TEAEs. Subject 522-53 (1200 µg) experienced headache and dizziness of moderate severity on Day 1. Both TEAEs resolved without treatment the next day and were considered as unlikely to be related to the study drug.

In Period 2, a total of 4 of 8 subjects (50.0%) experienced at least 1 TEAE. General disorders and administration site conditions occurred in 2 of 8 subjects (25.0%). The TEAEs that were experienced by 1 of 8 subjects (12.5%) each were catheter site pain, catheter site phlebitis, dyspepsia, headache, and rhinalgia.

The majority of TEAEs in Period 2 were of mild severity. Overall, 3 of 8 subjects (37.5%) experienced mild TEAEs. Only 1 of 8 subjects (12.5%) experienced a moderate TEAE. Subject 522-29 experienced an increase in headache intensity of moderate severity on Day 2. The TEAE resolved without treatment 2 days later and was considered as possibly related to the study drug.

A total of 6 subjects experienced adverse reactions (defined as TEAEs considered possibly, probably, or definitely related to study medication) during the study; 4 subjects in Period 1 and 2 subjects in Period 2. All adverse reactions were considered possibly related to study medication. Subject 522-29 (Period 2, 600 µg) had 2 adverse reactions of headache that were each recorded as a TEAE: a mild headache that increased in severity to moderate.

A total of 6 subjects experienced adverse reactions during the study: 4 of 24 subjects (16.7%) in Period 1 and 2 of 8 subjects (25.0%) in Period 2. All adverse reactions were considered possibly related to study medication. Subject 522-29 (Period 2) had 2 adverse reactions of headache that were each recorded as a TEAE: a mild headache that increased in severity to moderate.

There were no TEAEs associated with clinical laboratory tests or vital signs. Two subjects had ENT examination findings that were interpreted as clinically significant by the PI on Day 4 in Period 1: Subject 522-37 (600 µg) had slight rhinorrhea and Subject 522-53 (1200 µg) had mild erythema to the left nostril mucosa.

13. CMC SECTION

Testosterone batch, 80402960, used in the clinical batches was fully tested by the applicant in accordance with USP specifications.

The drug product, TBS-2 is a viscous bioadhesive oil-based formulation containing solubilized testosterone intended for intranasal application for the treatment of anorgasmia in women.

The drug product is formulated with the following compendial inactive ingredients: castor oil, oleoyl polyoxylglycerides, and colloidal silicon dioxide. TBS-2 is supplied in a white, non-aerosol, multi-dose, metered pump container. The containers are supplied separately as barrels (Albion 15 ml) and pumps (VP39/140H) with cap attached. The container closure is manufactured using materials acceptable for pharmaceutical use. See FIG. 39.

The container closure relies on atmospheric pressure and device design to deliver the required dose. When the actuator of the VP39/140 pump is pressed, a valve is opened in the pump mechanism. This allows atmospheric pressure to act on the piston, through the base of the gel-containing Albion 15 ml barrel, forcing it upwards. Consequently, the gel is forced upwards, through the tip of the device. The accurate and concise quantity of gel delivered is a function of the design of VP39/140 pump. When the actuation is stopped, a spring in the pump mechanism closes the valve, stops the effect of atmospheric pressure on the piston and returns the actuator to its starting position.

The patient is instructed to place his finger on the pump of the actuator and to advance the tip of the actuator until the finger on the pump reaches the base of the nose. The opening on the tip of the actuator must face the nasal mucosa. The patient depresses the pump and the gel is expelled onto the nasal mucosa. Each dose consists of two actuations, one actuation per nostril.

The compositions of the three different concentrations of the drug product to be used in this clinical trial are provided in Tables 3.2.P.1-1-3.

TABLE 3.2.P.1-1

Components, Quality, Quality Standards and Function-0.24% TBS-2 Gel

| Component | Amount (% w/w) | Amount per multiple dose dispenser (g) | Amount delivered per actuation (mg) | Function | Quality Standard |
|---|---|---|---|---|---|
| Testosterone | 0.24 | 0.024 | 0.30 | Active Ingredient | USP |
| Castor oil | 91.76 | 9.176 | 114.70 | Solvent | USP |
| Oleoyl poly-oxylglyczrides | 4.00 | 0.400 | 5.00 | Wetting agent (hydrophilic oil) | Ph. Eur./ NF |
| Colloidal silicon dioxide | 4.00 | 0.400 | 5.00 | Viscosity increasing agent | NF |
| Total | 100.00 | 10.0 | 125.00 | | |

TABLE 3.2.P.1-2

Components, Quality, Quality Standards and Function-0.48% TBS-2 Gel

| Component | Amount (% w/w) | Amount per multiple dose dispenser (g) | Amount delivered per actuation (mg) | Function | Quality Standard |
|---|---|---|---|---|---|
| Testosterone | 0.48 | 0.048 | 0.60 | Active Ingredient | USP |
| Castor oil | 91.52 | 9.152 | 114.40 | Solvent | USP |
| Oleoyl poly-oxylglycerides | 4.00 | 0.400 | 5.00 | Wetting agent (hydrophilic oil) | Ph. Eur./ NF |
| Colloidal silicon dioxide | 4.00 | 0.400 | 5.00 | Viscosity increasing agent | NF |
| Total | 100.00 | 10.0 | 125.00 | | |

TABLE 3.2.P.1-3

Components, Quality, Quality Standards and Function-0.72% TBS-2 Gel

| Component | Amount (% w/w) | Amount per multiple dose dispenser (g) | Amount delivered per actuation (mg) | Function | Quality Standard |
|---|---|---|---|---|---|
| Testosterone | 0.72 | 0.072 | 0.90 | Active Ingredient | USP |
| Castor oil | 91.28 | 9.128 | 114.10 | Solvent | USP |
| Oleoyl poly-oxylglycerides | 4.00 | 0.400 | 5.00 | Wetting agent (hydrophilic oil) | Ph. Eur./ NF |
| Colloidal silicon dioxide | 4.00 | 0.400 | 5.00 | Viscosity increasing agent | NF |
| Total | 100.00 | 10.0 | 125.00 | | |

A study is completed in accordance with USP<51> Antimicrobial Effectiveness Testing to establish that microbial growth is absent in the container closure system after filling and during use. This study is performed with a 4.5% testosterone gel filled in the multiple dose dispenser.

Sixteen (16) multiple dose dispensers are tested in this study. Each multiple dose dispensers is inoculated with 0.05 mL of one of the standardized microbial suspensions (*Candida albicans, Aspergillus brasiliensis, Sraphylococcus aureus, Pseudomonas aeruginosa*) through the tip of the piston. These microorganisms are chosen as they are the microorganisms recommended in USP<51> Antimicrobial Effectiveness Testing for nasal products. The theoretical concentration of the organisms used for the inoculation is between 100,000 and 1,000,000 microorganisms per mL. For the following 21 days, two actuations are performed on each multiple dose dispenser daily to reflect real use (2 actuations is equivalent to 1 dose).

The inoculated dispensers are incubated upright at 20-25° C. Each of the samples is examined at 1, 7, 14 and 21 days, subsequent to inoculation. The study is conducted over twenty-one (21) days. The Day 1 timepoint is chosen to assess the worst case scenario. Testing of the samples does occur following the daily actuations. For all the timepoints, the gel remaining in the barrel is tested. The piston is removed and the remaining gel in the barrel was subjected to further testing to determine the number of test organisms present, using 10 grams of the sample. The sample is examined at these intervals for any observed changes in appearance (i.e. colour, viscosity). Each dispenser is discarded after sampling. The results are presented in Table 3.2.P.2.5-1.

TABLE 3.2.P.2.5-1

Number of Microorganisms Surviving During Testing Period

| Organism | Initial Count | Number of Microorgasnisms surviving during testing period (Microorganisms per gram) | | | |
|---|---|---|---|---|---|
| | | Day 1 | Day 7 | Day 14 | Day 21 |
| S. aureus | 535,000 Log value 5.7 | Less than 10 (ND) Log value <1.0 | Less than 10 (ND) Log value <1.0 | Less than 10 (ND) Log value <1.0 | Less than 10 (ND) Log value <1.0 |
| P. aeruginosa | 405,000 Log value 5.6 | Less than 10 (ND) Log value <1.0 | Less than 10 (ND) Log value <1.0 | Less than 10 (ND) Log value <1.0 | Less than 10 (ND) Log value <1.0 |

TABLE 3.2.P.2.5-1-continued

Number of Microorganisms Surviving During Testing Period

| Organism | Initial Count | Number of Microorgasnisms surviving during testing period | | | |
|---|---|---|---|---|---|
| | | Day 1 | Day 7 | Day 14 | Day 21 |
| | | Microorganisms per gram | | | |
| C. albicans | 980,000 Log value 6.0 | Less than 10 (ND) Log value <1.0 | Less than 10 (ND) Log value <1.0 | Less than 10 (ND) Log value <1.0 | Less than 10 (ND) Log value <1.0 |
| A. brasiliensis | 675,000 Log value 5.8 | Less than 10 (ND) Log value <1.0 | Less than 10 (ND) Log value <1.0 | Less than 10 (ND) Log value <1.0 | Less than 10 (ND) Log value <1.0 |

ND—none detected; No changes were observed in the appearance of the product at each timepoint during the testing interval

TABLE 3.2.P.2.5-2

Criteria for Tested Microorganisms (Catergory 2)
Criteria for Tested Microorganisms (Category 2)

| | |
|---|---|
| Bacteria | Not less than 2.0 log reduction form the initial calculated count at 14 days, and no increase from the 14 day count at 28 days. |
| Yeast and Molds | No increase from the initial calculated count at 14 and 28 days |

In summary, the bacteria S. Aureus and P. Aeruginosa showed a reduction of not less than 2.0 from the initial count at 14 days and no increase from the 14 days count at 21 days. The yeast C. Albicans and A. Brasiliensis showed no increase from the initial calculated count at 14 and 21 days. Testosterone nasal gel packaged in a multiple dose dispenser meets the criteria for the Anitmicrobial Effectiveness Test.

Three different concentrations of TBS-2 clinical material, 0.24%, 0.48% and 0.72%, will be manufactured for the proposed clinical trial. The batch formulae for these batches are presented in Table 3.2.P.3.2-1.

TABLE 3.2.P.3.2-1

Batch Formulae for 0.24%, 0.48% and 0.72% TBS-2 at the 100 kg Batch Size

| Components | Quantity per Batch (kg) | | |
|---|---|---|---|
| | 0.24% TBS-2 | 0.48% TBS-2 | 0.72% TBS-2 |
| Testosterone, USP | 0.24 | 0.48 | 0.72 |
| Castor oil, USP | 91.76 | 91.52 | 91.28 |
| Oleoyl polyoxylglycerides, Ph. Eur./NF | 4.00 | 4.00 | 4.00 |
| Colloidal silicon dioxide, NF | 4.00 | 4.00 | 4.00 |
| Total | 100.00 | 100.00 | 100.00 |

The TBS-2 bulk gel is tested to the following specifications for batch release.

TABLE 3.2.P.5.1-1

Specification for TBS-2 Bulk Gel

| Test Parameter | Method/Reference | Acceptance Criteria | |
|---|---|---|---|
| Appearance | STM.GEN.001 | Slightly yellow gel | |
| Identification A | STM.TBS2.001 | Retention time of the peak in the sample corresponds to that of the Testosterone standard. | |
| Identification B | STM.TBS2.001 | UV spectrum of the sample corresponds to that of the Testosterone standard | |
| Assay | STM.TBS2.001 | 95.0-105.0% | |
| Related Compounds | STM.TBS2.002 | TBS1 RC4, | 0.2% |
| | | TBS1 RC5, | 0.5% |
| | | Single unknown impurity, | 0.2% |
| | | Total impurities, | 1.0% |
| Viscosity | USP<91 1> | Report results | |
| Water | USP<921>Method I | Report results | |
| Residual Solvents | USP<467> | The product complies with USP<467> requirements | |

TBS1 RC4-17,-hydroxyandrosta-4,6-dien-3-one (Delta-6-testosterone); EP Impurity I
TBS1 RC5-17,-hydroxyandrost-4-en-3one (Epitestosterone); EP Impurity C The TBS-2 gel packaged in the multiple dose dispenser is tested to the following specifications for batch release.

TABLE 3.2.P.5.1-2

Specification for TBS-2 Gel Packaged in Multiple Dose Dispenser

| Test Parameter | Method/Reference | Acceptance Criteria | |
|---|---|---|---|
| Appearance | STM.GEN.001 | White barrel and cap, filled with slightly yellow gel | |
| Identification A | STM.TBS2.001 | Retention time and spectrum corresponds to standard | |
| Identification B | STM.TBS2.001 | UV spectrum matches reference spectrum | |
| Delivered Dose Uniformity | STM.TBS2.003 | Meets USP <601> Mean (beginning doses & end doses) Min: Max: % RSD: | |
| Related Compounds | STM.TBS2.002 | TBS1 RC4, | 0.2% |
| | | TBS1 RC5, | 0.5% |
| | | Single unknown impurity, | 0.2% |
| | | Total impurities, | 1.0% |
| Residual Solvents | USP<467> | Complies with USP<467> | |
| Microbial Limits | USP<61>& <62> | Total aerobic microbial count <$10^2$ cfu/g | |
| | | Total combined yeasts/mould count <10 cfu/g | |
| | | P. aeruginosa | 0/g |

TBS1 RC4-17,-hydroxyandrosta-4,6-dien-3-one (Delta-6-testosterone); EP Impurity I
TBS1 RC5-17,-hydroxyandrost-4-en-3one (Epitestosterone); EP Impurity C Delivered Dose Uniformity as per USP has been added as a release test to verify the performance of the dispenser. In addition, the analytical procedure to test for related compounds has been modified. The viscosity and water content of the gel are tested upon release for information purposes only. These analytical procedures are described in this section.

Ten individual barrels are taken and tested for Delivered Dose Uniformity according to the method summarized in Table 3.2.P.5.2.1.1-1. Each dispenser is primed by actuating the pump 10 times. The drug content of the first dose, i.e. actuations #11 and #12 and the final dose (based on label claim of 10 doses, i.e. 20 actuations), i.e. actuation #29 and #30 are tested. The mean of the 10 doses (20 actuations) are reported.

TABLE 3.2.P.5.2.1.1-1

Summary of Chromatographic Conditions for Delivered Dose Uniformity

| | |
|---|---|
| Mobile Phase | Mobile Phase: Methanol:Water 60:40 |
| Column | Type: Thermo ODS Hypersil |
| | Dimensions: 100 cm × 4.6 mm |
| | Particle Size: 5 µm |
| Flow Rate | 1.0 mL/min |
| Column Temp. | 40° C. |
| Detector | 245 nm |
| Injection Volume | 5 L |
| Run Time | 9 minutes |
| Retention Time (RT) | Testosterone Typical RT 5.0 min |
| Standard and Sample Concentrations | For Delivered Dose: 600 µg/dose: Standard contains 15 µg/mL of testosterone Sample contains of 15 µg/mL of testosterone; 1200 µg/dose & 1800 µg/dose: Standard contains 30 µg/mL of testosterone Sample contains of 30 µg/mL of testosterone; |

The related compounds TBS1 RC4 (Impurity I/Δ-6-testosterone) and TBS1 RC5 (Impurity C/epitestosterone) in the finished product are analysed by HPLC, as well as the unknown impurities according to the method summarized in Table 3.2.P.5.2.1.2-1.

TABLE 3.2.P.5.2.1.2-1

Summary of Chromatographic Conditions for Related Compounds Method

| Mobile Phase | Mobile Phase A: Water, 100% Mobile Phase B: Acetonitrile: Methanol 60:40 | |
|---|---|---|
| | Filter and de-aerate each mobile phase Gradient Program | |
| Time | Mobile Phase A | Mobile Phase B |
| 0 | 70 | 30 |
| 5.0 | 70 | 30 |
| 15.0 | 20 | 80 |
| 20.0 | 0 | 100 |
| 25.0 | 0 | 100 |
| 30.0 | 70 | 30 |
| Column | Type: Hypersil BDS C18 Dimensions: 250 cm × 4.0 mm Particle Size: 5 µm | |
| Flow Rate | 1.0 mL/min | |
| Column Temp. | 40° C. | |
| Detector | 240 nm & 290 nm | |
| Injection Volume | 20 L | |
| Run Time | 30 minutes | |
| | Related Compound | Typical RT |
| Retention Time (RT) | Impurity I | 14.0 min |
| | Testosterone | 14.6 min |
| | Impurity C | 16.0 min |
| Standard and Sample Concentrations | Standard contains 0.75 µg/mL of testosterone and 2 µg/mL of Impurity I Sample contains of 48 µg/mL of testosterone | |

The measurement of the viscosity of TBS-2 is performed using a rotational viscosimeter. The results are reported for information purposes.

The content of water in the gel is determined using a direct titration measurement as per USP Method 1a. The results of the water content are reported for information purposes.

Assay and Delivered Dose Uniformity as per USP has been added as a release test to verify the performance of the dispenser. In addition, the analytical procedure to test for related compounds has been modified. The validation of these analytical procedures are described in this section.

The Assay and Delivered Dose method has been validated according to the parameters listed in Table 3.2.P.5.3.1-1.

TABLE 3.2.P.5.3.1-1

Assay and Delivered Dose Validation

| Test | Acceptance Criteria | Results |
|---|---|---|
| Linearity | $r^2 \geq 0.998$ | $r^2 = 0.999$ |
| Accuracy | Mean Recovery 98-102% Individual 98-102% | 0.24% and 0.48% Gel Mean = 100.6% (for all levels 50%, 100% and 150%) % RD = 0.6% 0.72% Gel Mean = 100.0% (for all levels 50%, 100% and 150%) % RD = 0.2% |
| System Precision | RSD ≤2.0% | At 15 µg/mL RSD 0.2% At 30 µg/mL RSD 0.4% |
| Method Precision | | 0.24% TBS-2 |
| | | Chemist 1  Chemist 2 |
| | | Mean  98.2%  98.2% |
| | | RSD  0.1%  0.3% |
| | | Absolute Difference 0.0 |
| Repeatability and Intermediate Precision Assay for 6 samples RSD ≤2.0% Absolute Difference between Chemist 1 and Chemist 2 is NMT 2% | | 0.48% TBS-2 Chemist 1  Chemist 2 Mean  96.6%  97.0% RSD  0.1%  0.2% Absolute Difference 0.4 0.72% TBS-2 Chemist 1  Chemist 2 Mean  99.0%  98.3% RSD  0.2%  0.1% Absolute Difference 0.7 |
| Stability of | Standard Solution for 0.24% and 0.48% | 5 Days |
| | Standard Solution for 0.72% | 5 Days |
| | Sample Solution for 0.24% and 0.48% | 5 Days |
| | Sample Solution for 0.72% | 5 Days |
| Selectivity | No interference of excipient mixture with testosterone peak | Complies |

Related Compounds/Degradation Products by HPLC. The method has been validated to the performance characteristics presented in Table 3.2.P.5.3.2-1 and 3.2.P.5.3.2-2.

TABLE 3.2.P.5.3.2-1

Analytical Validation for the Determination of Related Compounds by HPLC

| Test | Acceptance Criteria | | Results TBS1 RC4 (Limit: 0.2%) | Active (for unknown) (Limit: 0.2%) |
|---|---|---|---|---|
| Linearity | | Number of concentrations | 7 | 7 |
| | | Range (expressed as % and conc µg/mL) | 0.045 µg/mL to 2.252 µg/mL | 0.045 µg/mL to 2.324 µg/mL |
| | | Slope | 62.402 | 103.3735 |
| | | Y-intercept | 0.1604 | 0.1766 |
| | $r^2 \geq 0.99$ | Correlation coefficient ($r^2$) | 1.00 | 1.00 |
| LOQ | % RSD ≤10.0% of six injections at the LOQ concentration | Concentration % RSD | 0.1% 1.4% | 0.1% 2.1% |
| System Precision | | Conc.(s) (expressed as % "A") | 100% (Standard) | 100% (Standard) |
| | | Number of replicates | 6 | 6 |
| | % RSD ≤5.0% | Result average % RSD | 80.12765 0.2 | 46.88562 0.2 |
| Recovery At LOQ | Mean Recovery is between 80 to 120% | Number of replicates % Recovery at LOQ of specified limit % RSD at LOQ | 3 103.8 2.5 | 3 N/A |
| Recovery At 100% | Mean recovery is between 80 to 120% | Number of replicates % Recovery at 100% of specified limit % RSD | 3 101.2 1.4 | 3 N/A |
| Recovery At 150% | Mean recovery is between 80 to 120% | Number of replicates % Recovery at 150% of specified limit % RSD | 3 99.3 1.3 | 3 N/A |
| Method Precision | % RSD of mean result values of known related compound obtained from six samples: ≤10% | | TBS1 RC4 Chemist 1 Mean = 0.20% % RSD = 1.3 Chemist 2 Mean = 0.19% % RSD = 1.6 | TBS1 RC5 Chemist 1 Mean = 0.24% % RSD = 1.4 Chemist 2 Mean = 0.24% % RSD = 1.3 |

TABLE 3.2.P.5.3.2-2

Analytical Validation for the Determination of Related Compounds by HPLC

| Test | Acceptance Criteria | Results |
|---|---|---|
| Stability of Standard | The recovery of the standard solution is 80 to 120% | Standard solution is stable for 40 hours at room temperature |
| Stability of Sample Solution | Sample solution: The recovery of the testosterone and TBS 1 RC4 solution is 80 to 120% No significant change in known, unknown and total % of RCs over the specified length of time determined | Sample solution is stable for 1 Day at room temperature |
| Selectivity | The analytes of interest are free of interference. | Conforms |

It can be concluded that the analytical method meets the acceptance criteria described in the validation plan.

For the Phase I trial, three bulk gel batches of TBS-2 have been manufactured and are summarized in Table 3.2.P.5.4-1. Batch analysis data from the bulk gel batches IMP1 1005, IMP1 1006 and IMP1 1007 are presented in Tables 3.2.P.5.4-2 and batch analysis data from finished drug product batches IMP1 1008, IMP1 1009 and IMP1 1010 are presented in Table 3.2.P.5.4-3.

TABLE 3.2.P.5.4-1

Description of TBS-2 Batches

| | | | |
|---|---|---|---|
| Concentration | 0.24% | 0.48% | 0.72% |
| Bulk Batch No. | IMP11005 | IMP11006 | IMP11007 |
| Finished Product Batch No. | IMP11008 | IMP11009 | IMP11010 |
| Batch No. Testosterone | 80402960 | 80402960 | 80402960 |
| Equipment | 100 kg | 100 kg | 100 kg |
| Batch Size | | | |
| Filling Quantity per Multiple Dose Dispenser₁ | 10 g | 10 g | 10 g |

*Net fill weight 10 g ± 1.0 g

TABLE 3.2.P.5.4-2

Batch Analysis-TBS-2 Bulk Gel, Batches IMP1 1005, IMP1 1006 and IMP1 1007

| Test Parameter | Acceptance Criteria | IMP1 1005 | IMP1 1006 | IMP1 1007 |
|---|---|---|---|---|
| Appearance | Slightly yellow gel | Complies | Complies | Complies |
| Identification A | Retention time corresponds to standard | Complies | Complies | Complies |
| Identification B | UV spectrum corresponds to reference sample | Complies | Complies | Complies |
| Assay | 95.0-105.0% | 98.2% | 96.6% | 99.2% |
| Related Compounds | TBS1 RC4 ≤0.2% | BRT | BRT | BRT |
| | TBS1 RC5 ≤0.5% | 0.2% | 0.2% | 0.2% |
| | Each individual unknown imp. ≤0.2% | BRT | BRT | BRT |
| | Total imp. ≤1.0% | 0.2% | 0.2% | 0.2% |
| Viscosity | Report results | 13,820 mPas | 12,700 mPas | 13,000 mPas |
| Water | Report results | 0.2% | 0.2% | 0.2% |
| Residual | The product complies with USP <467> requirements | Complies | Complies | Complies |

TBS1 RC4-17.-hydroxyandrosta-4,6-dien-3-one (Delta-6-testosterone);
EP Impurity I TBS1 RC5-17.-hydroxyandrost-4-en-3one (Epitestosterone);
EP Impurity C
BRT-below reporting threshold

TABLE 3.2.P.5.4-3

Batch Analysis -TBS-2 Finished Product Filled in Multiple Dose Dispensers Batches IMP1 1008, IMP1 1009 and IMP1 1010

| Method | Specification | IMP11008 | IMP11009 | IMP11010 |
|---|---|---|---|---|
| Appearance | White Albion barrel and cap filled with slightly yellow gel | Complies | Complies | Complies |
| Identification A | Retention time corresponds to standard | Complies | Complies | Complies |
| Identification B | UV spectrum corresponds to reference sample | Complies | Complies | Complies |
| Delivered Dose Uniformity | Beginning Mean | 98.5% | 97.2% | 98.2% |
| | Min | 94.7% | 95.5% | 93.7% |
| | Max | 100.5% | 98.6% | 100.4% |
| | % RSD | 1.7% | 1.1% | 2.1% |
| | End Mean | 98.6% | 97.3% | 98.1% |
| | Min | 97.3% | 95.3% | 96.1% |
| | Max | 100.5% | 101.5% | 101.2% |
| | % RSD | 1.0% | 1.7% | 1.7% |
| Related Compounds | TBS1 RC4 ≤0.2% | BRT | BRT | BRT |
| | TBS1 RC5 ≤0.5% | 0.2% | 0.2% | 0.2% |
| | Max individual unknown imp. ≤0.2% | BRT | BRT | BRT |
| | Total imp. ≤1.0% | 0.2% | 0.2% | 0.2% |
| Residual Solvents | The product complies with USP <467> requirements | Complies | Complies | Complies |
| Microbial Limits | TAMC ≤$10^2$ cfu/g | <$10^2$ cfu/g | <$10^2$ cfu/g | <$10^2$ cfu/g |
| | TYMC ≤10 cfu/g | <10 cfu/g | <10 cfu/g | <10 cfu/g |
| | S. aureus-must be absent in 1 g | 0/g | 0/g | 0/g |
| | P. aeruginosa-must be absent in 1 g | 0/g | 0/g | 0/g |

TBS1 RC4-17.-hydroxyandrosta-4,6-dien-3-one (Delta-6-testosterone);
EP Impurity I TBS1 RC5-17.-hydroxyandrost-4-en-3one (Epitestosterone);
EP Impurity C
TAMC-total aerobic microbial count;
TYMC total combined yeasts/mould count BRT-below reporting threshold The only change made to the previous specification is the additional test for Delivered Dose Uniformity as per USP, to verify the performance of the dispenser. The following is a description of this test in the specification with a discussion concerning their suitability for intended use and a justification for the acceptable criterion.

The delivered dose of the gel discharged from the nasal actuator is analysed for the active content from a sample at the beginning and at the end of an individual multiple dose dispenser. Each, dispenser is primed by actuating the pump 10 times. The drug content of the first dose, i.e. actuations #11 and #12 and the final dose (based on label claim of 10 doses, i.e. 20 actuations), i.e. actuation #29 and #30 are tested using an in house HPLC method to determine the amount of active delivered from the nasal actuator, which is expressed as a percentage of the label claim.

The delivered dose uniformity test demonstrates the uniformity of the dose per actuation, and per total dose (2 actuations) and is consistent with the label claim, discharged from the nasal actuator.

The acceptance criteria proposed are based on USP<601> for Delivered Dose Uniformity and Guidance for Nasal Spray and Inhalation Solution, Suspension, and Spray Drug Products—Chemistry, Manufacturing and Controls Documentation:

The amount of active per determination is not outside of 80 to 120% of the LC for more than 2 of 20 determinations from 10 containers; none of the determinations is outside of 75 to 125% of the LC and the mean for each of the beginning and end determinations are not outside of 85 to 115% of LC.

TBS-2 is packaged in an Albion 15 ml barrel composed of polypropylene with a VP39/140H pump and cap. The barrel is filled with gel under vacuum using an Airlesssystems Laboratory filling unit (Airlesssystems, RD 149 Charleval 27380, France) to effectively expel 125 mg of gel.

The target fill weight for the Albion 15 ml barrel is 10.0±1.0 g.

The quality control measures are proposed for the packaging components. Material information on the Albion 15 ml Barrel with VP 39/140H Pump and Cap is provided in Table 3.2.P.7-1. In addition to the supplier release CoA, the container closure system is retested upon receipt to conform to the specifications summarized in Table 3.2.P.7-2 The CoA for the Albion 15 ml Barrel Lot 10318UV12101 is provided in Appendix 5. A Figure of the 15 ml Albion Bottle and the PMP VP 39/140H 15 Albion+Digital Actuator+Cap 15 ml Albion Rounded is provided at FIG. 39.

TABLE 3.2.P.7-1

Albion 15 ml Barrel with VP 39/140H Pump and Cap-Material Information

| Component | Material |
|---|---|
| Barrel | Polypropylene: PPR 7220<br>White colorant: PP 00121522 |
| Piston | Polytethylene PEHD PURELL GC 7260 |
| Base | Polypropylene: PPR 7220<br>White colourant: PP 00121522 |
| Insert | Polypropylene: PPH 7060 |
| Pen actuator | Polypropylene: PPC 11712<br>White colourant: PP0012 1522 |
| Snap on | Polypropylene: PPH 5060<br>White colourant: PP0012 1522 |
| Neck gasket | Thermoplastic: F217-5 906 |
| Stem gasket | Elastomer: 522C |
| Pump | |
| Body | PBT VALOX HX312C-1H1001 |
| Ball support | HD Polyethylene: Purell GB7250 |
| Ball | STAINLESS STEEL AISI 304L |
| Spring cap | POM HOSTAFORM C27021 |
| Return spring | STAINLESS STEEL 1.43 10 |
| Piston | HD Polyethylene: HOSTALEN GF4750<br>SILBIONE DM300 GMP |
| Stem | POM DELRIN 900PNC 10 |
| Pre compression spring | STAINLESS STEEL 1,43 10 |
| Turret | Polypropylene: PPH5060<br>White colourant: 85276 |

TABLE 3.2.P.7-2

Albion 15 ml Barrel with VP 39/140 Pump and Cap - Specifications

| Test Parameter | Acceptance Criteria |
|---|---|
| Appearance | Complies to current standard |
| Commodity no. of supplier | 153963PH (SEB 15 Albion PPBC/ 4625 FDP BC/4625) |
| Colour-white | Must comply |
| Design | Complies technical drawing no. 01484 Index A (14.06.2007) |
| Total height | 68.60 mm-69.70 mm |
| Outer diameter of bottle | 24.80 mm-25.50 mm |
| Outer diameter of mouth | 16.30 mm-16.45 mm |
| Compatibility with actuator | Must comply |
| Material type barrel-CoA | Polypropylene: PPR 7220,<br>Colourant: white PP00121522 |
| Material type piston-CoA | Polyethylene: HDPE Purell GC 7260 |
| Material type bottom-CoA | Polypropylene: PR 7220,<br>Colourant: white PP00121522 |
| Identity-IR-spectrum of barrel | Must comply to reference spectrum |
| Packaging | Must comply |
| Attributive testing | AQL must comply |
| Certificate of Conformity of supplier | Must be given and comply |

Three clinical batches bulk batches of TBS-2 (IMP1 1005, IMP1 1006 and IMP1 1007) were manufactured in a GMP facility. Each batch was then filled in the multiple dose dispenser as summarized in Table 3.2.P.8.1.

TABLE 3.2.P.8.1

Bulk Gel and Finished Product Batches

| Concentration | 0.24% | 0.48% | 0.72% |
|---|---|---|---|
| Bulk Batch No. | IMP11005 | IMP11006 | IMP11007 |
| Finished Product Batch No. | IMP11008 | IMP11009 | IMP11010 |

The bulk gel will stored under real time conditions 25±2° C., 60±5% RH and will be tested at the time intervals presented in Table 3.2.P.8.3.-2.

TABLE 3.2.P.8.3-2

Stability Schedule for TBS-2 Batches IMP1 1005, IMP1 1006 and IMP1 1007

| Storage Conditions (° C., % RH) | Strength | Batch Number | Product Type | Completed Test Intervals (Outstanding Test Intervals) |
|---|---|---|---|---|
| 25 ± 2° C., 60 ± 5% RH | 0.24% | IMP11005 | Bulk gel | 0, (1 m, 2 m, 3 m, 6 m, 9 m, 12 m, 18 m, 24 m, 36 m) |
| 25 ± 2° C., 60 ± 5% RH | 0.48% | IMP11006 | Bulk gel | 0, (1 m, 2 m, 3 m, 6 m, 9 m, 12 m, 18 m, 24 m, 36 m) |
| 25 ± 2° C., 60 ± 5% RH | 0.72% | IMP11007 | Bulk gel | 0, (1 m, 2 m, 3 m, 6 m, 9 m, 12 m, 18 m, 24 m, 36 m) |

TABLE 3.2.P.8.1-3

Stability Study Test Parameters of TBS-2 Bulk Gel and Corresponding Acceptance Criteria

| Test Parameter | Method/Reference | Acceptance Criteria | |
|---|---|---|---|
| Appearance | STM.GEN.001 | Slightly yellow gel | |
| Identification A | STM.TBS2.001 | Retention time and spectrum corresponds to standard | |
| Assay | STM.TBS2.001 | 95.0-105.0% | |
| Related Compounds | STM.TBS2.002 | TBS1 RC4, | 0.2% |
| | | TBS1 RC5, | 0.5% |
| | | Individual unknown impurity, | 0.2% |
| | | Total impurities, | 1.0% |
| Viscosity | USP <911> | Report results | |
| Water | USP <921> Method I | Report results | |

TBS1 RC4-17.-hydroxyandrosta-4,6-dien-3-one (Delta-6-testosterone); EP Impurity I TBS1 RC5-17.-hydroxyandrost-4-en-3one (Epitestosterone); EP Impurity C The multiple dose dispensers are stored under real time storage (25±2° C., 60±5% RH), intermediate time storage (30±2° C., 65±5% RH) and accelerated storage conditions (40±2° C., 75±5% RH) and tested to the schedule presented in Table 3.2.P.8.1-4. Ten (10) dispensers will be analyzed at each time point.

TABLE 3.2.P.8.1-4

Stability Schedule COMPLEO Finished Product Filled in Multiple Dose Dispenser

| Storage Conditions (° C., % RH) | Strength | Batch Number | Product Type | Completed Test Intervals (Outstanding Test Intervals) |
|---|---|---|---|---|
| 25 ± 2° C., 60 ± 5% RH | 0.24% | IMP1 1008 | Finished product in multiple dose dispenser | 0 m, (3 m, 6 m, 9 m, 12 m, 18 m, 24 m, 36 m) |
| 30 ± 2° C., 65 ± 5% RH | 0.24% | IMP1 1008 | Finished product in multiple dose dispenser | 0 m, (3 m, 6 m, 9 m, 12 m,) |
| 40 ± 2° C., 75 ± 5% RH | 0.24% | IMP1 1008 | Finished product in multiple dose dispenser | 0 m, (1 m, 2 m, 3 m, 6 m) |
| 25 ± 2° C., 60 ± 5% RH | 048% | IMP1 1009 | Finished product in multiple dose dispenser | 0 m, (3 m, 6 m, 9 m, 12 m, 18 m, 24 m, 36 m) |
| 30 ± 2° C., 65 ± 5% RH | 0.48% | IMP1 1009 | Finished product in multiple dose dispenser | 0 m, (3 m, 6 m, 9 m, 12 m) |
| 40 ± 2° C., 75 ± 5% RH | 0.48% | IMP1 1009 | Finished product in multiple dose dispenser | 0 m, (1 m, 2 m, 3 m, 6 m) |
| 25 ± 2° C., 60 ± 5% RH | 0.72% | IMP1 1010 | Finished product in multiple dose dispenser | 0 m, (3 m, 6 m, 9 m, 12 m, 18 m, 24 m, 36 m) |
| 30 ± 2° C., 65 ± 5% RH | 0.72% | IMP1 1010 | Finished product in multiple dose dispenser | 0 m, (3 m, 6 m, 9 m, 12 m) |
| 40 ± 2° C., 75 ± 5% RH | 0.72% | IMP1 1010 | Finished product in multiple dose dispenser | 0 m, (1 m, 2 m, 3 m, 6 m) |

The attributes used to confirm the quality of TBS-2 finished product and corresponding acceptance criteria are listed in Table 3.2.P.8. 1-5.

TABLE 3.2.P.8.1-5

Stability Study Test Parameters of TBS-2 Finished Product and Corresponding Acceptance Criteria

| Test Parameter | Method/Reference | Acceptance Criteria | |
|---|---|---|---|
| Appearance | STM.GEN.001 | White barrel and cap, filled with slightly yellow gel | |
| Identification A | STM.TBS2.001 | Retention time and spectrum corresponds to standard | |
| Delivered Dose Uniformity | STM.TBS2.003 | Meets USP <601> Mean (beginning doses & end doses) Min: Max: % RSD: | |
| Related Compounds | STM.TBS2.002 | TBS1 RC4, | 0.2% |
| | | TBS1 RC5, | 0.5% |
| | | Single unknown impurity, | 0.2% |
| | | Total impurities, | 1.0% |
| Microbial Limits | USP <61> & <62> | Total aerobic microbial count | <10² cfu/g |
| | | Total combined yeasts/mould count | <10 cfu/g |
| | | P. aeruginosa | 0/g |
| | | S. aureus | 0/g |

The results from the stability studies will be evaluated for any trends and a shelf life proposed after data has been generated. Room temperature, intermediate and accelerated stability studies are ongoing and updated data are available upon request.

TBS-2 bulk and finished product will be placed on a stability program as described in section 3.2.P.8.1. Stability updates will be provided as available.

A 4.5% testosterone gel inaccordance with this invention is packaged in the identical container closure system, the Albion 15 ml barrel composed of polypropylene with a VP39/140H pump and cap. The qualitative formulation is the same for the 4.5% gel as for the 0.24% 0.48% and 0.72% gels, only the proportion of castor oil and testosterone are different. Tables 3.2.P.8.3-1 and 3.2.P.8.3-2 provides supportive data for the stability of testosterone gel packaged in the Albion 15 ml barrel composed of polypropylene with a VP39/140H pump and cap. This supportive data indicates that the gel packaged in the dispenser provides adequate protection for potency and purity and are within acceptance criteria.

TABLE 3.2.P.8.3-1

Stability Data 4.5% Testosterone Gel Batch 1969 in Multiple Dose Dispensers, (25 ± 2° C., 60 ± 5% R.H., upright)

| Test | Specification | Time 0 | 3 months | 6 months | 9 months | 12 months |
|---|---|---|---|---|---|---|
| Appearance | White barrel and cap filled with slightly | Complies | Complies | | | |
| Identification | Retention time of peak in the sample corresponds to standard | Complies | Complies | | | |
| Delivered Dose Uniformity | Beginning and End must comply to USP<601> | Complies | Complies | | | |
| | Beginning | | | | | |
| | Mean | 100.5% | 100.2% | | | |
| | Min | 96.0% | 97.9% | | | |
| | Max | 103.6% | 102.1% | | | |
| | % RSD | 2.1% | 1.5% | | | |
| | End | | | | | |
| | Mean | 102.1% | 100.1% | | | |
| | Min | 99.9% | 98.9% | | | |
| | Max | 104.3% | 102.7% | | | |
| | % RSD | 1.3% | 1.1% | | | |
| Related Compounds | TBS1 RC4 ≤ 0.2 | BRT | BRT | | | |
| | TBS1 RC5 ≤ 0.5% | 0.3% | 0.3% | | | |
| | Max individual unknown imp. ≤ 0.2 % | BRT | BRT | | | |
| | Total imp. ≤ 1.0% | 0.3% | 0.3% | | | |
| Microbial Limits | TAMC < $10^2$ cfu/g | < 10 cfu/g | — | | | |
| | TYMC < 10 cfu/g | < 10 cfu/g | — | | | |
| | S. aureus — 0/g | 0/g | — | | | |
| | P. aeruginosa — 0/g | 0/g | — | | | |

BRT — below reporting threshold

TABLE 3.2.P.8.3-2

Stability Data 4.5% Testosterone Gel Batch 1969 in Multiple Dose Dispensers (40 ± 2° C., 75 ± 5% R.H., upright)

| Test | Specification | | Time 0 | 1 months | 2 months | 3 months | 6 months |
|---|---|---|---|---|---|---|---|
| Appearance | White barrel and cap filled with slightly | | Complies | Complies | Complies | Complies | |
| Identification | Retention time of peak in the sample corresponds to | | Complies | Complies | Complies | Complies | |
| Delivered Dose Uniformity | Beginning and End must comply to USP<601> | | Complies | Complies | Complies | Complies | |
| | Beginning | Mean | 100.5% | 105.0% | 102.3% | 100.6% | |
| | | Min | 96.0% | 103.4% | 100.5% | 99.2% | |
| | | Max | 103.6% | 106.2% | 104.7 | 101.4% | |
| | | % RSD | 2.1% | 0.8% | 1.5% | 0.6% | |
| | End | Mean | 102.1% | 104.6% | 102.6% | 100.3% | |
| | | Min | 99.9% | 103.5% | 100.5% | 99.3% | |
| | | Max | 104.3% | 107.0% | 104.5% | 101.4% | |
| | | % RSD | 1.3% | 1.0% | 1.1% | 0.6% | |

TABLE 3.2.P.8.3-2-continued

Stability Data 4.5% Testosterone Gel Batch 1969 in Multiple Dose Dispensers (40 ± 2° C., 75 ± 5% R.H., upright)

| Test | Specification | Time 0 | 1 months | 2 months | 3 months | 6 months |
|---|---|---|---|---|---|---|
| Related Compounds | TBS1 RC4 ≤0.2 | BRT | BRT | BRT | BRT | |
| | TBS1 RC5 ≤0.5% | 0.3% | 0.3% | 0.3% | 0.3% | |
| | Max individual unknown imp. ≤0.2% | BRT | 0.1% | 0.1% | 0.1% | |
| | Total imp. ≤1.0% | 0.3% | 0.4% | 0.4% | 0.4% | |
| Microbial Limits | TAMC <10$^2$ cfu/g | <10 cfu/g | — | — | — | |
| | TYMC <10 | <10 cfu/g | — | — | — | |
| | S. aureus - 0/g | 0/g | — | — | — | |
| | P. aeruginosa - 0/g | 0/g | — | — | — | |

BRT—below reporting threshold

14. DISCUSSION AND OVERALL CONCLUSIONS

A. Summary of Subjects

This was a phase 1, single-center, randomized, open-label parallel-group study of TBS-2 in 3 cohorts of subjects (Cohorts 1, 2, and 3) in Period 1 (single-dose) and a multiple-dose cohort in Period 2. A total of 24 healthy women received intranasal 600 μg, 1200 μg, or 1800 μg TBS-2 to evaluate the safety, tolerability, and PK of TBS-2.

B. Pharmacokinetic Conclusions

Results from the study indicate that the free testosterone concentrations and $AUC_{0-8}$, $AUC_{0-24}$, and $AUC_{0-t}$ parameters are dose proportional. While the total testosterone concentrations and parameters are clearly reflective of the dose, the strongest dose proportionality relationship is with the free testosterone. Dose proportionality is tested both by linear regression and by pair-wise dose comparison of parameters and both tests are equivocal in that free testosterone concentrations were dose proportional. Other analyte concentrations are less changed with the dose in the order of dihydrotestosterone with a minor change to estradiol with less and finally SHBG with the lest change.

Additionally equivalence between the single- and multi-dose profiles is not rejected for either of the free testosterone $AUC_{0-8}$ and $AUC_{0-24}$ parameters suggesting little if any accumulation of free testosterone following multiple dosing. However, this result is limited to the 3 subjects who received 1200 μg on each profile. Single-dose parameter calculations are performed on uncorrected concentrations of free testosterone, total testosterone and dihydrotestosterone for comparison to multiple-dose parameters. The pharmacokinetic analysis is based on 5 endogenous analytes that have reported normal ranges as well as baseline ranges. The following table presents the normal ranges, the baseline ranges observed and a break-down of the baseline ranges by dose cohort.

These data comparisons of the normal ranges with the pooled baseline ranges indicate that the pooled baseline ranges fall outside the normal ranges for free testosterone (min and max), dihydrotestosterone (max), estradiol (min) and SHBG (min and max).

C. Safety Conclusions

There have been no deaths, SAEs, or AEs leading to discontinuation during the study. Most TEAEs are in the system organ classes of general disorders (nasal related events) and administration site conditions and respiratory, thoracic, and mediastinal disorders. This is not unexpected given the venipuncture for PK blood sample draws and the intranasal study drug administration. Most TEAEs are mild in severity and are unlikely or not related to study medication.

TBS-2 is believed to be safe and well tolerated with respect to AEs and vital signs.

The disclosures of the patents, patent documents, articles, abstracts and other publications cited herein are incorporated herein by reference in their entireties as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

Having described our invention, we claim:

1. A method of treating a female for anorgasmia, said method comprising:
   (a) depositing an intranasal testosterone gel in an amount of between about 50 microliters and 150 microliters in

| Analyte | | Normal Range | Pooled Baseline | Dose Cohort | | |
|---|---|---|---|---|---|---|
| | | | | 600 (μg) | 1200 (μg) | 1800 (μg) |
| Free Testosterone (ng/dL) | Min | 0.166 | 0.10 | 0.10 | 0.13 | 0.15 |
| N = 112 | Max | 1.33 | 1.44 | 1.44 | 0.53 | 0.45 |
| Total Testosterone (ng/dL) | Min | 6.00 | 7.41 | 8.00 | 7.41 | 12.70 |
| N = 112 | Max | 86.00 | 58.00 | 58.00 | 41.10 | 43.90 |
| Dihydrotestosterone (ng/dL) | Min | 4.00 | 5.02 | 5.29 | 5.04 | 5.02 |
| N = 75 | Max | 22.00 | 32.60 | 22.10 | 25.30 | 32.60 |
| Estradiol (pg/mL) | Min | 20.00 | 17.00 | 20.90 | 17.00 | 17.70 |
| N = 112 | Max | 241.00 | 122.00 | 122.00 | 119.00 | 97.40 |
| SHBG (nmol/L) | Min | 18.00 | 15.30 | 15.30 | 16.00 | 25.20 |
| N = 112 | Max | 114.00 | 137.00 | 102.00 | 86.70 | 137.00 | each nasal cavity of each nostril of the female onto a mucosal membrane on an outer external nasal wall, opposite the nasal septum, preferably at about the middle to about the upper section of the outer external nasal wall and just under the cartilage section of the outer external nasal wall, to nasally deliver to the subject the intranasal testosterone gel to effectively treat the anorgasmia, wherein the testosterone gel comprises:
  (i) about 0.15% testosterone by weight of the intranasal testosterone gel, wherein the testosterone has a particle size of greater than 10 μm to prevent the testosterone particles from entering the respiratory tract following said nasal deposition; and
  (ii) a pharmaceutically acceptable vehicle; and
(b) squeezing or rubbing the exterior of the nose of the female following said nasal deposition to contact the nasally deposited intranasal testosterone gel with the nasal septum mucosal membrane within the nasal cavity, so that at least a portion of the deposited intranasal testosterone gel remains in contact with the mucosal membranes on the outer nasal wall and the nasal septum within the nasal cavity for sustained release of the testosterone from the intranasal testosterone gel over dose life.

2. The method of claim 1, wherein the intranasal testosterone gel is in an amount of about 100 microliters.

3. The method of claim 1, wherein said nasal deposition comprises depositing the intranasal testosterone gel into the nose of the female once or twice daily on demand.

4. The method of claim 1, wherein said nasal deposition comprises depositing the intranasal testosterone gel into the nose of the female at least once daily.

5. The method of claim 1, wherein said nasal deposition comprises depositing the intranasal testosterone gel into the nose of the female at least twice daily.

6. The method of claim 1, wherein the intranasal testosterone gel comprises:
  (a) 0.15% testosterone,
  (b) 91.85% castor oil,
  (c) 4.0% oleoyl polyoxylglycerides, and
  (d) 4.0% colloidal silicon dioxide.

7. A method of treating a female for hypoactive sexual desire disorder (HSDD), said method comprising:
(a) depositing an intranasal testosterone gel in an amount of between about 50 microliters and 150 microliters in each nasal cavity of each nostril of the female onto a mucosal membrane on an outer external nasal wall, opposite the nasal septum, preferably at about the middle to about the upper section of the outer external nasal wall and just under the cartilage section of the outer external nasal wall, to nasally deliver to the subject the intranasal testosterone gel to effectively treat the HSDD, wherein the testosterone gel comprises:
  (i) about 0.15% testosterone by weight of the intranasal testosterone gel, wherein the testosterone has a particle size of greater than 10 μm to prevent the testosterone particles from entering the respiratory tract following said nasal deposition; and
  (ii) a pharmaceutically acceptable vehicle; and
(b) squeezing or rubbing the exterior of the nose of the female following said nasal deposition to contact the nasally deposited intranasal testosterone gel with the nasal septum mucosal membrane within the nasal cavity, so that at least a portion of the deposited intranasal testosterone gel remains in contact with the mucosal membranes on the outer nasal wall and the nasal septum within the nasal cavity for sustained release of the testosterone from the intranasal testosterone gel over dose life.

8. The method of claim 7, wherein the intranasal testosterone gel is in an amount of about 100 microliters.

9. The method of claim 7, wherein said nasal deposition comprises depositing the intranasal testosterone gel into the nose of the female once or twice daily on demand.

10. The method of claim 7, wherein said nasal deposition comprises depositing the intranasal testosterone gel into the nose of the female at least once daily.

11. The method of claim 7, wherein said nasal deposition comprises depositing the intranasal testosterone gel into the nose of the female at least twice daily.

12. The method of claim 7, wherein the intranasal testosterone gel comprises:
  (a) 0.15% testosterone,
  (b) 91.85% castor oil,
  (c) 4.0% oleoyl polyoxylglycerides, and
  (d) 4.0% colloidal silicon dioxide.

* * * * *